US011807620B2

(12) United States Patent
Yang et al.

(10) Patent No.: US 11,807,620 B2
(45) Date of Patent: Nov. 7, 2023

(54) QUINAZOLINONE COMPOUNDS AND RELATED COMPOUNDS

(71) Applicant: PLEXIUM, INC., San Diego, CA (US)

(72) Inventors: Pengyu Yang, San Diego, CA (US); Mark Wilson, Ramona, CA (US); Mihai Azimioara, San Diego, CA (US)

(73) Assignee: Plexium, Inc., San Diego, CA (US)

( * ) Notice: Subject to any disclaimer, the term of this patent is extended or adjusted under 35 U.S.C. 154(b) by 78 days.

(21) Appl. No.: 17/180,644

(22) Filed: Feb. 19, 2021

(65) Prior Publication Data

US 2021/0269413 A1 Sep. 2, 2021

Related U.S. Application Data

(60) Provisional application No. 62/979,904, filed on Feb. 21, 2020.

(51) Int. Cl.
| | | |
|---|---|---|
| *C07D 401/04* | (2006.01) | |
| *C07D 401/14* | (2006.01) | |
| *C07D 487/04* | (2006.01) | |
| *C07D 498/08* | (2006.01) | |
| *C07D 498/18* | (2006.01) | |
| *C07D 413/14* | (2006.01) | |

(52) U.S. Cl.
CPC ......... *C07D 401/04* (2013.01); *C07D 401/14* (2013.01); *C07D 413/14* (2013.01); *C07D 487/04* (2013.01); *C07D 498/08* (2013.01); *C07D 498/18* (2013.01)

(58) Field of Classification Search
CPC .. C07D 401/04; C07D 401/14; C07D 487/04; C07D 498/08; C07D 498/18; C07D 413/14
See application file for complete search history.

(56) References Cited

U.S. PATENT DOCUMENTS

| 7,635,700 B2 | 12/2009 | Muller et al. |
| 8,921,385 B2 | 12/2014 | Muller et al. |
| 9,732,064 B2 | 8/2017 | Muller et al. |
| 11,001,566 B2 | 5/2021 | Lee et al. |
| 11,192,878 B2 * | 12/2021 | Hwang ................ C07D 401/14 |
| 2014/0228382 A1 | 8/2014 | DeWitt |
| 2017/0369471 A1 | 12/2017 | Muller et al. |
| 2018/0134684 A1 | 3/2018 | Bradner et al. |

FOREIGN PATENT DOCUMENTS

| KR | 20190044499 A | 4/2019 | |
| WO | WO 2008039489 A2 | 4/2008 | |
| WO | WO 2009042177 A1 | 4/2009 | |
| WO | WO 2017121388 A1 | 7/2017 | |
| WO | WO-2018208123 A1 * | 11/2018 | ............. A61K 31/53 |
| WO | WO-2020014489 A2 * | 1/2020 | ......... A61K 31/4545 |
| WO | WO 2020210630 A1 | 10/2020 | |
| WO | WO 2022032132 A1 | 2/2022 | |
| WO | WO 2022033548 A1 | 2/2022 | |

OTHER PUBLICATIONS

PubChem CID 147151006, National Center for Biotechnology Information. PubChem Compound Summary for CID 147151066. https://pubchem.ncbi.nlm.nih.gov/compound/147151066. Accessed Nov. 1, 2022, create date Aug. 12, 2020. (Year: 2020).*
Rowe, Raymond C, Paul J. Sheskey, and Marian E. Quinn. Handbook of Pharmaceutical Excipients. London: Pharmaceutical Press , 6th Edition, 2009, p. 238. (Year: 2009).*
Rowe, Raymond C, Paul J. Sheskey, and Marian E. Quinn. Handbook of Pharmaceutical Excipients. London: Pharmaceutical Press , 6th Edition, 2009, pp. 253, 254 and 766-770. (Year: 2009).*
Bolliger, J.L. et al. (2009, e-published Nov. 27, 2008) "Transition metal-free amination of aryl halides—A simple and reliable method for the efficient and high-yielding synthesis of N-arylated amines," *Tetrahedron*, 65(6):1180-1187.
Krönke, J. et al. (2013, e-published Nov. 29, 2013) "Lenalidomide Causes Selective Degradation of IKZF1 and IKZF3 in Multiple Myeloma Cells," *Science*, 343(6168):301-305.
Yang et al. (1999) "Palladium-catalyzed amination of aryl halides and sulfonates," *J. Organomet. Chem.* 576:125-146.
International Search Report and Written Opinion, dated Jun. 11, 2021, regarding International Application No. PCT/US2021/018865, 8 pages.

* cited by examiner

*Primary Examiner* — Laura L Stockton
(74) *Attorney, Agent, or Firm* — Sheppard Mullin Richter & Hampton LLP

(57) ABSTRACT

Disclosed are substituted quinazolinone compounds, pharmaceutical compositions comprising such compounds, and methods of using such compounds and compositions to treat diseases, disorders, or conditions such as those relating to unregulated protein function and/or levels.

24 Claims, No Drawings

QUINAZOLINONE COMPOUNDS AND RELATED COMPOUNDS

CROSS-REFERENCES TO RELATED APPLICATIONS

This application claims priority to U.S. Provisional Application No. 62/979,904 filed Feb. 21, 2020, which is incorporated herein in its entirety for all purposes.

FIELD

This invention is directed to substituted quinazolinone compounds, pharmaceutical compositions comprising such compounds, and methods of using such compounds and compositions to treat diseases, disorders, or conditions such as those relating to unregulated protein function and/or levels.

STATE OF THE ART

Ubiquitin-mediated proteolysis begins with ligation of one or more ubiquitin molecules to a particular protein substrate. Ubiquitination occurs through the activity of ubiquitin-activating enzymes (E1), ubiquitin-conjugating enzymes (E2), and ubiquitin-protein ligases (E3), acting sequentially to attach ubiquitin to lysine residues of substrate proteins. There are greater than 600 E3 ubiquitin ligases in human and each targets a specific substrate for ubiquitination and subsequent degradation by the proteosome. Cereblon (CRBN) functions as a unique substrate receptor of cullin-RING ligase 4 (CRL4). Various ligands including thalidomide bind to CRBN and alters it substrate specificity depending on compound shape. This results in multiple beneficial effects and/or teratogenicity. Lenalidomide, a thalidomide derivative approved by the US Food and Drug Administration, induces the degradation of oncoproteins such as Ikaros and casein kinase 1 alpha (CK1 alpha), resulting in anti-cancer effects. As such, compounds that bind to CRBN modulate the ubiquitin E3 ligase activity thereby targeting certain substrate proteins for ubiquitination.

Transcription factors are commonly deregulated in the pathogenesis of many cancers and are a major class of cancer cell dependencies. Such deregulation is often accompanied by mutation of a transcription factor. For example, the transcription factor IKZF1 is altered in about 2.23% of all cancers such as lung adenocarcinoma, colon adenocarcinoma, cutaneous melanoma, breast invasive ductal carcinoma having the greatest prevalence. My Cancer Genome, mycancergenome.org/content/gene/ikzf1/. Still further, IKZF1 and IKZF3 are essential transcription factors in multiple myeloma. Krönke, et al., *Lenalidomide Causes Selective Degradation of IKZF1 and IKZF3 in Multiple Myeloma Cells*, Science, 343(6168):301-305 (2013).

Targeting of the IKZF1 and/or IKZF3 transcription factors for degradation is of particular importance in the treatment of many mammalian cancers. Compounds that that bind to cereblon (CRBN) modulate the ubiquitin E3 ligase activity and those compounds where the E3 ligase protein degradation activity is directed against IKZF1 and/or IKZF3 transcription factors are of particular importance.

SUMMARY

The compounds disclosed herein bind to cereblon and degrade the IKZF1 and/or IKZF3 transcription factors and are, therefore, useful in treating cancers where one or more of these transcription factors are involved in the pathogenesis of the cancer.

In one embodiment, compounds of formula I are provided:

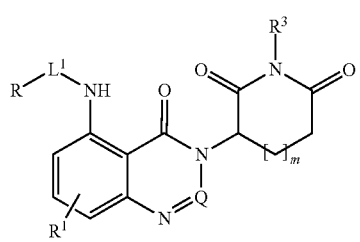

I or a pharmaceutical acceptable salt, solvate, stereoisomer, and/or tautomer thereof
wherein:
m is zero, one or two;
$L^1$ is a $C_1$-$C_4$ alkylene or $C_1$-$C_4$ alkylene substituted with 1 to 2 substituents selected from hydroxy, halo, cyano, and $C_1$-$C_4$ alkoxy;
Q is N or $CR^2$;
R is a substituted aryl having from 1 to 3 substituents wherein each substituent is independently selected from amino, substituted amino, alkyl, substituted alkyl, alkoxy, substituted alkoxy, aryl, substituted aryl, aryloxy, substituted aryloxy, arylalkyloxy, cyano, cycloalkyl, substituted cycloalkyl, cycoalkyloxy, substituted cycloalkyloxy, halo, heterocyclic, heterocyclic-$C_1$-$C_4$ alkylene, substituted heterocyclic, substituted heterocyclic-$C_1$-$C_4$ alkylene, heterocycloxy, substituted heterocycloxy, hydroxyl, guandino, substituted guanadino, and nitro;
$R^1$ is hydrogen, halo, or $C_1$-$C_4$ alkyl;
$R^2$ is hydrogen, $C_1$-$C_4$ alkyl, or cyclopropyl; and
$R^3$ is hydrogen, or —$CH_2$—$OR^5$ where $R^5$ is C(O)—$R^6$ or —P(O)($OR^7$)$_2$, where $R^6$ is $C_1$-$C_4$ alkyl, $C_1$-$C_4$ alkoxy, and where each $R^7$ is independently H or $C_1$-$C_4$ alkyl, wherein when R is 4-methoxyphenyl, Q is not N.

In one embodiment, the compounds of formula I are represented by formula I-A as follows:

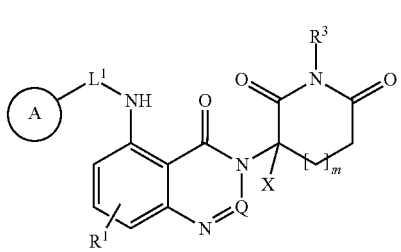

I-A or a pharmaceutical acceptable salt, solvate, stereoisomer, and/or tautomer thereof
wherein:
m is zero, one or two;
$R^1$ is hydrogen, halo, or $C_1$-$C_4$ alkyl;
$R^2$ is hydrogen, $C_1$-$C_4$ alkyl, or cyclopropyl;
$R^3$ is hydrogen, or —$CH_2$—$OR^5$ where $R^5$ is C(O)—$R^6$ or —P(O)($OR^7$)$_2$, where $R^6$ is $C_1$-$C_4$ alkyl, $C_1$-$C_4$ alkoxy, and where each $R^7$ is independently hydrogen or $C_1$-$C_4$ alkyl;

X is hydrogen or deuterium;

$L^1$ is a $C_1$-$C_4$ alkylene or $C_1$-$C_4$ alkylene substituted with 1 to 2 substituents selected from hydroxy, halo, cyano, and $C_1$-$C_4$ alkoxy;

Q is N or $CR^2$;

ring A is a substituted aryl group of from 6 to 14 carbon atoms having from 1 to 3 substituents wherein each substituent is independently selected from:
amino,
$C_1$-$C_4$ alkylamino,
di-($C_1$-$C_4$ alkyl)-amino
$C_1$-$C_4$ alkyl,
$C_1$-$C_4$ alkyl substituted with 1 to 3 substituents independently selected from amino, hydroxyl, or halo,
$C_1$-$C_4$ alkoxy,
$C_1$-$C_4$ alkoxy substituted with 1 to 3 substituents selected from amino, hydroxyl, or halo,
cyano,
halo,
hydroxyl, or
nitro.

In one embodiment, $L^1$ is a straight chain $C_1$-$C_4$ alkylene group and is preferably methylene or ethylene. In one embodiment, Q is N. In one embodiment, Q is $CR^2$.

In one embodiment, the substituted aryl groups preferably have from 1 to 3 substituents each of which are independently selected from $C_1$-$C_4$ alkyl, hydroxy-$C_1$-$C_4$ alkyl, $C_1$-$C_4$ alkoxy, amino, $C_1$-$C_4$ alkylamino, di-($C_1$-$C_4$ alkyl) amino, halo, cyano, nitro, and the like.

Representative examples of such substituted aryl groups include 2-methylphenyl, 3-methylphenyl, 4-methylphenyl, 2,4-dimethylphenyl, 2,6-dimethylphenyl, 3,5-dimethylphenyl, 2,4,6-trimethylphenyl, 2-methoxyphenyl, 3-methoxyphenyl, 4-methoxyphenyl, 2,4-dimethoxyphenyl, 2,6-dimethoxyphenyl, 2,5-dimethoxyphenyl, 3,4-dimethoxyphenyl, 3,5-dimethoxyphenyl, 2,4,6-trimethoxyphenyl, 2-fluorophenyl, 3-fluorophenyl, 4-fluorophenyl, 2,6-difluorophenyl, 3,5-difluorophenyl, 2,4-difluorophenyl, 2,5-difluorophenyl, 2,4,6-trifluorophenyl, 2-chlorophenyl, 3-chlorophenyl, 4-chlorophenyl, 2,6-dichlorophenyl, 3,5-dichlorophenyl, 2,4-dichlorophenyl, 2,5-dichlorophenyl, 2,4,6-trichlorophenyl, 2-methylphenyl, 3-methylphenyl, 4-methylphenyl, 2,6-dimethylphenyl, 3,5-dimethylphenyl, 2,4-dimethylphenyl, 2,4,6-trimethylphenyl, 2-hydroxymethylphenyl, 3-hydroxymethylphenyl, 4-hydroxymethylphenyl, 2-trifluoromethyl, 3-trifluoromethyl, 4-trifluoromethyl, 2,6-di-(trifluoromethyl)phenyl, 3,5-di-(trifluoromethyl)phenyl, 2-cyanophenyl, 3-cyanophenyl, 4-cyanophenyl, 2,4-dicyanophenyl, 2,6-dicyanophenyl, 2-methoxy-4-fluorophenyl, 2-ethyl-4-chlorophenyl, 3-ethyl-5,8-dichloronaphth-2-yl, and the like.

In one embodiment, the compounds of formula I are represented by formula I-B as follows:

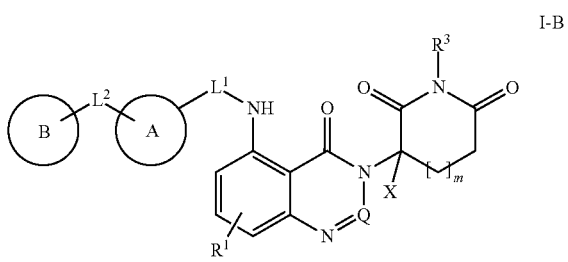

I-B or a pharmaceutical acceptable salt, solvate, stereoisomer, and/or tautomer thereof,
wherein:
m is zero, one or two;
X is hydrogen or deuterium;
$L^1$ is a $C_1$-$C_4$ alkylene or $C_1$-$C_4$ alkylene substituted with 1 to 2 substituents selected from hydroxy, halo, cyano, and $C_1$-$C_4$ alkoxy;
$L^2$ is a bond, $C_1$-$C_4$ alkylene, —O—$C_1$-$C_4$ alkylene or $C_1$-$C_4$ alkylene-O—;
Q is N or $CR^2$;
$R^1$ is hydrogen, halo, or $C_1$-$C_4$ alkyl;
$R^2$ is hydrogen, $C_1$-$C_4$ alkyl, or cyclopropyl;
$R^3$ is hydrogen, or —$CH_2$—$OR^5$ where $R^5$ is C(O)—$R^6$ or —P(O)$(OR^7)_2$, where $R^6$ is $C_1$-$C_4$ alkyl, $C_1$-$C_4$ alkoxy, and where each $R^7$ is independently hydrogen or $C_1$-$C_4$ alkyl;
Ring A is aryl or aryl having from 1 to 2 substituents wherein each substituent is independently selected from
amino,
$C_1$-$C_4$ alkylamino,
di-($C_1$-$C_4$ alkyl)-amino,
$C_1$-$C_4$ alkyl,
$C_1$-$C_4$ alkyl substituted with 1 to 3 substituents independently selected from amino, hydroxyl, or halo,
$C_1$-$C_4$ alkoxy,
$C_1$-$C_4$ alkoxy substituted with 1 to 3 substituents selected from amino,
hydroxyl, or halo,
halo,
hydroxy,
cyano, or
nitro; and
Ring B is aryl, substituted aryl, cycloalkyl, substituted cycloalkyl, heteroaryl, substituted heteroaryl, heterocylic or substituted heterocyclic wherein each substituted aryl, substituted cycloalkyl, substituted heteroaryl and substituted heterocyclic have from 1 to 3 substituents selected from
$C_1$-$C_4$ alkyl,
$C_1$-$C_4$ alkyl substituted with 1 to 3 substituents independently selected from amino, hydroxyl, or halo,
$C_1$-$C_4$ alkoxy, or
$C_1$-$C_4$ alkoxy substituted with 1 to 3 substituents selected from amino, hydroxyl, or halo.

Representative examples of Ring B-$L^2$-Ring A groups include 4-(morpholin-N-yl-$CH_2$)-phenyl, 2-fluoro-4-(morpholin-N-yl-$CH_2$)-phenyl, 3-fluoro-4-(morpholin-N-yl-$CH_2$)-phenyl, 2,6-difluoro-4-(morpholin-N-yl-$CH_2$)-phenyl, 3,5-difluoro-4-(morpholin-N-yl-$CH_2$)-phenyl, 2,3-difluoro-4-(morpholin-N-yl-$CH_2$)-phenyl, 3-(morpholin-N-yl-$CH_2$)-phenyl, 2-fluoro-3-(morpholin-N-yl-$CH_2$)-phenyl, 4-fluoro-3-(morpholin-N-yl-$CH_2$)-phenyl, 2,6-difluoro-3-(morpholin-N-yl-$CH_2$)-phenyl, 2,5-difluoro-3-(morpholin-N-yl-$CH_2$)-phenyl, 2,4-difluoro-3-(morpholin-N-yl-$CH_2$)-phenyl, 2-(morpholin-N-yl-$CH_2$)-phenyl, 3-fluoro-2-(morpholin-N-yl-$CH_2$)-phenyl, 4-fluoro-2-(morpholin-N-yl-$CH_2$)-phenyl, 5-fluoro-2-(morpholin-N-yl-$CH_2$)-phenyl, 6-fluoro-2-(morpholin-N-yl-$CH_2$)-phenyl, 3,6-difluoro-2-(morpholin-N-yl-$CH_2$)-phenyl, 3,5-difluoro-2-(morpholin-N-yl-$CH_2$)-phenyl, 4,6-difluoro-2-(morpholin-N-yl-$CH_2$)-phenyl, 2-chloro-4-(morpholin-N-yl-$CH_2$)-phenyl, 3-chloro-4-(morpholin-N-yl-$CH_2$)-phenyl, 2,6-dichloro-4-(morpholin-N-yl-$CH_2$)-phenyl, 3,5-dichloro-4-(morpholin-N-yl-$CH_2$)-phenyl, 2,3-dichloro-4-(morpholin-N-yl-$CH_2$)-phenyl, 3-(morpholin-N-yl-$CH_2$)-phenyl, 2-chloro-3-

(morpholin-N-yl-CH$_2$)-phenyl, 4-chloro-3-(morpholin-N-yl-CH$_2$)-phenyl, 2,6-dichloro-3-(morpholin-N-yl-CH$_2$)-phenyl, 2,5-dichloro-3-(morpholin-N-yl-CH$_2$)-phenyl, 2,4-dichloro-3-(morpholin-N-yl-CH$_2$)-phenyl, 2-(morpholin-N-yl-CH$_2$)-phenyl, 3-chloro-2-(morpholin-N-yl-CH$_2$)-phenyl, 4-chloro-2-(morpholin-N-yl-CH$_2$)-phenyl, 5-chloro-2-(morpholin-N-yl-CH$_2$)-phenyl, 6-chloro-2-(morpholin-N-yl-CH$_2$)-phenyl, 3,6-dichloro-2-(morpholin-N-yl-CH$_2$)-phenyl, 3,5-dichloro-2-(morpholin-N-yl-CH$_2$)-phenyl, 4,6-dichloro-2-(morpholin-N-yl-CH$_2$)-phenyl, 2-cyano-4-(morpholin-N-yl-CH$_2$)-phenyl, 2-cyano-6-fluoro-4-(morpholin-N-yl-CH$_2$)-phenyl, 4-benzyloxyphenyl, 4-(pyrid-2-yl-CH$_2$)-phenyl, 2-(pyrrolidin-N-yl-CH$_2$)-phenyl, 2-(piperidin-N-yl-CH$_2$)-phenyl, 4-(morpholin-N-yl-CH$_2$)-phenyl; 4-(piperazin-N-yl-CH$_2$)-phenyl, 2-fluoro-4-(piperazin-N-yl-CH$_2$)-phenyl, 2,6-difluoro-4-(piperazin-N-yl-CH$_2$)-phenyl, 3-fluoro-4-(piperazin-N-yl-CH$_2$)-phenyl, 3,5-difluoro-4-(piperazin-N-yl-CH$_2$)-phenyl, 2,3-difluoro-4-(piperazin-N-yl-CH$_2$)-phenyl; 2-chloro-4-(piperazin-N-yl-CH$_2$)-phenyl, 2,6-dichloro-4-(piperazin-N-yl-CH$_2$)-phenyl, 3-chloro-4-(piperazin-N-yl-CH$_2$)-phenyl, 3,5-dichloro-4-(piperazin-N-yl-CH$_2$)-phenyl, 2,3-dichloro-4-(piperazin-N-yl-CH$_2$)-phenyl, 2-cyclohexylphenyl, 2-cyclopentylphenyl, 4-(4,4-dimethylpiperidin-yl-CH$_2$)-phenyl, 4-(4,4-difluoropiperidin-yl-CH$_2$)-phenyl, 4-(4-trifluoromethylpiperidin-yl-CH$_2$)-phenyl, 4-(4-isopropylpiperidin-yl-CH$_2$)-phenyl, 4-(N'-isopropylpiperazin-N-yl-CH$_2$)-phenyl, 4-[(4-methoxypiperidin-N-yl)-CH$_2$-]phen-1-yl, 4-[(4-isopropoxypiperidin-N-yl)-CH$_2$-]phen-1-yl; 4-[(4-t-butoxypiperidin-N-yl)-CH$_2$-]phen-1-yl; 4-[(4-methoxy-4-ethylpiperidin-N-yl)-CH$_2$-]phen-1-yl; 3-methyl-4-[(4-methoxy-4-ethylpiperidin-N-yl)-CH$_2$-]phen-1-yl; 3-methyl-4-[(4-methoxy-4-methylpiperidin-N-yl)-CH$_2$-]phen-1-yl and 2-methyl-4-[(4-methoxy-4-ethylpiperidin-N-yl)-CH$_2$-]phen-1-yl.

In one embodiment, each member ring A set forth above is combined with each member ring B either or both of which is optionally substituted as per above.

In another embodiment, the compounds of formula I are represented by formula I-C as follows:

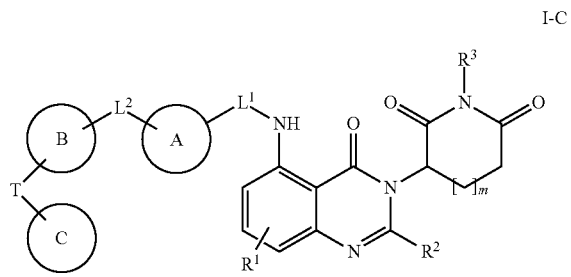

I-C or a pharmaceutical acceptable salt, solvate, stereoisomer, and/or tautomer thereof
wherein
m is zero, one or two;
L$^1$ is a C$_1$-C$_4$ alkylene or C$_1$-C$_4$ alkylene substituted with 1 to 2 substituents selected from hydroxy, halo, cyano, and C$_1$-C$_4$ alkoxy;
L$^2$ is a bond, C$_1$-C$_4$ alkylene, —O—C$_1$-C$_4$ alkylene or C$_1$-C$_4$ alkylene-O—;
X is hydrogen or deuterium;
T is a covalent bond or C$_1$-C$_4$ alkylene;
R$^1$ is hydrogen, halo, or C$_1$-C$_4$ alkyl;
R$^2$ is hydrogen, C$_1$-C$_4$ alkyl, or cyclopropyl;

R$^3$ is hydrogen, or —CH$_2$—OR$^5$ where R$^5$ is C(O)—R$^6$ or —P(O)(OR$^7$)$_2$, where R$^6$ is C$_1$-C$_4$ alkyl, C$_1$-C$_4$ alkoxy, and where each R$^7$ is independently hydrogen or C$_1$-C$_4$ alkyl;
Ring A is aryl or substituted aryl having from 1 to 3 substituents wherein each substituent is independently selected from:
amino,
C$_1$-C$_4$ alkylamino,
di-(C$_1$-C$_4$ alkyl)-amino
cyano,
halo,
nitro,
C$_1$-C$_4$ alkyl,
C$_1$-C$_4$ alkyl substituted with 1 to 3 substituents independently selected from amino, hydroxyl, or halo,
C$_1$-C$_4$ alkoxy,
C$_1$-C$_4$ alkoxy substituted with 1 to 3 substituents selected from amino, hydroxyl, or halo;
Ring B is aryl, substituted aryl, heteroaryl, substituted heteroaryl, heterocylic or substituted heterocyclic having 1 to 3 substituents selected from
amino,
C$_1$-C$_4$ alkylamino,
di-(C$_1$-C$_4$ alkyl)-amino
cyano,
halo,
nitro,
C$_1$-C$_4$ alkyl,
C$_1$-C$_4$ alkyl substituted with 1 to 3 substituents independently selected from amino, hydroxyl, or halo,
C$_1$-C$_4$ alkoxy,
C$_1$-C$_4$ alkoxy substituted with 1 to 3 substituents selected from amino, hydroxyl, or halo; and
Ring C is selected aryl, substituted aryl, cycloalkyl, substituted cycloalkyl, heteroaryl, substituted heteroaryl, heterocyclic or substituted heterocyclic wherein each substituted aryl, substituted cycloalkyl, substituted heteroaryl and substituted heterocyclic have from 1 to 3 substituents selected from
amino,
C$_1$-C$_4$ alkylamino,
di-(C$_1$-C$_4$ alkyl)-amino
cyano,
halo,
nitro,
C$_1$-C$_4$ alkyl,
C$_1$-C$_4$ alkyl substituted with 1 to 3 substituents independently selected from amino, hydroxyl, or halo,
C$_1$-C$_4$ alkoxy,
C$_1$-C$_4$ alkoxy substituted with 1 to 3 substituents selected from amino, hydroxyl, or halo.

Representative examples of ring C-T-ring B-L$^2$-ring A-groups include the following:
3-[(2-fluoro-4-cyanophenyl)-N'-piperazinyl-N—CH$_2$-]phen-1-yl;
4-[(2-fluoro-4-cyanophenyl)-N'-piperazinyl-N—CH$_2$-]phen-1-yl;
4-[(2-fluoro-4-cyanophenyl)-N'-octahydropyrrolo-[3,4-c]-pyrrol-N-yl-CH$_2$]-phen-1-yl;
4-[(2-chloro-4-cyanophenyl)-N'-piperazin-N-yl-CH$_2$-]phen-1-yl;
4-[(4-fluorophenyl)-N'-piperazin-N-yl-CH$_2$-]phen-1-yl;
4-[(2,4-difluorophenyl)-N'-piperazin-N-yl-CH$_2$-]phen-1-yl;
4-[(3,5-difluorophenyl)-N'-piperazin-N-yl-CH$_2$-]phen-1-yl;
4-[(5-fluoropyrid-2-yl)-N'-piperazin-N-yl-CH$_2$-]phen-1-yl;
4-[(pyrid-2-yl)-N'-piperazin-N-yl-CH$_2$-]phen-1-yl;

4-[(pyrid-3-yl)-N'-piperazin-N-yl-CH$_2$-]phen-1-yl;
4-[(pyrid-4-yl)-N'-piperazin-N-yl-CH$_2$-]phen-1-yl;
4-[(2,3-dichlorophenyl)-N'-piperazin-N-yl-CH$_2$-]phen-1-yl
4-[(4-cyanophenyl)-N'-piperazin-N-yl-CH$_2$-]phen-1-yl;
4-[{(5-cyanopyrid-2-yl)-N'-2-methylpiperazin-N-yl-CH$_2$-]phen-1-yl; 2-4-[(3-trifluoromethylphenyl)-N'-piperazin-N-yl-CH$_2$-]phen-1-yl;
4-[(2-methoxyphenyl)-N'-piperazin-N-yl-CH$_2$-]phen-1-yl;
4-(3-(N-morpholino)-azetidin-N-yl-CH$_2$-phen-1-yl;
2-fluoro-4-[3-(N-morpholino)-azetidin-N-yl-CH$_2$-]pheny-1-yl;
2-methyl-4-[3-(N-morpholino)-azetidin-N-yl-CH$_2$-]pheny-1-yl;
3-methyl-4-[3-(N-morpholino)-azetidin-N-yl-CH$_2$-]pheny-1-yl;
3-fluoro-4-[(3-(N-morpholino)-azetidin-N-yl-CH$_2$-]pheny-1-yl;
2,6-difluoro-4-(3-(N-morpholino)-azetidin-N-yl-CH$_2$-pheny-1-yl;
3,5-difluoro-4-(3-(N-morpholino)-azetidin-N-yl-CH$_2$-pheny-1-yl;
3,6-difluoro-4-(3-(N-morpholino)-azetidin-N-yl-CH$_2$-pheny-1-yl;
2-fluoro-4-(3-(N-piperidinyl)-azetidin-N-yl-CH$_2$-pheny-1-yl;
3-fluoro-4-(3-(N-piperidinyl)-azetidin-N-yl-CH$_2$-pheny-1-yl;
2,6-difluoro-4-(3-(N-piperidinyl)-azetidin-N-yl-CH$_2$-pheny-1-yl;
3,5-difluoro-4-(3-(N-piperidinyl)-azetidin-N-yl-CH$_2$-pheny-1-yl;
3,6-difluoro-4-(3-(N-piperidinyl)-azetidin-N-yl-CH$_2$-pheny-1-yl;
2-fluoro-4-(3-(N-piperazinyl)-azetidin-N-yl-CH$_2$-pheny-1-yl;
3-fluoro-4-(3-(N-piperazinyl)-azetidin-N-yl-CH$_2$-pheny-1-yl;
2,6-difluoro-4-(3-(N-piperazinyl)-azetidin-N-yl-CH$_2$-pheny-1-yl;
3,5-difluoro-4-(3-(N-piperazinyl)-azetidin-N-yl-CH$_2$-pheny-1-yl,
4-cyano-(3-(N-piperidinyl)-azetidin-N-yl-CH$_2$-pheny-1-yl;
3-cyano-(3-(N-piperidinyl)-azetidin-N-yl-CH$_2$-pheny-1-yl;
4-[(pyrid-2-yl)-azetidin-N-yl-CH$_2$-]phen-1-yl;
4-[(pyrid-3-yl)-azetidin-N-yl-CH$_2$-]phen-1-yl;
4-[(pyrid-4-yl)-azetidin-N-yl-CH$_2$-]phen-1-yl;
4-[(pyrazol-N-yl)-azetidin-N-yl-CH$_2$-]phen-1-yl;
4-[(pyrrolidin-N-yl)-azetidin-N-yl-CH$_2$-]phen-1-yl;
4-[3-(2,6-dimethyl-N-morpholino)-azetidin-N-yl-CH$_2$-]pheny-1-yl;
4-[3-(3,3-dimethyl-N-morpholino)-azetidin-N-yl-CH$_2$-]pheny-1-yl;
4-[3-(2,2-dimethyl-N-morpholino)-azetidin-N-yl-CH$_2$-]pheny-1-yl;
4-[3-(8-oxa-3-aza-bicyclo[3.2.1]-octan-N-yl)-azetidin-N-yl-CH$_2$-]pheny-1-yl;
4-[(4-pyrrol-N-yl-piperidin-N-yl)-CH$_2$-]phen-1-yl;
3-methyl-4-[(N'-cyclopropylpiperazin-N-yl-CH$_2$-]phen-1-yl;
3-methyl-4-[(N'-cyclobutylpiperazin-N-yl-CH$_2$-]phen-1-yl; and
4-[4-(morpholin-N-yl)-piperidin-N-yl-CH$_2$-]phen-1-yl.

In one embodiment, each member ring A specifically set forth above is combined with each member ring B specifically set forth above which, in turn, is combined with each member of ring C specifically as set forth above, all of which are optionally substituted as per above.

In one embodiment, there is provided a pharmaceutical composition comprising a pharmaceutically acceptable excipient and an effective amount of a compound of formula I.

In one embodiment, there is provided a pharmaceutical composition comprising a pharmaceutically acceptable excipient and an effective amount of a compound of formula I-A.

In one embodiment, there is provided a pharmaceutical composition comprising a pharmaceutically acceptable excipient and an effective amount of a compound of formula I-B.

In one embodiment, there is provided a pharmaceutical composition comprising a pharmaceutically acceptable excipient and an effective amount of a compound of formula I-C.

In one embodiment, compounds of formula II are provided:

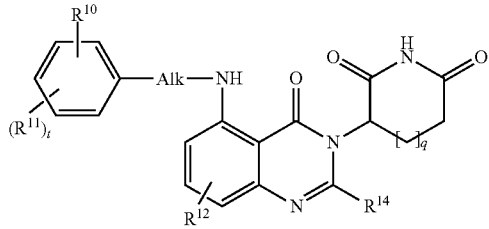

II or a pharmaceutical acceptable salt, solvate, stereoisomer, and/or tautomer thereof wherein:

q is zero, one or two;
t is zero, one or two;
Alk is a $C_1$-$C_4$ alkylene group or a substituted $C_1$-$C_4$ alkylene group;
$R^{10}$ is -(L)$_m$-(Q)$_n$-(L$^1$-)$_p$H where
   each of m, n, and p is independently zero or one;
   L is $C_1$-$C_4$ alkylene or substituted $C_1$-$C_4$ alkylene;
   Q is $C_6$-$C_{10}$ aryl, substituted $C_6$-$C_{10}$ aryl, $C_3$-$C_6$ cycloalkyl, substituted $C_6$-$C_{10}$ cycloalkyl, $C_1$-$C_6$ heteroaryl, $C_1$-$C_6$ substituted heteroaryl, $C_1$-$C_6$ heterocyclic, and $C_1$-$C_6$ substituted heterocyclic;
   L$^1$ is $C_1$-$C_4$ alkylene, substituted $C_1$-$C_4$ alkylene; $C_6$-$C_{10}$ aryl, substituted $C_6$-$C_{10}$ aryl, $C_3$-$C_6$ cycloalkyl, substituted $C_6$-$C_{10}$ cycloalkyl, $C_1$-$C_6$ heteroaryl, $C_1$-$C_6$ substituted heteroaryl, $C_1$-$C_6$ heterocyclic, and $C_1$-$C_6$ substituted heterocyclic;
provided that when m, n and t are zero then p is not zero;
each $R^{11}$ is independently $C_1$-$C_4$ alkyl, $C_1$-$C_4$ haloalkyl having from 1 to 3 halo groups, $C_1$-$C_4$ alkoxy, $C_1$-$C_4$ haloalkyl having from 1 to 3 halo groups, halo, hydroxy,
$R^{12}$ is hydrogen or $C_1$-$C_4$ alkyl; and
$R^{14}$ is hydrogen or methyl.

In one embodiment, there is provided a pharmaceutical composition comprising a pharmaceutically acceptable excipient and an effective amount of a compound of formula I, formula I-A, formula I-B, formula I-C or formula II.

In one embodiment, there is provided a method for degrading one or more transcription factors selected from IKZF1 and/or IKZF3 which method comprises selecting a compound or compounds of formula I and contacting said compound or compounds with cereblon under conditions which generates an EG3 ligase that targets protein degradation of IKZF1, and/or IKZF3, and contacting said EG3 ligase with the IKZF1 and/or IKZF3 transcription factors under conditions wherein one or both of said transcription factors is or are degraded by ubiquitination.

In one embodiment, there is provided a method to increase ubiquitination activity against one or more of the IKZF1 and/or IKZF3 transcription factors in a subject, which method comprises administering to said subject an effective amount of a compound of formula I or a pharmaceutical composition comprising a pharmaceutically acceptable excipient and an effective amount of a compound of formula I.

In one embodiment, there is provided a method to treat cancer in a subject which method comprises selecting a subject whose cancer is mediated in part by one or more of the the IKZF1 and/or IKZF3 transcription factors and administering to said subject an effective amount of a compound of formula I or a pharmaceutical composition comprising a pharmaceutically acceptable excipient and an effective amount of a compound of formula I.

In one embodiment of the methods provided above, the IKZF-1 transcription factor is degraded.

In one embodiment of the methods provided above, the IKZF-3 transcription factor is degraded.

In one embodiment of the methods provided above, both the IKZF-1 and the IKZF-3 transcription factors are degraded.

In one embodiment of the methods provided above, the degradation of IKZF-1 is greater than the degradation of IKZF-3.

In one embodiment of the methods provided above, the degradation of IKZF-3 is greater than the degradation of IKZF-1.

In one embodiment of the methods provided above, the degradation of IKZF-1 and IKZF-3 are equivalent.

In one embodiment of the methods provided above, a compound of formula I-A is employed.

In one embodiment of the methods provided above, a compound of formula I-B is employed.

In one embodiment of the methods provided above, a compound of formula I-C is employed.

In one embodiment of the methods provided above, a compound of formula II is employed.

Representative examples of compounds within the scope of formulae 1, 1-A, 1-B and 1-C above are set forth in the following Table 1 below where each of which include their pharmaceutical acceptable salts, solvates, hydrates, and/or tautomers thereof.

TABLE 1

| No. | Structure | Name |
|---|---|---|
| 1 | 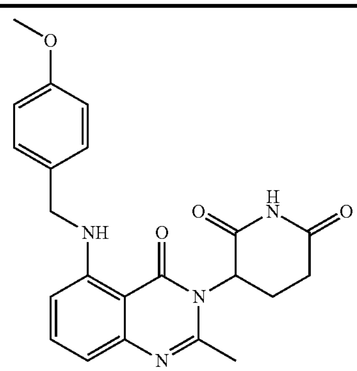 | 3-(5-((4-methoxy-benzyl)-amino)-2-methyl-4-oxoquinazolin-3(4H)-yl)piperidine-2,6-dione |
| 2 | 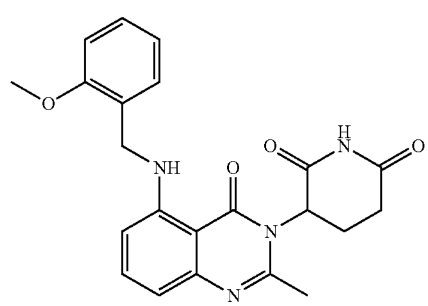 [SMILES: COc1ccccc1CNc1cccc2nc(C)n(C3CCC(=O)NC3=O)c(=O)c12] | 3-(5-((2-methoxybenzyl)-amino)-2-methyl-4-oxoquinazolin-3(4H)-yl)piperidine-2,6-dione |
| 3 | 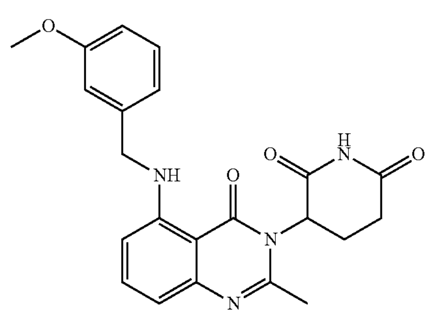 [SMILES: COc1cccc(CNc2cccc3nc(C)n(C4CCC(=O)NC4=O)c(=O)c23)c1] | 3-(5-((3-methoxybenzyl)-amino)-2-methyl-4-oxoquinazolin-3(4H)-yl)piperidine-2,6-dione |

TABLE 1-continued

| No. | Structure | Name |
| --- | --- | --- |
| 4 | 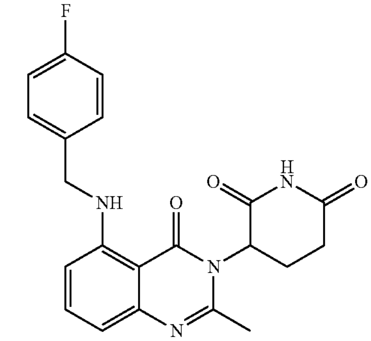 [SMILES: Cc1nc2cccc(NCc3ccc(F)cc3)c2c(=O)n1C1CCC(=O)NC1=O] | 3-(5-((4-fluorobenzyl)-amino)-2-methyl-4-oxoquinazolin-3(4H)-yl)piperidine-2,6-dione |
| 5 | 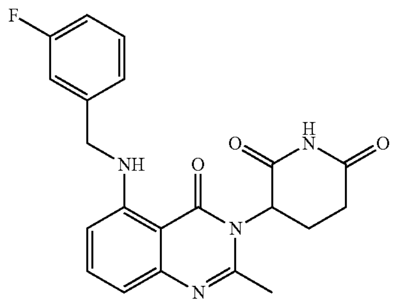 [SMILES: Cc1nc2cccc(NCc3cccc(F)c3)c2c(=O)n1C1CCC(=O)NC1=O] | 3-(5-((3-fluorobenzyl)-amino)-2-methyl-4-oxoquinazolin-3(4H)-yl)piperidine-2,6-dione |
| 6 | 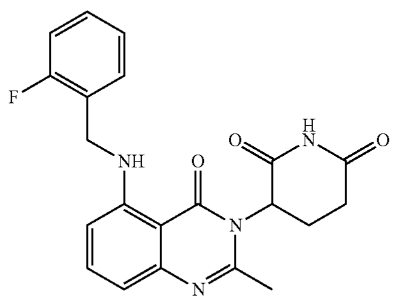 [SMILES: Cc1nc2cccc(NCc3ccccc3F)c2c(=O)n1C1CCC(=O)NC1=O] | 3-(5-((2-fluorobenzyl)-amino)-2-methyl-4-oxoquinazolin-3(4H)-yl)piperidine-2,6-dione |
| 7 | 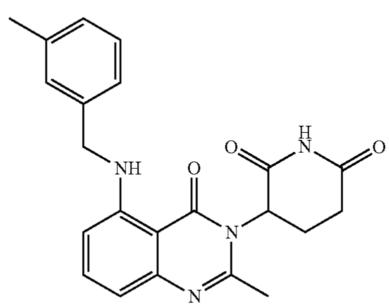 [SMILES: Cc1cccc(CNc2cccc3nc(C)n(C4CCC(=O)NC4=O)c(=O)c23)c1] | 3-(5-((3-methylbenzyl)-amino)-2-methyl-4-oxoquinazolin-3(4H)-yl)piperidine-2,6-dione |
| 8 | 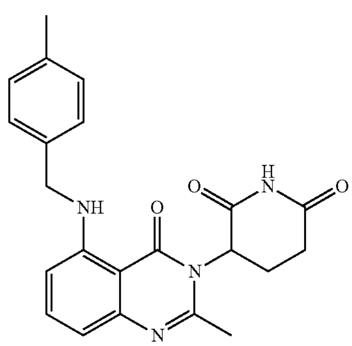 [SMILES: Cc1ccc(CNc2cccc3nc(C)n(C4CCC(=O)NC4=O)c(=O)c23)cc1] | 3-(5-((4-methylbenzyl)-amino)-2-methyl-4-oxoquinazolin-3(4H)-yl)piperidine-2,6-dione |

TABLE 1-continued

| No. | Structure | Name |
| --- | --- | --- |
| 9 | 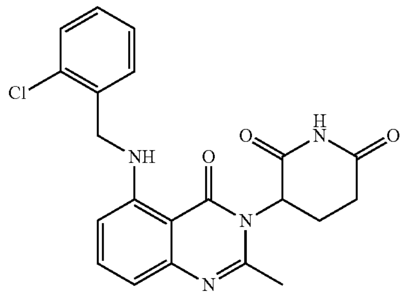 [SMILES: Cc1nc2cccc(NCc3ccccc3Cl)c2c(=O)n1C1CCC(=O)NC1=O] | 3-(5-((2-chlorobenzyl)-amino)-2-methyl-4-oxoquinazolin-3(4H)-yl)piperidine-2,6-dione |
| 10 | 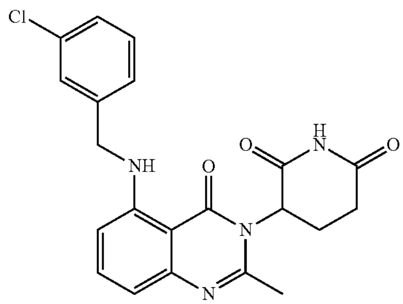 [SMILES: Cc1nc2cccc(NCc3cccc(Cl)c3)c2c(=O)n1C1CCC(=O)NC1=O] | 3-(5-((3-chlorobenzyl)-amino)-2-methyl-4-oxoquinazolin-3(4H)-yl)piperidine-2,6-dione |
| 11 | 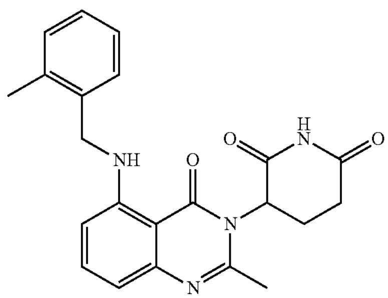 [SMILES: Cc1ccccc1CNc1cccc2nc(C)n(C3CCC(=O)NC3=O)c(=O)c12] | 3-(5-((2-methylbenzyl)-amino)-2-methyl-4-oxoquinazolin-3(4H)-yl)piperidine-2,6-dione |
| 12 | 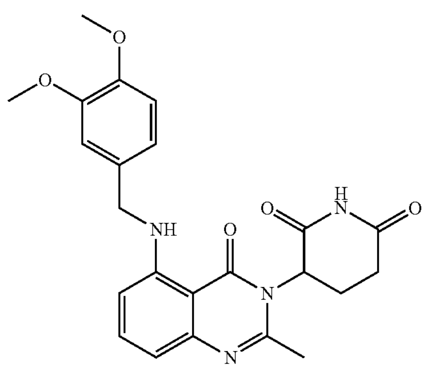 [SMILES: COc1ccc(CNc2cccc3nc(C)n(C4CCC(=O)NC4=O)c(=O)c23)cc1OC] | 3-(5-((3,4-dimethoxy-benzyl)-amino)-2-methyl-4-oxoquinazolin-3(4H)-yl)piperidine-2,6-dione |
| 13 | 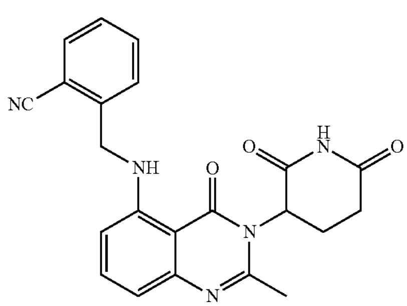 [SMILES: Cc1nc2cccc(NCc3ccccc3C#N)c2c(=O)n1C1CCC(=O)NC1=O] | 3-(5-((2-cyanobenzyl)-amino)-2-methyl-4-oxoquinazolin-3(4H)-yl)piperidine-2,6-dione |

TABLE 1-continued

| No. | Structure | Name |
|---|---|---|
| 14 | 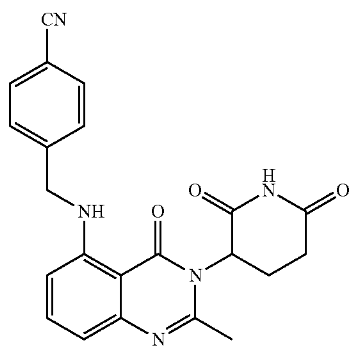 [SMILES: Cc1nc2cccc(NCc3ccc(C#N)cc3)c2c(=O)n1C1CCC(=O)NC1=O] | 3-(5-((4-cyanobenzyl)-amino)-2-methyl-4-oxoquinazolin-3(4H)-yl)piperidine-2,6-dione |
| 15 | 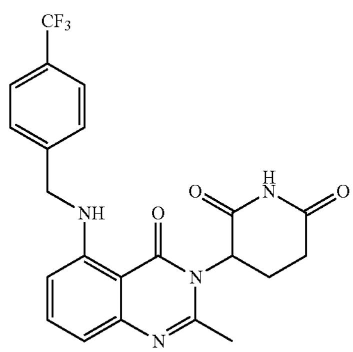 | 3-(5-((4-trifluoromethyl-benzyl)-amino)-2-methyl-4-oxoquinazolin-3(4H)-yl)piperidine-2,6-dione |
| 16 | 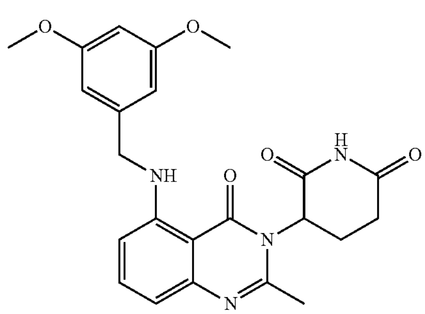 [SMILES: COc1cc(CNc2cccc3nc(C)n(C4CCC(=O)NC4=O)c(=O)c23)cc(OC)c1] | 3-(5-((3,5-dimethoxy-benzyl)-amino)-2-methyl-4-oxoquinazolin-3(4H)-yl)piperidine-2,6-dione |
| 17 | 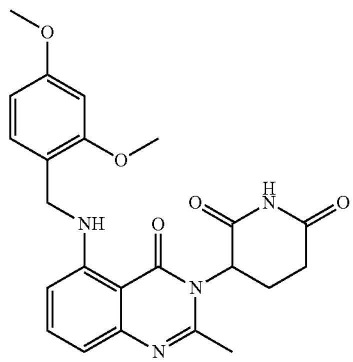 [SMILES: COc1ccc(CNc2cccc3nc(C)n(C4CCC(=O)NC4=O)c(=O)c23)c(OC)c1] | 3-(5-((2,4-dimethoxy-benzyl)-amino)-2-methyl-4-oxoquinazolin-3(4H)-yl)piperidine-2,6-dione |

TABLE 1-continued

| No. | Structure | Name |
|---|---|---|
| 18 | 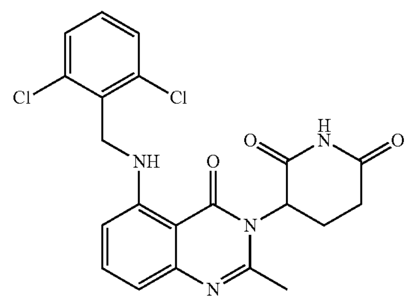 [SMILES: Cc1nc2cccc(NCc3c(Cl)cccc3Cl)c2c(=O)n1C1CCC(=O)NC1=O] | 3-(5-((2,6-dichlorobenzyl)-amino)-2-methyl-4-oxoquinazolin-3(4H)-yl)piperidine-2,6-dione |
| 19 | 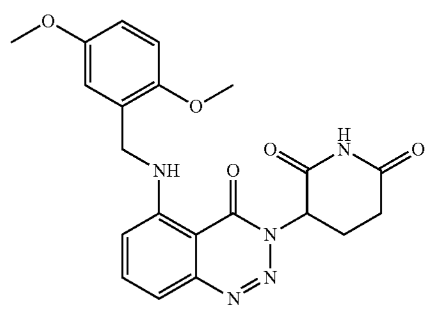 [SMILES: COc1ccc(OC)c(CNc2cccc3nnn(C4CCC(=O)NC4=O)c(=O)c23)c1] | 3-(5-((2,5-dimethoxybenzyl)amino)-4-oxobenzo[d][1,2,3]triazin-3(4H)-yl)piperidine-2,6-dione |
| 20 | 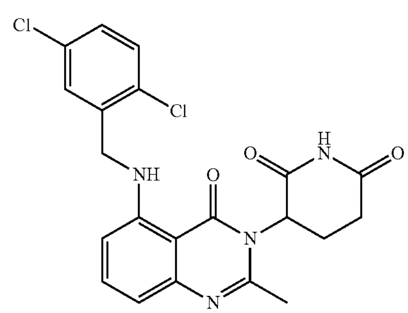 [SMILES: Cc1nc2cccc(NCc3cc(Cl)ccc3Cl)c2c(=O)n1C1CCC(=O)NC1=O] | 3-(5-((2,5-dichlorobenzyl)amino)-2-methyl-4-oxoquinazolin-3(4H)-yl)piperidine-2,6-dione |
| 21 | 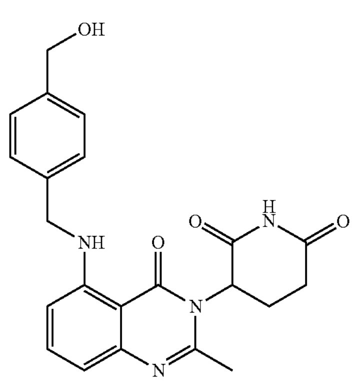 [SMILES: Cc1nc2cccc(NCc3ccc(CO)cc3)c2c(=O)n1C1CCC(=O)NC1=O] | 3-(5-((4-(hydroxymethyl)benzyl)amino)-2-methyl-4-oxoquinazolin-3(4H)-yl)piperidine-2,6-dione |

TABLE 1-continued

| No. | Structure | Name |
| --- | --- | --- |
| 22 | 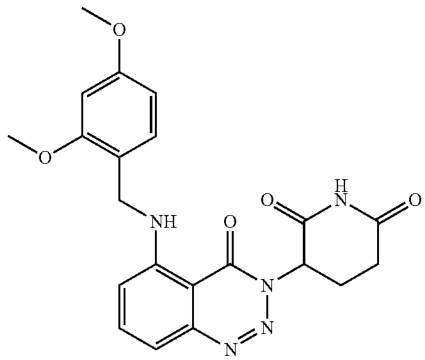 [SMILES: COc1ccc(CNc2cccc3nnn(C4CCC(=O)NC4=O)c(=O)c23)c(OC)c1] | 3-(5-((2,4-dimethoxybenzyl)amino)-4-oxobenzo[d][1,2,3]triazin-3(4H)-yl)piperidine-2,6-dione |
| 23 | 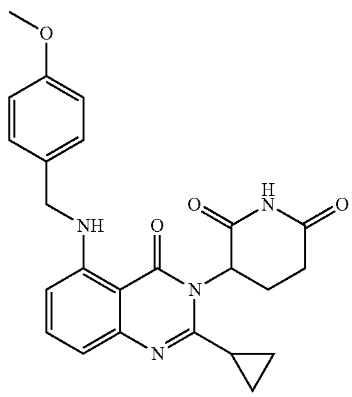 [SMILES: COc1ccc(CNc2cccc3nc(C4CC4)n(C4CCC(=O)NC4=O)c(=O)c23)cc1] | 3-(2-cyclopropyl-5-((4-methoxybenzyl)amino)-4-oxoquinazolin-3(4H)-yl)piperidine-2,6-dione |
| 24 | 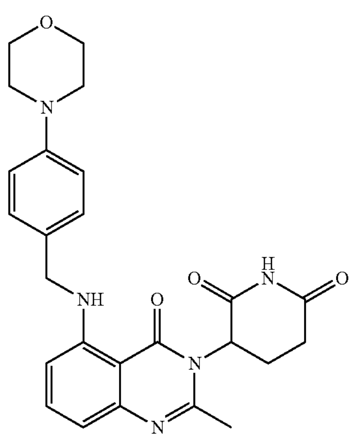 [SMILES: Cc1nc2cccc(NCc3ccc(N4CCOCC4)cc3)c2c(=O)n1C1CCC(=O)NC1=O] | 3-(2-methyl-5-((4-morpholinobenzyl)amino)-4-oxoquinazolin-3(4H)-yl)piperidine-2,6-dione |
| 25 | 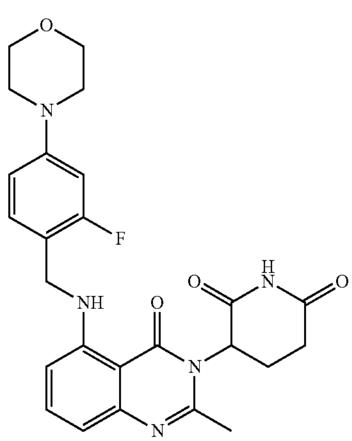 [SMILES: Cc1nc2cccc(NCc3ccc(N4CCOCC4)cc3F)c2c(=O)n1C1CCC(=O)NC1=O] | 3-(5-((2-fluoro-4-morpholinobenzyl)amino)-2-methyl-4-oxoquinazolin-3(4H)-yl)piperidine-2,6-dione |

TABLE 1-continued

| No. | Structure | Name |
|---|---|---|
| 26 | 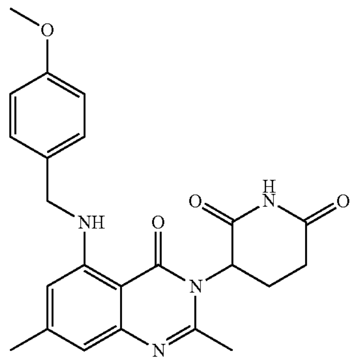 [SMILES: COc1ccc(CNc2cc(C)cc3nc(C)n(C4CCC(=O)NC4=O)c(=O)c23)cc1] | 3-(5-((4-methoxybenzyl)amino)-2,7-dimethyl-4-oxoquinazolin-3(4H)-yl)piperidine-2,6-dione |
| 27 | 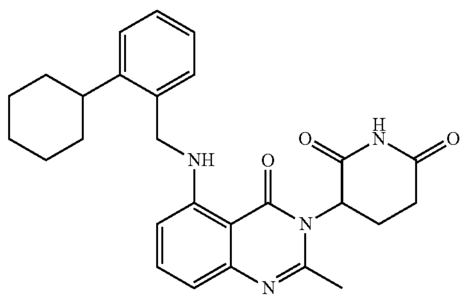 [SMILES: Cc1nc2cccc(NCc3ccccc3C3CCCCC3)c2c(=O)n1C1CCC(=O)NC1=O] | 3-(5-((2-cyclohexylbenzyl)amino)-2-methyl-4-oxoquinazolin-3(4H)-yl)piperidine-2,6-dione |
| 28 | 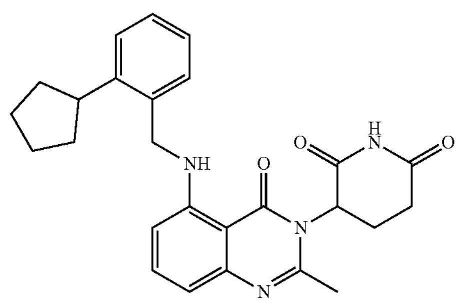 [SMILES: Cc1nc2cccc(NCc3ccccc3C3CCCC3)c2c(=O)n1C1CCC(=O)NC1=O] | 3-(5-((2-cyclopentylbenzyl)amino)-2-methyl-4-oxoquinazolin-3(4H)-yl)piperidine-2,6-dione |
| 29 | 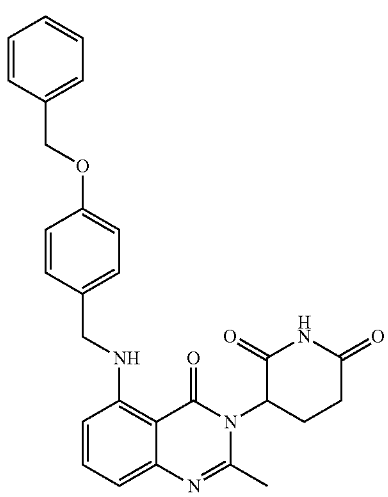 [SMILES: Cc1nc2cccc(NCc3ccc(OCc4ccccc4)cc3)c2c(=O)n1C1CCC(=O)NC1=O] | 3-(5-((4-(benzyloxy)benzyl)amino)-2-methyl-4-oxoquinazolin-3(4H)-yl)piperidine-2,6-dione |

TABLE 1-continued

| No. | Structure | Name |
|---|---|---|
| 30 | cancelled | |
| 31 | 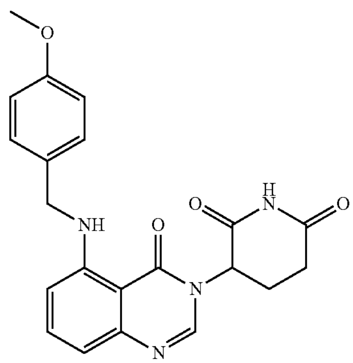 [SMILES: COc1ccc(CNc2cccc3ncn(C4CCC(=O)NC4=O)c(=O)c23)cc1] | 3-(5-((4-methoxybenzyl)amino)-4-oxoquinazolin-3(4H)-yl)piperidine-2,6-dione |
| 32 | 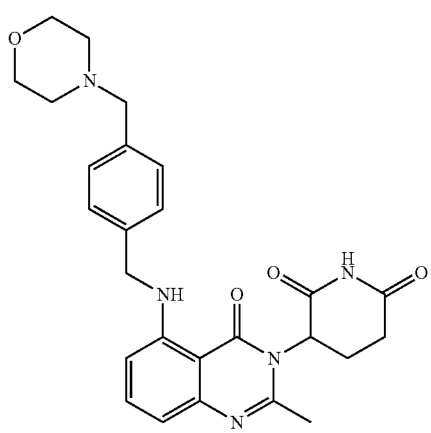 [SMILES: Cc1nc2cccc(NCc3ccc(CN4CCOCC4)cc3)c2c(=O)n1C1CCC(=O)NC1=O] | 3-(2-methyl-5-((4-(morpholinomethyl)benzyl)amino)-4-oxoquinazolin-3(4H)-yl)piperidine-2,6-dione |
| 33 | 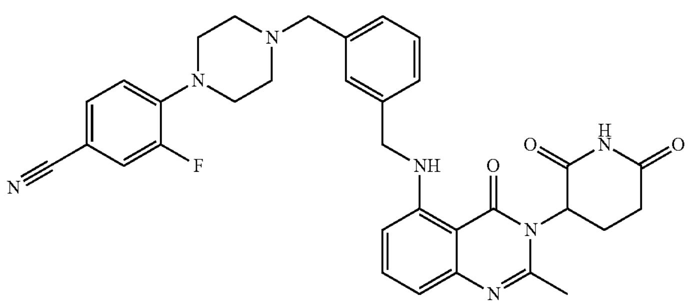 [SMILES: Cc1nc2cccc(NCc3cccc(CN4CCN(c5ccc(C#N)cc5F)CC4)c3)c2c(=O)n1C1CCC(=O)NC1=O] | 4-(4-(3-(((3-(2,6-dioxopiperidin-3-yl)-2-methyl-4-oxo-3,4-dihydroquinazolin-5-yl)amino)methyl)benzyl)piperazin-1-yl)-3-fluorobenzonitrile |

TABLE 1-continued

| No. | Structure | Name |
|---|---|---|
| 34 | 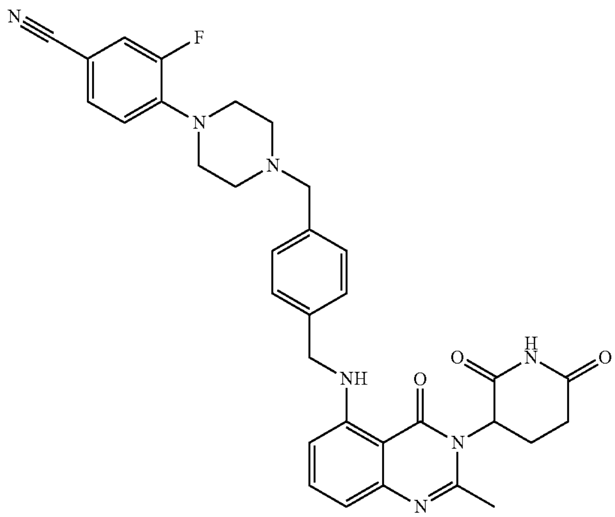 [SMILES: Cc1nc2cccc(NCc3ccc(CN4CCN(c5ccc(C#N)cc5F)CC4)cc3)c2c(=O)n1C1CCC(=O)NC1=O] | 4-(4-(4-(((3-(2,6-dioxopiperidin-3-yl)-2-methyl-4-oxo-3,4-dihydroquinazolin-5-yl)amino)methyl)benzyl)piperazin-1-yl)-3-fluorobenzonitrile |
| 35 | 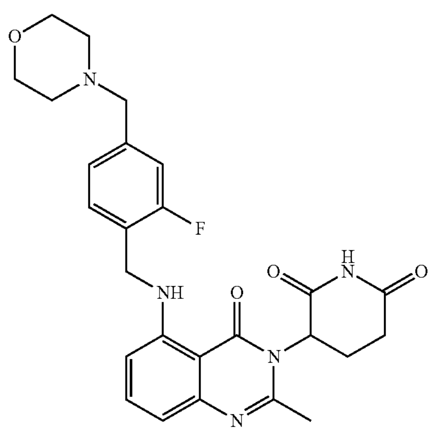 [SMILES: Cc1nc2cccc(NCc3ccc(CN4CCOCC4)cc3F)c2c(=O)n1C1CCC(=O)NC1=O] | 3-(5-((2-fluoro-4-(morpholinomethyl)benzyl)amino)-2-methyl-4-oxoquinazolin-3(4H)-yl)piperidine-2,6-dione |
| 36 | 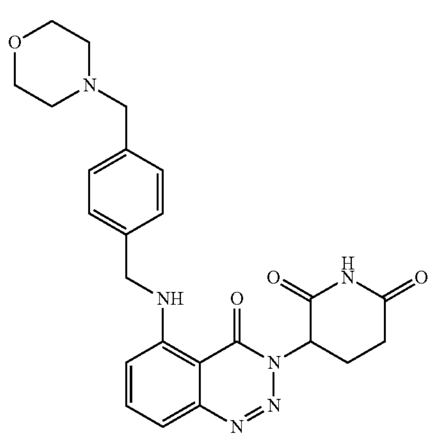 [SMILES: O=C1CCC(n2nnc3cccc(NCc4ccc(CN5CCOCC5)cc4)c3c2=O)C(=O)N1] | 3-(5-((4-(morpholinomethyl)benzyl)amino)-4-oxobenzo[d][1,2,3]triazin-3(4H)-yl)piperidine-2,6-dione |

TABLE 1-continued

| No. | Structure | Name |
|---|---|---|
| 37 | 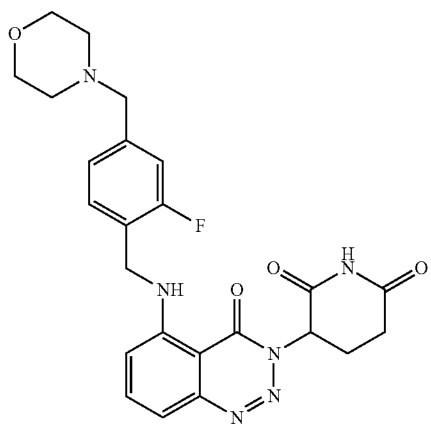 [SMILES: O=C1CCC(n2nnc3cccc(NCc4ccc(CN5CCOCC5)cc4F)c3c2=O)C(=O)N1] | 3-(5-((2-fluoro-4-(morpholinomethyl)benzyl)amino)-4-oxobenzo[d][1,2,3]triazin-3(4H)-yl)piperidine-2,6-dione |
| 38 | 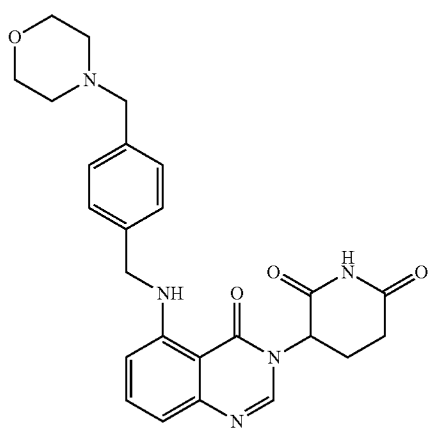 [SMILES: O=C1CCC(n2cnc3cccc(NCc4ccc(CN5CCOCC5)cc4)c3c2=O)C(=O)N1] | 3-(5-((4-(morpholinomethyl)benzyl)amino)-4-oxoquinazolin-3(4H)-yl)piperidine-2,6-dione |
| 39 | 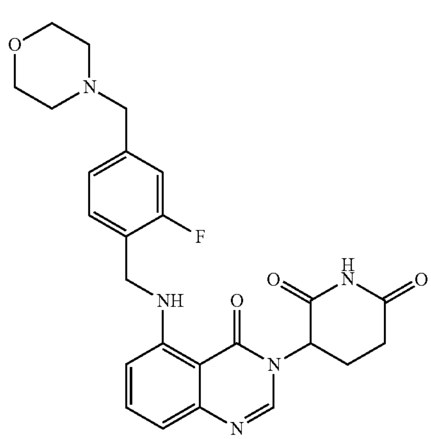 [SMILES: O=C1CCC(n2cnc3cccc(NCc4ccc(CN5CCOCC5)cc4F)c3c2=O)C(=O)N1] | 3-(5-((2-fluoro-4-(morpholinomethyl)benzyl)amino)-4-oxoquinazolin-3(4H)-yl)piperidine-2,6-dione |

TABLE 1-continued
| No. | Structure | Name |
|---|---|---|
| 40 | 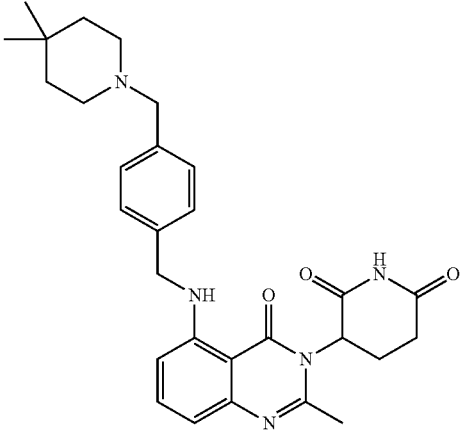 | 3-(5-((4-((4,4-dimethylpiperidin-1-yl)methyl)benzyl)amino)-2-methyl-4-oxoquinazolin-3(4H)-yl)piperidine-2,6-dione |
| 41 | 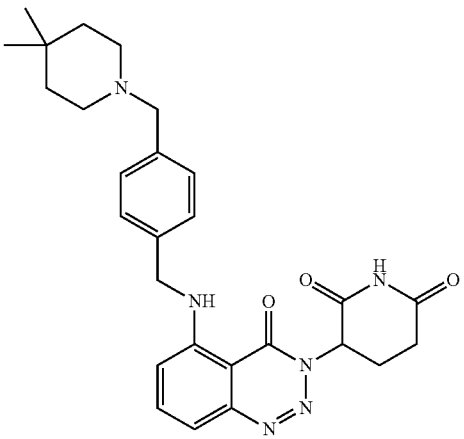 | 3-(5-((4-((4,4-dimethylpiperidin-1-yl)methyl)benzyl)amino)-4-oxobenzo[d][1,2,3]triazin-3(4H)-yl)piperidine-2,6-dione |
| 42 | 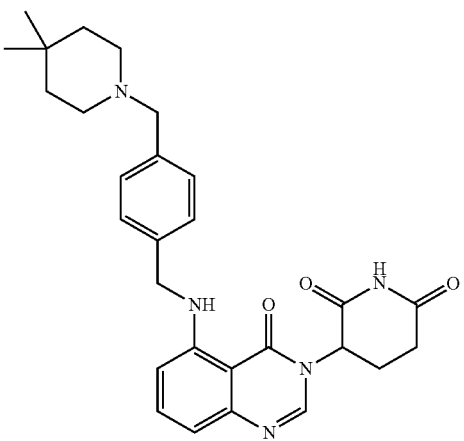 | 3-(5-((4-((4,4-dimethylpiperidin-1-yl)methyl)benzyl)amino)-4-oxoquinazolin-3(4H)-yl)piperidine-2,6-dione |

TABLE 1-continued

| No. | Structure | Name |
|---|---|---|
| 43 | 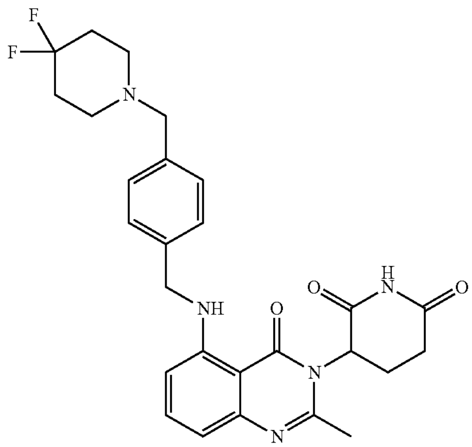 [SMILES: Cc1nc2cccc(NCc3ccc(CN4CCC(F)(F)CC4)cc3)c2c(=O)n1C1CCC(=O)NC1=O] | 3-(5-((4-((4,4-difluoropiperidin-1-yl)methyl)benzyl)amino)-2-methyl-4-oxoquinazolin-3(4H)-yl)piperidine-2,6-dione |
| 44 | 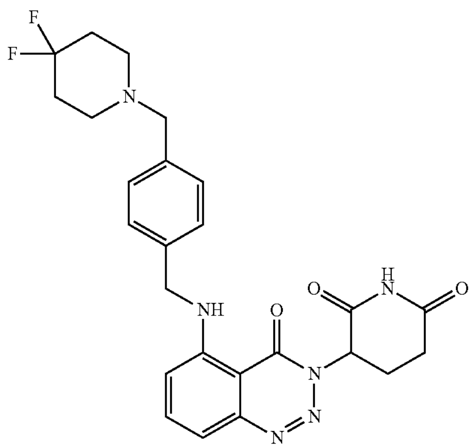 [SMILES: O=C1CCC(n2nnc3cccc(NCc4ccc(CN5CCC(F)(F)CC5)cc4)c3c2=O)C(=O)N1] | 3-(5-((4-((4,4-difluoropiperidin-1-yl)methyl)benzyl)amino)-4-oxobenzo[d][1,2,3]triazin-3(4H)-yl)piperidine-2,6-dione |
| 45 | 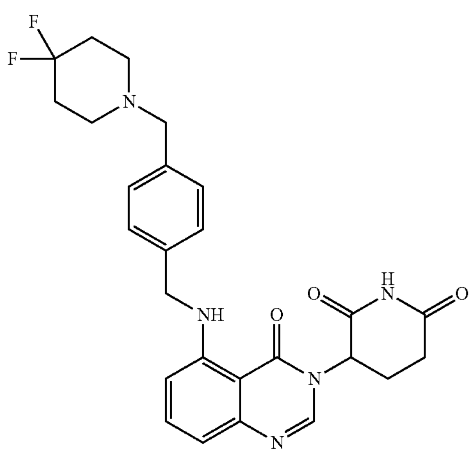 [SMILES: O=C1CCC(n2cnc3cccc(NCc4ccc(CN5CCC(F)(F)CC5)cc4)c3c2=O)C(=O)N1] | 3-(5-((4-((4,4-difluoropiperidin-1-yl)methyl)benzyl)amino)-4-oxoquinazolin-3(4H)-yl)piperidine-2,6-dione |

TABLE 1-continued

| No. | Structure | Name |
|---|---|---|
| 46 | 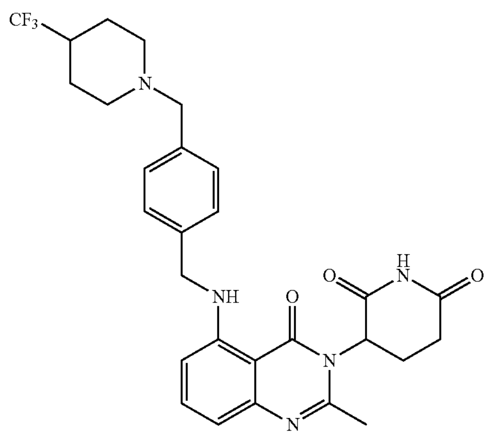 [SMILES: Cc1nc2cccc(NCc3ccc(CN4CCC(C(F)(F)F)CC4)cc3)c2c(=O)n1C1CCC(=O)NC1=O] | 3-(2-methyl-4-oxo-5-((4-((4-(trifluoromethyl)piperidin-1-yl)methyl)benzyl)amino)quinazolin-3(4H)-yl)piperidine-2,6-dione |
| 47 | 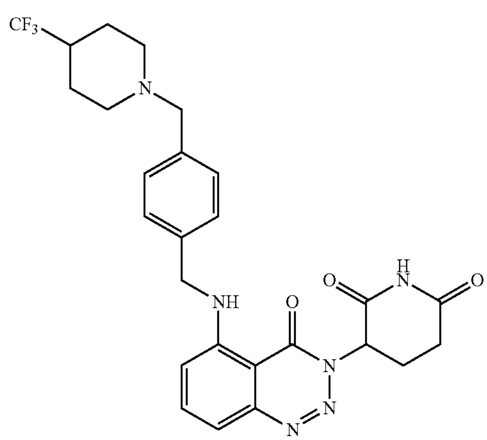 [SMILES: O=C1CCC(n2nnc3cccc(NCc4ccc(CN5CCC(C(F)(F)F)CC5)cc4)c3c2=O)C(=O)N1] | 3-(4-oxo-5-((4-((4-(trifluoromethyl)piperidin-1-yl)methyl)benzyl)amino)benzo[d][1,2,3]triazin-3(4H)-yl)piperidine-2,6-dione |
| 48 | 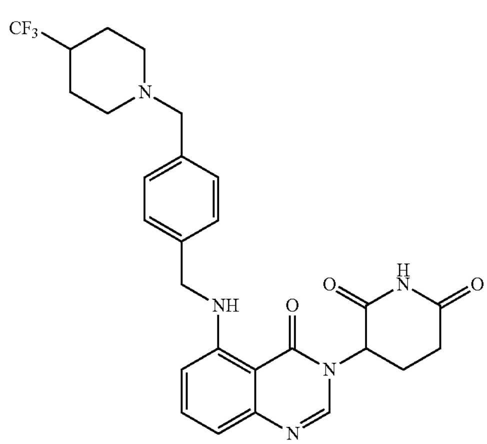 [SMILES: O=C1CCC(n2cnc3cccc(NCc4ccc(CN5CCC(C(F)(F)F)CC5)cc4)c3c2=O)C(=O)N1] | 3-(4-oxo-5-((4-((4-(trifluoromethyl)piperidin-1-yl)methyl)benzyl)amino)quinazolin-3(4H)-yl)piperidine-2,6-dione |

TABLE 1-continued

| No. | Structure | Name |
|---|---|---|
| 49 | 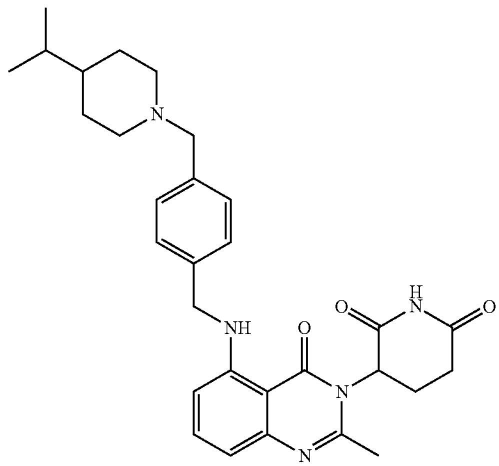 | 3-(5-((4-((4-isopropylpiperidin-1-yl)methyl)benzyl)amino)-2-methyl-4-oxoquinazolin-3(4H)-yl)piperidine-2,6-dione |
| 50 | 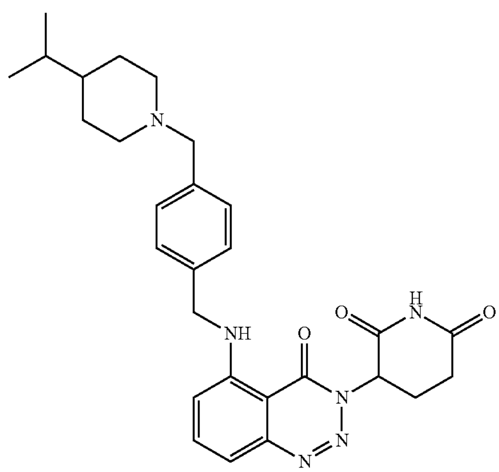 | 3-(5-((4-((4-isopropylpiperidin-1-yl)methyl)benzyl)amino)-4-oxobenzo[d][1,2,3]triazin-3(4H)-yl)piperidine-2,6-dione |
| 51 | 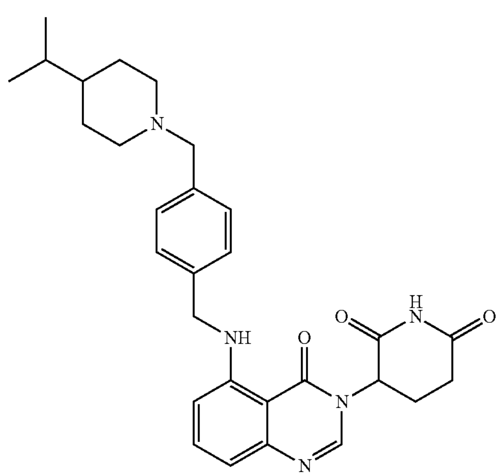 | 3-(5-((4-((4-isopropylpiperidin-1-yl)methyl)benzyl)amino)-4-oxoquinazolin-3(4H)-yl)piperidine-2,6-dione |

TABLE 1-continued

| No. | Structure | Name |
|---|---|---|
| 52 | 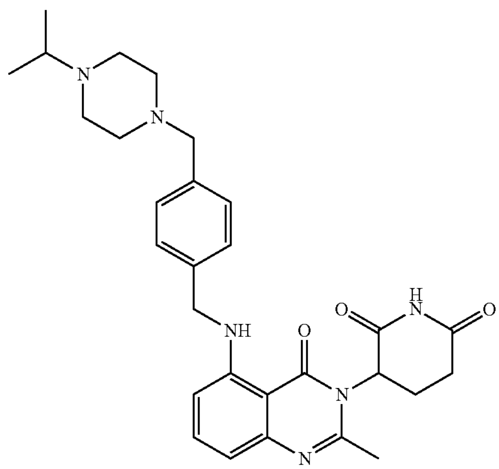 | 3-(5-((4-((4-isopropylpiperazin-1-yl)methyl)benzyl)amino)-2-methyl-4-oxoquinazolin-3(4H)-yl)piperidine-2,6-dione |
| 53 | 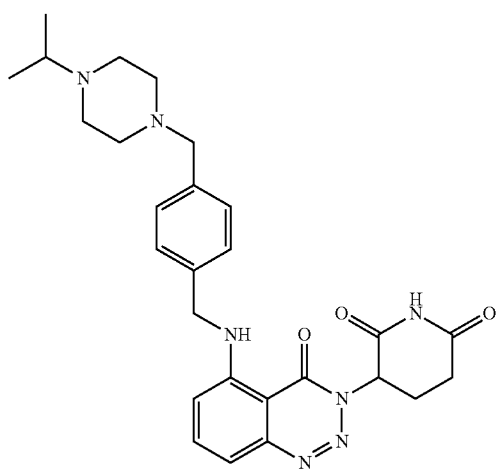 | 3-(5-((4-((4-isopropylpiperazin-1-yl)methyl)benzyl)amino)-4-oxobenzo[d][1,2,3]triazin-3(4H)-yl)piperidine-2,6-dione |
| 54 | 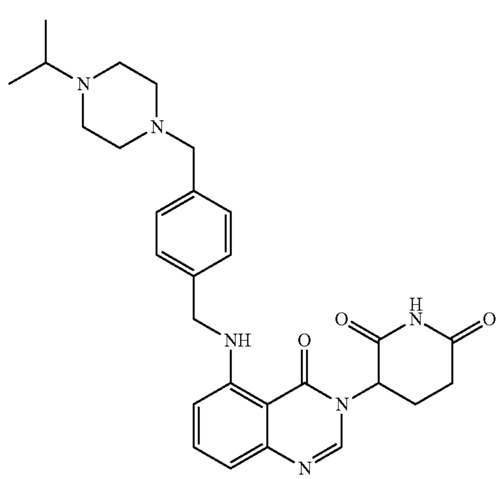 | 3-(5-((4-((4-isopropylpiperazin-1-yl)methyl)benzyl)amino)-4-oxoquinazolin-3(4H)-yl)piperidine-2,6-dione |

TABLE 1-continued

| No. | Structure | Name |
|---|---|---|
| 55 | 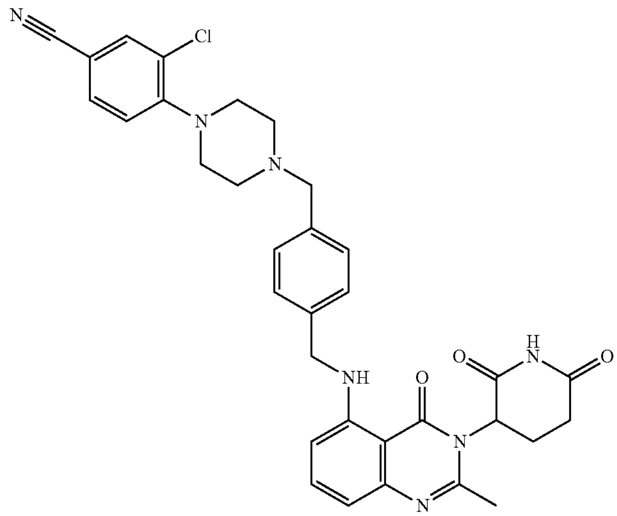 [SMILES: Cc1nc2cccc(NCc3ccc(CN4CCN(c5ccc(C#N)cc5Cl)CC4)cc3)c2c(=O)n1C1CCC(=O)NC1=O] | 3-chloro-4-(4-(4-(((3-(2,6-dioxopiperidin-3-yl)-2-methyl-4-oxo-3,4-dihydroquinazolin-5-yl)amino)methyl)benzyl)piperazin-1-yl)benzonitrile |
| 56 | 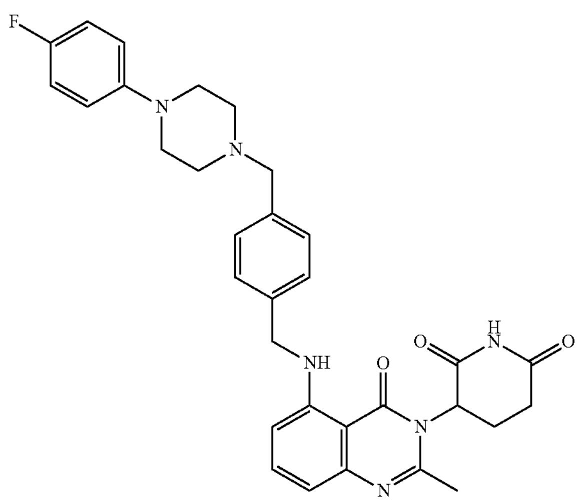 [SMILES: Cc1nc2cccc(NCc3ccc(CN4CCN(c5ccc(F)cc5)CC4)cc3)c2c(=O)n1C1CCC(=O)NC1=O] | 3-(5-((4-((4-(4-fluorophenyl)piperazin-1-yl)methyl)benzyl)amino)-2-methyl-4-oxoquinazolin-3(4H)-yl)piperidine-2,6-dione |
| 57 | 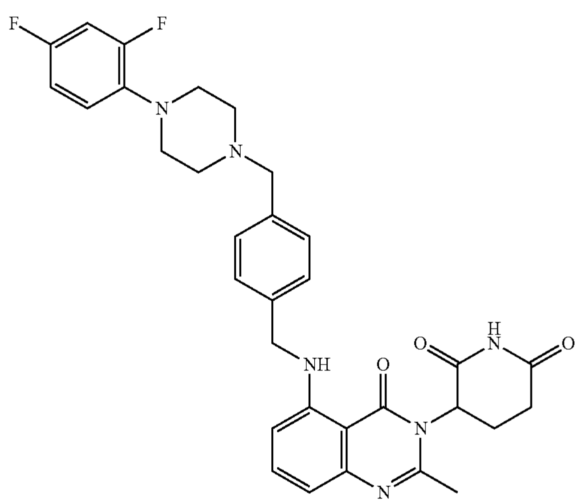 [SMILES: Cc1nc2cccc(NCc3ccc(CN4CCN(c5ccc(F)cc5F)CC4)cc3)c2c(=O)n1C1CCC(=O)NC1=O] | 3-(5-((4-((4-(2,4-difluorophenyl)piperazin-1-yl)methyl)benzyl)amino)-2-methyl-4-oxoquinazolin-3(4H)-yl)piperidine-2,6-dione |

TABLE 1-continued

| No. | Structure | Name |
|---|---|---|
| 58 | 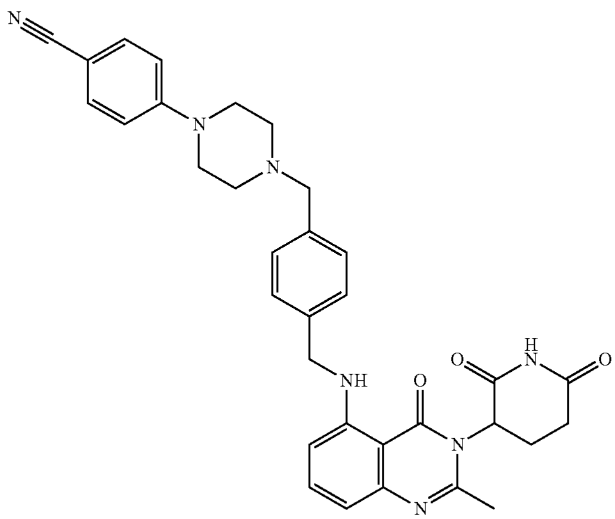 [SMILES: Cc1nc2cccc(NCc3ccc(CN4CCN(c5ccc(C#N)cc5)CC4)cc3)c2c(=O)n1C1CCC(=O)NC1=O] | 4-(4-(4-(((3-(2,6-dioxopiperidin-3-yl)-2-methyl-4-oxo-3,4-dihydroquinazolin-5-yl)amino)methyl)benzyl)piperazin-1-yl)benzonitrile |
| 59 | 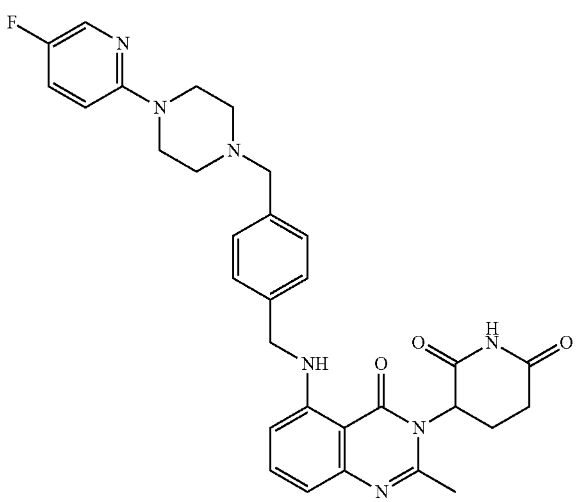 [SMILES: Cc1nc2cccc(NCc3ccc(CN4CCN(c5ccc(F)cn5)CC4)cc3)c2c(=O)n1C1CCC(=O)NC1=O] | 3-(5-((4-((4-(5-fluoropyridin-2-yl)piperazin-1-yl)methyl)benzyl)amino)-2-methyl-4-oxoquinazolin-3(4H)-yl)piperidine-2,6-dione |
| 60 | 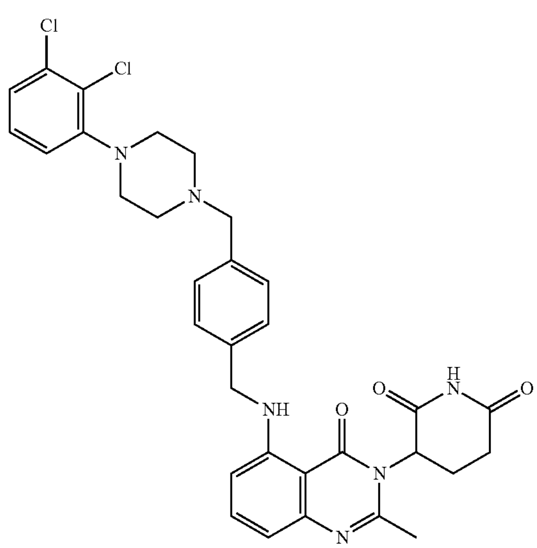 [SMILES: Cc1nc2cccc(NCc3ccc(CN4CCN(c5cccc(Cl)c5Cl)CC4)cc3)c2c(=O)n1C1CCC(=O)NC1=O] | 3-(5-((4-((4-(2,3-dichlorophenyl)piperazin-1-yl)methyl)benzyl)amino)-2-methyl-4-oxoquinazolin-3(4H)-yl)piperidine-2,6-dione |

TABLE 1-continued

| No. | Structure | Name |
|---|---|---|
| 61 | 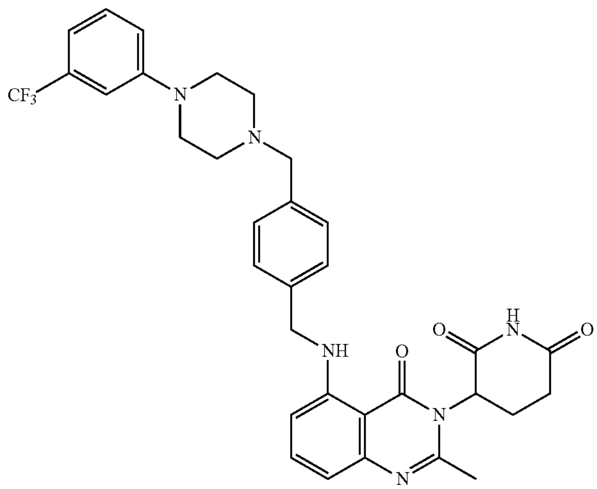 [SMILES: Cc1nc2cccc(NCc3ccc(CN4CCN(c5cccc(C(F)(F)F)c5)CC4)cc3)c2c(=O)n1C1CCC(=O)NC1=O] | 3-(2-methyl-4-oxo-5-((4-((4-(3-(trifluoromethyl)phenyl)piperazin-1-yl)methyl)benzyl)amino)quinazolin-3(4H)-yl)piperidine-2,6-dione |
| 62 | 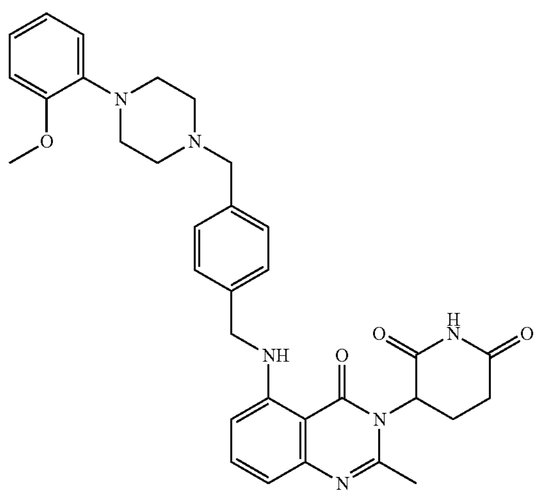 [SMILES: COc1ccccc1N1CCN(Cc2ccc(CNc3cccc4nc(C)n(C5CCC(=O)NC5=O)c(=O)c34)cc2)CC1] | 3-(5-((4-((4-(2-methoxyphenyl)piperazin-1-yl)methyl)benzyl)amino)-2-methyl-4-oxoquinazolin-3(4H)-yl)piperidine-2,6-dione |
| 63 | 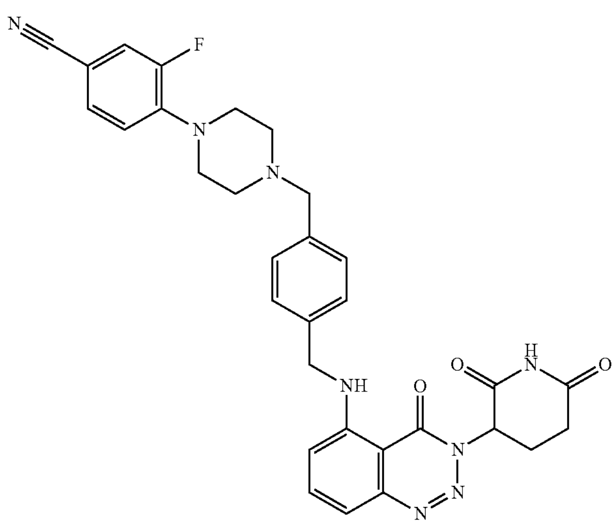 | 4-(4-(4-(((3-(2,6-dioxopiperidin-3-yl)-4-oxo-3,4-dihydrobenzo[d][1,2,3]triazin-5-yl)amino)methyl)benzyl)piperazin-1-yl)-3-fluorobenzonitrile |

TABLE 1-continued

| No. | Structure | Name |
|---|---|---|
| 64 | 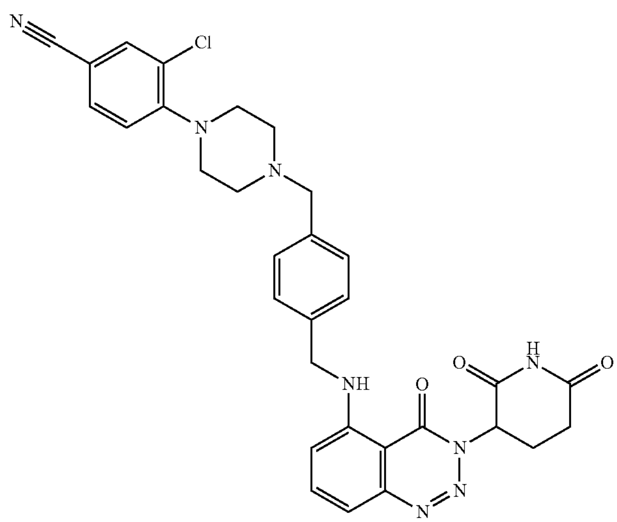 | 3-chloro-4-(4-(4-(((3-(2,6-dioxopiperidin-3-yl)-4-oxo-3,4-dihydrobenzo[d][1,2,3]triazin-5-yl)amino)methyl)benzyl)piperazin-1-yl)benzonitrile |
| 65 | 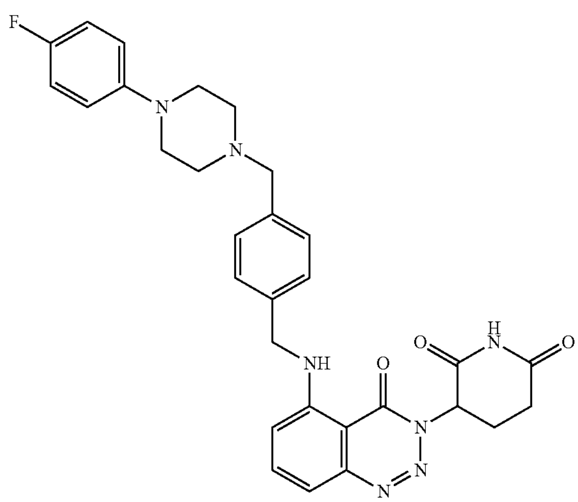 [SMILES: O=C1CCC(n2nnc3cccc(NCc4ccc(CN5CCN(c6ccc(F)cc6)CC5)cc4)c3c2=O)C(=O)N1] | 3-(5-((4-((4-(4-fluorophenyl)piperazin-1-yl)methyl)benzyl)amino)-4-oxobenzo[d][1,2,3]triazin-3(4H)-yl)piperidine-2,6-dione |
| 66 | 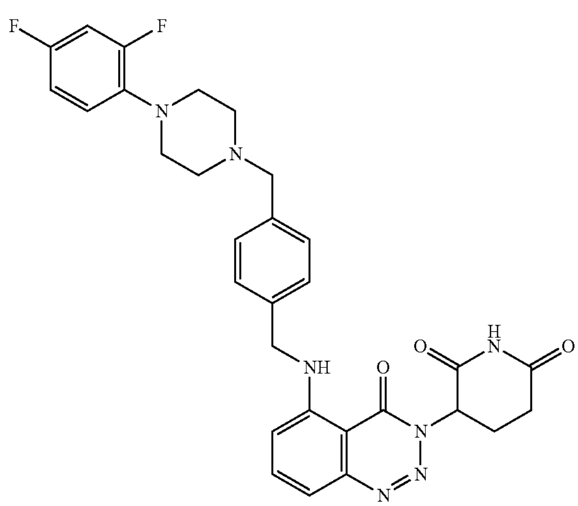 [SMILES: O=C1CCC(n2nnc3cccc(NCc4ccc(CN5CCN(c6ccc(F)cc6F)CC5)cc4)c3c2=O)C(=O)N1] | 3-(5-((4-((4-(2,4-difluorophenyl)piperazin-1-yl)methyl)benzyl)amino)-4-oxobenzo[d][1,2,3]triazin-3(4H)-yl)piperidine-2,6-dione |

TABLE 1-continued

| No. | Structure | Name |
|---|---|---|
| 67 | 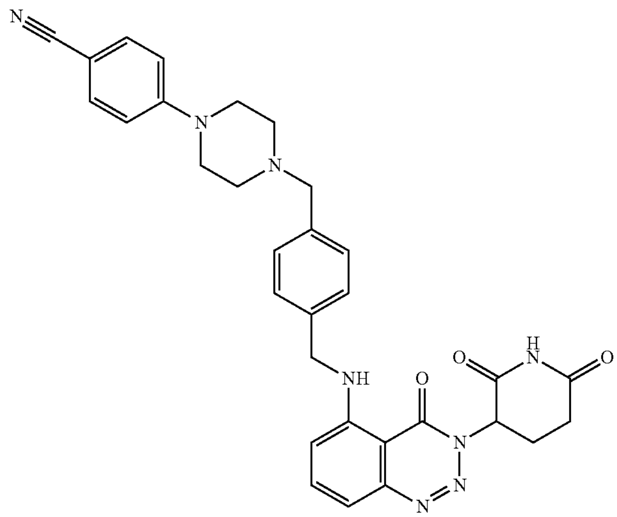 [SMILES: N#Cc1ccc(N2CCN(Cc3ccc(CNc4cccc5nnn(C6CCC(=O)NC6=O)c(=O)c45)cc3)CC2)cc1] | 4-(4-(4-(((3-(2,6-dioxopiperidin-3-yl)-4-oxo-3,4-dihydrobenzo[d][1,2,3]triazin-5-yl)amino)methyl)benzyl)piperazin-1-yl)benzonitrile |
| 68 | 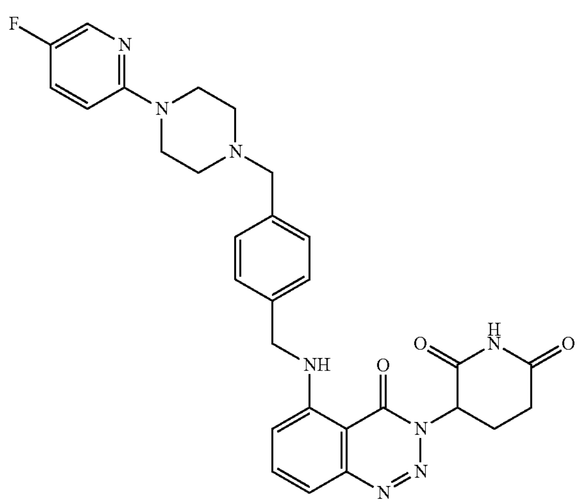 [SMILES: O=C1CCC(n2nnc3cccc(NCc4ccc(CN5CCN(c6ccc(F)cn6)CC5)cc4)c3c2=O)C(=O)N1] | 3-(5-((4-((4-(5-fluoropyridin-2-yl)piperazin-1-yl)methyl)benzyl)amino)-4-oxobenzo[d][1,2,3]triazin-3(4H)-yl)piperidine-2,6-dione |
| 69 | 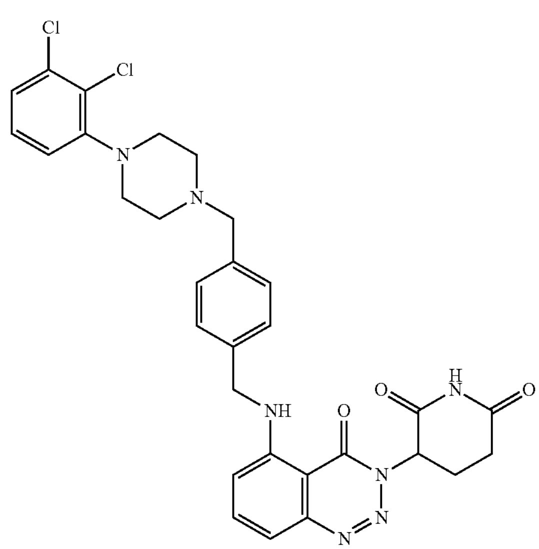 | 3-(5-((4-((4-(2,3-dichlorophenyl)piperazin-1-yl)methyl)benzyl)amino)-4-oxobenzo[d][1,2,3]triazin-3(4H)-yl)piperidine-2,6-dione |

TABLE 1-continued

| No. | Structure | Name |
|---|---|---|
| 70 | 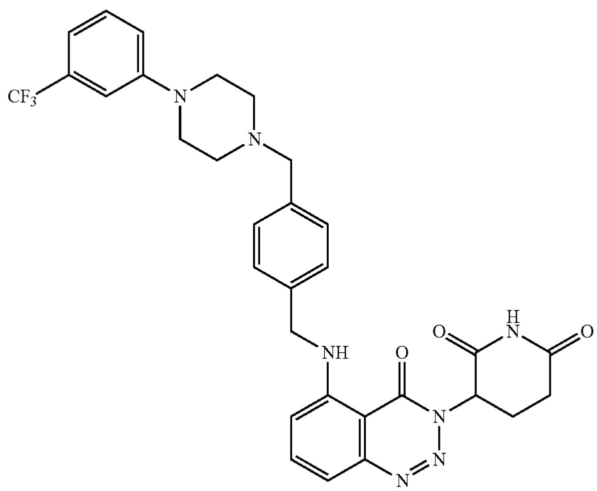 [SMILES: O=C1CCC(n2nnc3cccc(NCc4ccc(CN5CCN(c6cccc(C(F)(F)F)c6)CC5)cc4)c3c2=O)C(=O)N1] | 3-(4-oxo-5-((4-((4-(3-(trifluoromethyl)phenyl)piperazin-1-yl)methyl)benzyl)amino)benzo[d][1,2,3]triazin-3(4H)-yl)piperidine-2,6-dione |
| 71 | 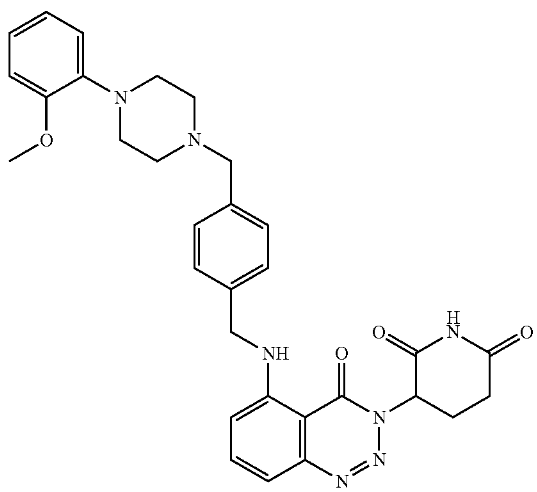 | 3-(5-((4-((4-(2-methoxyphenyl)piperazin-1-yl)methyl)benzyl)amino)-4-oxobenzo[d][1,2,3]triazin-3(4H)-yl)piperidine-2,6-dione |
| 72 | 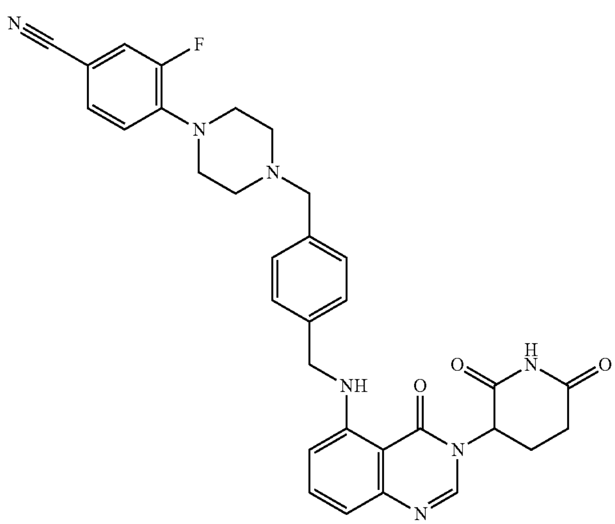 | 4-(4-(4-(((3-(2,6-dioxopiperidin-3-yl)-4-oxo-3,4-dihydroquinazolin-5-yl)amino)methyl)benzyl)piperazin-1-yl)-3-fluorobenzonitrile |

TABLE 1-continued

| No. | Structure | Name |
|---|---|---|
| 73 | 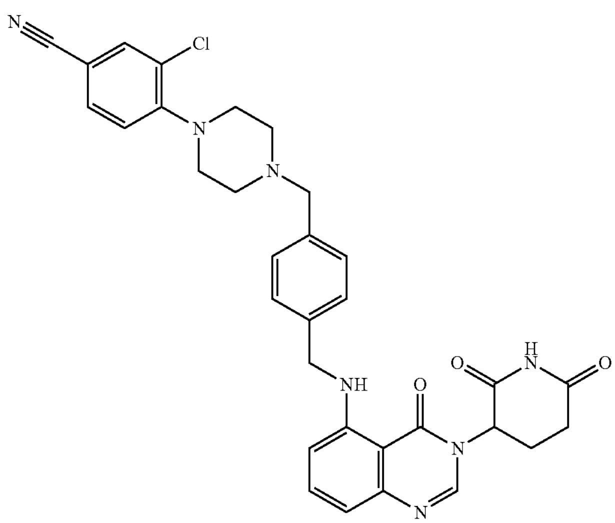 | 3-chloro-4-(4-(4-(((3-(2,6-dioxopiperidin-3-yl)-4-oxo-3,4-dihydroquinazolin-5-yl)amino)methyl)benzyl)piperazin-1-yl)benzonitrile |
| 74 | 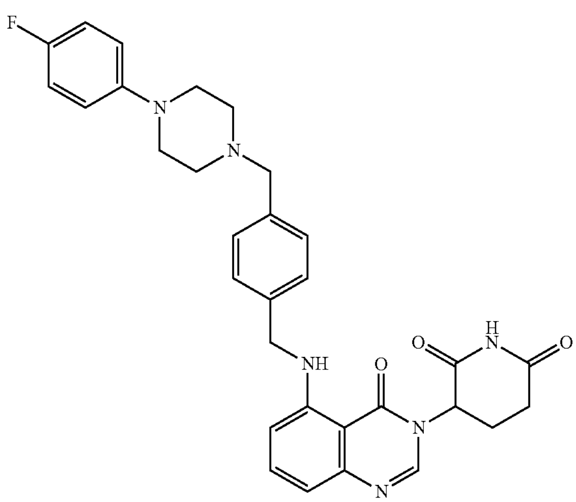 [SMILES: O=C1CCC(n2cnc3cccc(NCc4ccc(CN5CCN(c6ccc(F)cc6)CC5)cc4)c3c2=O)C(=O)N1] | 3-(5-((4-((4-(4-fluorophenyl)piperazin-1-yl)methyl)benzyl)amino)-4-oxoquinazolin-3(4H)-yl)piperidine-2,6-dione |
| 75 | 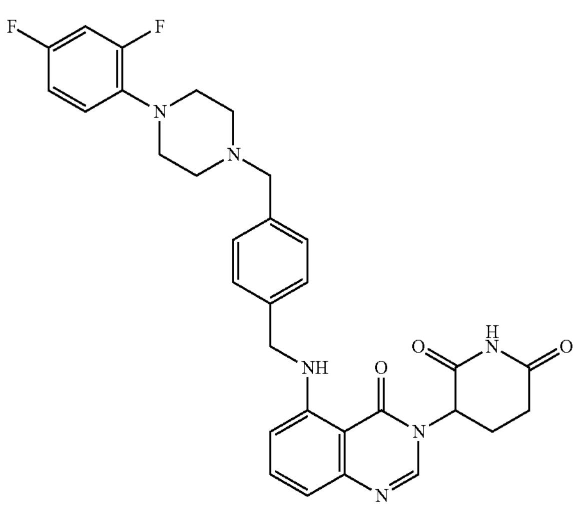 [SMILES: O=C1CCC(n2cnc3cccc(NCc4ccc(CN5CCN(c6ccc(F)cc6F)CC5)cc4)c3c2=O)C(=O)N1] | 3-(5-((4-((4-(2,4-difluorophenyl)piperazin-1-yl)methyl)benzyl)amino)-4-oxoquinazolin-3(4H)-yl)piperidine-2,6-dione |

TABLE 1-continued

| No. | Structure | Name |
|---|---|---|
| 76 | 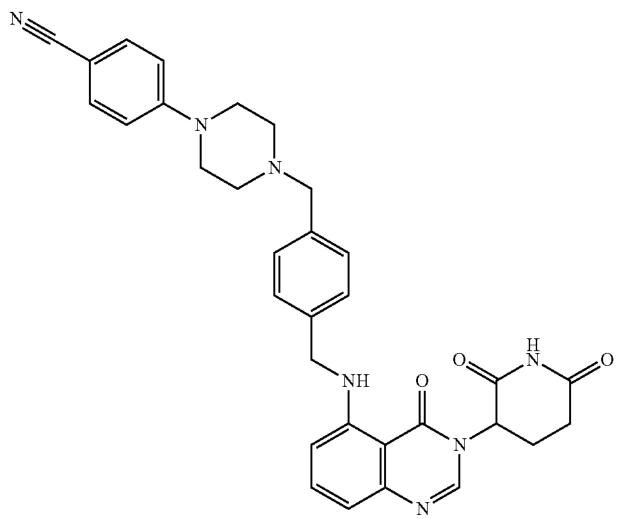 [SMILES: N#Cc1ccc(N2CCN(Cc3ccc(CNc4cccc5ncn(C6CCC(=O)NC6=O)c(=O)c45)cc3)CC2)cc1] | 4-(4-(4-(((3-(2,6-dioxopiperidin-3-yl)-4-oxo-3,4-dihydroquinazolin-5-yl)amino)methyl)benzyl)piperazin-1-yl)benzonitrile |
| 77 | 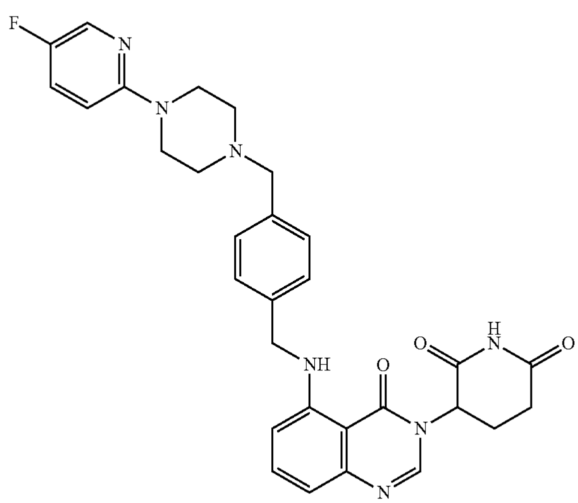 [SMILES: O=C1CCC(n2cnc3cccc(NCc4ccc(CN5CCN(c6ccc(F)cn6)CC5)cc4)c3c2=O)C(=O)N1] | 3-(5-((4-((4-(5-fluoropyridin-2-yl)piperazin-1-yl)methyl)benzyl)amino)-4-oxoquinazolin-3(4H)-yl)piperidine-2,6-dione |
| 78 | 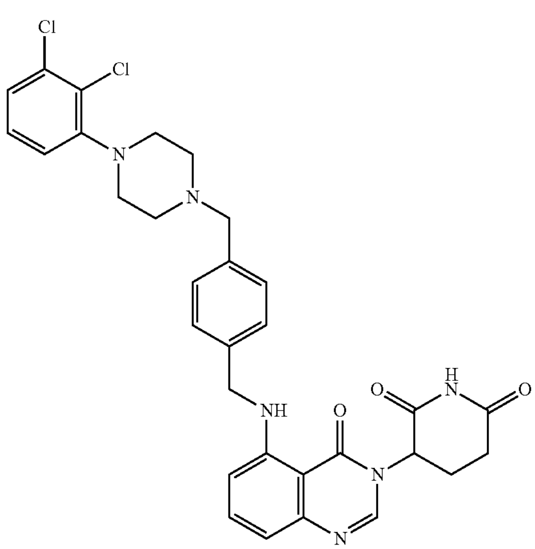 | 3-(5-((4-((4-(2,3-dichlorophenyl)piperazin-1-yl)methyl)benzyl)amino)-4-oxoquinazolin-3(4H)-yl)piperidine-2,6-dione |

TABLE 1-continued

| No. | Structure | Name |
|---|---|---|
| 79 | 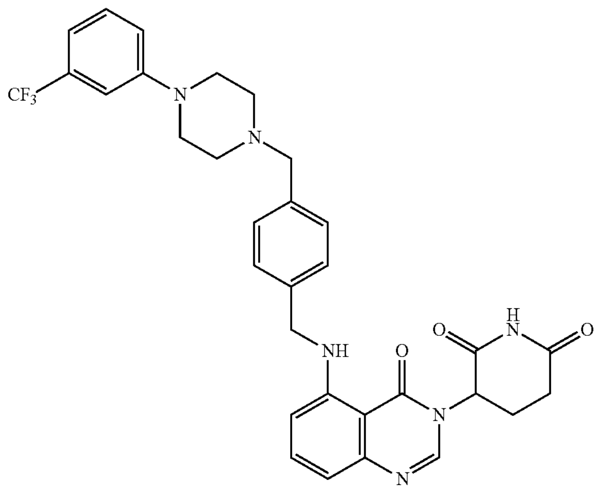 [SMILES: O=C1CCC(n2cnc3cccc(NCc4ccc(CN5CCN(c6cccc(C(F)(F)F)c6)CC5)cc4)c3c2=O)C(=O)N1] | 3-(4-oxo-5-((4-((4-(3-(trifluoromethyl)phenyl)piperazin-1-yl)methyl)benzyl)amino)quinazolin-3(4H)-yl)piperidine-2,6-dione |
| 80 | 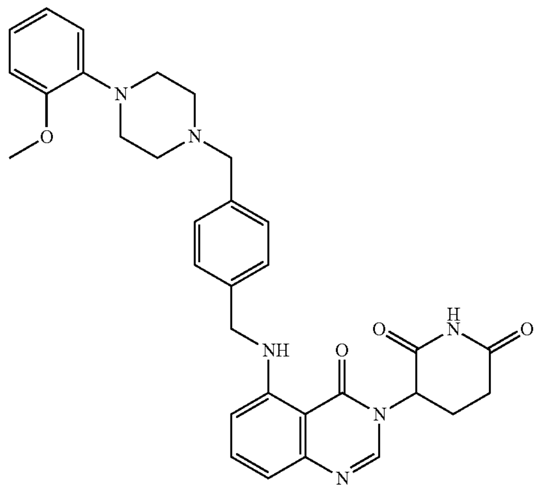 | 3-(5-((4-((4-(2-methoxyphenyl)piperazin-1-yl)methyl)benzyl)amino)-4-oxoquinazolin-3(4H)-yl)piperidine-2,6-dione |
| 81 | 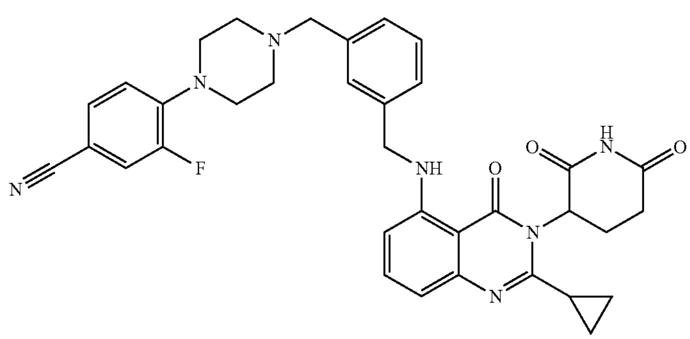 [SMILES: N#Cc1ccc(N2CCN(Cc3cccc(CNc4cccc5nc(C6CC6)n(C6CCC(=O)NC6=O)c(=O)c45)c3)CC2)c(F)c1] | 4-(4-(3-(((2-cyclopropyl-3-(2,6-dioxopiperidin-3-yl)-4-oxo-3,4-dihydroquinazolin-5-yl)amino)methyl)benzyl)piperazin-1-yl)-3-fluorobenzonitrile |
| 82 | 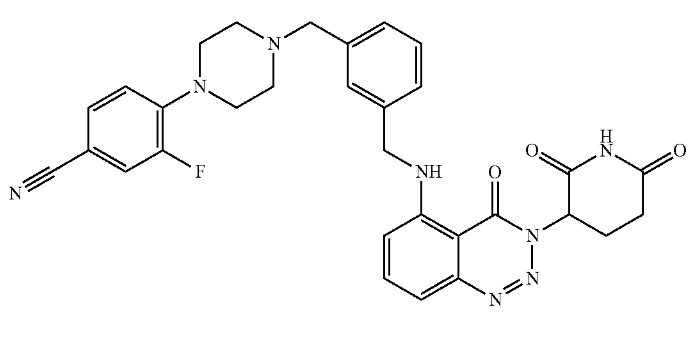 [SMILES: N#Cc1ccc(N2CCN(Cc3cccc(CNc4cccc5ncn(C6CCC(=O)NC6=O)c(=O)c45)c3)CC2)c(F)c1] | 4-(4-(3-(((3-(2,6-dioxopiperidin-3-yl)-4-oxo-3,4-dihydrobenzo[d][1,2,3]triazin-5-yl)amino)methyl)benzyl)piperazin-1-yl)-3-fluorobenzonitrile |

TABLE 1-continued

| No. | Structure | Name |
| --- | --- | --- |
| 83 | 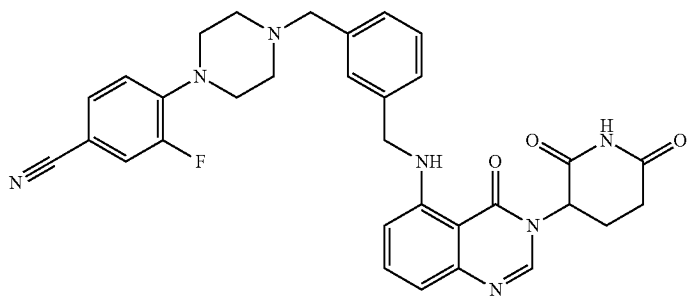 | 4-(4-(3-(((3-(2,6-dioxopiperidin-3-yl)-4-oxo-3,4-dihydroquinazolin-5-yl)amino)methyl)benzyl)piperazin-1-yl)-3-fluorobenzonitrile |
| 84 | 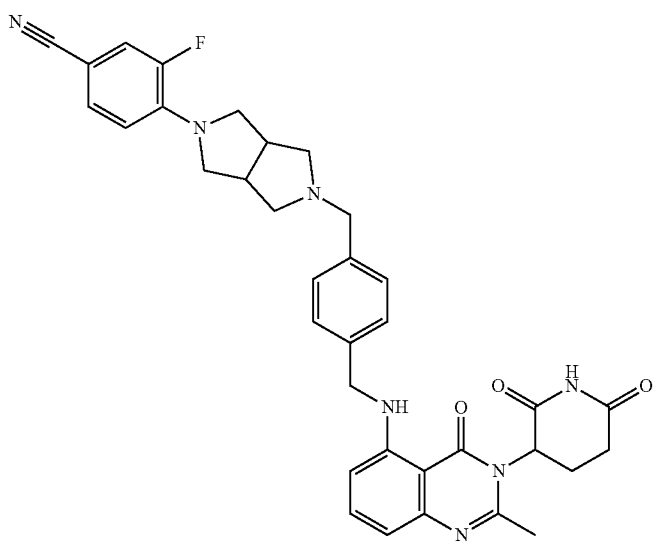 [SMILES: Cc1nc2cccc(NCc3ccc(CN4CC5CN(c6ccc(C#N)cc6F)CC5C4)cc3)c2c(=O)n1C1CCC(=O)NC1=O] | 4-(5-(4-(((3-(2,6-dioxopiperidin-3-yl)-2-methyl-4-oxo-3,4-dihydroquinazolin-5-yl)amino)methyl)benzyl)hexahydropyrrolo[3,4-c]pyrrol-2(1H)-yl)-3-fluorobenzonitrile |
| 85 | 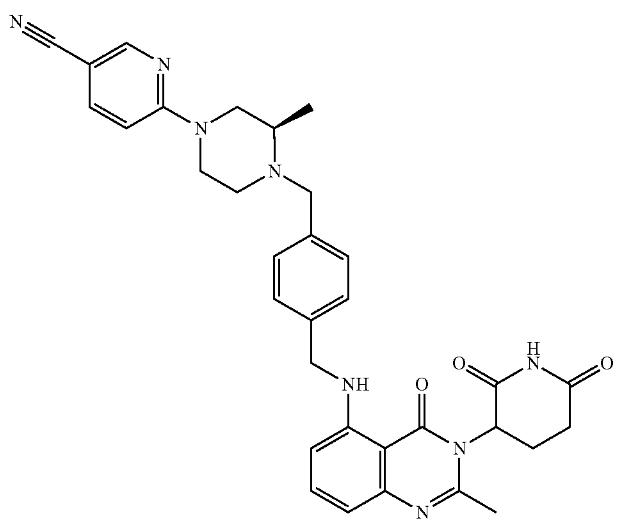 [SMILES: Cc1nc2cccc(NCc3ccc(CN4CCN(c5ccc(C#N)cn5)C[C@H]4C)cc3)c2c(=O)n1C1CCC(=O)NC1=O] | 6-((3R)-4-(4-(((3-(2,6-dioxopiperidin-3-yl)-2-methyl-4-oxo-3,4-dihydroquinazolin-5-yl)amino)methyl)benzyl)-3-methylpiperazin-1-yl)nicotinonitrile |

TABLE 1-continued

| No. | Structure | Name |
|---|---|---|
| 86 | 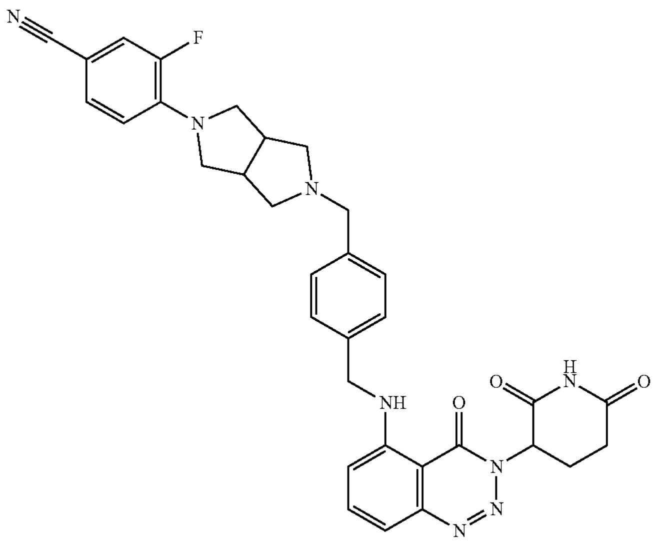 [SMILES: N#Cc1ccc(N2CC3CN(Cc4ccc(CNc5cccc6nnn(C7CCC(=O)NC7=O)c(=O)c56)cc4)CC3C2)c(F)c1] | 4-(5-(4-(((3-(2,6-dioxopiperidin-3-yl)-4-oxo-3,4-dihydrobenzo[d][1,2,3]triazin-5-yl)amino)methyl)benzyl)hexahydropyrrolo[3,4-c]pyrrol-2(1H)-yl)-3-fluorobenzonitrile |
| 87 | 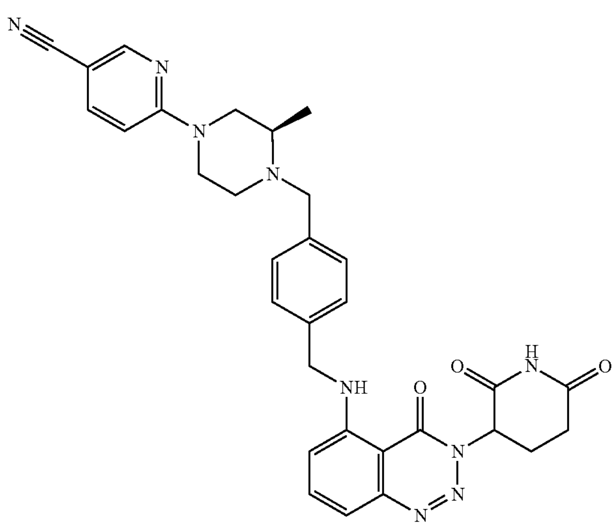 | 6-((3R)-4-(4-(((3-(2,6-dioxopiperidin-3-yl)-4-oxo-3,4-dihydrobenzo[d][1,2,3]triazin-5-yl)amino)methyl)benzyl)-3-methylpiperazin-1-yl)nicotinonitrile |
| 88 | 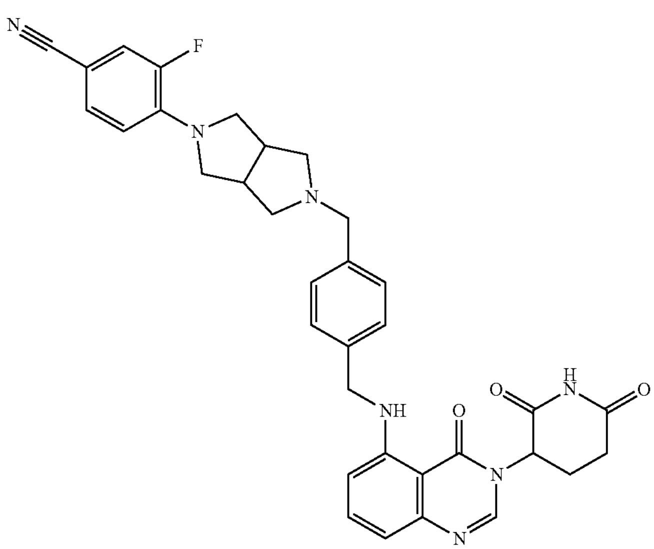 [SMILES: N#Cc1ccc(N2CC3CN(Cc4ccc(CNc5cccc6ncn(C7CCC(=O)NC7=O)c(=O)c56)cc4)CC3C2)c(F)c1] | 4-(5-(4-(((3-(2,6-dioxopiperidin-3-yl)-4-oxo-3,4-dihydroquinazolin-5-yl)amino)methyl)benzyl)hexahydropyrrolo[3,4-c]pyrrol-2(1H)-yl)-3-fluorobenzonitrile |

TABLE 1-continued

| No. | Structure | Name |
|---|---|---|
| 89 | 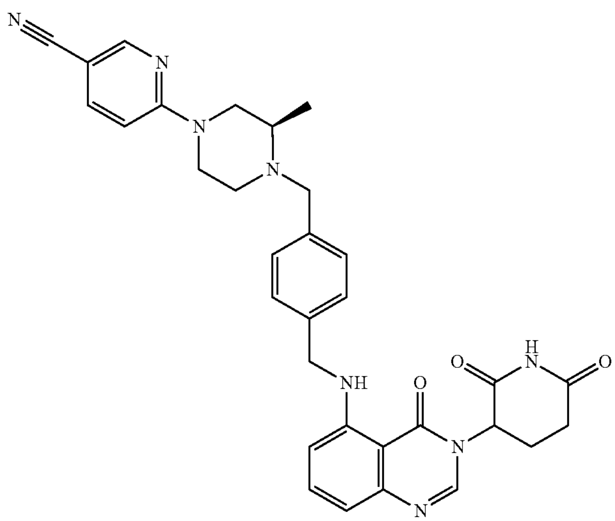 | 6-((3R)-4-(4-(((3-(2,6-dioxopiperidin-3-yl)-4-oxo-3,4-dihydroquinazolin-5-yl)amino)methyl)benzyl)-3-methylpiperazin-1-yl)nicotinonitrile |
| 90 | 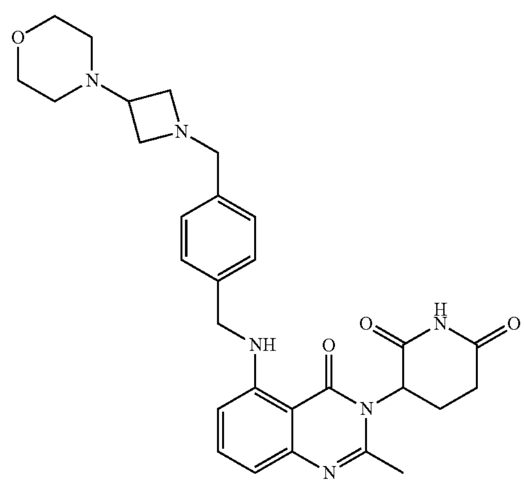 | 3-(2-methyl-5-((4-((3-morpholinoazetidin-1-yl)methyl)benzyl)amino)-4-oxoquinazolin-3(4H)-yl)piperidine-2,6-dione |
| 91 | 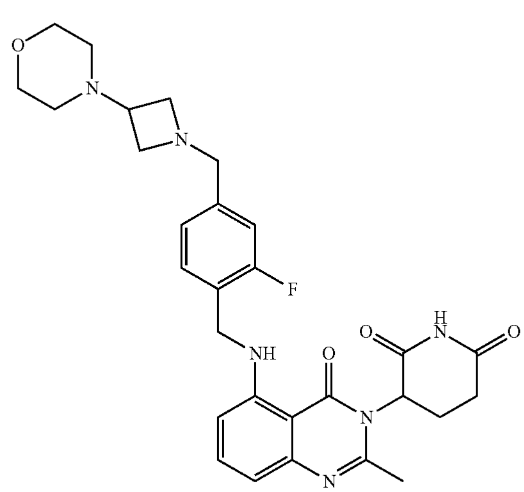 | 3-(5-((2-fluoro-4-((3-morpholinoazetidin-1-yl)methyl)benzyl)amino)-2-methyl-4-oxoquinazolin-3(4H)-yl)piperidine-2,6-dione |

TABLE 1-continued

| No. | Structure | Name |
|---|---|---|
| 92 | 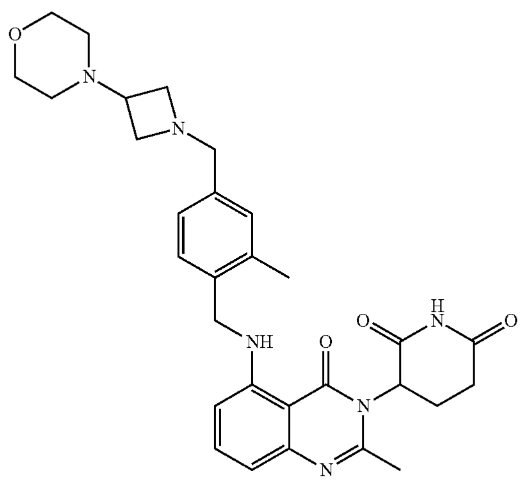 | 3-(2-methyl-5-((2-methyl-4-((3-morpholinoazetidin-1-yl)methyl)benzyl)amino)-4-oxoquinazolin-3(4H)-yl)piperidine-2,6-dione |
| 93 | 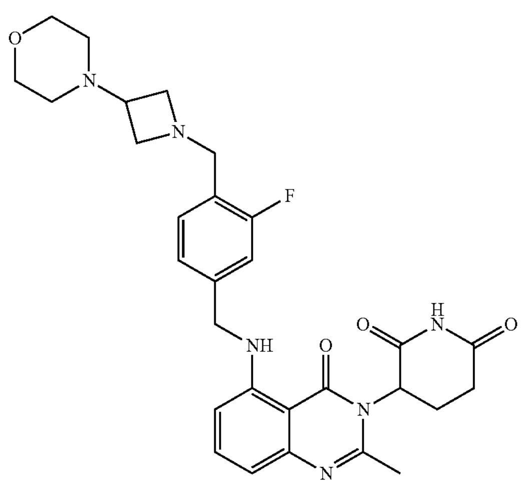 | 3-(5-((3-fluoro-4-((3-morpholinoazetidin-1-yl)methyl)benzyl)amino)-2-methyl-4-oxoquinazolin-3(4H)-yl)piperidine-2,6-dione |
| 94 | 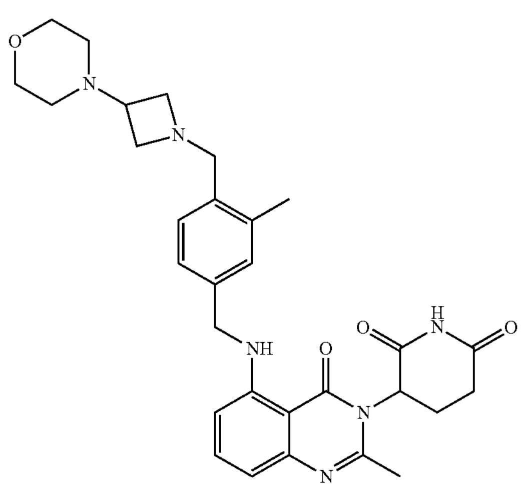 | 3-(2-methyl-5-((3-methyl-4-((3-morpholinoazetidin-1-yl)methyl)benzyl)amino)-4-oxoquinazolin-3(4H)-yl)piperidine-2,6-dione |

TABLE 1-continued

| No. | Structure | Name |
|---|---|---|
| 95 | 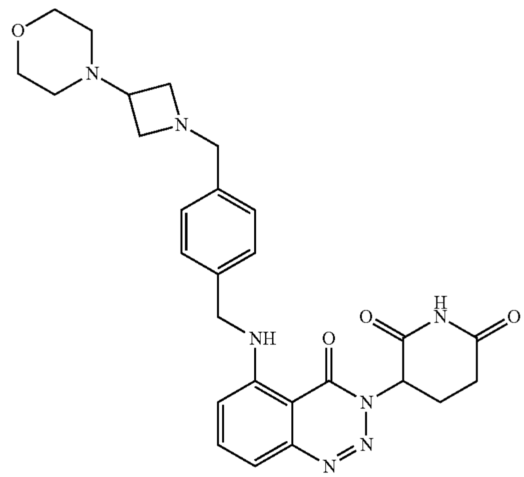 | 3-(5-((4-((3-morpholinoazetidin-1-yl)methyl)benzyl)amino)-4-oxobenzo[d][1,2,3]triazin-3(4H)-yl)piperidine-2,6-dione |
| 96 | 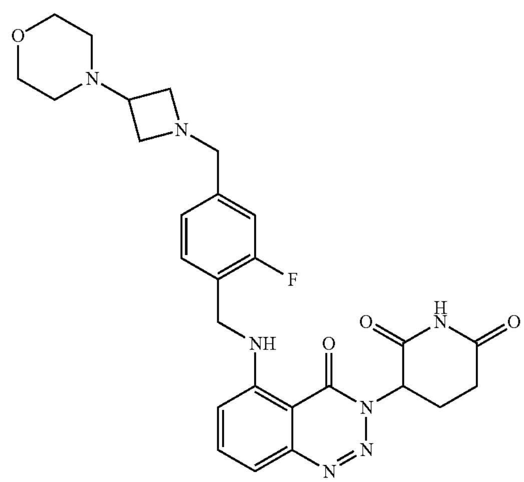 | 3-(5-((2-fluoro-4-((3-morpholinoazetidin-1-yl)methyl)benzyl)amino)-4-oxobenzo[d][1,2,3]triazin-3(4H)-yl)piperidine-2,6-dione |
| 97 | 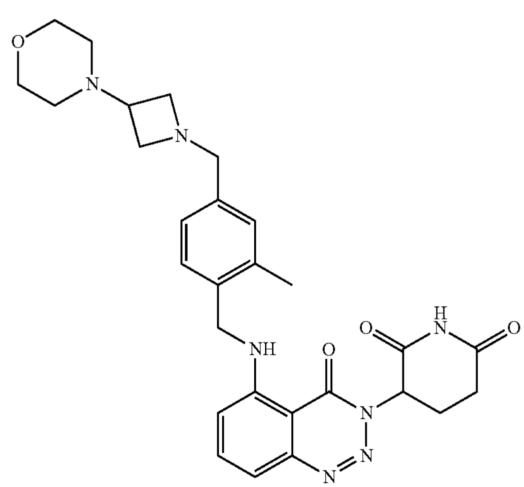 | 3-(5-((2-methyl-4-((3-morpholinoazetidin-1-yl)methyl)benzyl)amino)-4-oxobenzo[d][1,2,3]triazin-3(4H)-yl)piperidine-2,6-dione |

TABLE 1-continued
| No. | Structure | Name |
|---|---|---|
| 98 | 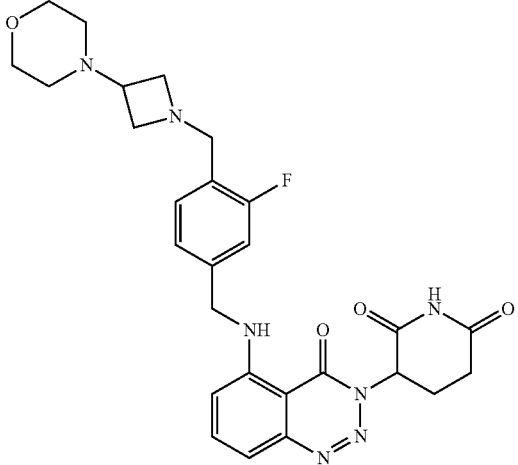 | 3-(5-(((3-fluoro-4-((3-morpholinoazetidin-1-yl)methyl)benzyl)amino)-4-oxobenzo[d][1,2,3]triazin-3(4H)-yl)piperidine-2,6-dione |
| 99 | 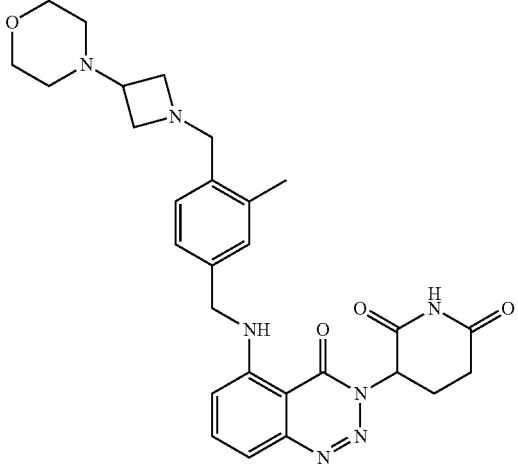 | 3-(5-(((3-methyl-4-((3-morpholinoazetidin-1-yl)methyl)benzyl)amino)-4-oxobenzo[d][1,2,3]triazin-3(4H)-yl)piperidine-2,6-dione |
| 100 | 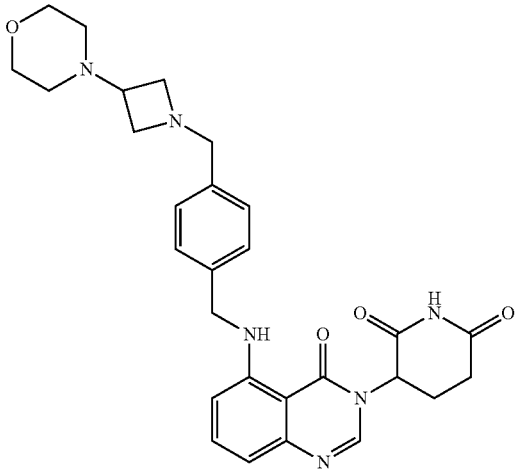 | 3-(5-((4-((3-morpholinoazetidin-1-yl)methyl)benzyl)amino)-4-oxoquinazolin-3(4H)-yl)piperidine-2,6-dione |

TABLE 1-continued

| No. | Structure | Name |
| --- | --- | --- |
| 101 | 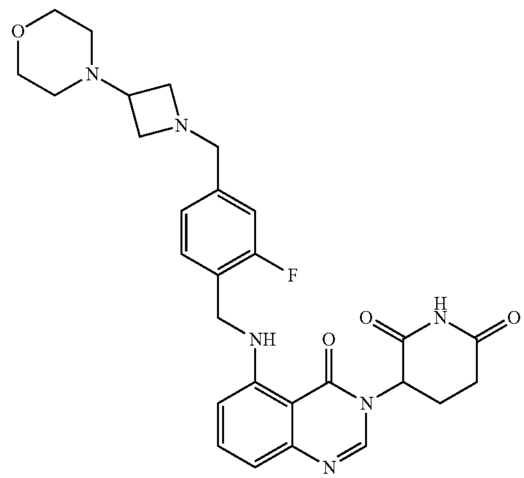 | 3-(5-((2-fluoro-4-((3-morpholinoazetidin-1-yl)methyl)benzyl)amino)-4-oxoquinazolin-3(4H)-yl)piperidine-2,6-dione |
| 102 | 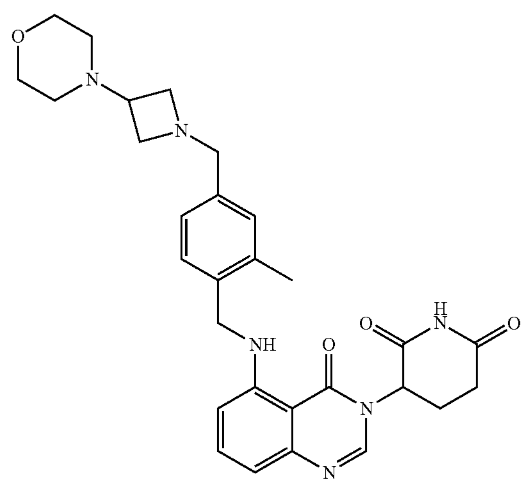 | 3-(5-((2-methyl-4-((3-morpholinoazetidin-1-yl)methyl)benzyl)amino)-4-oxoquinazolin-3(4H)-yl)piperidine-2,6-dione |
| 103 | 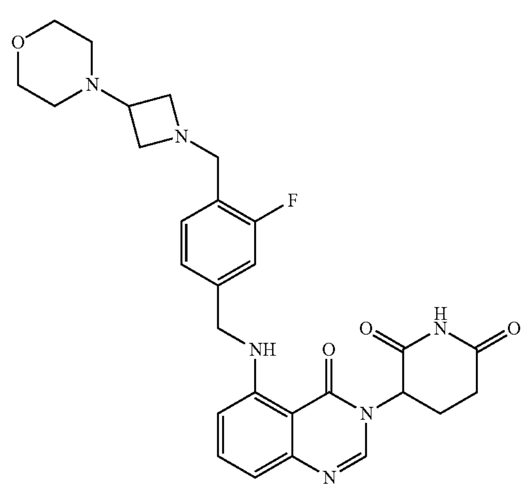 | 3-(5-((3-fluoro-4-((3-morpholinoazetidin-1-yl)methyl)benzyl)amino)-4-oxoquinazolin-3(4H)-yl)piperidine-2,6-dione |

TABLE 1-continued

| No. | Structure | Name |
|---|---|---|
| 104 | 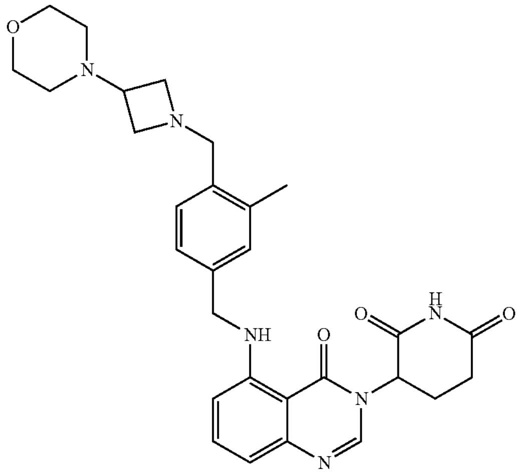 | 3-(5-((3-methyl-4-((3-morpholinoazetidin-1-yl)methyl)benzyl)amino)-4-oxoquinazolin-3(4H)-yl)piperidine-2,6-dione |
| 105 | 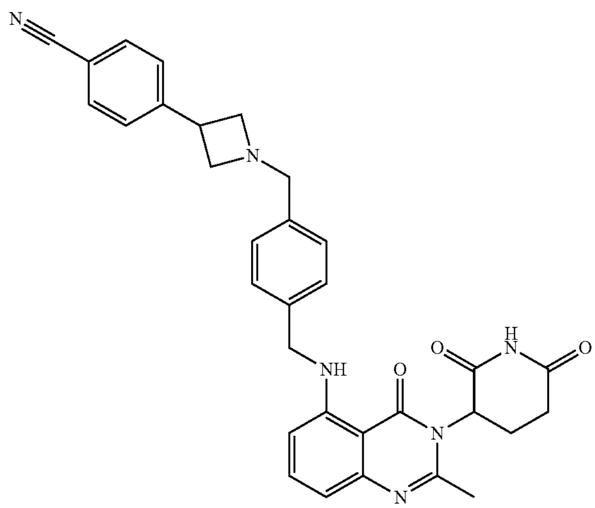 [SMILES: Cc1nc2cccc(NCc3ccc(CN4CC(c5ccc(C#N)cc5)C4)cc3)c2c(=O)n1C1CCC(=O)NC1=O] | 4-(1-(4-(((3-(2,6-dioxopiperidin-3-yl)-2-methyl-4-oxo-3,4-dihydroquinazolin-5-yl)amino)methyl)benzyl)azetidin-3-yl)benzonitrile |
| 106 | 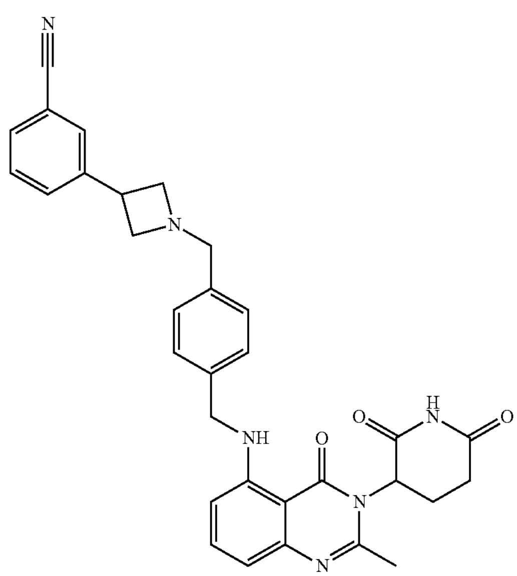 [SMILES: Cc1nc2cccc(NCc3ccc(CN4CC(c5cccc(C#N)c5)C4)cc3)c2c(=O)n1C1CCC(=O)NC1=O] | 3-(1-(4-(((3-(2,6-dioxopiperidin-3-yl)-2-methyl-4-oxo-3,4-dihydroquinazolin-5-yl)amino)methyl)benzyl)azetidin-3-yl)benzonitrile |

TABLE 1-continued

| No. | Structure | Name |
|-----|-----------|------|
| 107 | 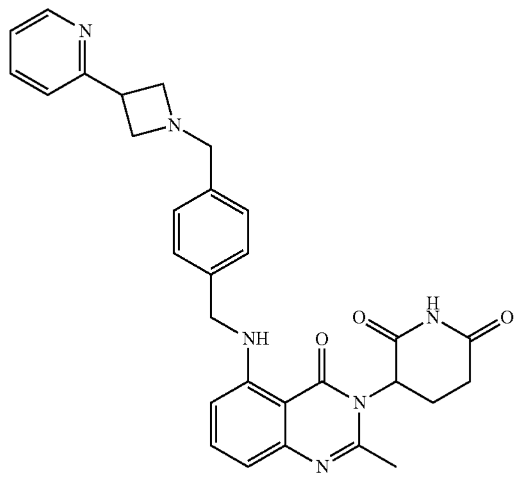 [SMILES: Cc1nc2cccc(NCc3ccc(CN4CC(c5ccccn5)C4)cc3)c2c(=O)n1C1CCC(=O)NC1=O] | 3-(2-methyl-4-oxo-5-((4-((3-(pyridin-2-yl)azetidin-1-yl)methyl)benzyl)amino)quinazolin-3(4H)-yl)piperidine-2,6-dione |
| 108 | 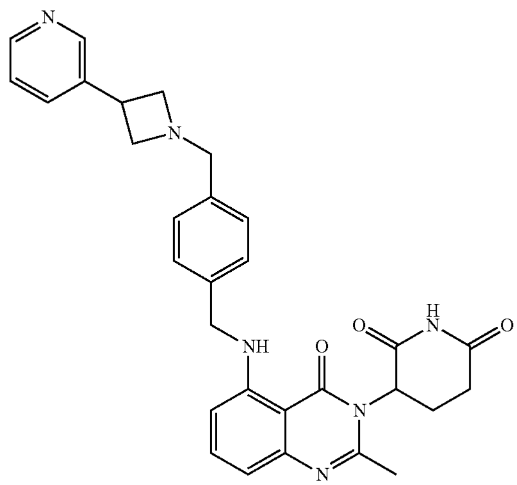 [SMILES: Cc1nc2cccc(NCc3ccc(CN4CC(c5cccnc5)C4)cc3)c2c(=O)n1C1CCC(=O)NC1=O] | 3-(2-methyl-4-oxo-5-((4-((3-(pyridin-3-yl)azetidin-1-yl)methyl)benzyl)amino)quinazolin-3(4H)-yl)piperidine-2,6-dione |
| 109 | 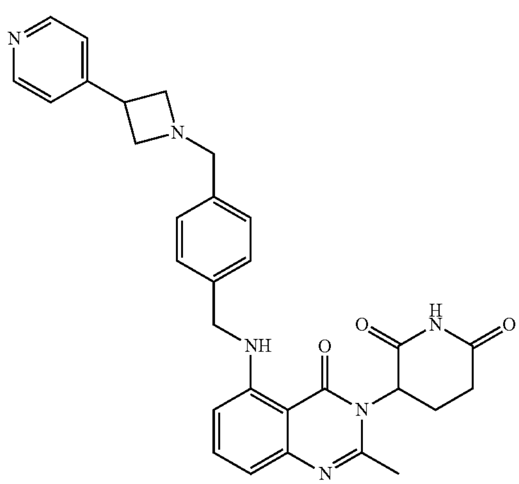 [SMILES: Cc1nc2cccc(NCc3ccc(CN4CC(c5ccncc5)C4)cc3)c2c(=O)n1C1CCC(=O)NC1=O] | 3-(2-methyl-4-oxo-5-((4-((3-(pyridin-4-yl)azetidin-1-yl)methyl)benzyl)amino)quinazolin-3(4H)-yl)piperidine-2,6-dione |

TABLE 1-continued

| No. | Structure | Name |
|---|---|---|
| 110 | 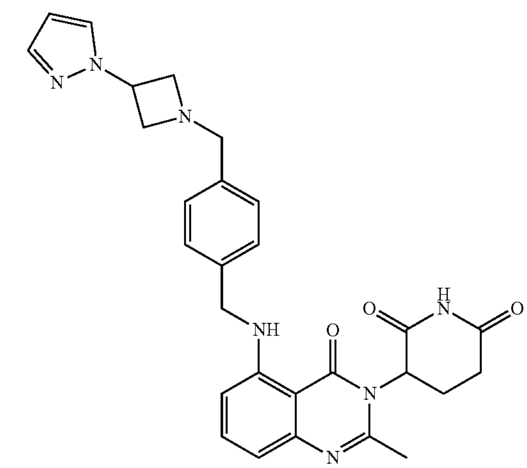 [SMILES: Cc1nc2cccc(NCc3ccc(CN4CC(n5cccn5)C4)cc3)c2c(=O)n1C1CCC(=O)NC1=O] | 3-(5-((4-((3-(1H-pyrazol-1-yl)azetidin-1-yl)methyl)benzyl)amino)-2-methyl-4-oxoquinazolin-3(4H)-yl)piperidine-2,6-dione |
| 111 | 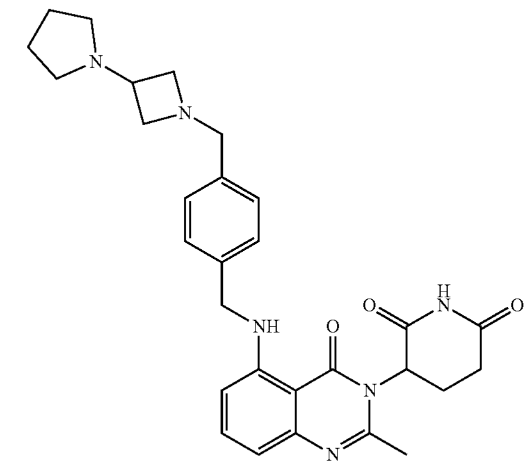 [SMILES: Cc1nc2cccc(NCc3ccc(CN4CC(N5CCCC5)C4)cc3)c2c(=O)n1C1CCC(=O)NC1=O] | 3-(2-methyl-4-oxo-5-((4-((3-(pyrrolidin-1-yl)azetidin-1-yl)methyl)benzyl)amino)quinazolin-3(4H)-yl)piperidine-2,6-dione |
| 112 | 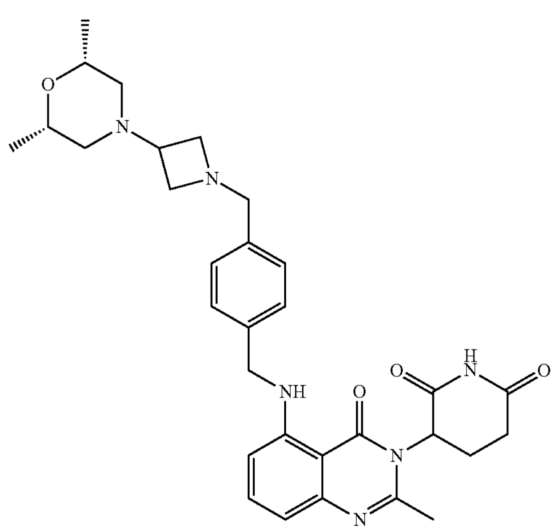 [SMILES: Cc1nc2cccc(NCc3ccc(CN4CC(N5C[C@@H](C)O[C@@H](C)C5)C4)cc3)c2c(=O)n1C1CCC(=O)NC1=O] | 3-(5-((4-((3-((2R,6S)-2,6-dimethylmorpholino)azetidin-1-yl)methyl)benzyl)amino)-2-methyl-4-oxoquinazolin-3(4H)-yl)piperidine-2,6-dione |

TABLE 1-continued

| No. | Structure | Name |
|-----|-----------|------|
| 113 | 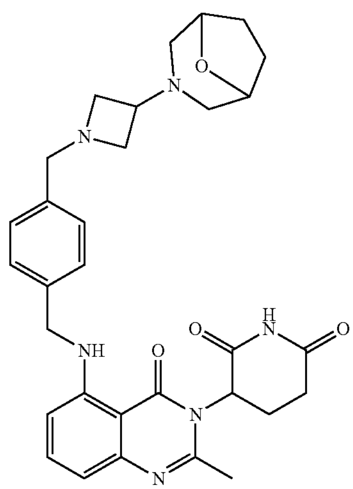 [SMILES: Cc1nc2cccc(NCc3ccc(CN4CC(N5CC6CCC(C5)O6)C4)cc3)c2c(=O)n1C1CCC(=O)NC1=O] | 3-(5-((4-((3-(8--oxa-3-azabicyclo[3.2.1]octan-3-yl)azetidin-1-yl)methyl)benzyl)amino)-2-methyl-4-oxoquinazolin-3(4H)-yl)piperidine-2,6-dione |
| 114 | 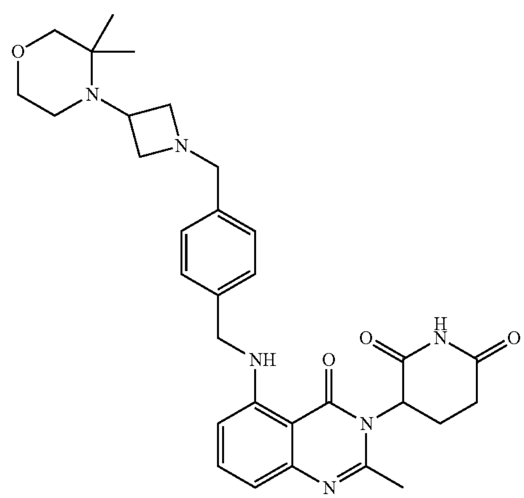 [SMILES: Cc1nc2cccc(NCc3ccc(CN4CC(N5CCOCC5(C)C)C4)cc3)c2c(=O)n1C1CCC(=O)NC1=O] | 3-(5-((4-((3-(3,3-dimethylmorpholino)azetidin-1-yl)methyl)benzyl)amino)-2-methyl-4-oxoquinazolin-3(4H)-yl)piperidine-2,6-dione |
| 115 | 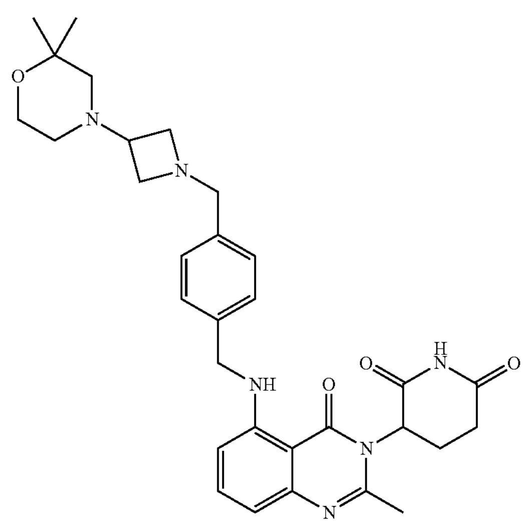 [SMILES: Cc1nc2cccc(NCc3ccc(CN4CC(N5CCOC(C)(C)C5)C4)cc3)c2c(=O)n1C1CCC(=O)NC1=O] | 3-(5-((4-((3-(2,2-dimethylmorpholino)azetidin-1-yl)methyl)benzyl)amino)-2-methyl-4-oxoquinazolin-3(4H)-yl)piperidine-2,6-dione |

TABLE 1-continued

| No. | Structure | Name |
| --- | --- | --- |
| 116 | 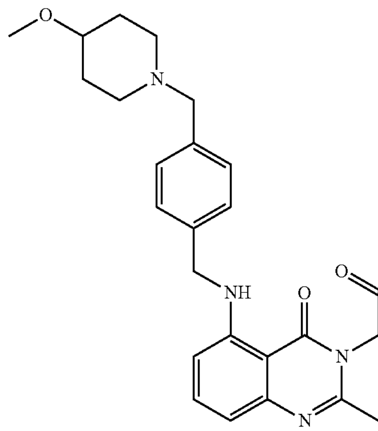 | 3-(5-((4-((4-methoxypiperidin-1-yl)methyl)benzyl)amino)-2-methyl-4-oxoquinazolin-3(4H)-yl)piperidine-2,6-dione |
| 117 | 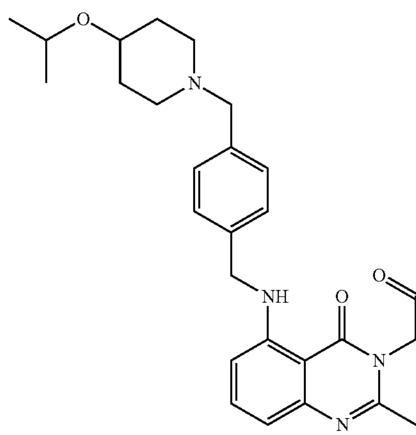 | 3-(5-((4-((4-isopropoxypiperidin-1-yl)methyl)benzyl)amino)-2-methyl-4-oxoquinazolin-3(4H)-yl)piperidine-2,6-dione |
| 118 | 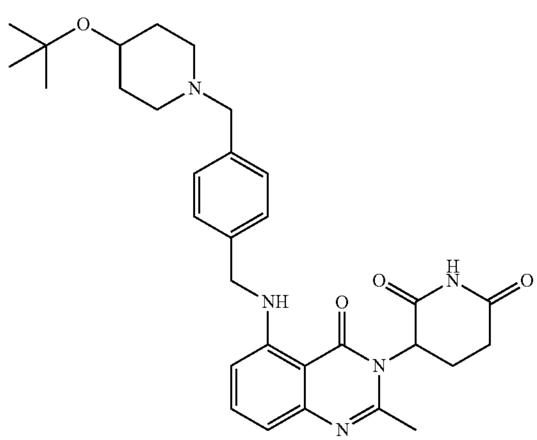 [SMILES: Cc1nc2cccc(NCc3ccc(CN4CCC(OC(C)(C)C)CC4)cc3)c2c(=O)n1C1CCC(=O)NC1=O] | 3-(5-((4-((4-(tert-butoxy)piperidin-1-yl)methyl)benzyl)amino)-2-methyl-4-oxoquinazolin-3(4H)-yl)piperidine-2,6-dione |

TABLE 1-continued

| No. | Structure | Name |
|---|---|---|
| 119 | 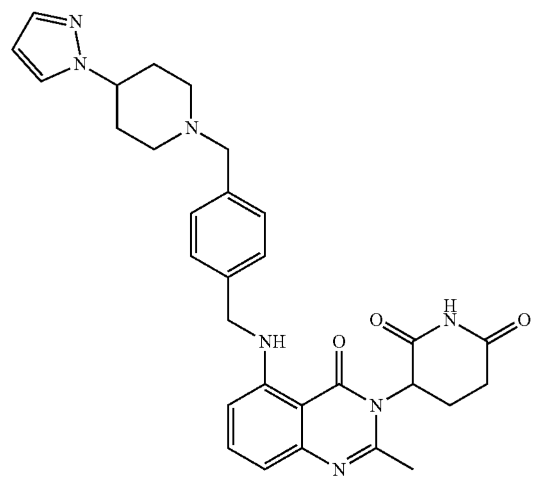 [SMILES: Cc1nc2cccc(NCc3ccc(CN4CCC(n5cccn5)CC4)cc3)c2c(=O)n1C1CCC(=O)NC1=O] | 3-(5-((4-((4-(1H-pyrazol-1-yl)piperidin-1-yl)methyl)benzyl)amino)-2-methyl-4-oxoquinazolin-3(4H)-yl)piperidine-2,6-dione |
| 120 | 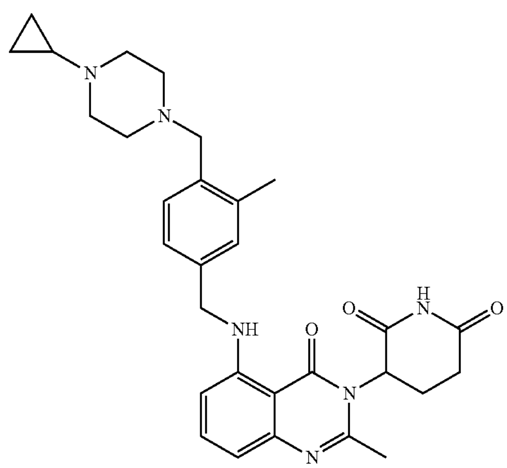 [SMILES: Cc1cc(CNc2cccc3nc(C)n(C4CCC(=O)NC4=O)c(=O)c23)ccc1CN1CCN(C2CC2)CC1] | 3-(5-((4-((4-cyclopropylpiperazin-1-yl)methyl)-3-methylbenzyl)amino)-2-methyl-4-oxoquinazolin-3(4H)-yl)piperidine-2,6-dione |
| 121 | 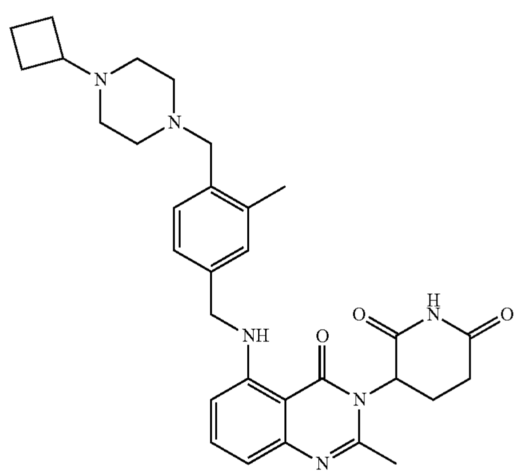 [SMILES: Cc1cc(CNc2cccc3nc(C)n(C4CCC(=O)NC4=O)c(=O)c23)ccc1CN1CCN(C2CCC2)CC1] | 3-(5-((4-((4-cyclobutylpiperazin-1-yl)methyl)-3-methylbenzyl)amino)-2-methyl-4-oxoquinazolin-3(4H)-yl)piperidine-2,6-dione |

TABLE 1-continued

| No. | Structure | Name |
|---|---|---|
| 122 | 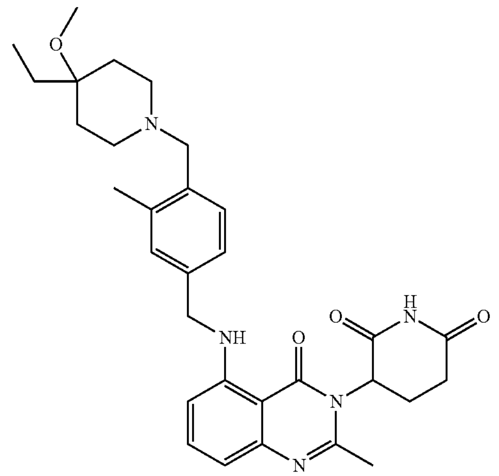 [SMILES: CCC1(OC)CCN(Cc2ccc(CNc3cccc4nc(C)n(C5CCC(=O)NC5=O)c(=O)c34)cc2C)CC1] | 3-(5-((4-((4-ethyl-4-methoxypiperidin-1-yl)methyl)-3-methylbenzyl)amino)-2-methyl-4-oxoquinazolin-3(4H)-yl)piperidine-2,6-dione |
| 123 | 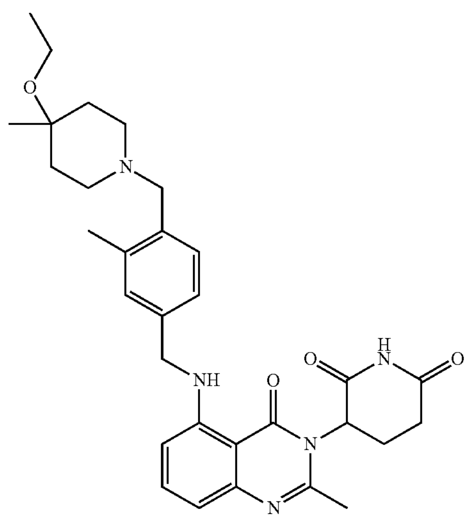 [SMILES: CCOC1(C)CCN(Cc2ccc(CNc3cccc4nc(C)n(C5CCC(=O)NC5=O)c(=O)c34)cc2C)CC1] | 3-(5-((4-((4-ethoxy-4-methylpiperidin-1-yl)methyl)-3-methylbenzyl)amino)-2-methyl-4-oxoquinazolin-3(4H)-yl)piperidine-2,6-dione |
| 124 | 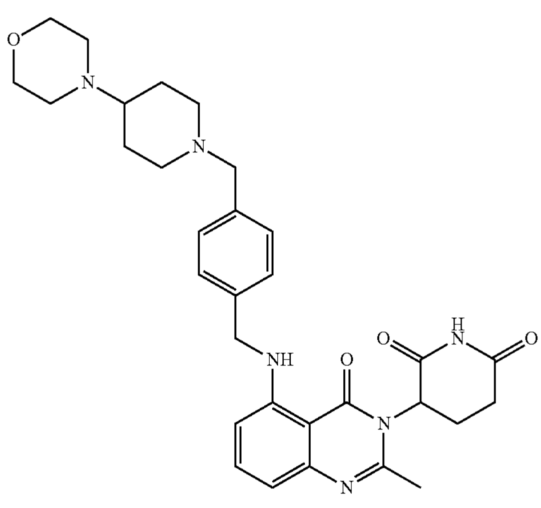 [SMILES: Cc1nc2cccc(NCc3ccc(CN4CCC(N5CCOCC5)CC4)cc3)c2c(=O)n1C1CCC(=O)NC1=O] | 3-(2-methyl-5-((4-((4-morpholinopiperidin-1-yl)methyl)benzyl)amino)-4-oxoquinazolin-3(4H)-yl)piperidine-2,6-dione |

TABLE 1-continued

| No. | Structure | Name |
|---|---|---|
| 125 | 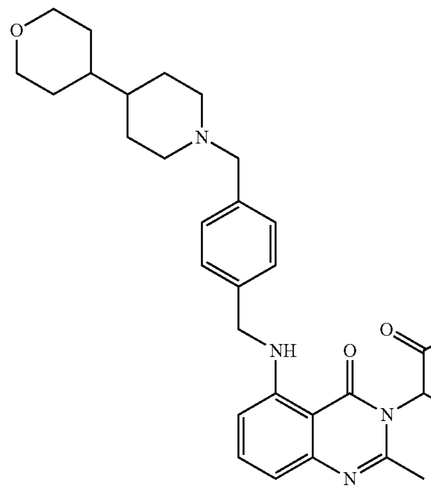 | 3-(2-methyl-4-oxo-5-((4-((4-(tetrahydro-2H-pyran-4-yl)piperidin-1-yl)methyl)benzyl)amino)quinazolin-3(4H)-yl)piperidine-2,6-dione |
| 126 | 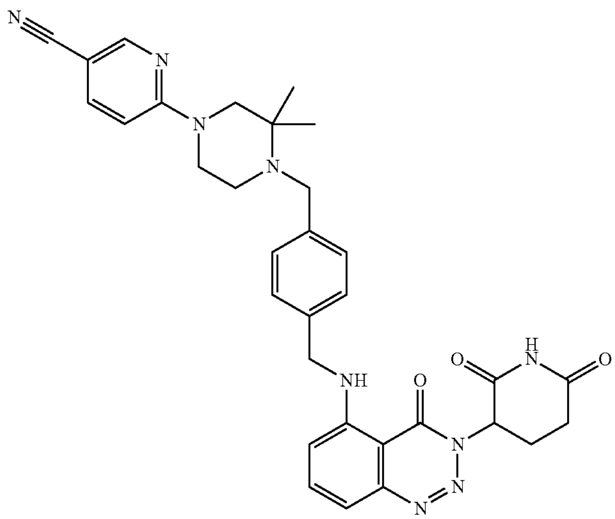 [SMILES: CC1(C)CN(c2ccc(C#N)cn2)CCN1Cc1ccc(CNc2cccc3nnn(C4CCC(=O)NC4=O)c(=O)c23)cc1] | 6-(4-(4-(((3-(2,6-dioxopiperidin-3-yl)-4-oxo-3,4-dihydrobenzo[d][1,2,3]triazin-5-yl)amino)methyl)benzyl)-3,3-dimethylpiperazin-1-yl)nicotinonitrile |

In one embodiment, there is provided a human EG3 ligase which comprises a compound a formula I bound to or complexed with human cereblon. Said EG3 ligase targets protein degradation of IKZF1, and/or IKZF3.

DETAILED DESCRIPTION

This invention is directed to compounds, pharmaceutical compositions comprising such compounds, and methods of using such compounds and compositions to treat diseases, disorders, or conditions relating to unregulated protein function and/or levels. However, prior to providing a detailed description of the invention, the following terms will first be defined. If not defined, terms used herein have their generally accepted scientific meaning.

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to a dose amount means that the dose may vary by +/−10%.

"Comprising" or "comprises" is intended to mean that the compositions and methods include the recited elements, but not excluding others.

"Consisting essentially of" when used to define compositions and methods, shall mean excluding other elements of any essential significance to the combination for the stated purpose.

Thus, a composition consisting essentially of the elements as defined herein would not exclude other materials or steps that do not materially affect the basic and novel characteristic(s) of the claimed invention.

"Consisting of" shall mean excluding more than trace elements of other ingredients and substantial method steps. Embodiments defined by each of these transition terms are within the scope of this invention.

"Alkyl" refers to monovalent saturated aliphatic hydrocarbyl groups having from 1 to 6 carbon atoms and preferably 1 to 4 carbon atoms. The number of carbon atoms in an alkyl can be quantified specifically by reciting, e.g., $C_1$-$C_4$ alkyl. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2CH$—), n-butyl ($CH_3CH_2CH_2CH_2$—), isobutyl (($CH_3$)$_2CHCH_2$—), sec-butyl (($CH_3$)($CH_3CH_2$)$CH$—), t-butyl (($CH_3$)$_3C$—), n-pentyl ($CH_3CH_2CH_2CH_2CH_2$—), and neopentyl (($CH_3$)$_3CCH_2$—).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminocarbonylamino, aminocarbonyloxy, amidino, aryl, substituted aryl, aryloxy, substituted aryloxy, carboxyl, carboxyl ester, (carboxyl ester) amino, (carboxyl ester)oxy, cyano, cycloalkyl, substituted cycloalkyl, cycloalkyloxy, substituted cycloalkyloxy, guanidino, substituted guanidino, halo, hydroxy, heteroaryl, substituted heteroaryl, heteroaryloxy, substituted heteroaryloxy, heterocyclic, substituted heterocyclic, heterocyclyloxy, substituted heterocyclyloxy, nitro, substituted sulfonyl, oxo and thio.

"Alkylene" refers to divalent saturated aliphatic hydrocarbyl groups having from 1 to 6 carbon atoms and preferably 1 to 4 carbon atoms. The number of carbon atoms in an alkylene can be quantified specifically by reciting, e.g., $C_1$-$C_4$ alkylene. The alkylene group can be straight or branched chain such as methylene, ethylene, n-propylene, iso-propylene, n-butylene and the like.

"Substituted alkylene" refers to an alkylene group having from 1 to 5, preferably 1 to 3, and more preferably, 1 to 2 substituents selected from alkoxy, amino, substituted amino, cyano, halo, nitro, and hydroxyl.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—. Acyl includes the "acetyl" group $CH_3$C(O)—.

"Acylamino" refers to the groups —$NR^{10}$C(O)alkyl, —$NR^{10}$C(O) substituted alkyl, —$NR^{10}$C(O)cycloalkyl, —$NR^{10}$C(O) substituted cycloalkyl, —$NR^{10}$C(O)aryl, —$NR^{10}$C(O) substituted aryl, —$NR^{10}$C(O)heteroaryl, —$NR^{10}$C(O) substituted heteroaryl, —$NR^{10}$C(O)heterocyclic, and —$NR^{10}$C(O) substituted heterocyclic wherein $R^{10}$ is hydrogen or alkyl.

"Acyloxy" refers to the groups alkyl-C(O)O—, substituted alkyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O.

"Amino" refers to the group —$NH_2$.

"Substituted amino" refers to the group —$NR^{11}R^{12}$ where $R^{11}$ and $R^{12}$ are independently selected from the group consisting of hydrogen, alkyl, substituted alkyl, aryl, substituted aryl, cycloalkyl, substituted cycloalkyl, heteroaryl, substituted heteroaryl, heterocyclic, substituted heterocyclic, and wherein $R^{11}$ and $R^{12}$ are optionally joined, together with the nitrogen bound thereto to form a heterocyclic or substituted heterocyclic group, provided that $R^{11}$ and $R^{12}$ are both not hydrogen.

"Aminocarbonyl" refers to the group —C(O)$NR^{13}R^{14}$ where $R^{13}$ and $R^{14}$ are independently selected from the group consisting of hydrogen, alkyl, substituted alkyl, aryl, substituted aryl, cycloalkyl, substituted cycloalkyl, heteroaryl, substituted heteroaryl, heterocyclic, and substituted heterocyclic and where $R^{13}$ and $R^{14}$ are optionally joined together with the nitrogen bound thereto to form a heterocyclic or substituted heterocyclic group.

"Aminocarbonylamino" refers to the group —$NR^{10}$C(O) $NR^{13}R^{14}$ where $R^{10}$ is hydrogen or alkyl and $R^{13}$ and $R^{14}$ are independently selected from the group consisting of hydrogen, alkyl, substituted alkyl, aryl, substituted aryl, cycloalkyl, substituted cycloalkyl, heteroaryl, substituted heteroaryl, heterocyclic, and substituted heterocyclic, and where $R^{13}$ and $R^{14}$ are optionally joined together with the nitrogen bound thereto to form a heterocyclic or substituted heterocyclic group.

"Aminocarbonyloxy" refers to the group —O—C(O) $NR^{13}R^{14}$ where $R^{13}$ and $R^{14}$ are independently selected from the group consisting of hydrogen, alkyl, substituted alkyl, aryl, substituted aryl, cycloalkyl, substituted cycloalkyl, heteroaryl, substituted heteroaryl, heterocyclic, and substituted heterocyclic and where $R^{13}$ and $R^{14}$ are optionally joined together with the nitrogen bound thereto to form a heterocyclic or substituted heterocyclic group.

"Oxo" refers to the group =O which when bound to a carbon atom (—C=O) is referred to a carbonyl group. "Thiooxo" refers to the group =S.

"Amidino" refers to the group —C(=$NR^{15}$)$NR^{13}R^{14}$ where $R^{13}$, $R^{14}$, and $R^{15}$ are independently selected from the group consisting of hydrogen, alkyl, substituted alkyl, aryl, substituted aryl, cycloalkyl, substituted cycloalkyl, heteroaryl, substituted heteroaryl, heterocyclic, and substituted heterocyclic and where $R^{13}$ and $R^{14}$ are optionally joined together with the nitrogen bound thereto to form a heterocyclic or substituted heterocyclic group.

"Aryl" or "Ar" refers to a monovalent aromatic carbocyclic group of from 6 to 14 carbon atoms having a single ring (e.g., phenyl) or multiple condensed rings (e.g., naphthyl, fluorenyl or anthryl) which condensed rings may or may not be aromatic (e.g., 2-benzoxazolinone, 2H-1,4-benzoxazin-3 (4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkoxy, acyl, acylamino, acyloxy, amino, substituted amino, aminocarbonyl, aminocarbonylamino, aminocarbonyloxy, amidino, aryl, substituted aryl, aryloxy, substituted aryloxy, carboxyl, carboxyl ester, (carboxyl ester) amino, (carboxyl ester)oxy, cyano, cycloalkyl, substituted cycloalkyl, cycloalkyloxy, substituted cycloalkyloxy, guanidino, substituted guanidino, halo, hydroxy, heteroaryl, substituted heteroaryl, heteroaryloxy, substituted heteroaryloxy, heterocyclic, substituted heterocyclic, heterocyclyloxy, substituted heterocyclyloxy, nitro, $SO_3H$, substituted sulfonyl, and substituted sulfonyloxy.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the group —C(O)(O)-alkyl, —C(O)(O)-substituted alkyl, —C(O)(O)-aryl, —C(O)(O)-substituted-aryl, —C(O)(O)-cycloalkyl, —C(O)(O)-substituted cycloalkyl, —C(O)(O)-heteroaryl, —C(O)(O)-substituted heteroaryl, —C(O)(O)-heterocyclic, and —C(O)(O)-substituted heterocyclic.

"(Carboxyl ester)amino refers to the group —NR$^{10}$C(O)(O)-alkyl, —NR$^{10}$C(O)(O)-substituted alkyl, —NR$^{10}$C(O)(O)-aryl, —NR$^{10}$C(O)(O)-substituted-aryl, —NR$^{10}$C(O)(O)-cycloalkyl, —NR$^{10}$C(O)(O)-substituted cycloalkyl, —NR$^{10}$C(O)(O)-heteroaryl, —NR$^{10}$C(O)(O)-substituted heteroaryl, —NR$^{10}$C(O)(O)-heterocyclic, and —NR$^{10}$C(O)(O)-substituted heterocyclic wherein R$^{10}$ is alkyl or hydrogen.

"(Carboxyl ester)oxy refers to the group —O—C(O)O-alkyl, —O—C(O)O-substituted alkyl, —O—C(O)O-aryl, —O—C(O)O-substituted-aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclic, and —O—C(O)O-substituted heterocyclic.

"Cyano" refers to the group —CN.

"Cycloalkyl" refers to cyclic alkyl groups of from 3 to 10 carbon atoms having single or multiple cyclic rings including fused, bridged, and spiro ring systems. The number of carbon atoms in a cycloalkyl can be quantified specifically by reciting, e.g., C$_3$-C$_4$ cycloalkyl. The fused ring can be an aryl ring provided that the non-aryl part is joined to the rest of the molecule.

Examples of suitable cycloalkyl groups include, for instance, adamantyl, cyclopropyl, cyclobutyl, cyclopentyl, and cyclooctyl. Preferred cycloalkyl groups are cyclopropyl and cyclobutyl.

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thio, alkyl, substituted alkyl, alkoxy, substituted alkoxy, acyl, acylamino, acyloxy, amino, substituted amino, aminocarbonyl, aminocarbonylamino, aminocarbonyloxy, amidino, aryl, substituted aryl, aryloxy, substituted aryloxy, carboxyl, carboxyl ester, (carboxyl ester)amino, (carboxyl ester)oxy, cyano, cycloalkyl, substituted cycloalkyl, cycloalkyloxy, substituted cycloalkyloxy, guanidino, substituted guanidino, halo, hydroxy, heteroaryl, substituted heteroaryl, heteroaryloxy, substituted heteroaryloxy, heterocyclic, substituted heterocyclic, heterocyclyloxy, substituted heterocyclyloxy, nitro, SO$_3$H, substituted sulfonyl, and substituted sulfonyloxy. In one embodiment, an aryl, substituted aryl, heteroaryl, or substituted heteroaryl group can be fused to the cycloalkenyl group to form a bicyclic fused ring system provided that the point of attachment is through the cycloalkenyl group. Such groups include by way of example only 1,2,3,4-tetrahydronapthalen-1-yl.

"Cycloalkyloxy" refers to —O-cycloalkyl.

"Substituted cycloalkyloxy refers to —O-(substituted cycloalkyl).

"Guanidino" refers to the group —NHC(=NH)NH$_2$.

"Substituted guanidino" refers to —NR$^{15}$C(=NR$^{13}$)N(R$^{14}$)$_2$ where each of R$^{13}$, R$^{14}$ and R$^{15}$ is independently selected from the group consisting of hydrogen, alkyl, substituted alkyl, aryl, substituted aryl, heteroaryl, substituted heteroaryl, cycloalkyl, substituted cycloalkyl, heterocyclic, and substituted heterocyclic and where R$^{13}$ and one of R$^{14}$ are optionally joined together with the nitrogen bound thereto to form a heterocyclic or substituted heterocyclic group, and wherein said substituents are as defined herein.

"Halo" or "halogen" refers to fluoro, chloro, bromo and iodo.

"Hydroxy" or "hydroxyl" refers to the group —OH.

The term "heteroaryl," as used herein, alone or in combination, refers to 3 to 7 membered unsaturated heteromonocyclic rings, or fused polycyclic rings, each of which is 3 to 7 membered, in which at least one of the fused rings is unsaturated, wherein at least one atom is selected from the group consisting of O, S, and N. In some embodiments, a heteroaryl may comprise from 5 to 7 carbon atoms. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Non-limiting examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

Heteroaryl groups can include any number of ring atoms, such as, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, benzoisothiazole, benzimidazoles, and benzofuran. The heteroaryl groups can also be fused to aromatic ring systems that are themselves heteroaryls, such as pyrazolopyridines, imidazopyridines, pyrrolopyridines, furopyridines, pyrrolopyrimidines, azaindoles, and the like. Other fused systems include pyrrolozines, indolizines, and the like.

Other heteroaryl groups include heteroaryl rings linked by a bond, such as bipyridine.

Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

The terms "heterocycloalkyl" and, interchangeably, "heterocycle," or "heterocyclyl" as used herein, alone or in combination, each refer to a saturated or unsaturated (but not heteroaryl), monocyclic, bicyclic, or tricyclic heterocyclic radical containing at least one heteroatom as ring members wherein said bicyclic and tricyclic groups. Examples of bicyclic and tricyclic heterocycloalkyl groups include octahydropyrrolo-[3,4-c]-pyrrol-N-yl, 2-aza-(2.2.2)-bicyclooctanyl or 8-oxa-3-aza-bicyclo[3.2.1]-octanyl and the like. Each heteroatom may be independently selected from the group consisting of nitrogen, oxygen, and sulfur. In certain embodiments, a heterocycloalkyl may comprise from 1 to 4 heteroatoms as ring members. In further embodiments, a heterocycloalkyl may comprise from 1 to 2 heteroatoms ring members. In some embodiments, a heterocycloalkyl may comprise from 3 to 8 ring members in each ring. In further embodiments, a heterocycloalkyl may comprise from 3 to 7 ring members in each ring. In yet further embodiments, a heterocycloalkyl may comprise from 5 to 6 ring members in each ring.

"Heterocycloalkyl" and "heterocycle" are intended to include sugars, sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycloalkyl groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, epoxy, isoindolinyl, morpholinyl, piperazinyl, pyrrolidinyl, tetrahydropyridinyl, piperidinyl, thiomorpholinyl, and the like. The heterocycloalkyl groups may be optionally substituted unless specifically prohibited.

"Heterocycloalkyl" may refer to a saturated ring system having from 3 to 12 ring members and from 1 to 5 heteroatoms of N, O and S. The heteroatoms can also be oxidized, such as, but not limited to, S(O) and S(O)2. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, 4, or 5, or 1 to 2, 1 to 3, 1 to 4, 1 to 5, 2 to 3, 2 to 4, 2 to 5, 3 to 4 or 3 to 5. The heterocycloalkyl group can include any number of carbons, such as C3-6, C4-6, C5-6, C3-8, C4-8, C5-8, C6-8, C3-9, C3-10, C3-11, and C3-12. The heterocycloalkyl group can include groups such as aziridine, azetidine, pyrrolidine, piperidine, azepane, diazepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline, diazabicycloheptane, diazabicyclooctane, diazaspirooctane or diazaspirononane. Heterocycloalkyl groups can be unsubstituted or substituted. For example, heterocycloalkyl groups can be substituted with C1 6 alkyl or oxo (═O), among many others. Heterocycloalkyl groups can also include a double bond or a triple bond, such as, but not limited to dihydropyridine or 1,2,3,6-tetrahydropyridine.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane.

Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

Examples of heterocycle and heteroaryls include, but are not limited to, azetidine, pyrrole, furan, thiophene, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Sulfonyl" refers to the divalent group —S(O)$_2$—.

"Substituted sulfonyl" refers to the group —SO$_2$-alkyl, —SO$_2$-substituted alkyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic.

A substituted ring can be substituted with one or more fused and/or spiro cycles. Such fused cycles include a fused cycloalkyl, a fused heterocyclyl, a fused aryl, a fused heteroaryl ring, each of which rings can be unsubstituted or substituted. Such spiro cycles include a fused cycloalkyl and a fused heterocyclyl, each of which rings can be unsubstituted or substituted.

Unless otherwise defined, the term "optionally substituted" means that a substituent may or may not be bound to the underlying group modified as optionally substituted. In the event that the optional substituent is not defined for the underlying group, then the optional substituents are selected from $C_1$-$C_{10}$ or $C_1$-$C_6$ alkyl, substituted $C_1$-$C_{10}$ or $C_1$-$C_6$ alkyl, $C_6$-$C_{10}$ aryl, $C_3$-$C_8$ cycloalkyl, $C_2$-$C_{10}$ heterocyclyl, $C_1$-$C_{10}$ heteroaryl, substituted $C_6$-$C_{10}$ aryl, substituted $C_3$-$C_8$ cycloalkyl, substituted $C_2$-$C_{10}$ heterocyclyl, substituted $C_1$-$C_{10}$ heteroaryl, halo, nitro, cyano, —CO$_2$H or a $C_1$-$C_6$ alkyl ester thereof.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

It is understood that the above definitions are not intended to include impermissible substitution patterns (e.g., methyl substituted with 5 fluoro groups). Such impermissible substitution patterns are well known to the skilled artisan.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

The compounds of this invention may exist as solvates, especially hydrates. Hydrates may form during manufacture of the compounds or compositions comprising the compounds, or hydrates may form over time due to the hygroscopic nature of the compounds. Compounds of this invention may exist as organic solvates as well, including DMF, ether, and alcohol solvates among others. The identification and preparation of any particular solvate is within the skill of the ordinary artisan of synthetic organic or medicinal chemistry.

"Subject" refers to a mammal. The mammal can be a human or non-human animal mammalian organism.

"Treating" or "treatment" of a disease or disorder in a subject refers to 1) preventing the disease or disorder from occurring in a subject that is predisposed or does not yet display symptoms of the disease or disorder; 2) inhibiting the disease or disorder or arresting its development; or 3) ameliorating or causing regression of the disease or disorder.

"Effective amount" refers to the amount of a vaccine of this invention that is sufficient to treat the disease or disorder afflicting a subject or to prevent such a disease or disorder from arising in said subject or patient.

"Administration" refers to any art recognized form of administration to a subject including oral (including oral gavage), pulmonary, transdermal, sublingual, injection (e.g., intravenous, intramuscular), transmucosal (e.g., vaginal, nasal, etc.), and the like. The route of administration is selected by the attending clinician and is based on factors such as the age, weight and general health of the patient as well as the severity of the condition. In one embodiment, the compounds and pharmaceutical compositions of this invention are administered orally.

As used herein, the term "pharmaceutically acceptable salts" of compounds disclosed herein are within the scope of the present invention include acid or base addition salts which retain the desired pharmacological activity and is not biologically undesirable (e.g., the salt is not unduly toxic, allergenic, or irritating, and is bioavailable). When the compound of the present invention has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesolfonic acid) or acidic amino acids (such as aspartic acid and glutamic acid).

When the compound of the present invention has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$), ammonia or organic amines (e.g., dicyclohexylamine, trimethylamine, trimethylamine, pyridine, picoline, ethanolamine, diethanolamine, triethanolamine) or basic amino acids (e.g., arginine, lysine, and ornithine). Such salts can be prepared in situ during isolation and purification of the compounds or by separately reacting the purified compound in its free base or free acid form with a suitable acid or base, respectively, and isolating the salt thus formed.

For ease of reference, the following number system is used in the nomenclature of described compounds.

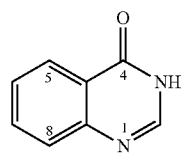 [SMILES: O=c1[nH]cnc2ccccc12]

General Synthetic Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, *Protecting Groups in Organic Synthesis*, Third Edition, Wiley, New York, 1999, and references cited therein.

The starting materials for the following reactions are generally known compounds or can be prepared by known procedures or obvious modifications thereof. For example, many of the starting materials are available from commercial suppliers such as SigmaAldrich (St. Louis, Mo., USA), Bachem (Torrance, Calif., USA), Emka-Chemce (St. Louis, Mo., USA). Others may be prepared by procedures, or obvious modifications thereof, described in standard reference texts such as *Fieser and Fieser's Reagents for Organic Synthesis*, Volumes 1-15 (John Wiley, and Sons, 1991), *Rodd's Chemistry of Carbon Compounds*, Volumes 1-5, and *Supplementals* (Elsevier Science Publishers, 1989), *Organic Reactions*, Volumes 1-40 (John Wiley, and Sons, 1991), *March's Advanced Organic Chemistry*, (J. Wiley, and Sons, 5th Edition, 2001), and *Larock's Comprehensive Organic Transformations* (VCH Publishers Inc., 1989).

Synthesis of Representative Compounds of the Invention

The general synthesis of the compounds of this invention is set forth in the reaction schemes below. Specifically, Scheme 1 illustrates one method for preparing compounds of formula I.

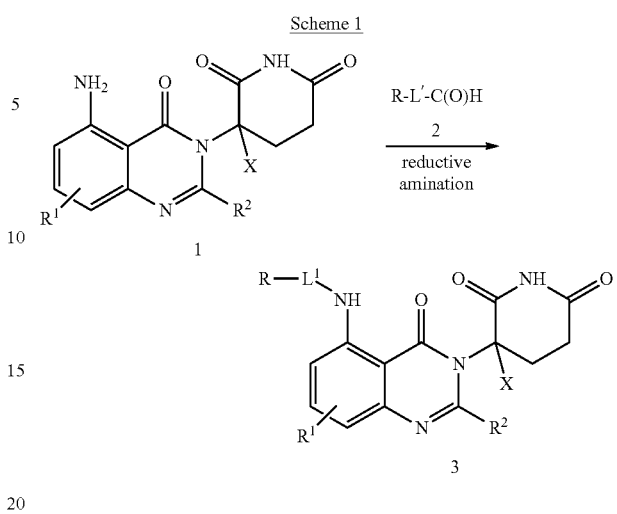

where R, $R^1$, $R^2$ and X are as defined herein and L' is a bond, a $C_1$-$C_3$ alkylene, or a $C_1$-$C_3$ alkylene substituted with 1 to 2 substituents selected from hydroxy, halo, cyano, and $C_1$-$C_2$ alkoxy.

In Scheme 1, the 5-aminoquinazolinones, compound 1, are either known in the art or can be prepared by art recognized procedures. For example, 2-(alkyl, hydroxyalkyl, cycloalkyl)-3-(4-glutamimide)-5-aminoquinazolinones are disclosed in U.S. Pat. No. 7,635,700 which is incorporated herein by reference in its entirety. Likewise, the aldehydes, compound 2, are either commercially available or otherwise known in the art. These include substituted benzaldehydes, 2-(substituted phenyl)-acetaldehyde, and 3-(substituted phenyl)-propanal.

As to the reaction in Scheme 1, this is a conventional reductive amination reaction wherein at least a stoichiometric equivalent of an aldehyde, compound 2, is combined with a 5-aminoquinazolinone, compound 1, preferably in an inert diluent such as methylene chloride, ethyl acetate, dimethylacetamide, and the like typically in the presence of acid catalyst (e.g, acetic acid, trifluoroacetic acid, zinc chloride). The reaction is typically maintained at from −15° to 65° C. The intermediate imine (not shown) is either reduced in situ provided a reducing agent is also present in the reaction (e.g., sodium cyanoborohydride, sodium triacetoxyborohydride or the like) or reduced in a second step within the same reaction vessel by addition of a stronger reducing agent, e.g., using at least a stoichiometric equivalent of sodium borohydride or similar reducing agents. Conventional workup of the reaction solution can be followed by isolation/purification processes such as crystallization, chromatography, high performance liquid chromatography (HPLC), and the like to provide for compound 3.

Scheme 2 provides an alternative reaction that can be used to prepare the compounds of this invention.

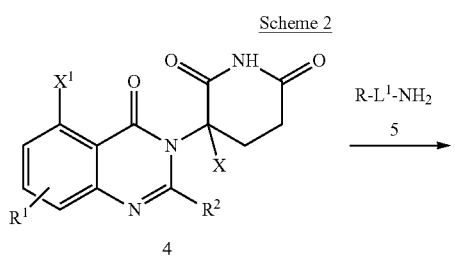

-continued

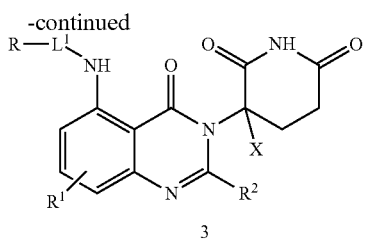

3 where $X^1$ is a sulfonate (such as triflate), fluoro, chloro, bromo or iodo and R, $R^1$, and $R^2$ are as defined above. In embodiments, Scheme 2 may comprise a cross-coupling reaction (such as transition metal-mediated cross-coupling of aryl halide or sulfonates with amines (Buchwald-Hartwig amination); see, for example, Yang et al. "Palladium-catalyzed amination of aryl halides and sulfonates," *J. Organomet. Chem.* 576:125-146 (1999); for transition metal-free based coupling reactions see Bolinger et al. "Transition metal-free amination of aryl halides-A simple and reliable method for the efficient and high-yielding synthesis of N-arylated amines," *Tetrahedron* 65(6):1180-1187 (2009)). Cross-coupling reactions are typically mediated by a palladium catalysts in the presence of phosphine ligands in a wide range of potential solvents depending on the exact nature of the coupling partners, though toluene is typical.

In Scheme 2, the 5-haloquinazolinones, compound 4, are either known in the art or can be prepared by art recognized procedures. For example, 2-(alkyl, hydroxyalkyl, cycloalkyl)-3-(4-glutamimide)-5-haloquinazolinones are disclosed in U.S. Pat. No. 7,635,700 which is incorporated herein by reference in its entirety. Likewise, the amines, compound 5, are either commercially available or otherwise known in the art.

As to the reaction in Scheme 2, this is a conventional displacement reaction wherein at least a stoichiometric equivalent of an amine, compound 5, is combined with a 5-halo quinazolinone, compound 4, preferably in an inert diluent such as dichloroethane, 1,4-dioxane, dimethylacetamide, and the like. The reaction is typically conducted in the presence of a base such as diisopropylethylamine so as to scavenge the acid generated. The reaction is typically maintained above room temperature, preferably above 100° C. a period of time sufficient for substantial completion of the reaction as measure by, e.g., thin layer chromatography. The resulting product, compound 3, is then recovered by conventional workup of the reaction solution which can be followed by isolation/purification processes such as crystallization, chromatography, high performance liquid chromatography (HPLC), and the like.

In some embodiments, a reactive functionality found on the phenyl ring (Ra) optionally can be further derivatized either before or after reductive amination or the displacement reaction provided that any derivatization conducted after imine formation but prior to reduction of the imine to the amine is compatible with the reduction conditions used. Non-limiting examples of such further modification of a reactive functional group include the following:

Alkylation of a primary amino group;
Esterification of a carboxyl group;
Conversion of an amino group to an amido (R—C(O) NH—) group;
Conversion of a carboxyl group to a reverse amido (R—NHC(O)—) group;
Conversion of a hydroxy group to an ester;
Addition of one or more amino acids to either a carboxyl or amino group;
Displacement of a halo group with an amino group;
Reduction of a cyano group to an methylamino group;
Reduction of a nitro group to an amino group;
Michael addition reactions; and
Any of the art recognized reactions that selectively modify the reactive functionality.

Methods

The compounds described herein bind to cereblon (CRBN) and that such binding modulates the activity of ubiquitin E3 ligase activity thereby targeting disease related proteins for ubiquitination. Specifically, the modified ubiquitin E3 ligase targets the transcription factors IKZF1 and/or IKZF3 for degradation. These transcription factors are deregulated in many cancers such as multiple myeloma (IKZF1 and IKZF3), B cell precursor acute lymphoblastic leukemia (IKZF-1) to name a few. The compounds described herein are useful to target IKZF1 and/or IKZF3 for ubiquitation and are useful in treating cancers where these transcription factors play in a role in the pathogenesis of the cancer.

Accordingly, in one embodiment, there is provided a method for modulating the activity of ubiquitin E3 ligase in a subject which method comprises administration of an effective amount of a compound of formula I to said subject wherein binding of said compound to cereblon results in the modulation of the activity of the E3 ligase thereby targeting IKZF1 and/or IKZF3 for ubiquitation. In one embodiment, modulation of activity of the E3 ligase results in ubiquitination of unregulated protein function and/or levels such as those associated with cancer.

In one embodiment, the compounds of this invention bind to cereblon as exemplified further below in Example 15.

Pharmaceutical Compositions

When so used, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors well-known to the skilled artisan. The drug can be administered at least once a day, preferably once or twice a day.

An effective amount of such inhibitors is readily ascertainable by the binding affinity to cereblon. Various formulations and drug delivery systems are available in the art. See, e.g., Gennaro, A. R., ed. (1995) *Remington's Pharmaceutical Sciences,* 18$^{th}$ ed., Mack Publishing Co.

As noted previously, an effective amount or a therapeutically effective amount or dose of an agent, e.g., a compound of this invention, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population), and the maximum tolerated dose (MTD), and the ED50 (the dose therapeutically effective in 50% of the population). The dose ratio of toxic to therapeutic effects is the therapeutic index, which can be expressed as the ratio LD50 or MTD/ED50. Agents that exhibit a high therapeutic index are preferred. Such an effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the condition being treated, the sex, age, and weight of the subject being treated, the severity of the affliction, the manner of administration, and the judgment of the prescribing physician. In one embodiment, an effective amount of a compound of this invention is administered to the patient. Preferably, the effective amount of a compound of this invention ranges from about 0.1 mg/kg to about 75 mg/kg and preferably at from about 1 mg/kg to about 30 mg/kg given at standard intervals well-known in the art.

This invention is not limited to any particular composition or pharmaceutical carrier, as such may vary. In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. One preferred manner of administration is intravenous using a dosage regimen that can be adjusted according to the degree of affliction. In one embodiment, the drug intravenous administration is conducted over a period of 30 minutes to 3 hours.

Other pharmaceutical compositions can take the form of tablets, pills, capsules, semisolids, powders, sustained release formulations, solutions, suspensions, elixirs, aerosols, or any other appropriate compositions.

The choice of formulation depends on various factors such as the mode of drug administration and bioavailability of the drug substance.

Pharmaceutical dosage forms of a compound of this invention may be manufactured by any of the methods well-known in the art, such as, for example, by conventional mixing, sieving, dissolving, melting, granulating, dragee-making, tableting, suspending, extruding, spray-drying, levigating, emulsifying, (nano-/micro-) encapsulating, entrapping, or lyophilization processes. As noted above, the compositions of this invention can include one or more physiologically acceptable inactive ingredients that facilitate processing of active molecules into preparations for pharmaceutical use.

The compositions are comprised of, in general, a compound of this invention in combination with at least one pharmaceutically acceptable excipient. Acceptable excipients are non-toxic, aid administration, and do not adversely affect the therapeutic benefit of the claimed compounds. Such excipient may be any solid, liquid, semi-solid or, in the case of an aerosol composition, gaseous excipient that is generally available to one of skill in the art. Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semi-solid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in an aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The compositions of this invention may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a compound of this invention that can be formulated in a compatible pharmaceutical carrier may also be prepared, placed in an appropriate container, and labeled for treatment of an indicated condition.

The amount of the compound in a formulation can vary within the full range employed by those skilled in the art. Typically, the formulation will contain, on a weight percent (wt %) basis, from about 0.01-99.99 wt % of a compound of this invention based on the total formulation, with the balance being one or more suitable pharmaceutical excipients. Preferably, the compound is present at a level of about 1-80 wt %. Representative pharmaceutical formulations are described below.

Combinations

The compounds described herein can be administered alone or in combination with one or more drugs at the discretion of the attending clinician and based on the age, weight, sex, and condition of the patient including the degree and extent of the underlying disease. When used in combination, each drug is administered at a dose that provides a therapeutic result for the indications that the drug is treating. Examples of drugs that can be co-administered with a compound of formula I as described herein include those set forth in U.S. Pat. No. 7,635,700 at columns 26-30 thereof. Examples of drugs that can be co-administered with a compound of formula I as described herein include:

FORMULATION EXAMPLES

The following are representative pharmaceutical formulations containing a compound of this invention.

| Ingredient | Quantity per tablet, mg |
|---|---|
| compound of this invention | 400 |
| Cornstarch | 50 |
| croscarmellose sodium | 25 |
| Lactose | 120 |
| magnesium stearate | 5 |

| Ingredient | Quantity per capsule, mg |
|---|---|
| compound of this invention | 200 |
| lactose, spray-dried | 148 |
| magnesium stearate | 2 |

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| Flavoring | 0.035 mL |
| Colorings | 0.5 mg |
| distilled water | q.s. to 100 mL |

| Ingredient | Amount |
|---|---|
| compound of this invention | 0.2 mg-20 mg |
| sodium acetate buffer solution, | 2.0 mL |
| 0.4M HCl (1N) or NaOH (1N) | q.s. to suitable pH |
| water (distilled, sterile) | q.s. to 20 mL |

Formulation Example 5—Suppository Formulation

A suppository of total weight 2.5 g is prepared by mixing the compound of this invention with Witepsol® H-15 (triglycerides of saturated vegetable fatty acid; Riches-Nelson, Inc., New York), and has the following composition:

| Ingredient | Amount |
|---|---|
| Compound of this invention | 500 mg |
| Witepsol ® H-15 | balance |

The following synthetic and biological exaim not mples are offered to illustrate this invention and are not to be construed in any way as limiting the scope of this invention. Unless otherwise stated, all temperatures are in degrees Celsius.

EXAMPLES

This invention is further understood by reference to the following examples, which are intended to be purely exemplary of this invention. This invention is not limited in scope by the exemplified embodiments, which are intended as illustrations of single aspects of this invention only. Any methods that are functionally equivalent are within the scope of this invention. Various modifications of this invention in addition to those described herein will become apparent to those skilled in the art from the foregoing description and accompanying figures. Such modifications fall within the scope of the appended claims.

In the specification and in the examples below, the following abbreviations have the following meanings. If not defined, these abbreviations have their art recognized meaning.

AcOH=acetic acid
ACN=acetonitrile
d=doublet
dd=doublet of doublets
ddd=doublet of doublets of doublets
ddt=doublet of doublet of triplets
dt=doublet of triplets
dtd=doublet of triplet of doublets
δ=delta from trimethylsilane
DCE=dichloroethane
DCM=dichloromethane
DIPEA=N,N-diisopropylethylamine
DMA=N,N-dimethylacetamide
DMP=2,2,-dimethoxypropane
DMSO=dimethylsulfoxide
eq.=equivalents
EtOH=ethanol
g=gram
h=hour
HATU=1-[Bis(dimethylamino)methylene]-1H-1,2,3-triazolo[4,5-b]pyridinium 3-oxide hexafluorophosphate
$^1$H-NMR=proton nuclear magnetic resonance
HPLC=high performance liquid chromatography
J=coupling constant
LC/MS=liquid chromatography/mass spec
m=multiplet
MeOH=methanol
mg=milligrams
MHz=mega Hertz
mL=milliliters
mmol=millimole
MS (ESI)=mass spectrometry (electrosrapy ionization)
NaBH$_3$CN=sodium cyanoborohydride
PDL=poly-D-lysine
q=quadruplet
rt=room temperature
s=singlet
t=triplet
td=triplet of doublets
TFA=trifluoroacetic acid
THF=tetrahydrofuran
TLC=thin layer chromatography
ug=microgram Example 1—Preparation of 3-(5-((4-methoxybenzyl)amino)-2-methyl-4-oxoquinazolin-3(4H)-yl)piperidine-2,6-dione

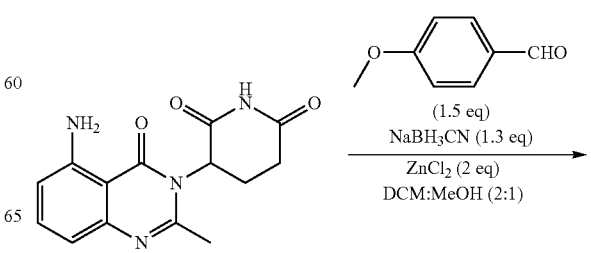

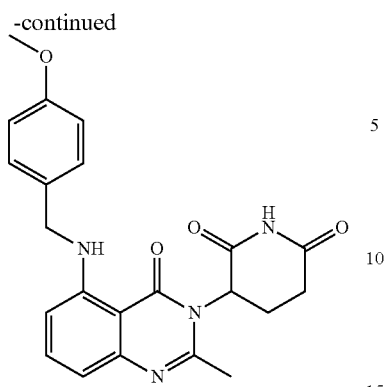

Into a 40 mL screw cap vial were added 3-(5-amino-2-methyl-4-oxoquinazolin-3(4H)-yl)piperidine-2,6-dione (226.4 mg, 1 eq, 0.791 mmol), DCM (10 mL), methanol (5 mL), 4-methoxybenzaldehyde (163.6 mg, 1.5 eq, 1.2 mmol), sodium cyanoborohydride (80.2 mg, 1.61 eq, 1.28 mmol) and zinc chloride (368.2 mg, 3.416 eq, 2.702 mmol). The reaction mixture was stirred at about 50° C. for 3 days. LC/MS indicated the reaction was complete. The reaction mixture was filtered and concentrated/adsorbed onto Celite and purified with a 0-100% (1:3 EtOH)/heptanes gradient on 25 g silica gel column to obtain 312.5 mg (97% yield) of the title compound as a white solid.

MS (ESI) m/z [M+H]=407.1; $^1$H NMR (499 MHz, DMSO-d6) δ 10.97 (s, 1H), 8.67 (t, J=5.6 Hz, 1H), 7.44 (t, J=8.1 Hz, 1H), 7.30 (d, J=10.0 Hz 2H), 6.91 (d, J=10.0 Hz, 2H), 6.65 (d, J=5.6 Hz, 1H), 6.49 (d, J=5.6 Hz, 1H), 5.18 (dd, J=11.6, 5.7 Hz, 1H), 4.34 (d, J=5.6 Hz, 2H), 3.73 (s, 3H), 2.82 (m, 1H), 2.64 (m, 1H), 2.60 (m, 1H), 2.58 (s, 3H), 2.16 (m, 1H).

Example 2—Preparation of 3-(5-((2-methoxybenzyl)amino)-2-methyl-4-oxoquinazolin-3(4H)-yl)piperidine-2,6-dione

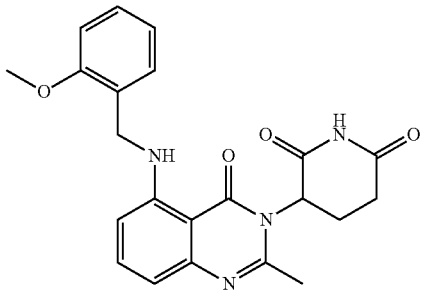 [SMILES: COc1ccccc1CNc1cccc2nc(C)n(C3CCC(=O)NC3=O)c(=O)c12]

The title compound was prepared as per Example 1 using 3-(5-amino-2-methyl-4-oxoquinazolin-3(4H)-yl)piperidine-2,6-dione and 2-methoxybenzaldehyde to afford 51.7 mg (72.8% yield) of the title compound as a yellow solid.

MS (ESI) m/z [M+H]=407.1; $^1$H NMR (499 MHz, DMSO-d6) δ 10.97 (s, 1H), 8.70 (t, J=5.6 Hz, 1H), 7.43 (t, J=8.1 Hz, 1H), 7.23-7.19 (m, 2H), 7.02 (dd, J=8.3, 1.1 Hz, 1H), 6.88 (t, J=10.0 Hz, 1H), 6.64 (d, J=10.0 Hz, 1H), 6.42 (d, J=10.0 Hz, 1H), 5.18 (dd, J=11.6, 5.7 Hz, 1H), 4.38 (d, J=5.6 Hz, 2H), 3.82 (s, 3H), 2.82 (m, 1H), 2.64 (m, 2H), 2.56 (s, 3H), 2.16 (m, 1H).

Example 3—Preparation of 3-(5-((3-methoxybenzyl)amino)-2-methyl-4-oxoquinazolin-3(4H)-yl)piperidine-2,6-dione

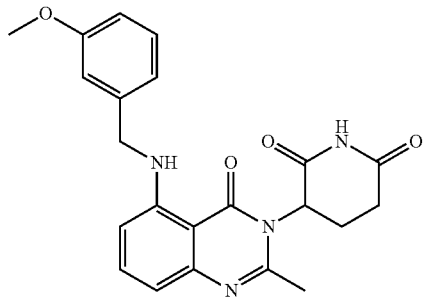 [SMILES: COc1cccc(CNc2cccc3nc(C)n(C4CCC(=O)NC4=O)c(=O)c23)c1]

The title compound was prepared as per Example 1 from 3-(5-amino-2-methyl-4-oxoquinazolin-3(4H)-yl)piperidine-2,6-dione and 3-methoxybenzaldehyde to afford 46.8 mg (65% yield) of the title compound as a yellow solid.

MS (ESI) m/z [M+H]=407.1; $^1$H NMR (499 MHz, DMSO-d6) δ 10.98 (s, 1H), 8.76 (t, J=5.9 Hz, 1H), 7.42 (dt, J=10.5, 8.1 Hz, 1H), 7.25 (td, J=8.1, 6.2 Hz, 1H), 6.96-6.84 (m, 2H), 6.84-6.79 (m, 1H), 6.68-6.60 (m, 1H), 6.43 (t, J=8.4 Hz, 1H), 5.19 (dd, J=11.4, 5.7 Hz, 1H), 4.41 (d, J=5.8 Hz, 2H), 3.72 (s, 3H), 2.83 (ddd, J=16.3, 13.4, 5.4 Hz, 1H), 2.70-2.57 (m, 1H), 2.56 (s, 3H), 2.32-2.23 (m, 1H), 2.25 (m, 1H).

Example 4—Preparation of 3-(5-((4-fluorobenzyl)amino)-2-methyl-4-oxoquinazolin-3(4H)-yl)piperidine-2,6-dione

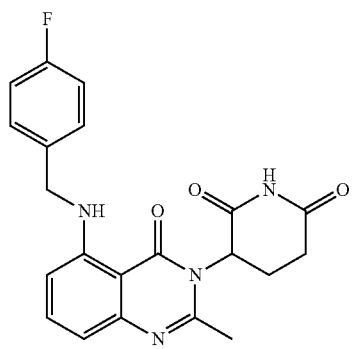

The title compound was prepared as per Example 1 from 3-(5-amino-2-methyl-4-oxoquinazolin-3(4H)-yl)piperidine-2,6-dione and 4-fluorobenzaldehyde to afford 46.9 mg (68% yield) of the title compound as a yellow solid.

MS (ESI) m/z [M+H]=395.1; $^1$H NMR (499 MHz, DMSO-d6) δ 10.98 (s, 1H), 8.78 (t, J=6.0 Hz, 1H), 7.47-7.31 (m, 3H), 7.16 (dtd, J=8.8, 6.9, 2.1 Hz, 2H), 6.65 (ddd, J=11.9, 7.9, 0.9 Hz, 1H), 6.46-6.40 (m, 1H), 5.19 (dd, J=11.5, 5.7 Hz, 1H), 4.43 (d, J=5.8 Hz, 2H), 2.83 (ddd, J=16.2, 13.4, 5.3 Hz, 1H), 2.70-2.57 (m, 1H), 2.56 (s, 3H), 2.32-2.24 (m, 1H), 2.16 (ddd, J=10.2, 5.9, 3.8 Hz, 1H).

Example 5—Preparation of 3-(5-((3-fluorobenzyl)amino)-2-methyl-4-oxoquinazolin-3(4H)-yl)piperidine-2,6-dione

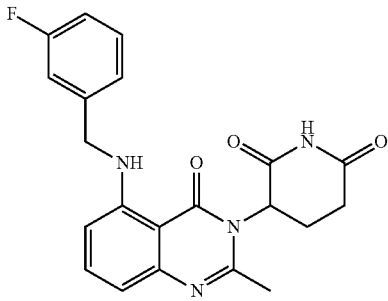 [SMILES: Cc1nc2cccc(NCc3cccc(F)c3)c2c(=O)n1C1CCC(=O)NC1=O]

The title compound was prepared per Example 1 from 3-(5-amino-2-methyl-4-oxoquinazolin-3(4H)-yl)piperidine-2,6-dione and 3-fluorobenzaldehyde to afford 32.8 mg (48% yield) of the title compound as a yellow solid.

MS (ESI) m/z [M+H]=395.1; $^1$H NMR (499 MHz, DMSO-d6) δ 11.00 (s, 1H), 8.84 (t, J=6.1 Hz, 1H), 7.49-7.33 (m, 2H), 7.23-7.08 (m, 2H), 7.06 (dt, J=8.4, 4.1 Hz, 1H), 6.65 (dd, J=11.7, 7.8 Hz, 1H), 6.41 (dd, J=8.3, 5.1 Hz, 1H), 5.20 (dd, J=11.5, 5.7 Hz, 1H), 4.49 (t, J=5.1 Hz, 2H), 2.84 (ddd, J=16.5, 13.6, 5.6 Hz, 1H), 2.67 (dd, J=12.2, 4.3 Hz, 1H), 2.57 (s, 3H), 2.33-2.24 (m, 1H), 2.17 (ddt, J=11.9, 6.3, 3.1 Hz, 1H).

Example 6—Preparation of 3-(5-((2-fluorobenzyl)amino)-2-methyl-4-oxoquinazolin-3(4H)-yl)piperidine-2,6-dione

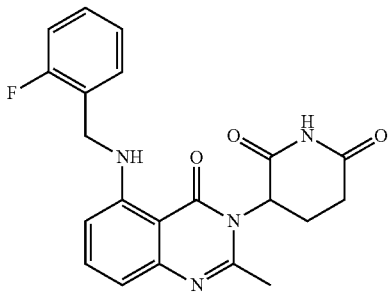 [SMILES: Cc1nc2cccc(NCc3ccccc3F)c2c(=O)n1C1CCC(=O)NC1=O]

The title compound was prepared as per Example 1 from 3-(5-amino-2-methyl-4-oxoquinazolin-3(4H)-yl)piperidine-2,6-dione and 2-fluorobenzaldehyde to afford 54.1 mg (79% yield) of the title compound as a light yellow solid.

MS (ESI) m/z [M+H]=395.1; $^1$H NMR (499 MHz, DMSO-d6) δ 10.99 (s, 1H), 8.74 (t, J=6.0 Hz, 1H), 7.45 (t, J=8.1 Hz, 1H), 7.38-7.34 (m, 2H), 7.26-7.18 (m, 1H), 7.15 (td, J=7.5, 1.2 Hz, 1H), 6.68 (d, J=10 Hz, 1H), 6.47 (d, J=10 Hz, 1H), 5.19 (dd, J=11.7, 5.7 Hz, 1H), 4.50 (d, J=5.9 Hz, 2H), 2.88-2.78 (m, 1H), 2.69-2.58 (m, 2H), 2.56 (s, 3H), 2.20-2.11 (m, 1H).

Example 7—Preparation of 3-(2-methyl-5-((3-methylbenzyl)amino)-4-oxoquinazolin-3(4H)-yl)piperidine-2,6-dione

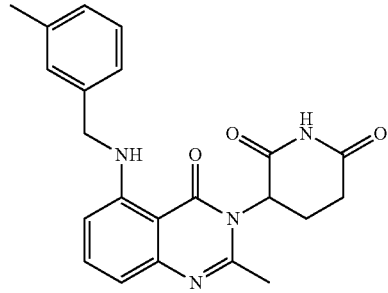 [SMILES: Cc1cccc(CNc2cccc3nc(C)n(C4CCC(=O)NC4=O)c(=O)c23)c1]

The title compound was prepared as per Example 1 from 3-(5-amino-2-methyl-4-oxoquinazolin-3(4H)-yl)piperidine-2,6-dione and 3-methylbenzaldehyde to afford 39.8 mg (55% yield) of the title compound as a light yellow solid.

MS (ESI) m/z [M+H]=391.1; $^1$H NMR (499 MHz, DMSO-d6) δ 10.98 (s, 1H), 8.73 (t, J=5.8 Hz, 1H), 7.43 (q, J=8.1 Hz, 1H), 7.26-7.04 (m, 4H), 6.64 (ddd, J=11.9, 7.9, 1.0 Hz, 1H), 6.44 (dt, J=8.5, 1.6 Hz, 1H), 5.19 (dd, J=11.6, 5.7 Hz, 1H), 4.39 (d, J=5.5 Hz, 2H), 2.88-2.77 (m, 1H), 2.69-2.58 (m, 2H), 2.51 (s, 3H), 2.28 (s, 3H), 2.15 (ddd, J=11.5, 5.8, 3.5 Hz, 1H).

Example 8—Preparation of 3-(2-methyl-5-((4-methylbenzyl)amino)-4-oxoquinazolin-3(4H)-yl)piperidine-2,6-dione

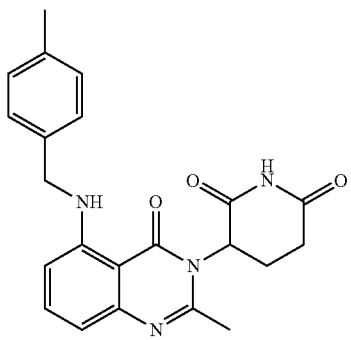 [SMILES: Cc1ccc(CNc2cccc3nc(C)n(C4CCC(=O)NC4=O)c(=O)c23)cc1]

The titled compound was prepared per Example 1 from 3-(5-amino-2-methyl-4-oxoquinazolin-3(4H)-yl)piperidine-2,6-dione and 4-methylbenzaldehyde to afford 16.0 mg (24% yield) of the title compound as an off-white solid.

MS (ESI) m/z [M+H]=391.1; $^1$H NMR (499 MHz, DMSO-d6) δ 10.97 (s, 1H), 8.71 (t, J=5.7 Hz, 1H), 7.42 (dt, J=9.5, 8.1 Hz, 1H), 7.26-7.24 m, 2H), 7.18-7.12 (m, 2H), 6.64 (d, J=10 Hz, 1H), 6.44 (d, J=10 Hz, 1H), 5.18 (dd, J=11.6, 5.7 Hz, 1H), 4.38 (d, J=5.6 Hz, 2H), 2.87-2.77 (m, 1H), 2.63-2.57 (m, 2H), 2.56 (s, 3H), 2.28 (s, 3H), 2.19-2.11 (m, 1H).

The following compounds indicated with an "*" were also prepared as per Example 1 above as set forth in Table 2 below (which includes compounds 1-8 exemplified above). Those compound without "*" are prophetic compounds:

TABLE 2

| No. | Structure | Name |
|---|---|---|
| 1* | 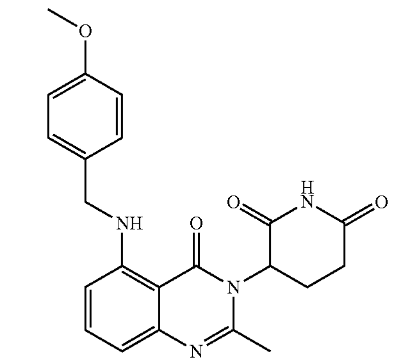 [SMILES: COc1ccc(CNc2cccc3nc(C)n(C4CCC(=O)NC4=O)c(=O)c23)cc1] | 3-(5-((4-methoxy-benzyl)-amino)-2-methyl-4-oxoquinazolin-3(4H)-yl)piperidine-2,6-dione |
| 2* | 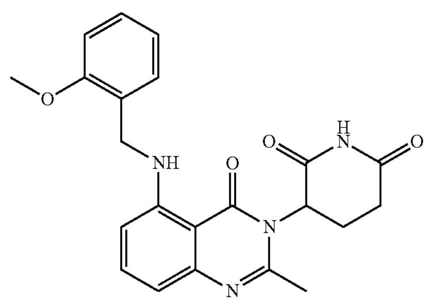 [SMILES: COc1ccccc1CNc1cccc2nc(C)n(C3CCC(=O)NC3=O)c(=O)c12] | 3-(5-((2-methoxybenzyl)-amino)-2-methyl-4-oxoquinazolin-3(4H)-yl)piperidine-2,6-dione |
| 3* | 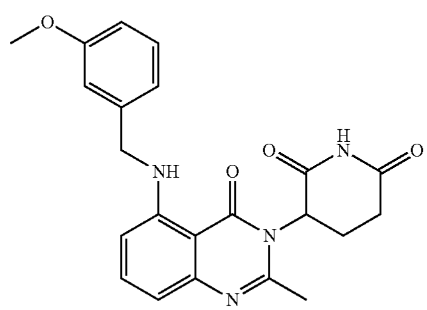 [SMILES: COc1cccc(CNc2cccc3nc(C)n(C4CCC(=O)NC4=O)c(=O)c23)c1] | 3-(5-((3-methoxybenzyl)-amino)-2-methyl-4-oxoquinazolin-3(4H)-yl)piperidine-2,6-dione |
| 4* | 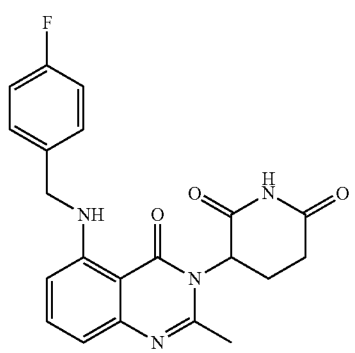 | 3-(5-((4-fluorobenzyl)-amino)-2-methyl-4-oxoquinazolin-3(4H)-yl)piperidine-2,6-dione |

TABLE 2-continued

| No. | Structure | Name |
| --- | --- | --- |
| 5* | 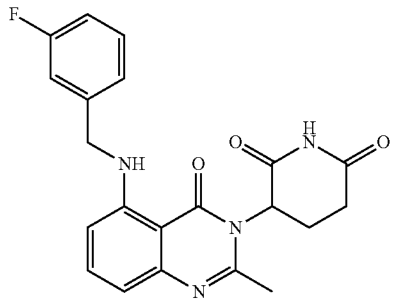 [SMILES: Cc1nc2cccc(NCc3cccc(F)c3)c2c(=O)n1C1CCC(=O)NC1=O] | 3-(5-((3-fluorobenzyl)-amino)-2-methyl-4-oxoquinazolin-3(4H)-yl)piperidine-2,6-dione |
| 6* | 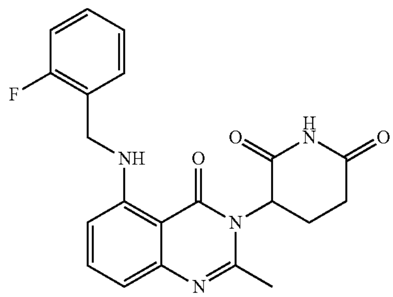 [SMILES: Cc1nc2cccc(NCc3ccccc3F)c2c(=O)n1C1CCC(=O)NC1=O] | 3-(5-((2-fluorobenzyl)-amino)-2-methyl-4-oxoquinazolin-3(4H)-yl)piperidine-2,6-dione |
| 7* | 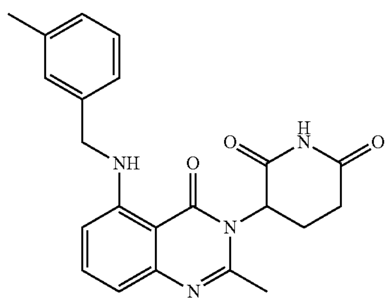 [SMILES: Cc1cccc(CNc2cccc3nc(C)n(C4CCC(=O)NC4=O)c(=O)c23)c1] | 3-(5-((3-methylbenzyl)-amino)-2-methyl-4-oxoquinazolin-3(4H)-yl)piperidine-2,6-dione |
| 8* | 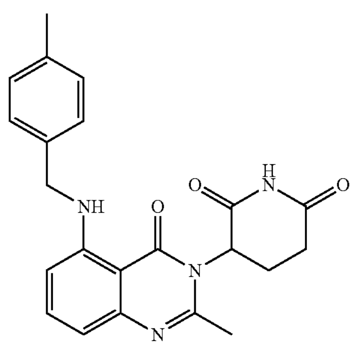 [SMILES: Cc1ccc(CNc2cccc3nc(C)n(C4CCC(=O)NC4=O)c(=O)c23)cc1] | 3-(5-((4-methylbenzyl)-amino)-2-methyl-4-oxoquinazolin-3(4H)-yl)piperidine-2,6-dione |
| 9* | 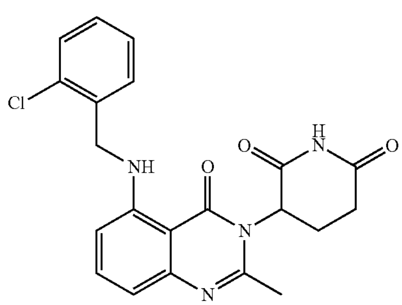 [SMILES: Cc1nc2cccc(NCc3ccccc3Cl)c2c(=O)n1C1CCC(=O)NC1=O] | 3-(5-((2-chlorobenzyl)-amino)-2-methyl-4-oxoquinazolin-3(4H)-yl)piperidine-2,6-dione |

TABLE 2-continued
| No. | Structure | Name |
|---|---|---|
| 10* | 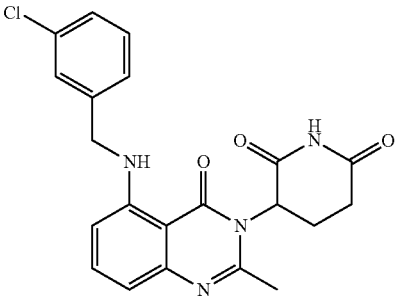 [SMILES: Cc1nc2cccc(NCc3cccc(Cl)c3)c2c(=O)n1C1CCC(=O)NC1=O] | 3-(5-((3-chlorobenzyl)-amino)-2-methyl-4-oxoquinazolin-3(4H)-yl)piperidine-2,6-dione |
| 11* | 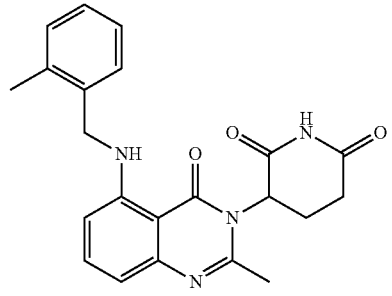 [SMILES: Cc1ccccc1CNc1cccc2nc(C)n(C3CCC(=O)NC3=O)c(=O)c12] | 3-(5-((2-methylbenzyl)-amino)-2-methyl-4-oxoquinazolin-3(4H)-yl)piperidine-2,6-dione |
| 12* | 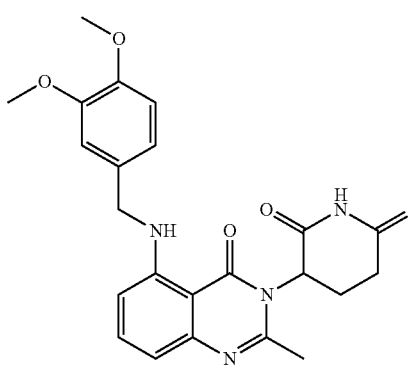 | 3-(5-((3,4-dimethoxy-benzyl)-amino)-2-methyl-4-oxoquinazolin-3(4H)-yl)piperidine-2,6-dione |
| 13* | 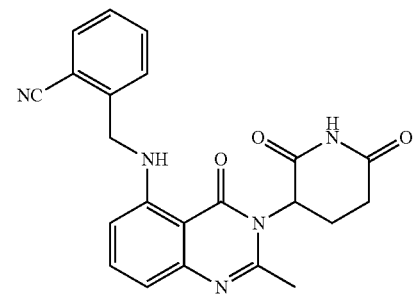 | 3-(5-((2-cyanobenzyl)-amino)-2-methyl-4-oxoquinazolin-3(4H)-yl)piperidine-2,6-dione |

TABLE 2-continued

| No. | Structure | Name |
| --- | --- | --- |
| 14* | 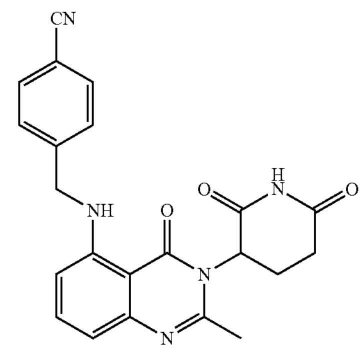 | 3-(5-((4-cyanobenzyl)-amino)-2-methyl-4-oxoquinazolin-3(4H)-yl)piperidine-2,6-dione |
| 15* | 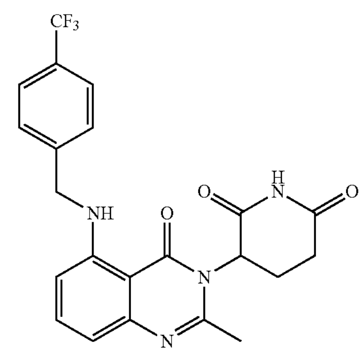 | 3-(5-((4-trifluoromethyl-benzyl)-amino)-2-methyl-4-oxoquinazolin-3(4H)-yl)piperidine-2,6-dione |
| 16* | 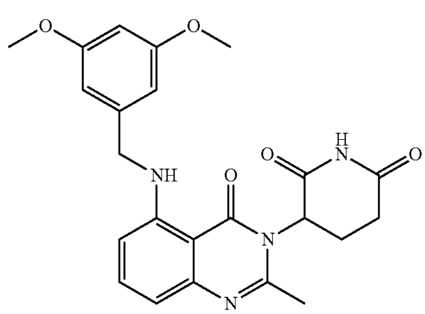 [SMILES: COc1cc(CNc2cccc3nc(C)n(C4CCC(=O)NC4=O)c(=O)c23)cc(OC)c1] | 3-(5-((3,5-dimethoxy-benzyl)-amino)-2-methyl-4-oxoquinazolin-3(4H)-yl)piperidine-2,6-dione |
| 17* | 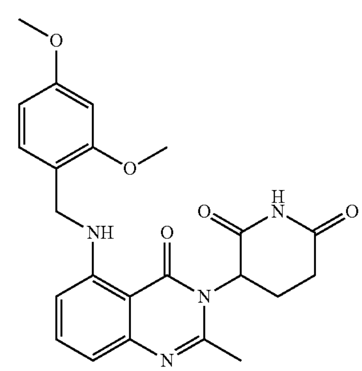 [SMILES: COc1ccc(CNc2cccc3nc(C)n(C4CCC(=O)NC4=O)c(=O)c23)c(OC)c1] | 3-(5-((2,4-dimethoxy-benzyl)-amino)-2-methyl-4-oxoquinazolin-3(4H)-yl)piperidine-2,6-dione |

TABLE 2-continued

| No. | Structure | Name |
| --- | --- | --- |
| 18* | 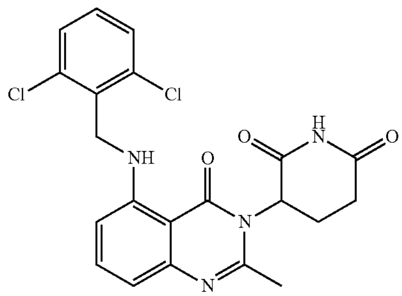 [SMILES: Cc1nc2cccc(NCc3c(Cl)cccc3Cl)c2c(=O)n1C1CCC(=O)NC1=O] | 3-(5-((2,6-dichlorobenzyl)-amino)-2-methyl-4-oxoquinazolin-3(4H)-yl)piperidine-2,6-dione |
| 19* | 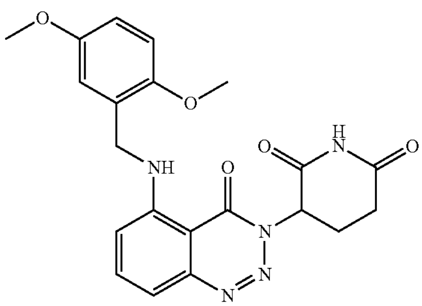 [SMILES: COc1ccc(OC)c(CNc2cccc3nnn(C4CCC(=O)NC4=O)c(=O)c23)c1] | 3-(5-((2,5-dimethoxybenzyl)amino)-4-oxobenzo[d][1,2,3]triazin-3(4H)-yl)piperidine-2,6-dione |
| 20* | 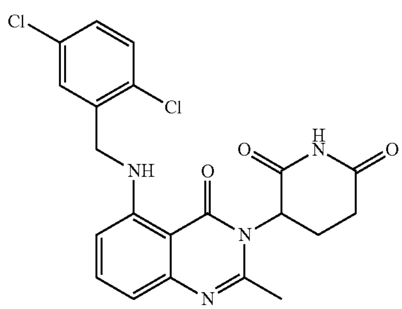 [SMILES: Cc1nc2cccc(NCc3cc(Cl)ccc3Cl)c2c(=O)n1C1CCC(=O)NC1=O] | 3-(5-((2,5-dichlorobenzyl)amino)-2-methyl-4-oxoquinazolin-3(4H)-yl)piperidine-2,6-dione |
| 21* | 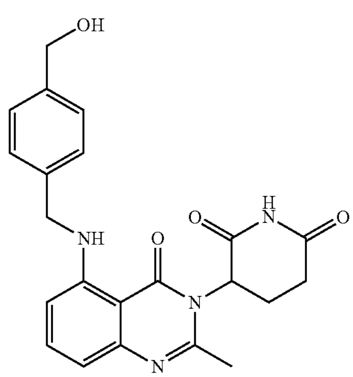 [SMILES: Cc1nc2cccc(NCc3ccc(CO)cc3)c2c(=O)n1C1CCC(=O)NC1=O] | 3-(5-((4-(hydroxymethyl)benzyl)amino)-2-methyl-4-oxoquinazolin-3(4H)-yl)piperidine-2,6-dione |

TABLE 2-continued

| No. | Structure | Name |
|---|---|---|
| 22 | 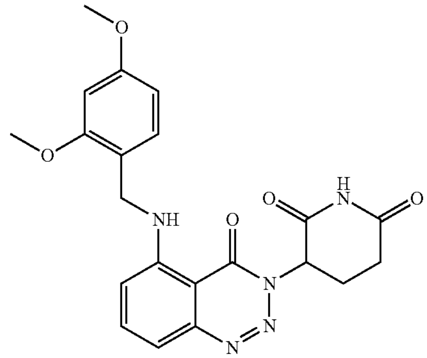 [SMILES: COc1ccc(CNc2cccc3nnn(C4CCC(=O)NC4=O)c(=O)c23)c(OC)c1] | 3-(5-((2,4-dimethoxybenzyl)amino)-4-oxobenzo[d][1,2,3]triazin-3(4H)-yl)piperidine-2,6-dione |
| 23 | 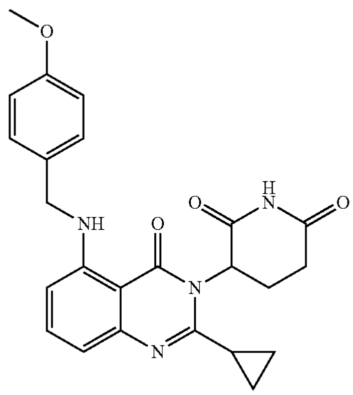 [SMILES: COc1ccc(CNc2cccc3nc(C4CC4)n(C4CCC(=O)NC4=O)c(=O)c23)cc1] | 3-(2-cyclopropyl-5-((4-methoxybenzyl)amino)-4-oxoquinazolin-3(4H)-yl)piperidine-2,6-dione |
| 24* | 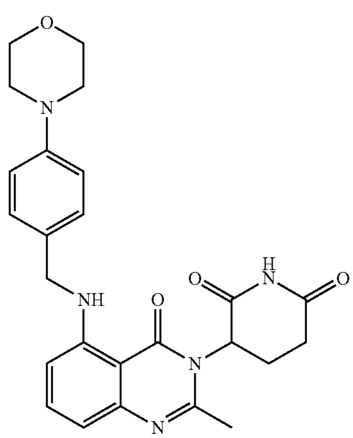 [SMILES: Cc1nc2cccc(NCc3ccc(N4CCOCC4)cc3)c2c(=O)n1C1CCC(=O)NC1=O] | 3-(2-methyl-5-((4-morpholinobenzyl)amino)-4-oxoquinazolin-3(4H)-yl)piperidine-2,6-dione |
| 25 | 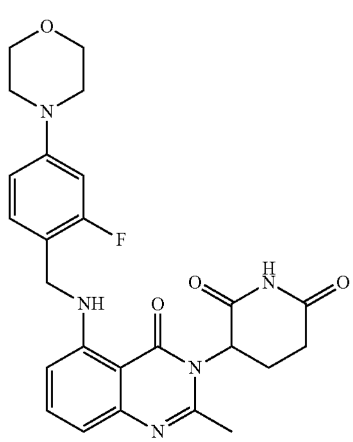 [SMILES: Cc1nc2cccc(NCc3ccc(N4CCOCC4)cc3F)c2c(=O)n1C1CCC(=O)NC1=O] | 3-(5-((2-fluoro-4-morpholinobenzyl)amino)-2-methyl-4-oxoquinazolin-3(4H)-yl)piperidine-2,6-dione |

TABLE 2-continued

| No. | Structure | Name |
| --- | --- | --- |
| 26 | 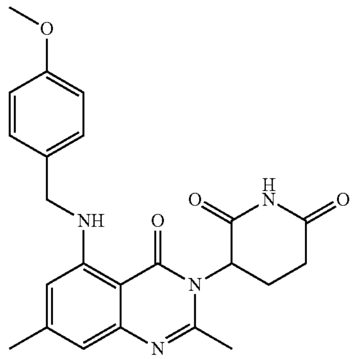 [SMILES: COc1ccc(CNc2cc(C)cc3nc(C)n(C4CCC(=O)NC4=O)c(=O)c23)cc1] | 3-(5-((4-methoxybenzyl)amino)-2,7-dimethyl-4-oxoquinazolin-3(4H)-yl)piperidine-2,6-dione |
| 27 | 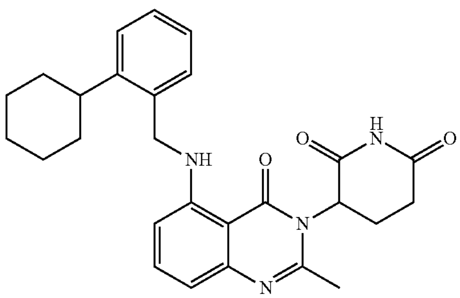 [SMILES: Cc1nc2cccc(NCc3ccccc3C3CCCCC3)c2c(=O)n1C1CCC(=O)NC1=O] | 3-(5-((2-cyclohexylbenzyl)amino)-2-methyl-4-oxoquinazolin-3(4H)-yl)piperidine-2,6-dione |
| 28 | 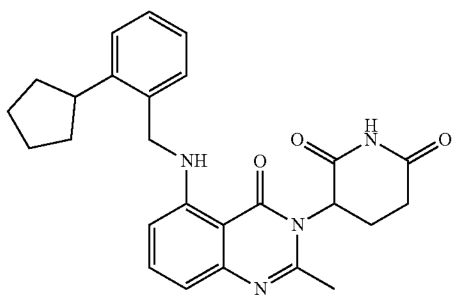 [SMILES: Cc1nc2cccc(NCc3ccccc3C3CCCC3)c2c(=O)n1C1CCC(=O)NC1=O] | 3-(5-((2-cyclopentylbenzyl)amino)-2-methyl-4-oxoquinazolin-3(4H)-yl)piperidine-2,6-dione |
| 29* | 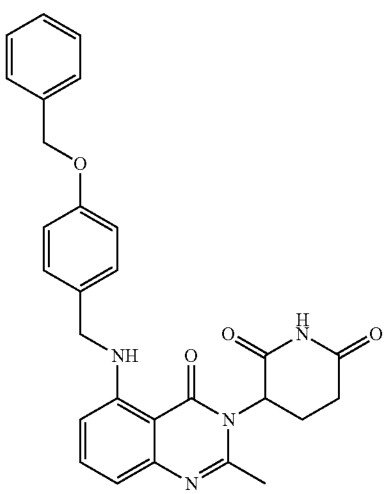 [SMILES: Cc1nc2cccc(NCc3ccc(OCc4ccccc4)cc3)c2c(=O)n1C1CCC(=O)NC1=O] | 3-(5-((4-(benzyloxy)benzyl)amino)-2-methyl-4-oxoquinazolin-3(4H)-yl)piperidine-2,6-dione |

TABLE 2-continued

| No. | Structure | Name |
|---|---|---|
| 31 | 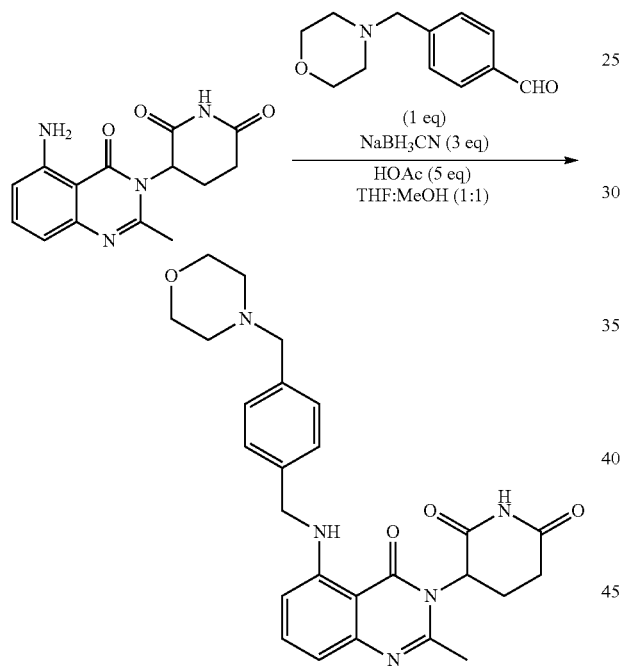 | 3-(5-((4-methoxybenzyl)amino)-4-oxoquinazolin-3(4H)-yl)piperidine-2,6-dione |

Example 32—Preparation of 3-(2-methy-5-((4-(morpholinomethyl)benzyl)amino)-4-oxoquinazolin-3 (4H)-yl)piperidine-2,6-dione To a solution of 3-(5-amino-2-methyl-4-oxoquinazolin-3 (4H)-yl)piperidine-2,6-dione (300 mg, 1.04 mmol) in THF: MeOH (1:1) (6 mL) were added 4-(morpholinomethyl)-benzaldehyde (215 mg, 1.04 mmol), AcOH (0.3 ml) and stirred at rt for 2 h, added NaBH$_3$CN (201 mg, 3.14 mmol) stirred at rt for 16 h. The progress of the reaction is monitored by TLC. After completion of the reaction by TLC the reaction was quenched with saturated NaHCO$_3$ solution (20 mL) extracted with EtOAc (2×20 mL). The combined organic layer was washed with saturated brine solution (20 mL) dried over anhydrous Na$_2$SO$_4$ and concentrated. The crude was purified by Prep HPLC by using 0.1% FA/ACN to obtain 10 mg (2%) of the title compound as an off white solid. MS (ESI) m z=476.2 [M+H]. $^1$H NMR (400 MHz, MeOH-d4) δ 7.44-7.37 (m, 3H), 6.71 (d, J=8.0 Hz, 2H), 6.48 (d, J=8.4 Hz, 2H), 5.19 (t, J=10.8 Hz, 1H), 4.57 (s, 2H), 3.85 (br s, 2H), 3.75-3.47 (m, 4H), 2.88-2.70 (m, 6H), 2.65 (s, 3H), 2.21-2.19 (m, 1H).

Example 33—Preparation of 4-(4-(3-(((3-(2,6-dioxopiperidin-3-yl)-2-methyl-4-oxo-3,4-dihydroquinazolin-5-yl)amino)methyl)benzyl)piperazin-1-yl)-3-fluorobenzonitrile

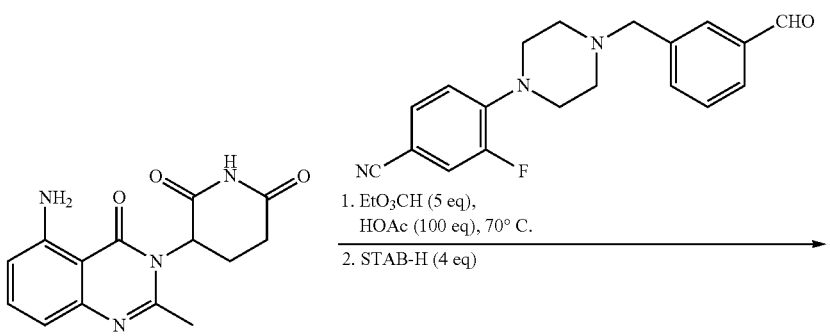

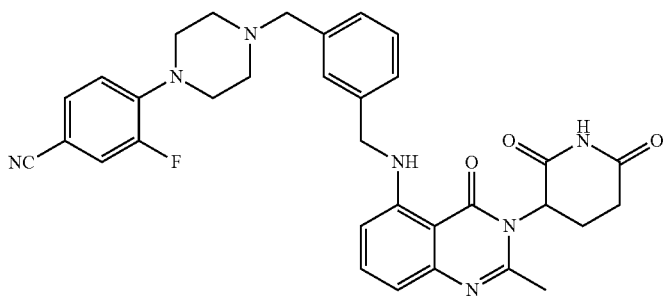

3-(5-amino-2-methyl-4-oxo-quinazolin-3-yl)piperidine-2,6-dione (1.00 eq, 50 mg, 0.175 mmol) and 3-fluoro-4-[4-[(3-formylphenyl)methyl]piperazin-1-yl]benzonitrile (1.00 eq, 56 mg, 0.175 mmol) were dissolved/suspended in 1,4-Dioxane (5 mL) and treated with triethyl orthoformate (5.00 eq, 0.15 mL, 0.873 mmol) and acetic acid (1 mL). The mixture became homogenous. Stirring was continued for 48 h at 70° C. An aliquot of the reaction mixture was treated with sodium triactetoxyborohydride (STAB-H) in and methanol (1 mL). The crude LCMS data indicated the presence of the desired product. The reaction mixture was treated with sodium triacetoxyborohydride (4.00 eq, 148 mg, 0.699 mmol) and stirred at 70° C. for 2 h, then at rt for 18 h. The reaction mixture was diluted with methanol (5 mL) and stirred for 5 h. The crude reaction mixture was purified by Prep-HPLC (C-18) water/ACN gradient to afford 18 mg (17% yield) of the title compound. MS (ESI) m/z 594.3 for [M+H].

Example 34—Preparation of 4-(4-(4-(((3-(2,6-dioxopiperidin-3-yl)-2-methyl-4-oxo-3,4-dihydroquinazolin-5-yl)amino)methyl)benzyl)piperazin-1-yl)-3-fluorobenzonitrile

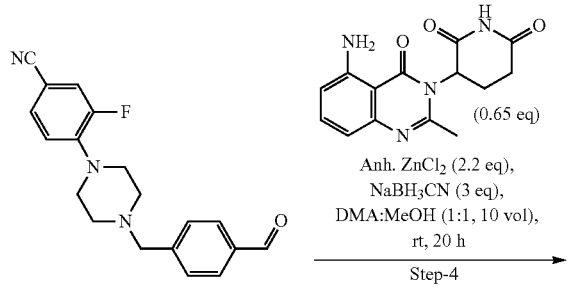

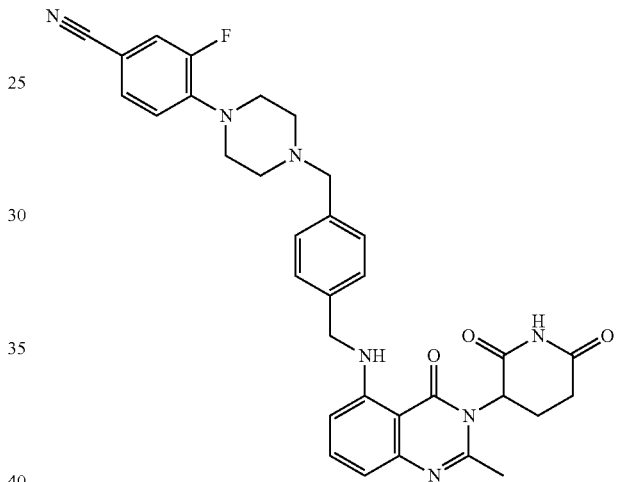

To a stirred solution of 3-(5-amino-2-methyl-4-oxoquinazolin-3(4H)-yl)piperidine-2,6-dione (100 mg, 0.34 mmol) and 3-fluoro-4-(4-(4-formylbenzyl)piperazin-1-yl)benzonitrile (160 mg, 0.52 mmol) in MeOH:DMA (1:1, 10 vol) was added anhydrous ZnCl2 (104 mg, 0.76 mmol) and stirred at rt for 4 h. Cooled the reaction mixture to 0° C. and added sodium NaCNBH$_3$ (66 mg, 1.04 mmol) portion wise. The resultant reaction mixture was stirred at rt for 16 h. The progress of the reaction was monitored by TLC and LCMS. After completion. The reaction mixture was diluted with DCM and washed the organic layer with water. Separated organic layer was dried over anhydrous sodium sulphate and evaporated to get crude residue. Resultant crude residue was purified by prep-HPLC (Ammonium acetate:water method) and fractions are lyophilized to obtain 65 mg (32%) pure desired products as an off-white solid.

MS (ESI) m/z 594.6 [M+H]. $^1$H NMR (499 MHz, DMSO-d6) δ 10.98 (s, 1H), 8.76 (t, J=5.8 Hz, 1H), 7.71-7.64 (m, 1H), 7.55 (dd, J=8.5, 2.0 Hz, 1H), 7.43 (q, J=8.1 Hz, 1H), 7.33-7.26 (m, 4H), 7.10 (td, J=8.8, 1.8 Hz, 1H), 6.64 (ddd, J=11.4, 7.9, 0.9 Hz, 1H), 6.46 (dd, J=8.2, 3.6 Hz, 1H), 5.19 (dd, J=11.5, 5.7 Hz, 1H), 4.43 (d, J=5.8 Hz, 2H), 3.50 (m, 2H), 3.17-3.16 (m, 8H), 2.87-2.78 (m, 1H), 2.64-2.56 (m, 1H), 2.56 (s, 3H), 2.32-2.24 (m, 1H), 2.16-2.15 (m, 1H).

Example 96—Preparation of 3-(5-((2-fluoro-4-((3-morpholinoazetidin-1-yl)methyl)benzyl)amino)-2-methyl-4-oxoquinazolin-3(4H)-yl)piperidine-2,6-dione

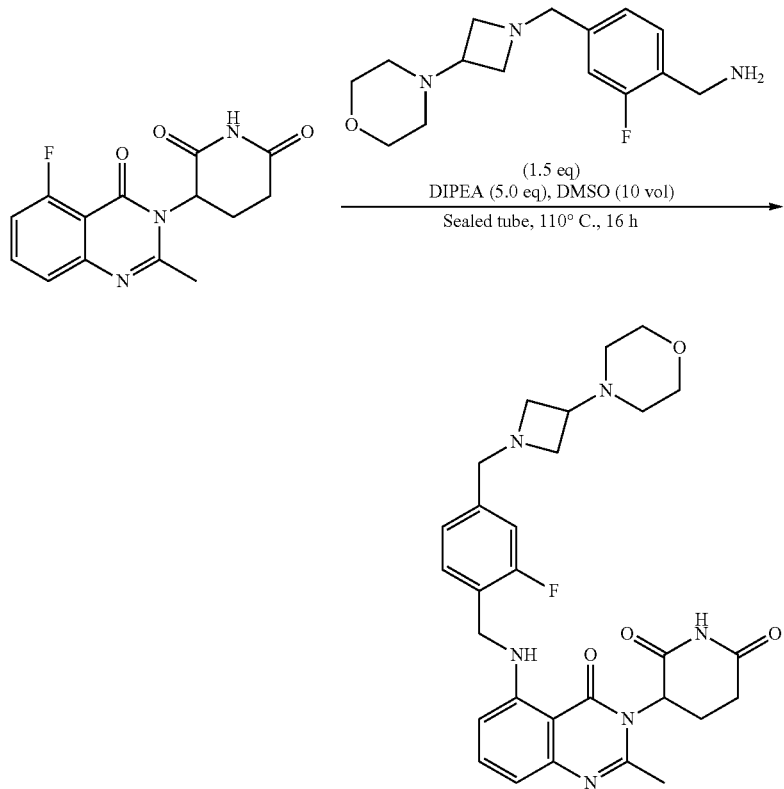

A mixture of (2-fluoro-4-((3-morpholinoazetidin-1-yl)methyl)phenyl)methanamine TFA salt (0.300 g, 1.07 mmol), 3-(5-fluoro-2-methyl-4-oxoquinazolin-3(4H)-yl)piperidine-2,6-dione (0.186 g, 0.644 mmol) and DIPEA (0.694 mg, 5.37 mmol) in DMSO (4 mL), in a sealed tube, was stirred at 110° C. for 16 h. After completion of starting materials, the reaction mixture was quenched with 10% Formic acid in DMSO (1 mL) and further diluted with water (5 mL). The mixture was extracted with EtOAc (3×15 mL) and the organic layer was concentrated. The crude residue was purified by RP-HPLC (0.1% TFA in water/ACN), and fractions are lyophilized to obtain 3-(5-((2-fluoro-4-((3-morpholinoazetidin-1-yl)methyl)benzyl)amino)-2-methyl-4-oxoquinazolin-3(4H)-yl)piperidine-2,6-dione (30 mg, 5% yield) as light brown solid.

MS (ESI) m/z 547.49 [M−H]−. 1H NMR (400 MHz, DMSO-d6) δ 11.00 (s, 1H), 8.75 (m, 1H), 7.48-7.40 (m, 3H), 7.28-7.25 (d, J=7.2 Hz, 1H), 6.70 (d, J=8.0 Hz, 1H), 6.46 (d, J=8.0 Hz, 1H), 5.23-5.19 (m, 1H), 4.53 (d, J=5.2 Hz, 2H), 4.35 (s, 2H), 4.07-4.00 (m, 4H), 3.59 (m, 4H), 3.30-3.23 (m, 1H), 2.88-2.81 (m, 1H), 2.61-2.53 (m, 5H), 2.35-2.32 (m, 4H), 2.18-2.16 (m, 1H).

Example 101—Preparation of 3-(5-((2-fluoro-4-((3-morpholinoazetidin-1-yl)methyl)benzyl)amino)-4-oxoquinazolin-3(4H)-yl)piperidine-2,6-dione

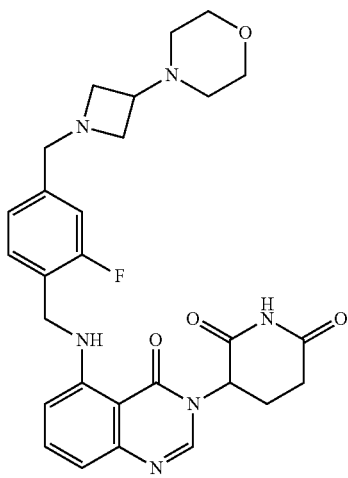 [SMILES: O=C1CCC(n2cnc3cccc(NCc4ccc(CN5CC(N6CCOCC6)C5)cc4F)c3c2=O)C(=O)N1]

The title compound was prepared per Example 35 from 3-(5-fluoro-4-oxoquinazolin-3(4H)-yl)piperidine-2,6-dione (from Step F under the Preparation of Starting Materials in the next section) and (2-fluoro-4-((3-morpholinoazetidin-1-yl)methyl)phenyl)methanamine afford 21 mg (5.5% yield) of the title compound as a light yellow solid.

MS (ESI) m/z 533.21 [M+H]+. 1H NMR (400 MHz, DMSO-d6) δ 11.10 (s, 1H), 8.87 (m, 1H), 8.21 (s, 1H), 7.53 (t, J=8.0 Hz, 1H), 7.45 (t, J=8.0 Hz, 1H), 7.40 (m, 1H), 7.28-7.6 (d, J=8.0 Hz, 1H), 6.78 (d, J=8.0 Hz, 1H), 6.57 (d, J=8.4 Hz, 1H), 5.37 (m, 1H), 4.54 (d, J=5.6 Hz, 2H), 4.35 (s, 2H), 4.08-3.99 (m, 4H), 3.59 (m, 4H), 3.30-3.23 (m, 1H), 2.82 (m, 1H), 2.67-2.60 (m, 2H), 2.35 (m, 4H), 2.15-2.12 (m, 1H).

Preparation of Starting Materials

A. 3-(5-fluoro-4-oxoquinazolin-3(4H)-yl)piperidine-2,6-dione

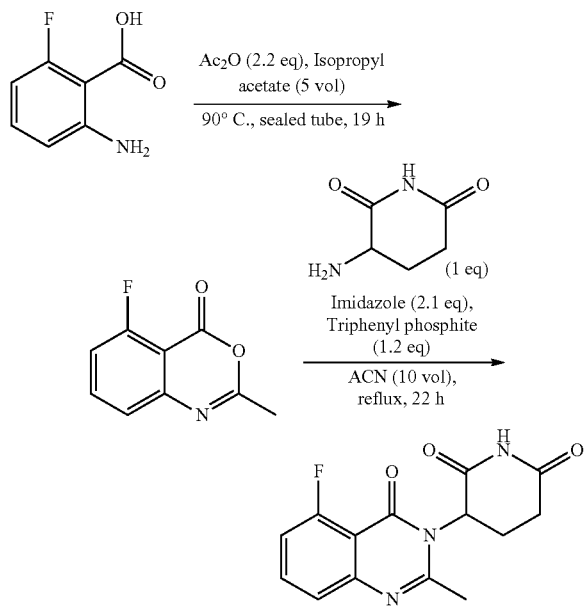

To a solution of 2-amino-6-fluorobenzoic acid (5.0 g, 32.2 mmol) in isopropyl acetate (25.0 mL) in a sealed tube, Ac2O (6.6 mL, 70.90 mmol) was added and heated at 90° C. for 16 h. After completion, the volatiles were evaporated to get the residue. Triturated with pentane (20 mL) to obtain 5-fluoro-2-methyl-4H-benzo[d][1,3]oxazin-4-one (5.8 g) as light yellow solid and and used in the next step without further purification. 1H NMR (400 MHz, CDCl3) δ 7.77-7.72 (m, 1H), 7.36-7.34 (d, J=8.0 Hz, 1H), 7.21-7.16 (t, J=9.4 Hz, 1H), 2.46 (s, 3H).

To a solution of 5-fluoro-2-methyl-4H-benzo[d][1,3]oxazin-4-one (11.7 g, 65.31 mmol) in acetonitrile (117 mL), 3-aminopiperidine-2,6-dione hydrochloride (10.44 g, 65.31 mmol), imidazole (9.33 g, 137.1 mmol) and triphenyl phosphite (23.91 g, 77.06 mmol) were added and then heated the mixture at reflux for 22 h. The progress of the reaction was monitored by TLC and LC-MS. After completion, the reaction mixture was cooled to room temperature, and diluted with water (30 mL) and stirred for 30 minutes. The solid was collected by filtration and washed with acetonitrile (3×10 mL). The solid was further refluxed with methanol (50 mL) for 12 h and then filtered to obtain 3-(5-fluoro-2-methyl-4-oxoquinazolin-3(4H)-yl)piperidine-2,6-dione (10.96 g, 58% over 2 steps) as an off white solid. 1H NMR (400 MHz, DMSO-d6) δ 11.03 (s, 1H), 5.26-5.22 (m, 1H), 7.45-7.43 (d, 1H), 7.84-7.78 (m, 1H), 7.28-7.23 (m, 1H), 2.88-2.78 (m, 1H), 2.67-2.60 (m, 5H), 2.19 (m, 1H).

B. (2-fluoro-4-((3-morpholinoazetidin-1-yl)methyl)phenyl)methanamine

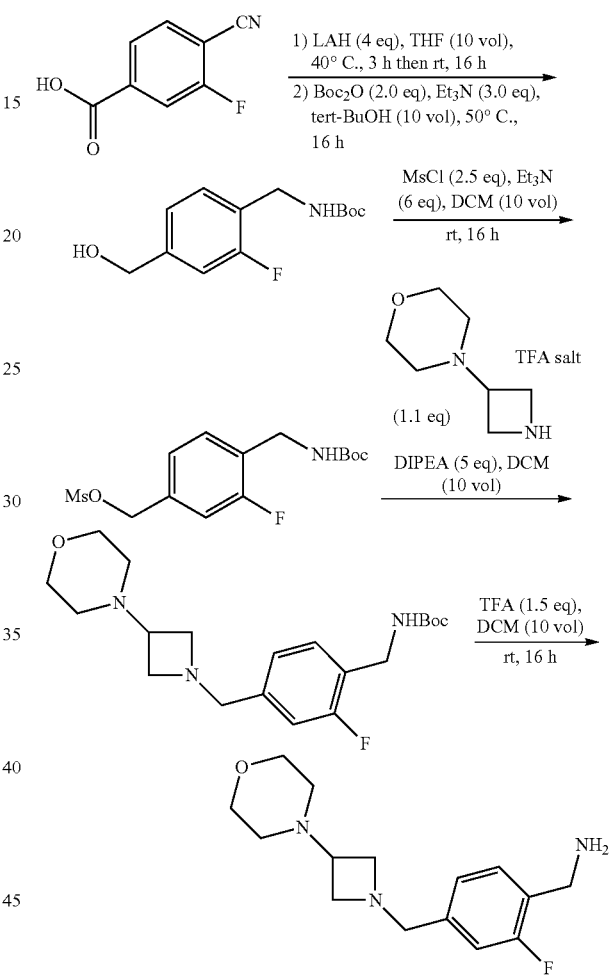

To a solution of Lithium aluminum hydride (48.45 mL, 2.5 M solution in THF, 121.12 mmol, 4.0 eq) at 40° C. under argon gas, a solution of 4-cyano-3-fluorobenzoic acid (5 g, 30.28 mmol) in THF (50 mL) was added drop wise and stirred the mixture at 40° C. for 3 h and then at rt for 16 h. After completion, the reaction mixture was cooled to 0° C., and quenched with sequential addition of water (5 mL), 15% NaOH solution (15 mL) and water (5 mL). The reaction mixture was filtered over celite bed and the filtrate was concentrated to obtain (4-(aminomethyl)-3-fluorophenyl)methanol (4.0 g, 85% yield) and used in the next step without further purification. MS (ESI) m/z 156.11 [M+H]+. 1H NMR (400 MHz, DMSO-d6) δ 7.40 (t, J=8.8 Hz, 1H), 7.09 (d, J=8.4 Hz, 1H), 7.05-7.02 (d, J=11.2 Hz, 1H), 5.23 (m, 1H), 4.47 (d, J=4.0 Hz, 2H), 3.71 (s, 2H), 1.80 (br s, 2H).

A mixture of (4-(aminomethyl)-3-fluorophenyl)methanol (4.5 g, 29.0 mmol), Boc-anhydride (12.66 g, 58.0 mmol, 2.0 eq), triethylamine (8.80 g, 87.0 mmol, 3.0 eq) in tert-BuOH (45 mL) was stirred at 50° C. for 16 h. After completion, the reaction mixture was diluted with water (50 mL) and extracted with DCM (3×100 mL). The combined organic layer was dried over anhydrous sodium sulfate and concentrated. The crude residue was purified by flash chromatography (silica gel) using 50% EtOAc in pentane as eluent to obtain tert-butyl (2-fluoro-4-(hydroxymethyl)benzyl)carbamate (5.0 g, 67% yield). MS (ESI) m/z 200.13 [M-56+H]$^+$. $^1$H NMR (400 MHz, DMSO-d$_6$) δ 7.36-7.34 (m, 1H), 7.25-7.21 (t, J=7.6 Hz, 1H), 7.10-7.04 (m, 2H), 5.26 (t, J=6.0 Hz, 1H), 4.47 (d, J=6.0 Hz, 2H), 4.12 (m, 2H), 1.39 (s, 9H).

To a solution of tert-butyl (2-fluoro-4-(hydroxymethyl)benzyl)carbamate (5.0 g, 19.6 mmol) and triethylamine (16 mL, 117.6 mmol, 6.0 eq) in DCM (50 mL), MsCl (3.7 mL, 49.0 mmol, 2.5 eq) was added and stirred the mixture at rt for 16 h. After completion, the reaction mixture was concentrated under reduced pressure to obtain 4-(((tert-butoxycarbonyl)-amino)methyl)-3-fluorobenzyl methanesulfonate (4.1 g, 62% yield) as yellow liquid and used in the next step without further purification.

To a solution of 4-(((tert-butoxycarbonyl)amino)methyl)-3-fluorobenzyl methanesulfonate (2.0 g, 6.00 mmol, 1.0 eq) and 4-(azetidin-3-yl)morpholine (TFA salt) (1.10 g, 6.60 mmol, 1.1 eq) in DCM (20 mL), DIPEA (3.8 g, 30.00 mmol, 5.0 eq) was added and stirred at rt for 16 h. After completion, the mixture was diluted with water (60 mL) and extracted with DCM (3×80 mL). The combined organic layer was dried over anhydrous sodium sulphate and concentrated. The crude product was purified by flash chromatography (silica gel) using 5% MeOH in DCM as eluent to obtain tert-butyl (2-fluoro-4-((3-morpholinoazetidin-1-yl)methyl)benzyl)carbamate (1.1 g, 48% yield). MS (ESI) m/z 380.41 [M+H]$^+$. $^1$H NMR (400 MHz, DMSO-d$_6$) δ 7.35-7.34 (m, 1H), 7.23-7.18 (t, J=7.6 Hz, 1H), 7.07-7.01 (m, 2H), 4.13 (d, J=6.0 Hz, 2H), 3.56-3.53 (m, 6H), 2.87-2.81 (m, 3H), 2.21 (m, 4H), 1.39 (s, 9H), 0.95 (m, 2H).

To a solution of tert-butyl (2-fluoro-4-((3-morpholinoazetidin-1-yl)methyl)benzyl)carbamate (1.1 g, 2.90 mmol, 1.0 eq) in DCM (10 mL), TFA (2 mL) was added slowly and stirred the mixture at rt for 16 h. After completion, the mixture was concentrated under vacuum to obtain (2-fluoro-4-((3-morpholinoazetidin-1-yl)methyl)phenyl)methanamine (0.80 g, 96% yield) as a TFA salt and used in the next step without further purification. MS (ESI) m/z 280.23 [M+H]. $^1$H NMR (400 MHz, DMSO-d$_6$) δ 8.35 (br s, 2H), 7.61-7.57 (t, J=8.0 Hz, 1H), 7.43 (d, J=10.4 Hz, 1H), 7.37 (d, J=8.0 Hz, 1H), 4.42 (s, 2H), 4.13 (m, 5H), 3.60-3.50 (m, 2H), 2.67 (m, 4H), 1.28 (m, 4H).

C. 4-(azetidin-3-yl)morpholine

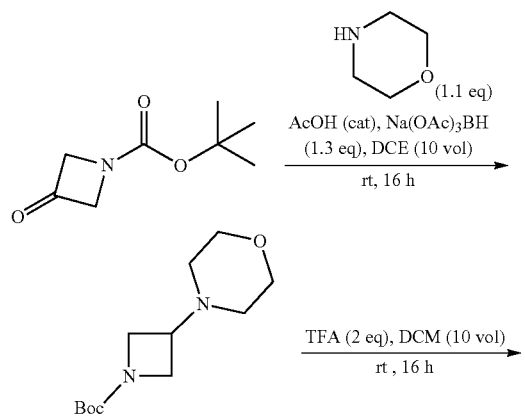

To a solution of tert-butyl 3-oxoazetidine-1-carboxylate (5.0 g, 29.21 mmol), morpholine (2.80 g, 32.13 mmol, 1.1 eq), AcOH (1 mL) in DCE (50 mL), sodium triacetoxy borohydride (8.05 g, 37.97 mmol, 1.3 eq) was added and stirred the mixture at rt for 16 h. The reaction mixture was diluted with saturated sodium bicarbonate solution (50 mL) and extracted with DCM (3×100 mL). The combined organic layer was dried over anhydrous sodium sulfate and concentrated. The crude was triturated with diethylether to obtain tert-butyl 3-morpholinoazetidine-1-carboxylate (3.70 g, 52% yield) and used in the next step without further purification. MS (ESI) m/z 243.25 [M+H]$^+$.

To a solution of tert-butyl 3-morpholinoazetidine-1-carboxylate (2.0 g, 8.25 mmol) in DCM (20 mL), Trifluoroacetic acid (4 mL) was added and stirred at rt for 16 h. After completion, the reaction mixture was concentrated under vacuum to obtain 4-(azetidin-3-yl)morpholine (TFA salt, 1.1 g, 94% yield) and used in the next step without further purification.

MS (ESI) m/z 143.15 [M+H]$^+$. $^1$H NMR (400 MHz, DMSO-d$_6$) δ 8.94 (br s, 1H), 4.03 (m, 4H), 3.68-3.66 (m, 5H), 2.64 (m, 4H).

D. 3-fluoro-4-(4-(4-formylbenzyl)piperazin-1-yl)benzonitrile a. 3-Fluoro-4-(piperazin-1-yl)benzonitrile

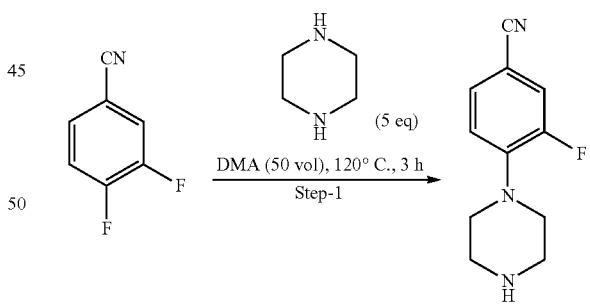

A solution of 3,4-difluorobenzonitrile (5.0 g, 35.9 mmol), piperazine (14.0 g, 179.72 mmol) in DMA (250 mL) stirred at 120° C. for 3 h. The progress of the reaction is monitored by TLC. After completion, the reaction was quenched in cool water (500 ml) and extract with DCM (900 ml), organic layer was evaporated get to solid material. After wash with pet-ether (2×200 mL) and then dried to get 3-fluoro-4-(piperazin-1-yl)benzonitrile (24.3 g) as an off-white solid.

MS (ESI) m/z 206.39 [M+H]$^+$. $^1$H NMR (400 MHz, DMSO-d6) δ 7.12-7.07 (t, J=8.0 Hz, 1H), 7.68-7.64 (m, 1H), 3.09-3.06 (m, 4H), 2.84-2.81 (m, 4H), 7.56-7.53 (m, 1H).

b. 3-Fluoro-4-(4-(4-(hydroxymethyl)benzyl)piperazin-1-yl)benzonitrile

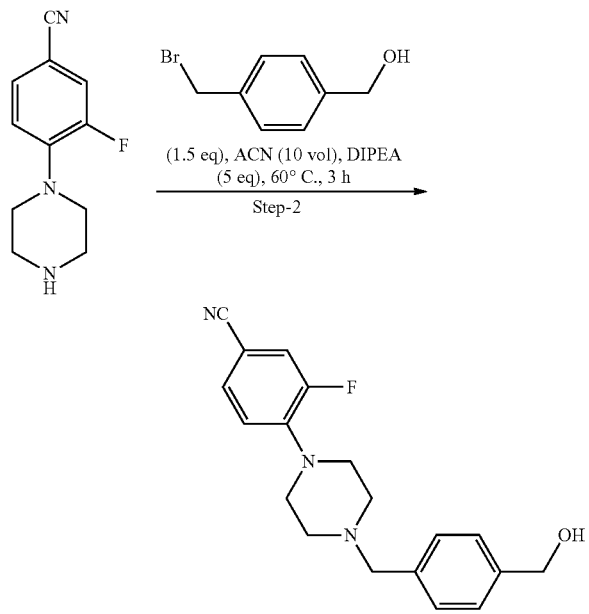

To a solution of 3-fluoro-4-(piperazin-1-yl)benzonitrile (4.0 g, 19.4 mmol), (4-(bromomethyl)phenyl)methanol (5.87 g, 29.2 mmol) in acetonitrile (40 mL), DIPEA (90.4 ml, 97.4 mmol) was added and allowed the mixture to stirred at 60° C. for 3 h in a seal tube. The progress of the reaction is monitored by TLC. After completion, the reaction was quenched in water (2×250 ml) and extract with ethyl acetate (2×400 ml), organic layer was evaporated get to solid material. After triturate with ACN (2 ml) and ether (40 ml) and then dried to obtain solid 3-fluoro-4-(4-(4-(hydroxymethyl)benzyl)piperazin-1-yl)benzonitrile (4.7 g, 37.06% yield) as an off-white solid. MS (ESI) m/z 326.30 [M+H]$^+$. $^1$H NMR (400 MHz, DMSO-d6) δ 7.98 (s, 1H), 5.14-5.11 (t, J=8.0 Hz, 1H), 3.50 (s, 2H), 4.48-4.47 (d, J=4.0 Hz, 2H), 3.18-3.15 (t, J=4.0 Hz, 4H), 2.51-2.49 (m, 4H), 7.69-7.65 (m, 1H), 7.56-7.54 (m, 1H), 7.27 (s, 4H), 7.12-7.08 (t, J=8.0 Hz, 1H).

c. 3-fluoro-4-(4-(4-formylbenzyl)piperazin-1-yl)benzonitrile

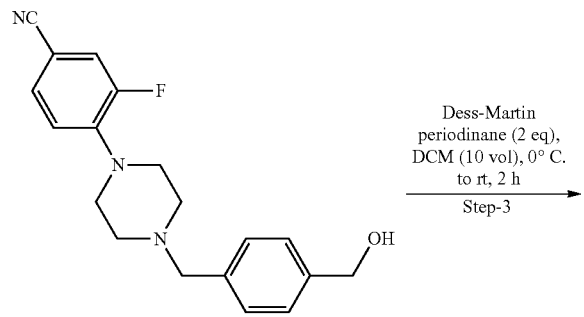

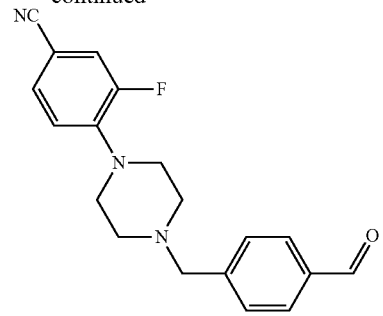

In a 100 mL round bottom flask, 3-fluoro-4-(4-(4-(hydroxymethyl)benzyl)piperazin-1-yl)benzonitrile (5) (4.7 g, 14.4 mmol) was dissolved in DCM (47 mL) and DMP (12.26, 28.9 mmol) was added at 0° C. and allowed the mixture to stirred at rt for 2 h. The progress of the reaction is monitored by TLC. After completion, the reaction was filtrate and filtrate layer was evaporated get to crude material. After triturate with ACN (3 ml) and ether (40 ml), then dried to get 3-fluoro-4-(4-(4-formylbenzyl)piperazin-1-yl)benzonitrile (6) (3.0 g, 64.23% yield) as off-white solid. MS (ESI) m/z 324.45 [M+H]$^+$. $^1$H NMR (400 MHz, DMSO-d6) δ 10.00 (s, 1H), 7.90 (d, J=1.6 Hz, 2H), 7.120 (t, J=8.8 Hz, 1H), 3.642 (s, 2H), 3.197 (t, J=4.8 Hz, 4H), 2.559-2.497 (m, 4H), 7.66 (d, J=2 Hz, 1H), 7.58-7.55 (m, 3H).

E. 3-(5-fluoro-4-oxoquinazolin-3(4H)-yl)piperidine-2,6-dione

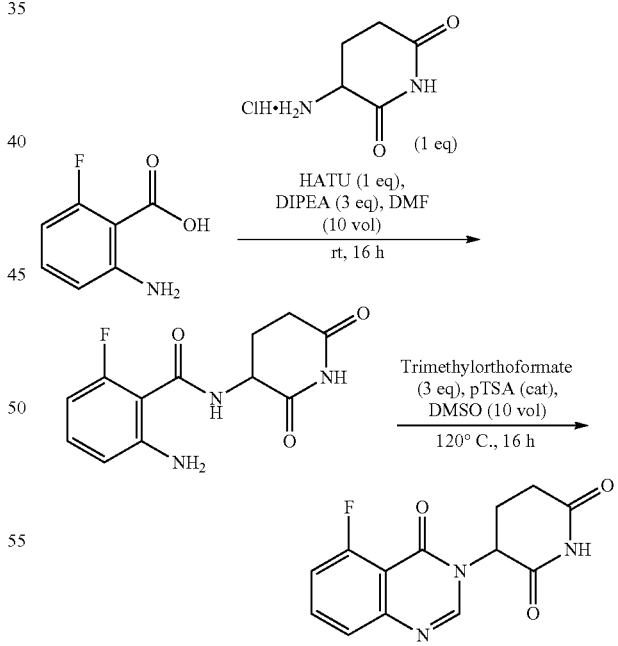

a. To a solution of 2-amino-6-fluorobenzoic acid (5.0 g, 32.23 mmol) in DMF (50 mL), HATU (18.38 g, 48.35 mmol, 1.5 eq), DIPEA (16.66 g, 128.93 mmol, 4.0 eq) and 3-aminopiperidine-2,6-dione hydrochloride (6.90 g, 41.90 mmol, 1.3 eq) were added and stirred the mixture at rt for 16 h. After completion, the mixture was poured in to ice cold water (50 mL) and filtered the suspension. The solid was washed with cold water (10 mL), pentane (20 mL) and dried under vacuum to obtain 2-amino-N-(2,6-dioxopiperidin-3-yl)-6-fluorobenzamide 3 (6.52 g, 76% yield) as light brown solid and used in the next step without further purification. MS (ESI) m/z 265.98 [M+H]⁺. ¹H NMR (400 MHz, DMSO-d6) δ 10.90 (s, 1H), 8.53-8.51 (dd, J=8.0, 2.0 Hz, 1H), 7.11 (m, 1H), 6.52 (d, J=8.0 Hz, 1H), 6.32 (dd, J=8.4, 1.6 Hz, 1H), 5.99 (s, 2H), 4.77-4.70 (m, 1H), 2.82-2.74 (m, 1H), 2.55 (m, 1H), 2.14-2.04 (m, 1H), 1.99-1.96 (m, 1H).

b. A mixture of 2-amino-N-(2,6-dioxopiperidin-3-yl)-6-fluorobenzamide (2.0 g, 7.54 mmol), trimethyl ortho formate (2.4 g, 22.62 mmol, 3.0 eq), p-toluene sulfonic acid (0.2 g, 1.51 mmol, 0.2 eq) in DMSO (20 mL) in a sealed tube was heated at 120° C. for 16 h. After completion, the reaction mixture diluted with water (20 mL) and filtered to collect the solid. The solid was washed with ether (10 mL) and dried under vacuum to get 3-(5-fluoro-4-oxoquinazolin-3(4H)-yl) piperidine-2,6-dione (1.2 g, 63% yield) as a brown solid. and used in the next step without further purification. MS (ESI) m/z 276.08 [M+H]⁺. ¹H NMR (400 MHz, DMSO-d6) δ 11.17 (s, 1H), 8.38 (s, 1H), 7.88-7.82 (m, 1H), 7.54 (d, J=8.0 Hz, 1H), 7.37-7.32 (dd, J=10.8, 8.4 Hz, 1H), 5.45 (br s, 1H), 2.85-2.82 (m, 1H), 2.70-2.63 (m, 2H), 2.18-2.14 (m, 1H).

Triazinyl derivatives can be synthesized using the compound synthesized in Preparation F below.

F. 3-(5-fluoro-4-oxobenzo[d][1,2,3]triazin-3(4H)-yl) piperidine-2,6-dione

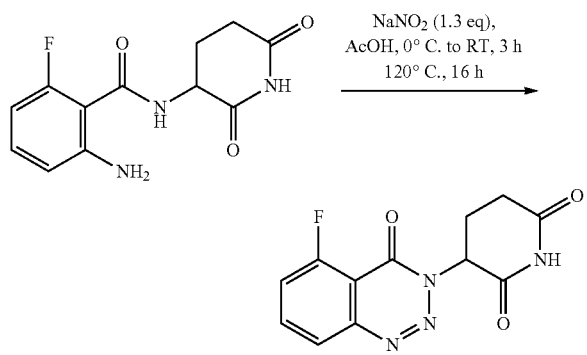

To a solution of 2-amino-N-(2,6-dioxopiperidin-3-yl)-6-fluorobenzamide (2.5 g, 9.4 mmol) in AcOH (20 mL) at 0° C., sodium nitrite (0.975 g, 14.0 mmol, 1.5 eq) was added slowly and stirred at rt for 3 h. After completion, the reaction mixture was diluted with ice cold water (30 mL), filtered and dried under vacuum to obtain 3-(5-fluoro-4-oxobenzo[d][1,2,3]triazin-3(4H)-yl)piperidine-2,6-dione (1.9 g, 73% yield) as off-white solid and used in the next step without further purification. MS (ESI) m/z 276.97 [M+H]⁺. ¹H NMR (400 MHz, DMSO-d6) δ 11.20 (s, 1H), 8.18-8.08 (m 2H), 7.82-7.76 (dd, J=9.2, 0.8 Hz, 1H), 6.00-5.95 (m, 1H), 3.00-2.91 (m, 1H), 2.73-2.62 (m, 2H), 2.30-2.24 (m, 1H).

G. 4-(morpholinomethyl)benzaldehyde

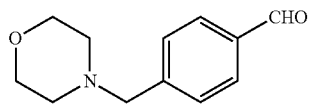 [SMILES: O=Cc1ccc(CN2CCOCC2)cc1]

The title compound was prepared as per Example A from morpholine to afford 1.19 g (64% yield) of the title compound as an off-white solid.

MS (ESI) m/z [M+H]=206.2; ¹H NMR (499 MHz, DMSO) δ 10.00 (s, 1H), 7.87 (d, J=7.6 Hz, 2H), 7.55 (d, J=7.6 Hz, 2H), 3.56-3.57 (m, 6H), 2.78-2.36 (m, 4H).

H. 3-fluoro-4-(4-(3-formylbenzyl)piperazin-1-yl) benzonitrile

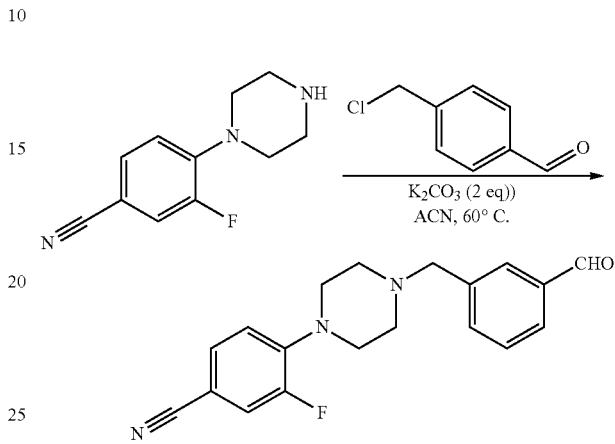

3-Fluoro-4-piperazinobenzonitrile (1.10 eq, 256 mg, 1.25 mmol) was dissolved in ACN (5 mL) and treated with 3-(chloromethyl)benzaldehyde (1.00 eq, 175 mg, 1.13 mmol) and powdered potassium carbonate (2.00 eq, 313 mg, 2.26 mmol). The mixture was stirred at 60° C. for 24 h. The reaction mixture was cooled to rt, filtered, and concentrated to yield 352 mg (96% yield) of the title compound as an amber oil.

MS (ESI) m/z [M+H]=324.3; ¹H NMR (500 MHz, DMSO-d₆) δ 10.02 (s, 1H), 7.87 (s, 1H), 7.82 (dt, J=7.5, 1.4 Hz, 1H), 7.71-7.62 (m, 2H), 7.59 (d, J=7.5 Hz, 1H), 7.55 (dd, J=8.8, 2.0 Hz, 1H), 7.11 (t, J=8.8 Hz, 1H), 3.63 (s, 2H), 3.22-3.16 (m, 4H), 2.57-2.51 (m, 4H).

I. 3-(5-amino-2-cyclopropyl-4-oxoquinazolin-3(4H)-yl)piperidine-2,6-dione

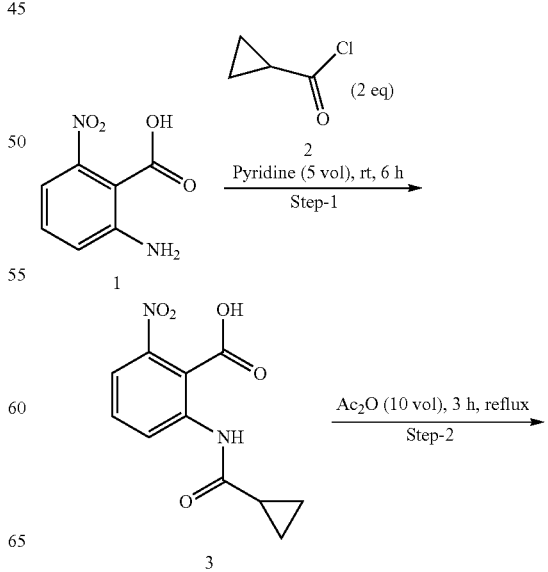

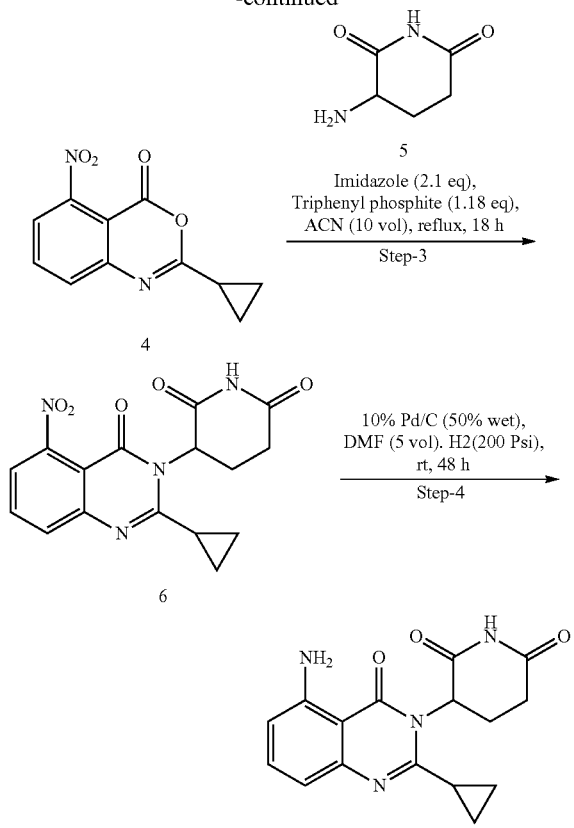

a. To a stirred solution of 2-amino-6-nitrobenzoic acid 1 (15.0 g, 82.30 mmol) in pyridine (70 mL) at 0° C., cyclopropane carbonyl chloride 2 (17.20 g, 164.6 mmol) was added and allowed the mixture to stir at room temperature for 12 h. After completion (monitored by TLC), the reaction mixture was quenched by adding 20% citric acid solution (500 mL), and extracted with ethyl acetate (3×400 mL). The organic layer was concentrated to get solid material which was washed with dichloromethane (300 mL) and dried to obtain 2-(cyclopropanecarboxamido)-6-nitrobenzoic acid 3 (14 g, 67.94% yield) as light yellow solid which was used as such in next step. MS (ESI) m/z 249.11 [M−H]⁻.

b. A solution of 2-(cyclopropanecarboxamido)-6-nitrobenzoic acid 3 (14.0 g, 55.95 mmol) in Ac₂O (70 mL) stirred at 90° C. for 1 h in a seal tube. The progress of the reaction is monitored by TLC. After completion, the solvent was evaporated and the residue was diluted with pet-ether (400 mL). The precipitated solid was filtered and washed again with pet ether (2×50 mL) and then dried to get 2-cyclopropyl-5-nitro-4H-benzo[d][1,3]oxazin-4-one (13.6 g) as an off-white solid which was used as such in next step. MS (ESI) m/z 233.27 [M+H]⁺. ¹H NMR (400 MHz, DMSO-d6) δ 7.85-7.83 (t, J=8.0 Hz, 1H), 2.00-1.91 (m, 1H), 7.67-7.65 (m, 1H), 1.35-1.31 (m, 2H), 7.48-7.46-2.66 (m, 1H), 1.20-1.15 (m, 2H).

c. To a solution of 2-cyclopropyl-5-nitro-4H-benzo[d][1,3]oxazin-4-one 4 (13.6 g, 58.57 mmol) in acetonitrile (136 mL), 3-aminopiperidine-2,6-dione 5 (9.6 g, 58.57 mmol, HCl salt), imidazole (7.97 g, 117.1 mmol) and triphenyl phosphite (21.42 g, 69.11 mmol) were added and stirred at 90° C. for 18 h. The progress of the reaction was monitored by TLC. After completion, the solvent was evaporated and purified by silica gel (230-400#) using 5% MeOH in DCM as eluent to get 3-(2-cyclopropyl-5-nitro-4-oxoquinazolin-3(4H)-yl)piperidine-2,6-dione 6 (500 mg, 2.79% yield) as an off-white solid. MS (ESI) m/z 343.23 [M+H]⁺. ¹H NMR (400 MHz, DMSO-d6) δ 7.98 (s, 1H), 7.78-7.77 (d, J=4.0 Hz, 2H), 7.42 (s, 1H), 5.39-5.36 (t, J=4.0 Hz, 1H), 3.03-2.71 (m, 3H), 2.20 (s, 1H), 1.96 (s, 1H), 1.45 (s, 1H), 1.29 (s, 1H), 1.18-1.16 (d, J=8.0 Hz, 2H).

d. In a 100 mL round bottom flask, 3-(5-amino-2-cyclopropyl-4-oxoquinazolin-3(4H)-yl)piperidine-2,6-dione 6 (0.5 g, 1.4 mmol) was dissolved in THF:DMF (5 mL, 1:1) and 10% Pd/C (260 mg, 50% wet) was added. The reaction was hydrogenated under balloon pressure at RT for 12 h. After completion, the reaction mixture was filtered and washed with MeOH (150 mL) and DMF (100 mL). The filtrate was evaporated under reduced pressure to get the crude which was diluted with water (5 mL). The precipitated solid was filtered and washed with diethyl ether (10 mL) and dried to get 3-(5-amino-2-cyclopropyl-4-oxoquinazolin-3(4H)-yl)piperidine-2,6-dione (150 mg, 42% yield) as off-white solid. MS (ESI) m/z 313.25 [M+H]⁺. ¹H NMR (400 MHz, DMSO-d6) δ 7.35-7.31 (t, J=8.0 Hz, 1H), 7.011 (s, 2H), 10.98 (s, 1H), 6.55-6.53 (m, 2H), 5.63-5.59 (m, 1H), 2.70-2.61 (m, 2H), 2.94-2.85 (m, 1H), 2.17-2.15 (d, J=8.0 Hz, 2H), 1.16-0.92 (m, 4H).

The following compounds indicated with an "*" were also prepared as per Examples 32, 33, 34, 96, and 101 above as set forth in Table 3 below (which includes compounds 32-34, 96 and 101 exemplified above). Those compound without "*" are prophetic compounds:

TABLE 3

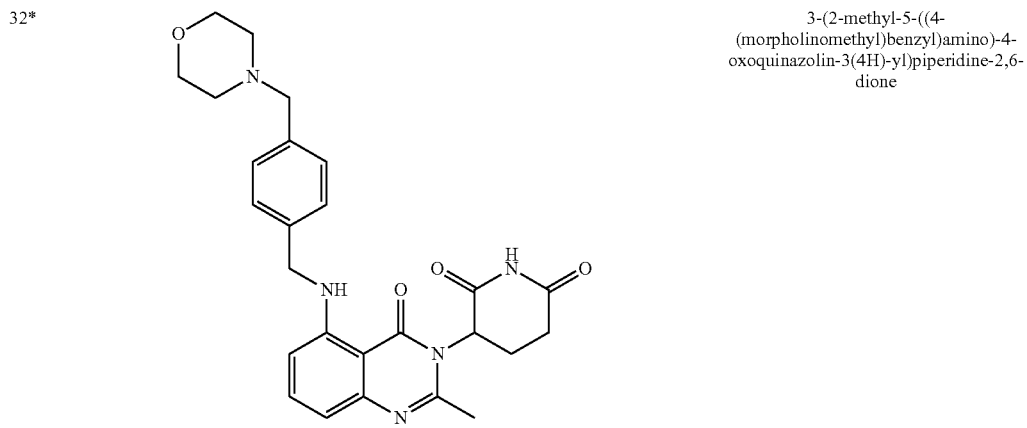

| 32* | | 3-(2-methyl-5-((4-(morpholinomethyl)benzyl)amino)-4-oxoquinazolin-3(4H)-yl)piperidine-2,6-dione |

33* 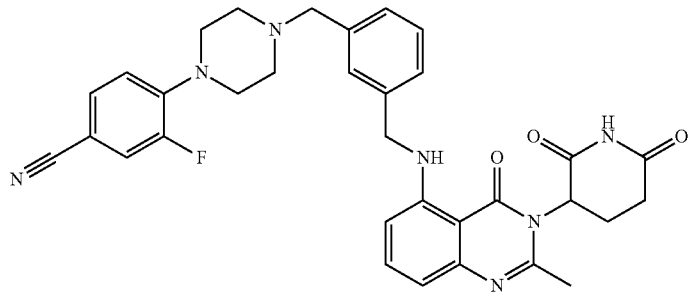 [SMILES: Cc1nc2cccc(NCc3cccc(CN4CCN(c5ccc(C#N)cc5F)CC4)c3)c2c(=O)n1C1CCC(=O)NC1=O] 4-(4-(3-(((3-(2,6-dioxopiperidin-3-yl)-2-methyl-4-oxo-3,4-dihydroquinazolin-5-yl)amino)methyl)benzyl)piperazin-1-yl)-3-fluorobenzonitrile
34* 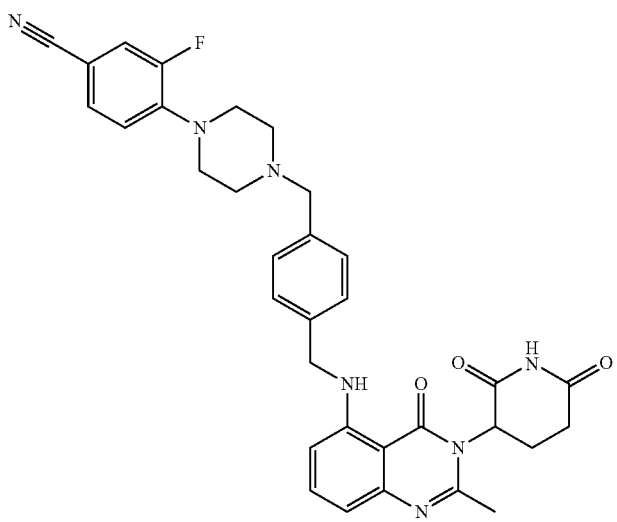 [SMILES: Cc1nc2cccc(NCc3ccc(CN4CCN(c5ccc(C#N)cc5F)CC4)cc3)c2c(=O)n1C1CCC(=O)NC1=O] 4-(4-(4-(((3-(2,6-dioxopiperidin-3-yl)-2-methyl-4-oxo-3,4-dihydroquinazolin-5-yl)amino)methyl)benzyl)piperazin-1-yl)-3-fluorobenzonitrile
35* 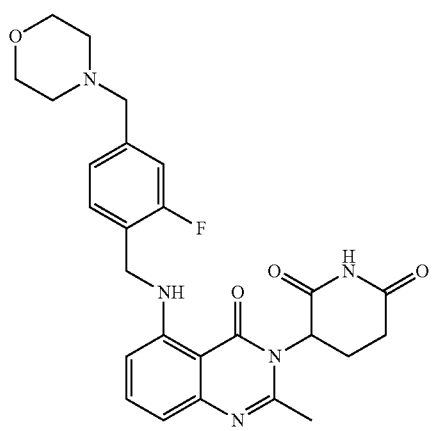 [SMILES: Cc1nc2cccc(NCc3ccc(CN4CCOCC4)cc3F)c2c(=O)n1C1CCC(=O)NC1=O] 3-(5-((2-fluoro-4-(morpholinomethyl)benzyl)amino)-2-methyl-4-oxoquinazolin-3(4H)-yl)piperidine-2,6-dione TABLE 3-continued
| | | |
|---|---|---|
| 36* | 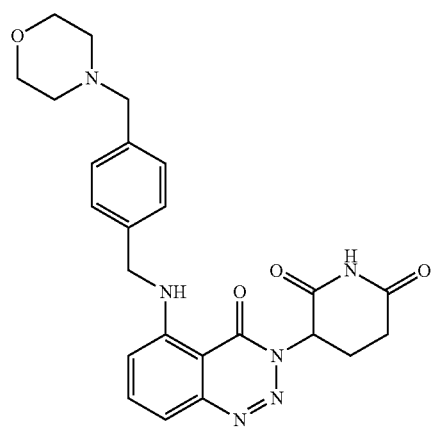 [SMILES: O=C1CCC(n2nnc3cccc(NCc4ccc(CN5CCOCC5)cc4)c3c2=O)C(=O)N1] | 3-(5-((4-(morpholinomethyl)benzyl)amino)-4-oxobenzo[d][1,2,3]triazin-3(4H)-yl)piperidine-2,6-dione |
| 37* | 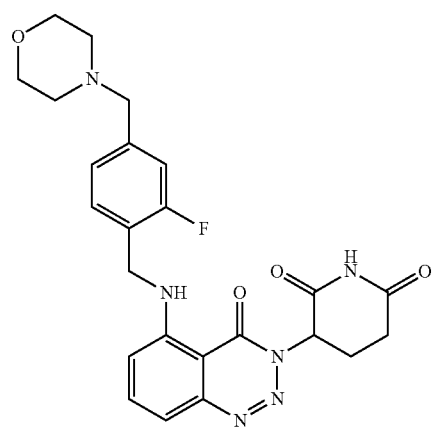 [SMILES: O=C1CCC(n2nnc3cccc(NCc4ccc(CN5CCOCC5)cc4F)c3c2=O)C(=O)N1] | 3-(5-((2-fluoro-4-(morpholinomethyl)benzyl)amino)-4-oxobenzo[d][1,2,3]triazin-3(4H)-yl)piperidine-2,6-dione |
| 38 | 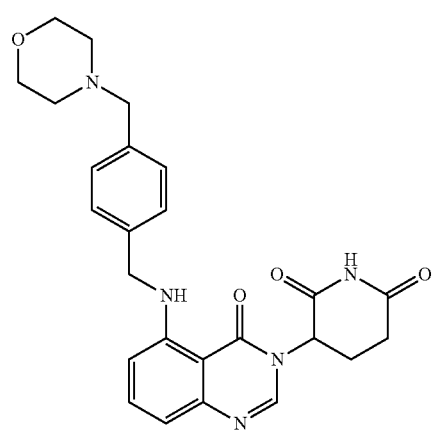 [SMILES: O=C1CCC(n2cnc3cccc(NCc4ccc(CN5CCOCC5)cc4)c3c2=O)C(=O)N1] | 3-(5-((4-(morpholinomethyl)benzyl)amino)-4-oxoquinazolin-3(4H)-yl)piperidine-2,6-dione |

TABLE 3-continued
| | | |
|---|---|---|
| 39 | 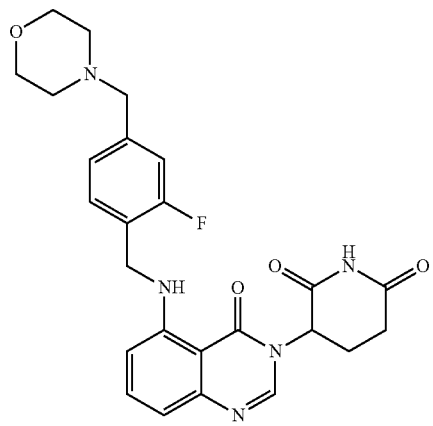 [SMILES: O=C1CCC(n2cnc3cccc(NCc4ccc(CN5CCOCC5)cc4F)c3c2=O)C(=O)N1] | 3-(5-((2-fluoro-4-(morpholinomethyl)benzyl)amino)-4-oxoquinazolin-3(4H)-yl)piperidine-2,6-dione |
| 40* | 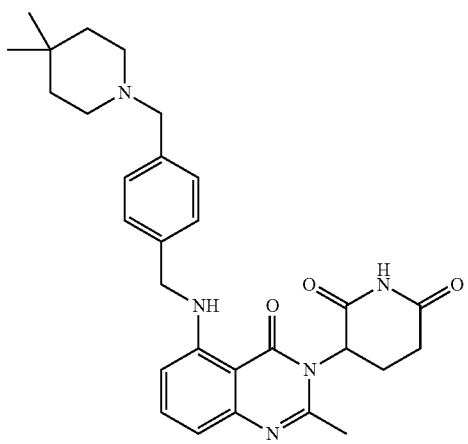 [SMILES: Cc1nc2cccc(NCc3ccc(CN4CCC(C)(C)CC4)cc3)c2c(=O)n1C1CCC(=O)NC1=O] | 3-(5-((4-((4,4-dimethylpiperidin-1-yl)methyl)benzyl)amino)-2-methyl-4-oxoquinazolin-3(4H)-yl)piperidine-2,6-dione |
| 41 | 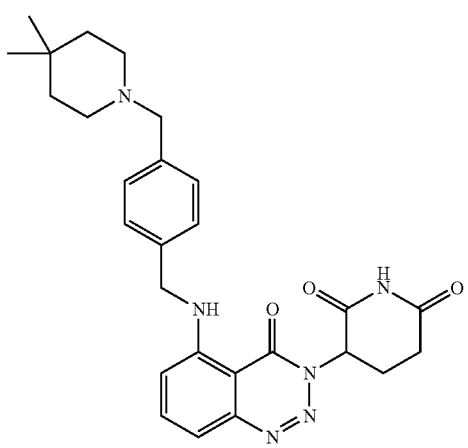 [SMILES: CC1(C)CCN(Cc2ccc(CNc3cccc4nnn(C5CCC(=O)NC5=O)c(=O)c34)cc2)CC1] | 3-(5-((4-((4,4-dimethylpiperidin-1-yl)methyl)benzyl)amino)-4-oxobenzo[d][1,2,3]triazin-3(4H)-yl)piperidine-2,6-dione |

TABLE 3-continued
| 42 | 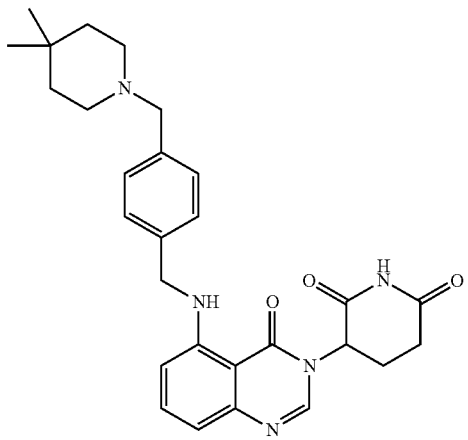 [SMILES: CC1(C)CCN(Cc2ccc(CNc3cccc4ncn(C5CCC(=O)NC5=O)c(=O)c34)cc2)CC1] | 3-(5-((4-((4,4-dimethylpiperidin-1-yl)methyl)benzyl)amino)-4-oxoquinazolin-3(4H)-yl)piperidine-2,6-dione |
| --- | --- | --- |
| 43 | 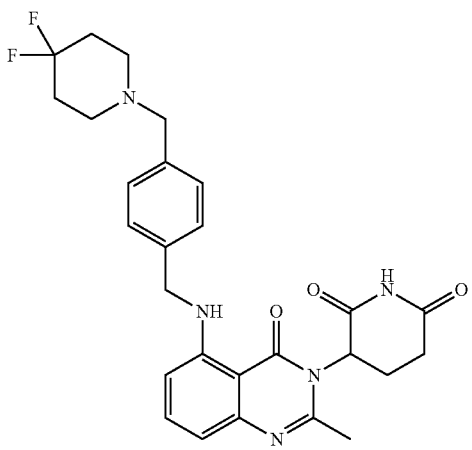 [SMILES: Cc1nc2cccc(NCc3ccc(CN4CCC(F)(F)CC4)cc3)c2c(=O)n1C1CCC(=O)NC1=O] | 3-(5-((4-((4,4-difluoropiperidin-1-yl)methyl)benzyl)amino)-2-methyl-4-oxoquinazolin-3(4H)-yl)piperidine-2,6-dione |
| 44 | 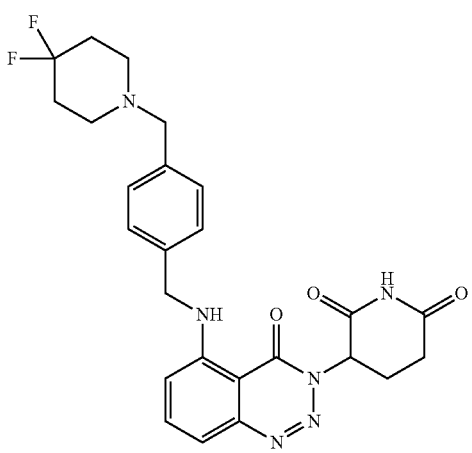 | 3-(5-((4-((4,4-difluoropiperidin-1-yl)methyl)benzyl)amino)-4-oxobenzo[d][1,2,3]triazin-3(4H)-yl)piperidine-2,6-dione |

TABLE 3-continued
| | | |
|---|---|---|
| 45 | 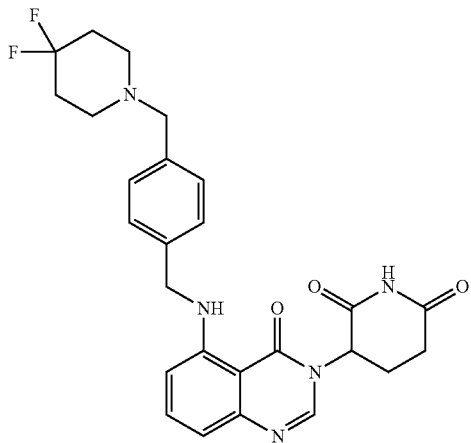 | 3-(5-(((4-((4,4-difluoropiperidin-1-yl)methyl)benzyl)amino)-4-oxoquinazolin-3(4H)-yl)piperidine-2,6-dione |
| 46 | 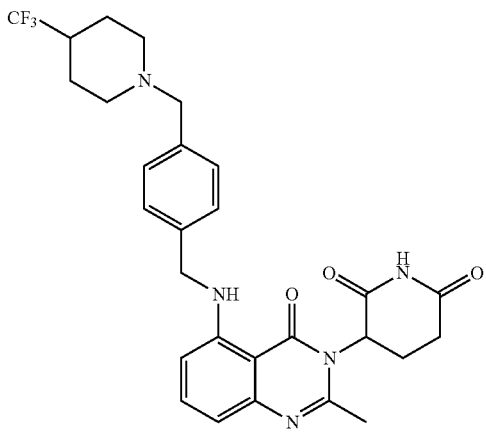 | 3-(2-methyl-4-oxo-5-(((4-((4-(trifluoromethyl)piperidin-1-yl)methyl)benzyl)amino)quinazolin-3(4H)-yl)piperidine-2,6-dione |
| 47 | 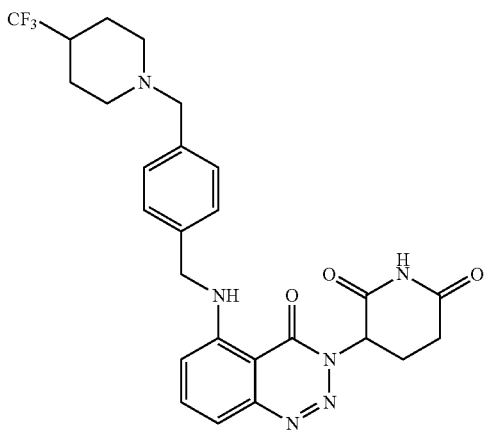 | 3-(4-oxo-5-(((4-((4-(trifluoromethyl)piperidin-1-yl)methyl)benzyl)amino)benzo[d][1,2,3]triazin-3(4H)-yl)piperidine-2,6-dione |

TABLE 3-continued
| 48 | 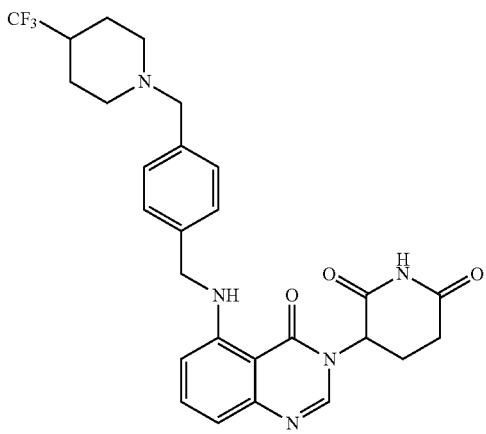 | 3-(4-oxo-5-((4-((4-(trifluoromethyl)piperidin-1-yl)methyl)benzyl)amino)quinazolin-3(4H)-yl)piperidine-2,6-dione |
| 49* | 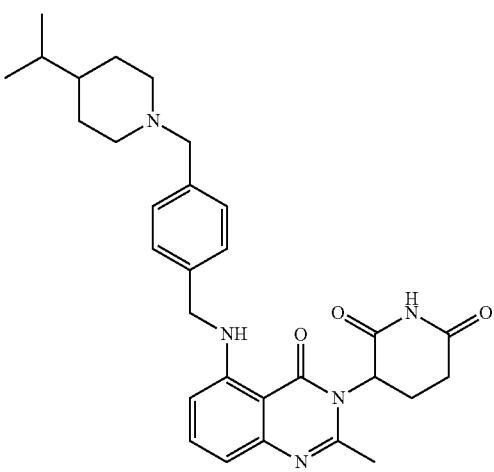 [SMILES: Cc1nc2cccc(NCc3ccc(CN4CCC(C(C)C)CC4)cc3)c2c(=O)n1C1CCC(=O)NC1=O] | 3-(5-((4-((4-isopropylpiperidin-1-yl)methyl)benzyl)amino)-2-methyl-4-oxoquinazolin-3(4H)-yl)piperidine-2,6-dione |
| 50* | 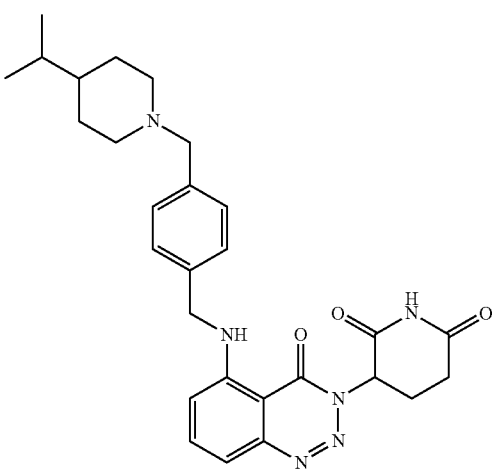 [SMILES: CC(C)C1CCN(Cc2ccc(CNc3cccc4nnn(C5CCC(=O)NC5=O)c(=O)c34)cc2)CC1] | 3-(5-((4-((4-isopropylpiperidin-1-yl)methyl)benzyl)amino)-4-oxobenzo[d][1,2,3]triazin-3(4H)-yl)piperidine-2,6-dione |

TABLE 3-continued
| 51 | 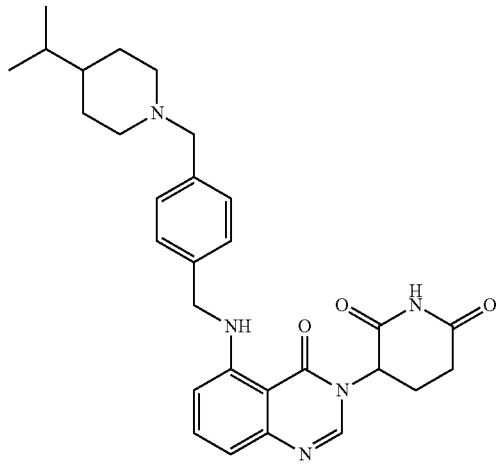 [SMILES: CC(C)C1CCN(Cc2ccc(CNc3cccc4ncn(C5CCC(=O)NC5=O)c(=O)c34)cc2)CC1] | 3-(5-((4-((4-isopropylpiperidin-1-yl)methyl)benzyl)amino)-4-oxoquinazolin-3(4H)-yl)piperidine-2,6-dione |
| 52* | 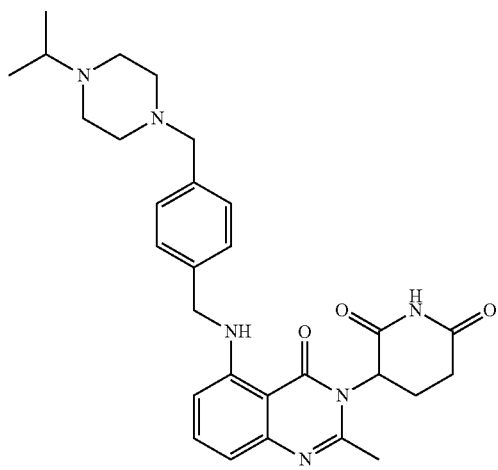 | 3-(5-((4-((4-isopropylpiperazin-1-yl)methyl)benzyl)amino)-2-methyl-4-oxoquinazolin-3(4H)-yl)piperidine-2,6-dione |
| 53 | 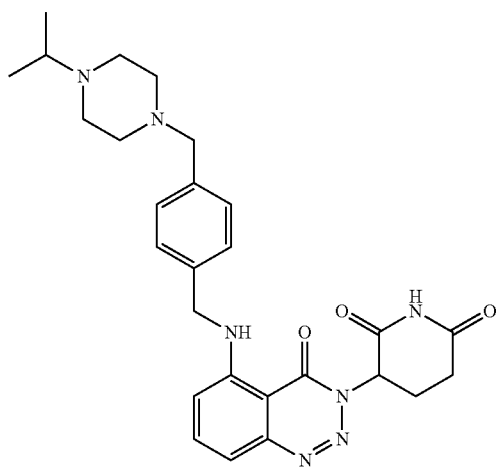 | 3-(5-((4-((4-isopropylpiperazin-1-yl)methyl)benzyl)amino)-4-oxobenzo[d][1,2,3]triazin-3(4H)-yl)piperidine-2,6-dione |

TABLE 3-continued
| | | |
|---|---|---|
| 54 | 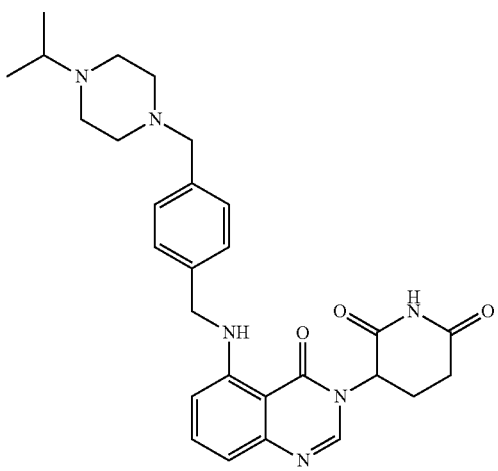 | 3-(5-(((4-((4-isopropylpiperazin-1-yl)methyl)benzyl)amino)-4-oxoquinazolin-3(4H)-yl)piperidine-2,6-dione |
| 55 | 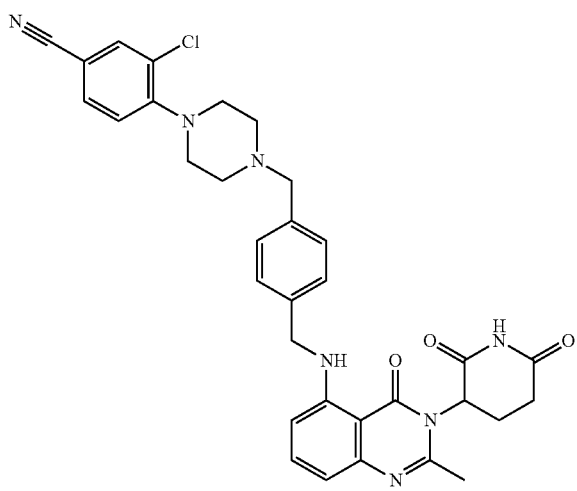 | 3-chloro-4-(4-(4-(((3-(2,6-dioxopiperidin-3-yl)-2-methyl-4-oxo-3,4-dihydroquinazolin-5-yl)amino)methyl)benzyl)piperazin-1-yl)benzonitrile |
| 56 | 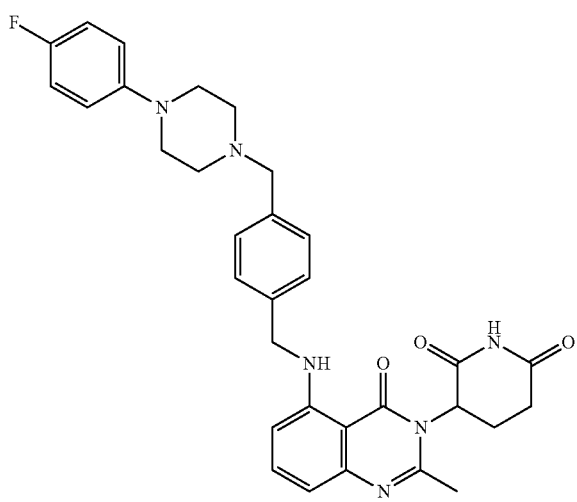 | 3-(5-(((4-((4-(4-fluorophenyl)piperazin-1-yl)methyl)benzyl)amino)-2-methyl-4-oxoquinazolin-3(4H)-yl)piperidine-2,6-dione |

TABLE 3-continued
| 57 | 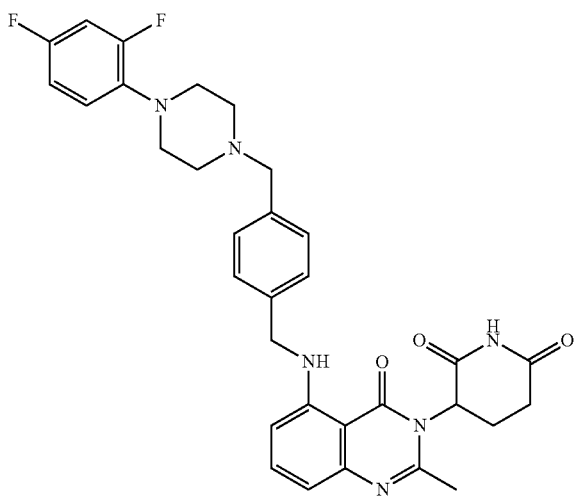 | 3-(5-((4-((4-(2,4-difluorophenyl)piperazin-1-yl)methyl)benzyl)amino)-2-methyl-4-oxoquinazolin-3(4H)-yl)piperidine-2,6-dione |
| --- | --- | --- |
| 58 | 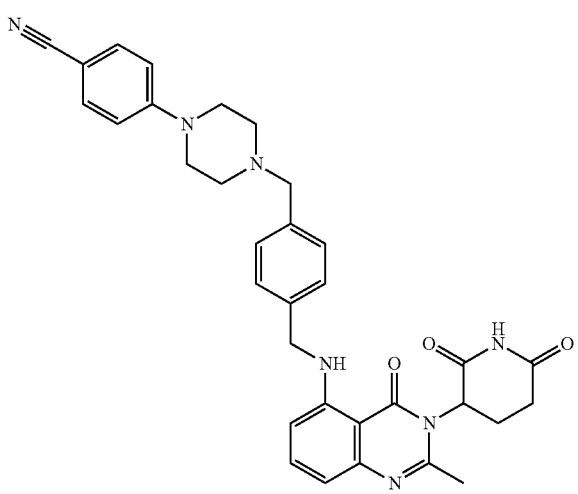 | 4-(4-(4-(((3-(2,6-dioxopiperidin-3-yl)-2-methyl-4-oxo-3,4-dihydroquinazolin-5-yl)amino)methyl)benzyl)piperazin-1-yl)benzonitrile |
| 59 | 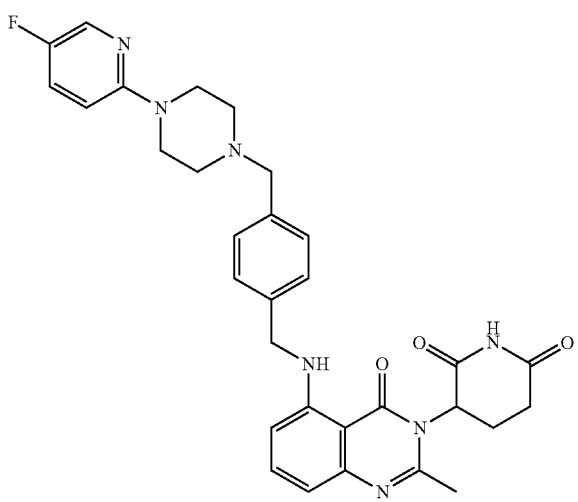 | 3-(5-((4-((4-(5-fluoropyridin-2-yl)piperazin-1-yl)methyl)benzyl)amino)-2-methyl-4-oxoquinazolin-3(4H)-yl)piperidine-2,6-dione |

| | | |
|---|---|---|
| 60 | 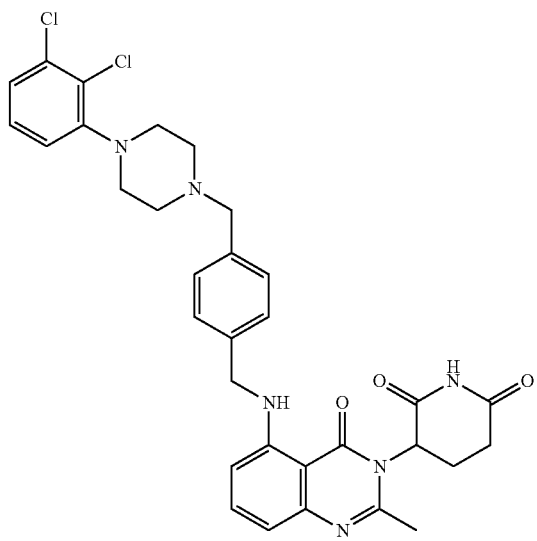 [SMILES: Cc1nc2cccc(NCc3ccc(CN4CCN(c5cccc(Cl)c5Cl)CC4)cc3)c2c(=O)n1C1CCC(=O)NC1=O] | 3-(5-((4-((4-(2,3-dichlorophenyl)piperazin-1-yl)methyl)benzyl)amino)-2-methyl-4-oxoquinazolin-3(4H)-yl)piperidine-2,6-dione |
| 61 | 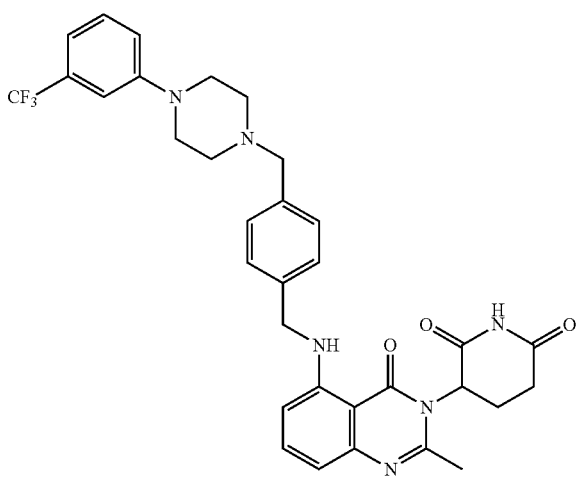 | 3-(2-methyl-4-oxo-5-((4-((4-(3-(trifluoromethyl)phenyl)piperazin-1-yl)methyl)benzyl)amino)quinazolin-3(4H)-yl)piperidine-2,6-dione |
| 62 | 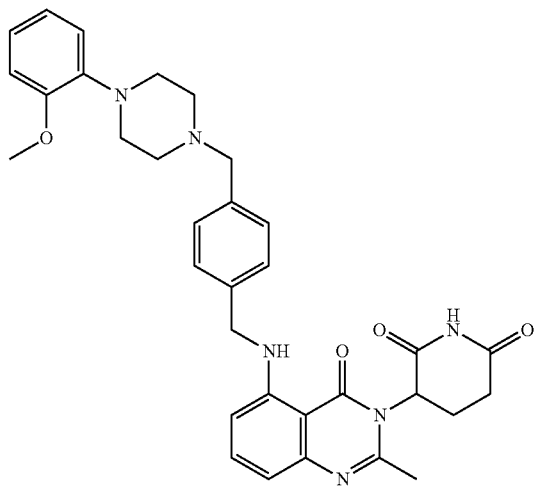 [SMILES: COc1ccccc1N1CCN(Cc2ccc(CNc3cccc4nc(C)n(C5CCC(=O)NC5=O)c(=O)c34)cc2)CC1] | 3-(5-((4-((4-(2-methoxyphenyl)piperazin-1-yl)methyl)benzyl)amino)-2-methyl-4-oxoquinazolin-3(4H)-yl)piperidine-2,6-dione |

TABLE 3-continued
| | | |
|---|---|---|
| 63* | 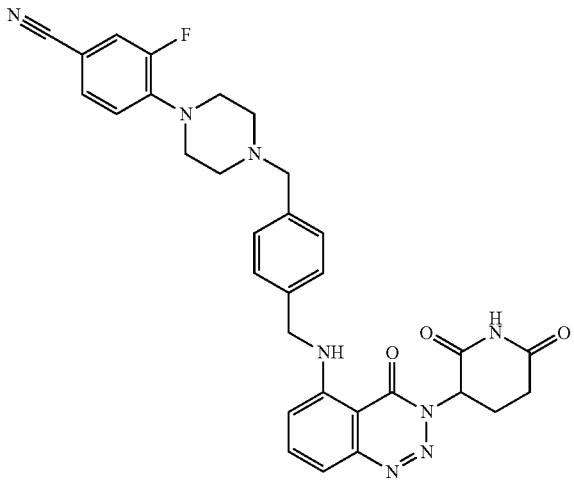 [SMILES: N#Cc1ccc(N2CCN(Cc3ccc(CNc4cccc5nnn(C6CCC(=O)NC6=O)c(=O)c45)cc3)CC2)c(F)c1] | 4-(4-(4-(((3-(2,6-dioxopiperidin-3-yl)-4-oxo-3,4-dihydrobenzo[d][1,2,3]triazin-5-yl)amino)methyl)benzyl)piperazin-1-yl)-3-fluorobenzonitrile |
| 64 | 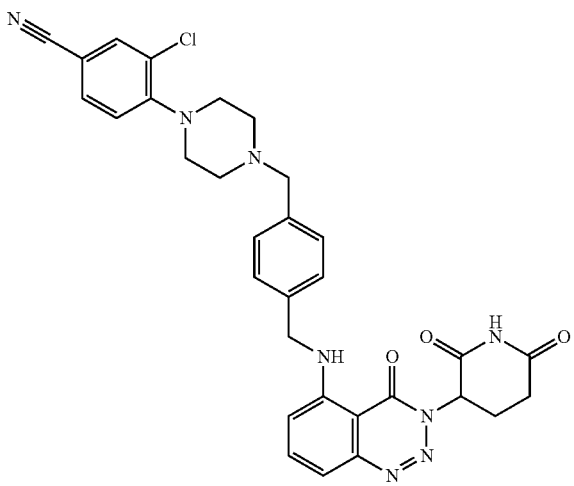 [SMILES: N#Cc1ccc(N2CCN(Cc3ccc(CNc4cccc5nnn(C6CCC(=O)NC6=O)c(=O)c45)cc3)CC2)c(Cl)c1] | 3-chloro-4-(4-(4-(((3-(2,6-dioxopiperidin-3-yl)-4-oxo-3,4-dihydrobenzo[d][1,2,3]triazin-5-yl)amino)methyl)benzyl)piperazin-1-yl)benzonitrile |
| 65 | 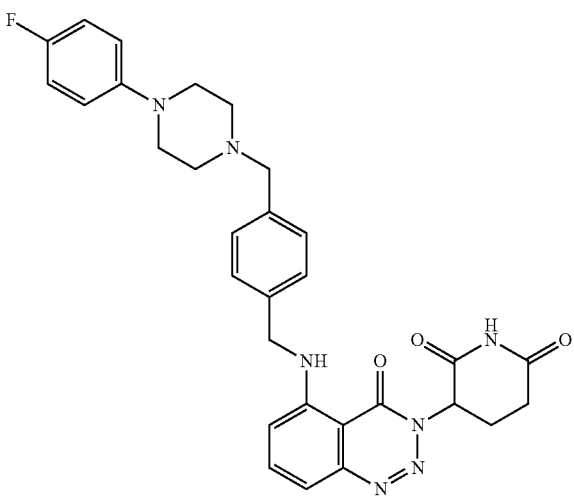 | 3-(5-((4-((4-(4-fluorophenyl)piperazin-1-yl)methyl)benzyl)amino)-4-oxobenzo[d][1,2,3]triazin-3(4H)-yl)piperidine-2,6-dione |

TABLE 3-continued
| | | |
|---|---|---|
| 66* | 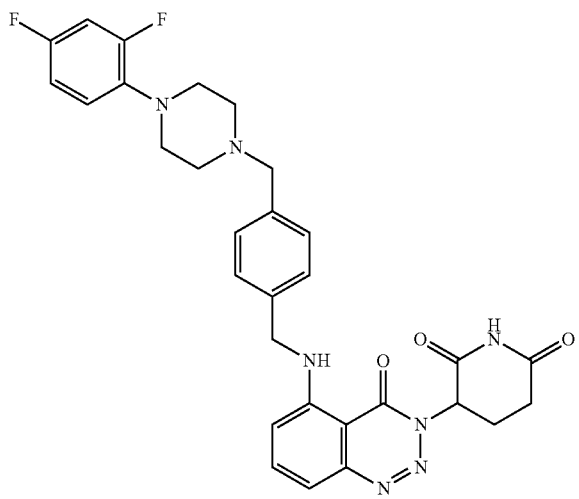 | 3-(5-((4-((4-(2,4-difluorophenyl)piperazin-1-yl)methyl)benzyl)amino)-4-oxobenzo[d][1,2,3]triazin-3(4H)-yl)piperidine-2,6-dione |
| 67 | 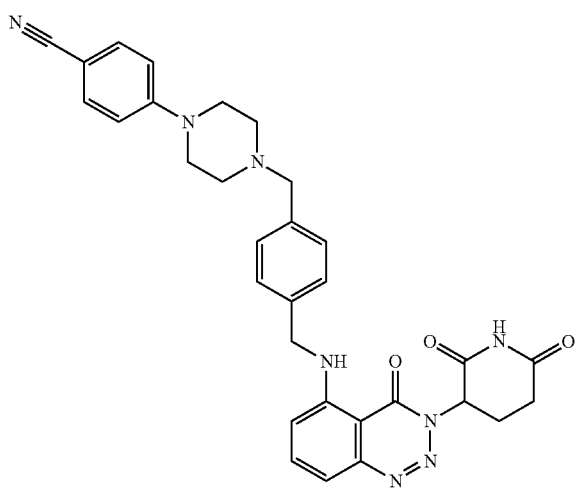 | 4-(4-(4-(((3-(2,6-dioxopiperidin-3-yl)-4-oxo-3,4-dihydrobenzo[d][1,2,3]triazin-5-yl)amino)methyl)benzyl)piperazin-1-yl)benzonitrile |
| 68* | 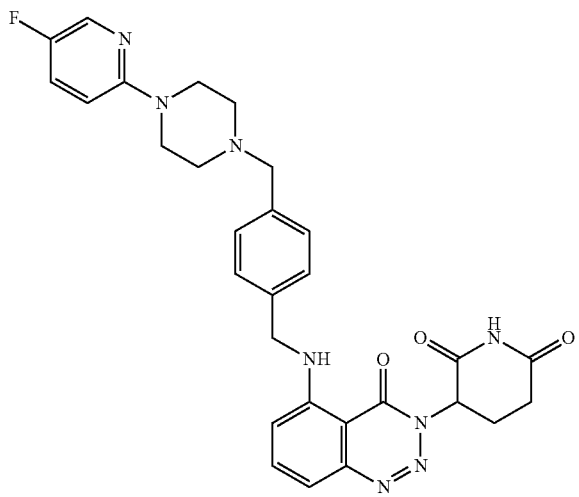 | 3-(5-((4-((4-(5-fluoropyridin-2-yl)piperazin-1-yl)methyl)benzyl)amino)-4-oxobenzo[d][1,2,3]triazin-3(4H)-yl)piperidine-2,6-dione |

TABLE 3-continued
| 69 | 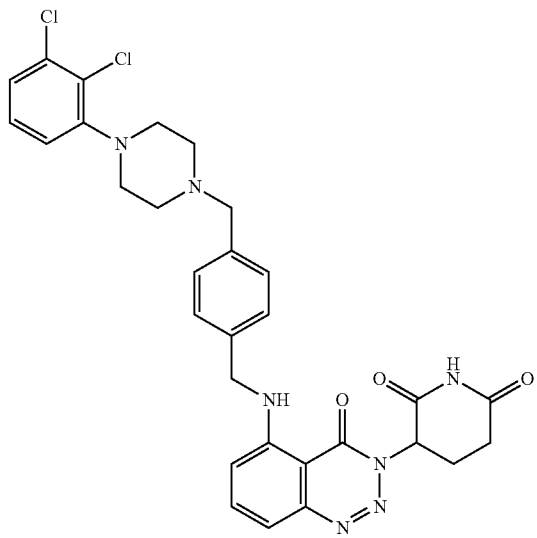 [SMILES: O=C1CCC(n2nnc3cccc(NCc4ccc(CN5CCN(c6cccc(Cl)c6Cl)CC5)cc4)c3c2=O)C(=O)N1] | 3-(5-((4-((4-(2,3-dichlorophenyl)piperazin-1-yl)methyl)benzyl)amino)-4-oxobenzo[d][1,2,3]triazin-3(4H)-yl)piperidine-2,6-dione |
| 70 | 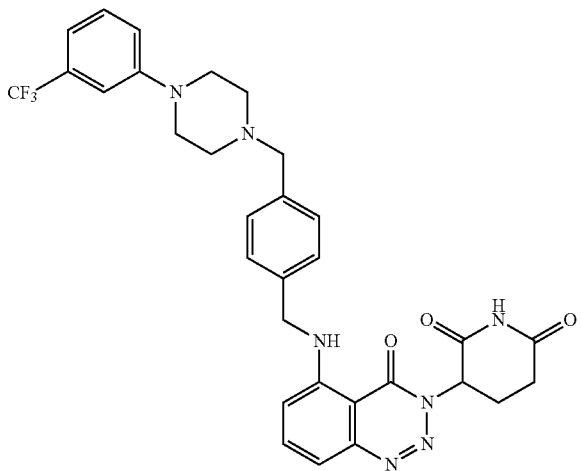 | 3-(4-oxo-5-((4-((4-(3-(trifluoromethyl)phenyl)piperazin-1-yl)methyl)benzyl)amino)benzo[d][1,2,3]triazin-3(4H)-yl)piperidine-2,6-dione |
| 71 | 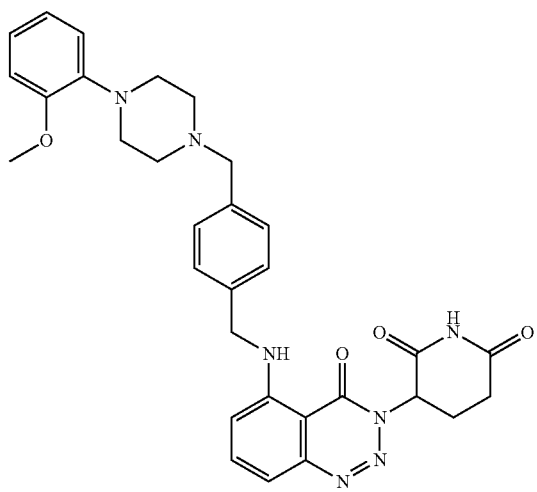 [SMILES: COc1ccccc1N1CCN(Cc2ccc(CNc3cccc4nnn(C5CCC(=O)NC5=O)c(=O)c34)cc2)CC1] | 3-(5-((4-((4-(2-methoxyphenyl)piperazin-1-yl)methyl)benzyl)amino)-4-oxobenzo[d][1,2,3]triazin-3(4H)-yl)piperidine-2,6-dione |

TABLE 3-continued
| 72 | 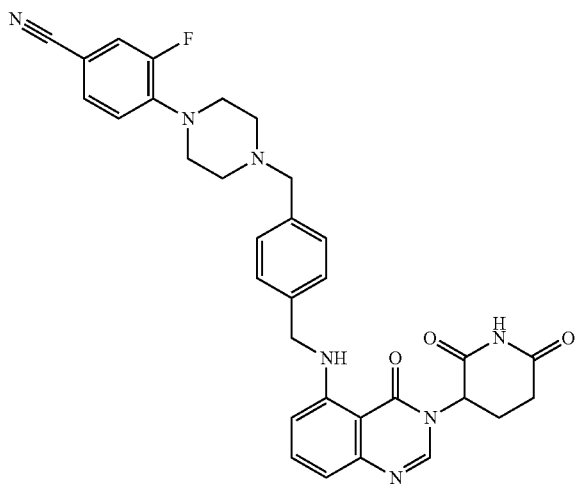 [SMILES: N#Cc1ccc(N2CCN(Cc3ccc(CNc4cccc5ncn(C6CCC(=O)NC6=O)c(=O)c45)cc3)CC2)c(F)c1] | 4-(4-(4-(((3-(2,6-dioxopiperidin-3-yl)-4-oxo-3,4-dihydroquinazolin-5-yl)amino)methyl)benzyl)piperazin-1-yl)-3-fluorobenzonitrile |
| --- | --- | --- |
| 73 | 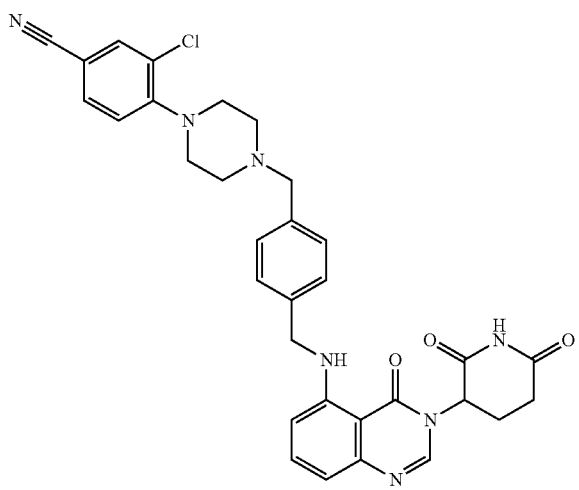 [SMILES: N#Cc1ccc(N2CCN(Cc3ccc(CNc4cccc5ncn(C6CCC(=O)NC6=O)c(=O)c45)cc3)CC2)c(Cl)c1] | 3-chloro-4-(4-(4-(((3-(2,6-dioxopiperidin-3-yl)-4-oxo-3,4-dihydroquinazolin-5-yl)amino)methyl)benzyl)piperazin-1-yl)benzonitrile |
| 74 | 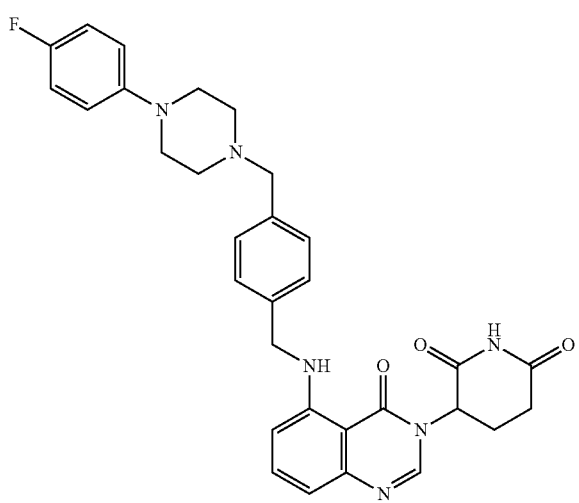 | 3-(5-((4-((4-(4-fluorophenyl)piperazin-1-yl)methyl)benzyl)amino)-4-oxoquinazolin-3(4H)-yl)piperidine-2,6-dione |

| | | |
|---|---|---|
| 75 | 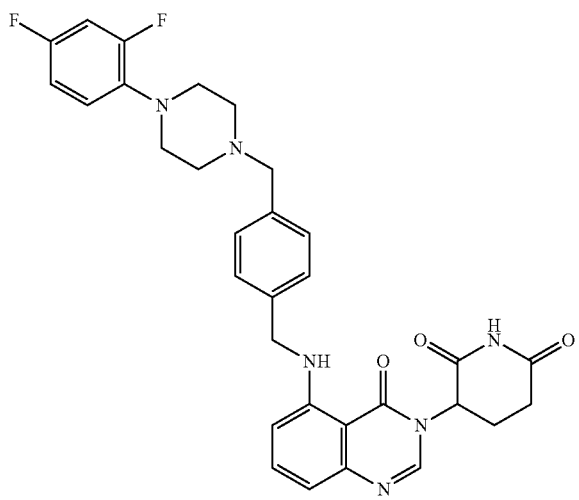 | 3-(5-((4-((4-(2,4-difluorophenyl)piperazin-1-yl)methyl)benzyl)amino)-4-oxoquinazolin-3(4H)-yl)piperidine-2,6-dione |
| 76 | 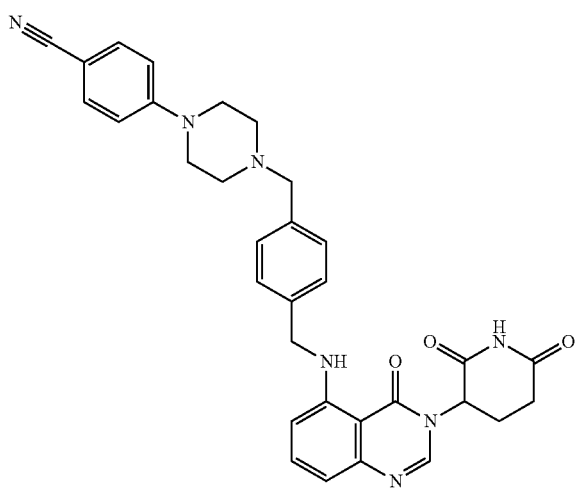 | 4-(4-(4-(((3-(2,6-dioxopiperidin-3-yl)-4-oxo-3,4-dihydroquinazolin-5-yl)amino)methyl)benzyl)piperazin-1-yl)benzonitrile |
| 77 | 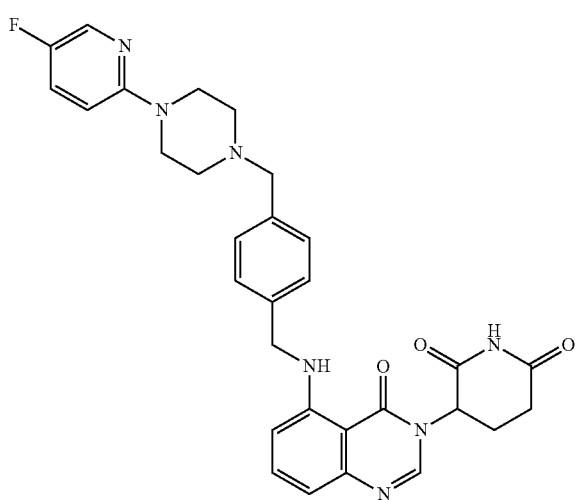 | 3-(5-((4-((4-(5-fluoropyridin-2-yl)piperazin-1-yl)methyl)benzyl)amino)-4-oxoquinazolin-3(4H)-yl)piperidine-2,6-dione |

TABLE 3-continued
| | | |
|---|---|---|
| 78 | 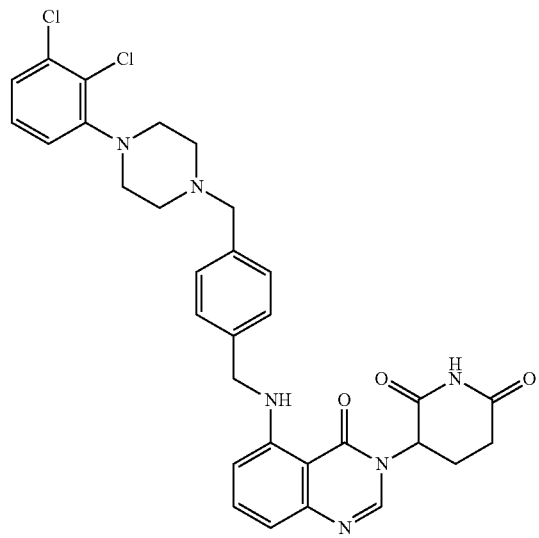 [SMILES: O=C1CCC(n2cnc3cccc(NCc4ccc(CN5CCN(c6cccc(Cl)c6Cl)CC5)cc4)c3c2=O)C(=O)N1] | 3-(5-((4-((4-(2,3-dichlorophenyl)piperazin-1-yl)methyl)benzyl)amino)-4-oxoquinazolin-3(4H)-yl)piperidine-2,6-dione |
| 79 | 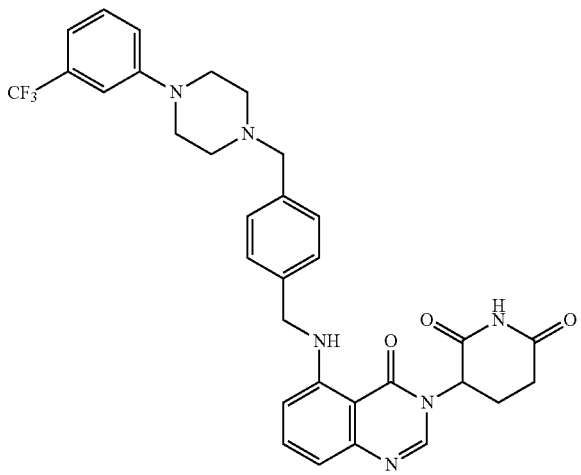 | 3-(4-oxo-5-((4-((4-(3-(trifluoromethyl)phenyl)piperazin-1-yl)methyl)benzyl)amino)quinazolin-3(4H)-yl)piperidine-2,6-dione |
| 80 | 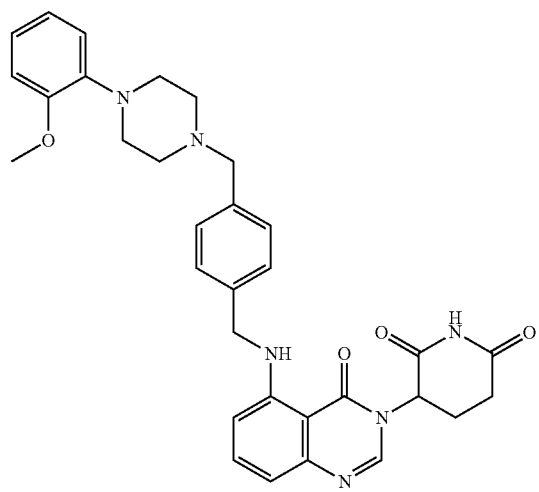 [SMILES: COc1ccccc1N1CCN(Cc2ccc(CNc3cccc4ncn(C5CCC(=O)NC5=O)c(=O)c34)cc2)CC1] | 3-(5-((4-((4-(2-methoxyphenyl)piperazin-1-yl)methyl)benzyl)amino)-4-oxoquinazolin-3(4H)-yl)piperidine-2,6-dione |

TABLE 3-continued

| | | |
|---|---|---|
| 81 | 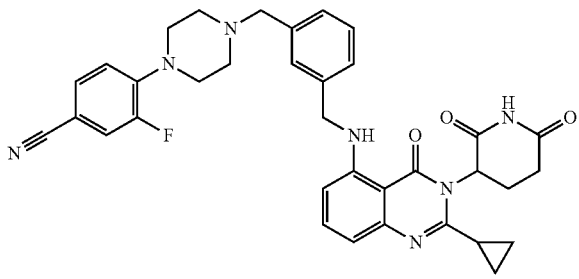 [SMILES: N#Cc1ccc(N2CCN(Cc3cccc(CNc4cccc5nc(C6CC6)n(C6CCC(=O)NC6=O)c(=O)c45)c3)CC2)c(F)c1] | 4-(4-(3-(((2-cyclopropyl-3-(2,6-dioxopiperidin-3-yl)-4-oxo-3,4-dihydroquinazolin-5-yl)amino)methyl)benzyl)piperazin-1-yl)-3-fluorobenzonitrile |
| 82* | 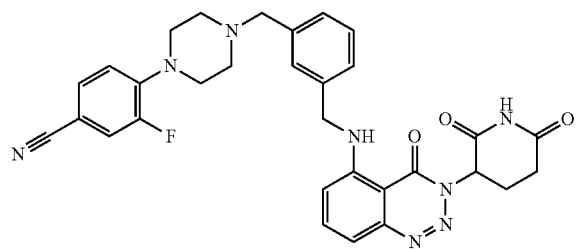 [SMILES: N#Cc1ccc(N2CCN(Cc3cccc(CNc4cccc5nnn(C6CCC(=O)NC6=O)c(=O)c45)c3)CC2)c(F)c1] | 4-(4-(3-(((3-(2,6-dioxopiperidin-3-yl)-4-oxo-3,4-dihydrobenzo[d][1,2,3]triazin-5-yl)amino)methyl)benzyl)piperazin-1-yl)-3-fluorobenzonitrile |
| 83 | 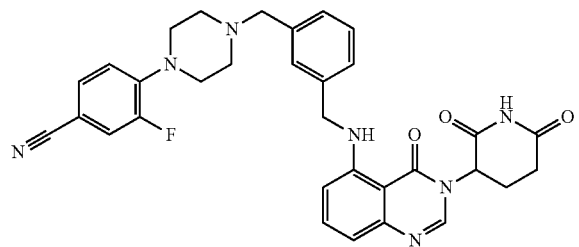 [SMILES: N#Cc1ccc(N2CCN(Cc3cccc(CNc4cccc5ncn(C6CCC(=O)NC6=O)c(=O)c45)c3)CC2)c(F)c1] | 4-(4-(3-(((3-(2,6-dioxopiperidin-3-yl)-4-oxo-3,4-dihydroquinazolin-5-yl)amino)methyl)benzyl)piperazin-1-yl)-3-fluorobenzonitrile |
| 84 | 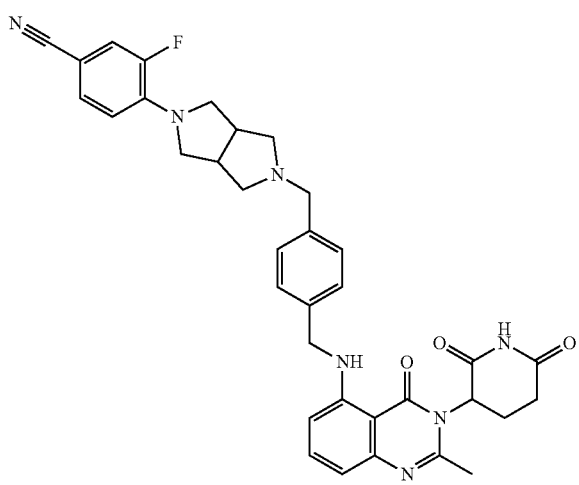 [SMILES: Cc1nc2cccc(NCc3ccc(CN4CC5CN(c6ccc(C#N)cc6F)CC5C4)cc3)c2c(=O)n1C1CCC(=O)NC1=O] | 4-(5-(4-(((3-(2,6-dioxopiperidin-3-yl)-2-methyl-4-oxo-3,4-dihydroquinazolin-5-yl)amino)methyl)benzyl)hexahydropyrrolo[3,4-c]pyrrol-2(1H)-yl)-3-fluorobenzonitrile |

TABLE 3-continued

| 85 | 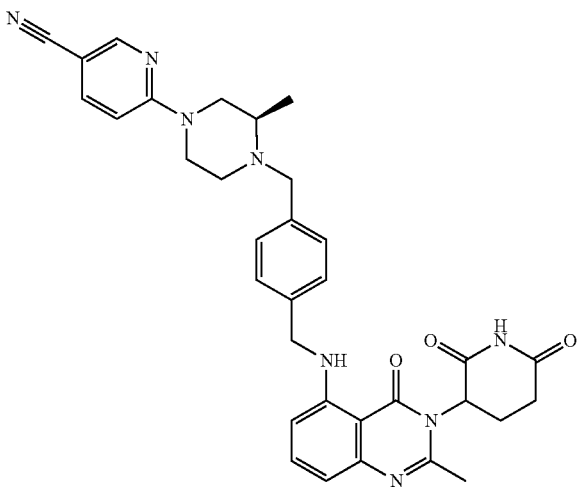 [SMILES: Cc1nc2cccc(NCc3ccc(CN4CCN(c5ccc(C#N)cn5)C[C@H]4C)cc3)c2c(=O)n1C1CCC(=O)NC1=O] | 6-((3R)-4-(4-(((3-(2,6-dioxopiperidin-3-yl)-2-methyl-4-oxo-3,4-dihydroquinazolin-5-yl)amino)methyl)benzyl)-3-methylpiperazin-1-yl)nicotinonitrile |
| --- | --- | --- |
| 86 | 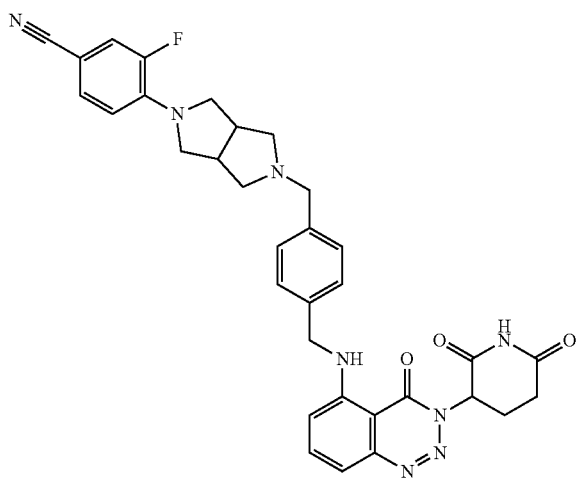 | 4-(5-(4-(((3-(2,6-dioxopiperidin-3-yl)-4-oxo-3,4-dihydrobenzo[d][1,2,3]triazin-5-yl)amino)methyl)benzyl)hexahydropyrrolo[3,4-c]pyrrol-2(1H)-yl)-3-fluorobenzonitrile |
| 87 | 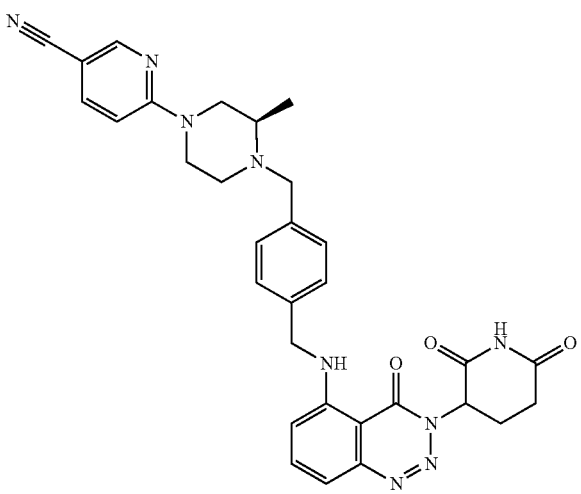 [SMILES: C[C@@H]1CN(c2ccc(C#N)cn2)CCN1Cc1ccc(CNc2cccc3nnn(C4CCC(=O)NC4=O)c(=O)c23)cc1] | 6-((3R)-4-(4-(((3-(2,6-dioxopiperidin-3-yl)-4-oxo-3,4-dihydrobenzo[d][1,2,3]triazin-5-yl)amino)methyl)benzyl)-3-methylpiperazin-1-yl)nicotinonitrile |

| | | |
|---|---|---|
| 88 | 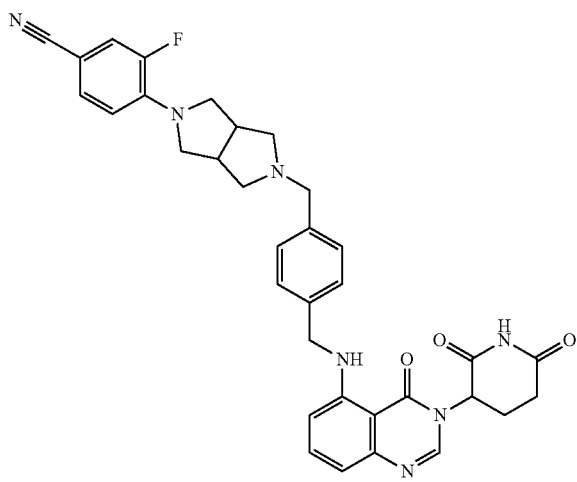 [SMILES: N#Cc1ccc(N2CC3CN(Cc4ccc(CNc5cccc6ncn(C7CCC(=O)NC7=O)c(=O)c56)cc4)CC3C2)c(F)c1] | 4-(5-(4-(((3-(2,6-dioxopiperidin-3-yl)-4-oxo-3,4-dihydroquinazolin-5-yl)amino)methyl)benzyl)hexahydropyrrolo[3,4-c]pyrrol-2(1H)-yl)-3-fluorobenzonitrile |
| 89 | 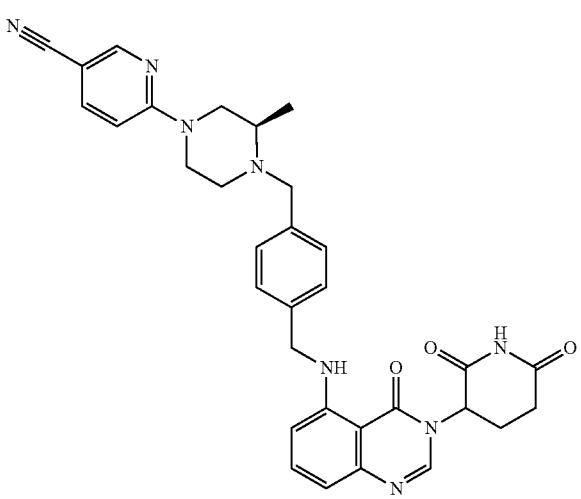 [SMILES: C[C@@H]1CN(c2ccc(C#N)cn2)CCN1Cc1ccc(CNc2cccc3ncn(C4CCC(=O)NC4=O)c(=O)c23)cc1] | 6-((3R)-4-(4-(((3-(2,6-dioxopiperidin-3-yl)-4-oxo-3,4-dihydroquinazolin-5-yl)amino)methyl)benzyl)-3-methylpiperazin-1-yl)nicotinonitrile |
| 90* | 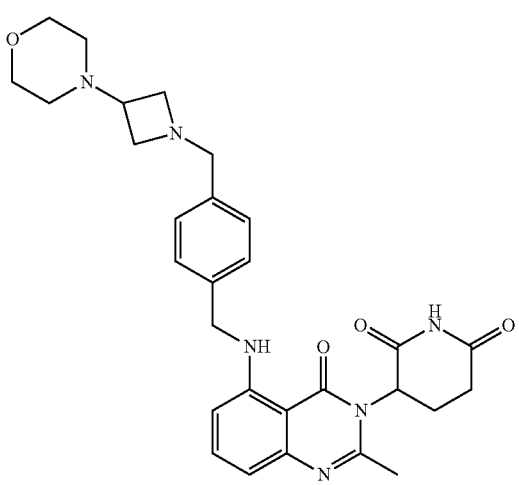 [SMILES: Cc1nc2cccc(NCc3ccc(CN4CC(N5CCOCC5)C4)cc3)c2c(=O)n1C1CCC(=O)NC1=O] | 3-(2-methyl-5-((4-((3-morpholinoazetidin-1-yl)methyl)benzyl)amino)-4-oxoquinazolin-3(4H)-yl)piperidine-2,6-dione |

TABLE 3-continued
| | | |
|---|---|---|
| 91* | 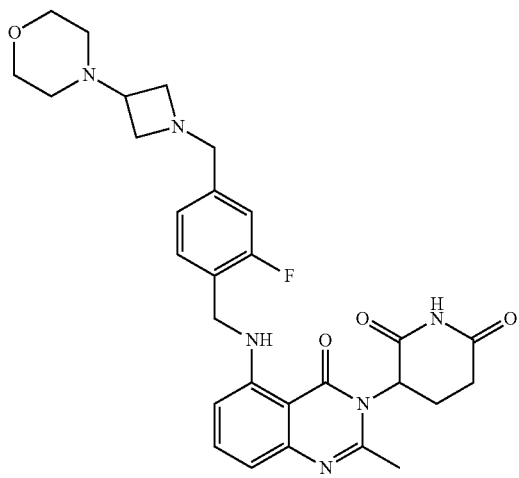 | 3-(5-(((2-fluoro-4-((3-morpholinoazetidin-1-yl)methyl)benzyl)amino)-2-methyl-4-oxoquinazolin-3(4H)-yl)piperidine-2,6-dione |
| 92 | 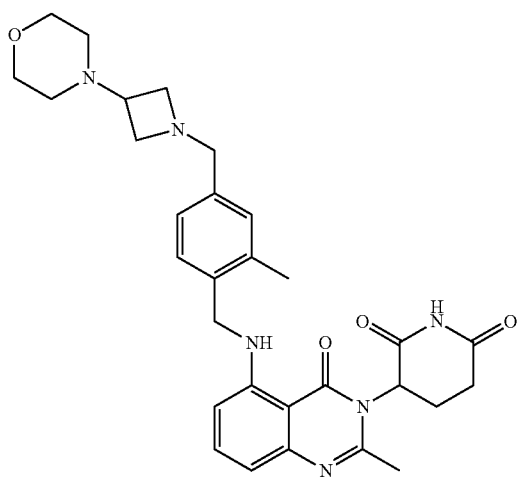 [SMILES: Cc1cc(CN2CC(N3CCOCC3)C2)ccc1CNc1cccc2nc(C)n(C3CCC(=O)NC3=O)c(=O)c12] | 3-(2-methyl-5-((2-methyl-4-((3-morpholinoazetidin-1-yl)methyl)benzyl)amino)-4-oxoquinazolin-3(4H)-yl)piperidine-2,6-dione |
| 93* | 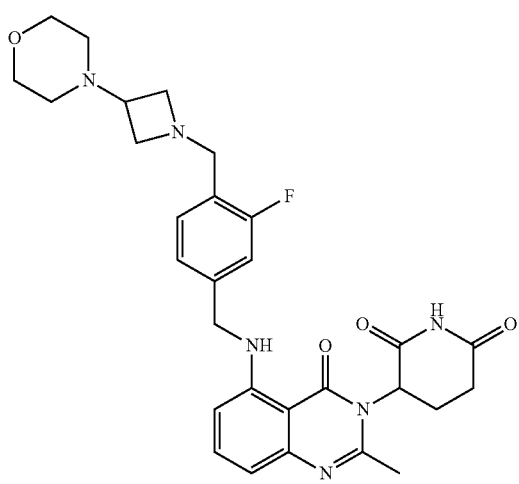 [SMILES: Cc1nc2cccc(NCc3ccc(CN4CC(N5CCOCC5)C4)c(F)c3)c2c(=O)n1C1CCC(=O)NC1=O] | 3-(5-(((3-fluoro-4-((3-morpholinoazetidin-1-yl)methyl)benzyl)amino)-2-methyl-4-oxoquinazolin-3(4H)-yl)piperidine-2,6-dione |

TABLE 3-continued
| 94 | 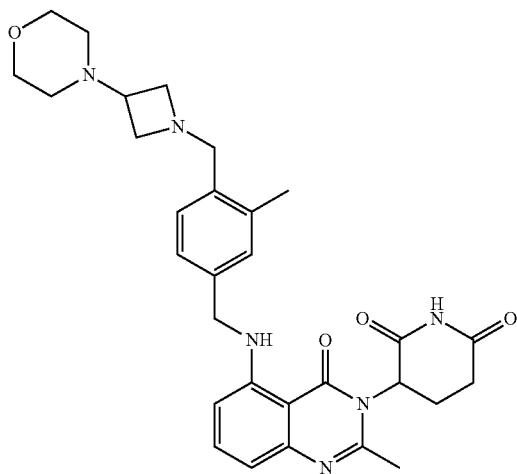 [SMILES: Cc1cc(CNc2cccc3nc(C)n(C4CCC(=O)NC4=O)c(=O)c23)ccc1CN1CC(N2CCOCC2)C1] | 3-(2-methyl-5-((3-methyl-4-((3-morpholinoazetidin-1-yl)methyl)benzyl)amino)-4-oxoquinazolin-3(4H)-yl)piperidine-2,6-dione |
| 95* | 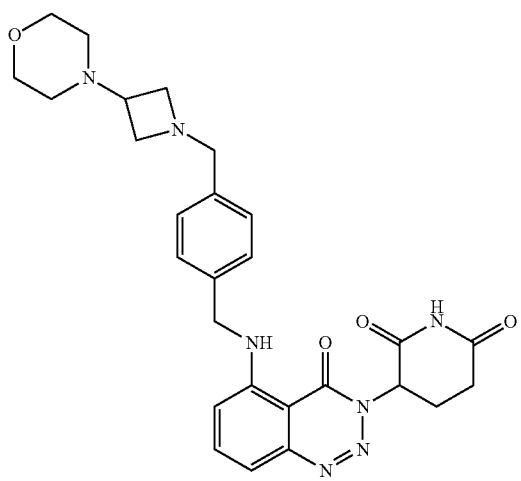 | 3-(5-((4-((3-morpholinoazetidin-1-yl)methyl)benzyl)amino)-4-oxobenzo[d][1,2,3]triazin-3(4H)-yl)piperidine-2,6-dione |
| 96* | 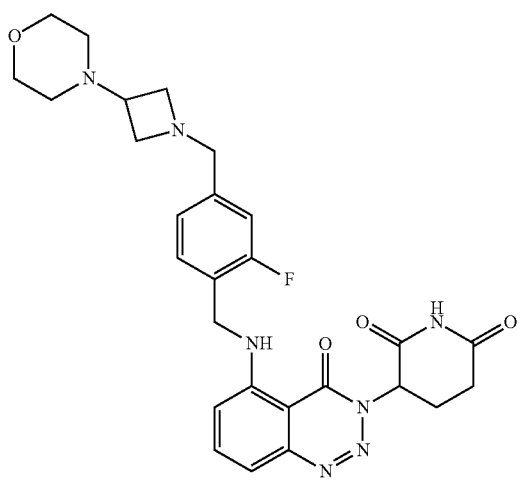 | 3-(5-((2-fluoro-4-((3-morpholinoazetidin-1-yl)methyl)benzyl)amino)-4-oxobenzo[d][1,2,3]triazin-3(4H)-yl)piperidine-2,6-dione |

TABLE 3-continued
| 97 | 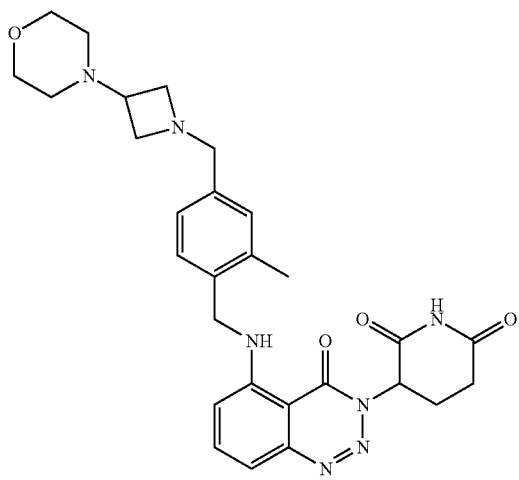 [SMILES: Cc1cc(CN2CC(N3CCOCC3)C2)ccc1CNc1cccc2nnn(C3CCC(=O)NC3=O)c(=O)c12] | 3-(5-((2-methyl-4-((3-morpholinoazetidin-1-yl)methyl)benzyl)amino)-4-oxobenzo[d][1,2,3]triazin-3(4H)-yl)piperidine-2,6-dione |
| 98* | 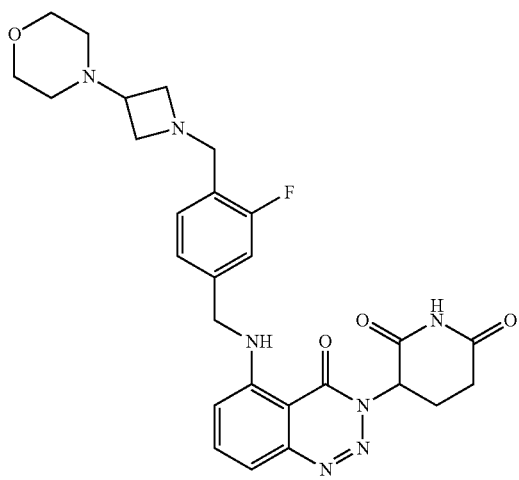 [SMILES: O=C1CCC(n2nnc3cccc(NCc4ccc(CN5CC(N6CCOCC6)C5)c(F)c4)c3c2=O)C(=O)N1] | 3-(5-((3-fluoro-4-((3-morpholinoazetidin-1-yl)methyl)benzyl)amino)-4-oxobenzo[d][1,2,3]triazin-3(4H)-yl)piperidine-2,6-dione |
| 99 | 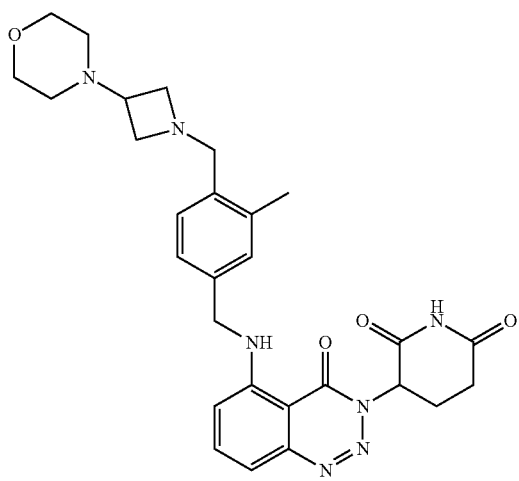 [SMILES: Cc1cc(CNc2cccc3nnn(C4CCC(=O)NC4=O)c(=O)c23)ccc1CN1CC(N2CCOCC2)C1] | 3-(5-((3-methyl-4-((3-morpholinoazetidin-1-yl)methyl)benzyl)amino)-4-oxobenzo[d][1,2,3]triazin-3(4H)-yl)piperidine-2,6-dione |

TABLE 3-continued
| 100 | 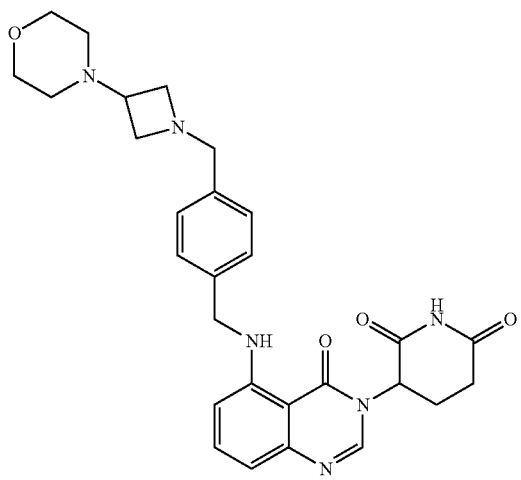 [SMILES: O=C1CCC(n2cnc3cccc(NCc4ccc(CN5CC(N6CCOCC6)C5)cc4)c3c2=O)C(=O)N1] | 3-(5-((4-((3-morpholinoazetidin-1-yl)methyl)benzyl)amino)-4-oxoquinazolin-3(4H)-yl)piperidine-2,6-dione |
| 101* | 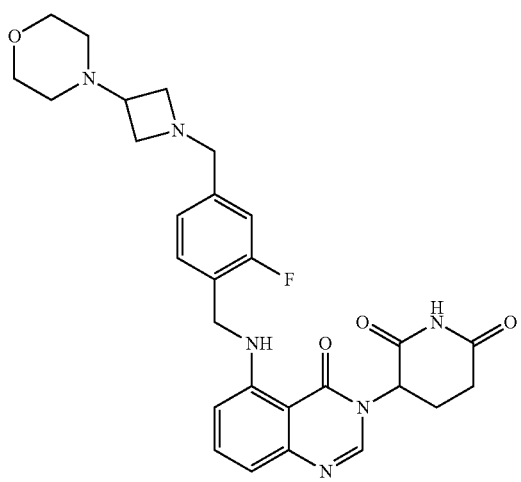 [SMILES: O=C1CCC(n2cnc3cccc(NCc4ccc(CN5CC(N6CCOCC6)C5)cc4F)c3c2=O)C(=O)N1] | 3-(5-((2-fluoro-4-((3-morpholinoazetidin-1-yl)methyl)benzyl)amino)-4-oxoquinazolin-3(4H)-yl)piperidine-2,6-dione |
| 102 | 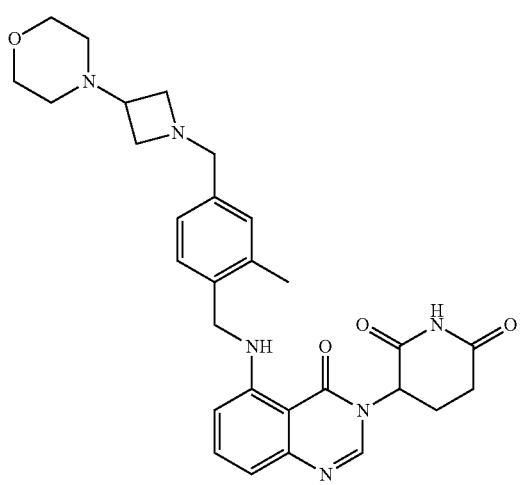 [SMILES: Cc1cc(CN2CC(N3CCOCC3)C2)ccc1CNc1cccc2ncn(C3CCC(=O)NC3=O)c(=O)c12] | 3-(5-((2-methyl-4-((3-morpholinoazetidin-1-yl)methyl)benzyl)amino)-4-oxoquinazolin-3(4H)-yl)piperidine-2,6-dione |

| | | |
|---|---|---|
| 103 | 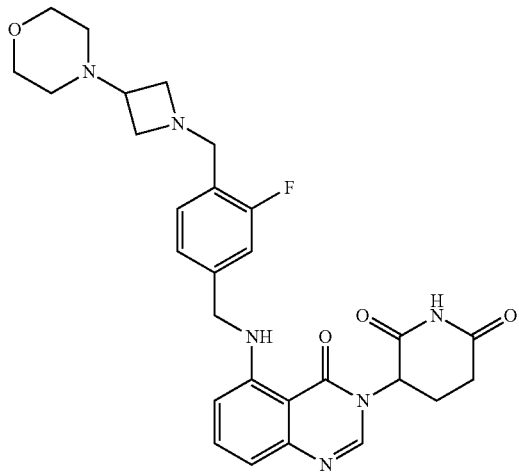 [SMILES: O=C1CCC(n2cnc3cccc(NCc4ccc(CN5CC(N6CCOCC6)C5)c(F)c4)c3c2=O)C(=O)N1] | 3-(5-(((3-fluoro-4-((3-morpholinoazetidin-1-yl)methyl)benzyl)amino)-4-oxoquinazolin-3(4H)-yl)piperidine-2,6-dione |
| 104 | 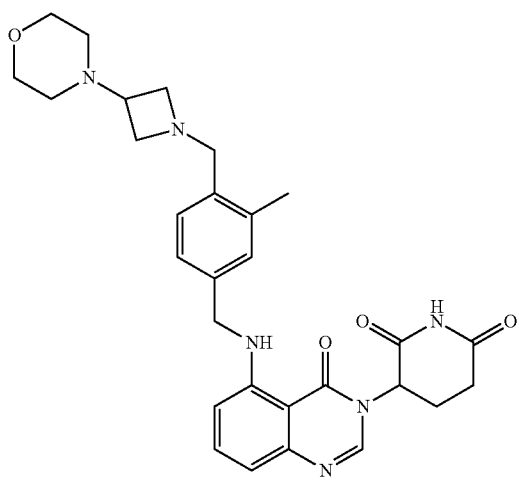 [SMILES: Cc1cc(CNc2cccc3ncn(C4CCC(=O)NC4=O)c(=O)c23)ccc1CN1CC(N2CCOCC2)C1] | 3-(5-(((3-methyl-4-((3-morpholinoazetidin-1-yl)methyl)benzyl)amino)-4-oxoquinazolin-3(4H)-yl)piperidine-2,6-dione |
| 105 | 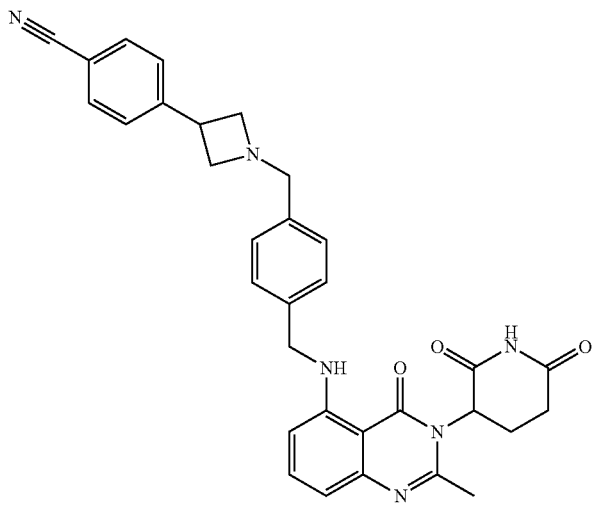 [SMILES: Cc1nc2cccc(NCc3ccc(CN4CC(c5ccc(C#N)cc5)C4)cc3)c2c(=O)n1C1CCC(=O)NC1=O] | 4-(1-(4-(((3-(2,6-dioxopiperidin-3-yl)-2-methyl-4-oxo-3,4-dihydroquinazolin-5-yl)amino)methyl)benzyl)azetidin-3-yl)benzonitrile |

TABLE 3-continued
| 106 | 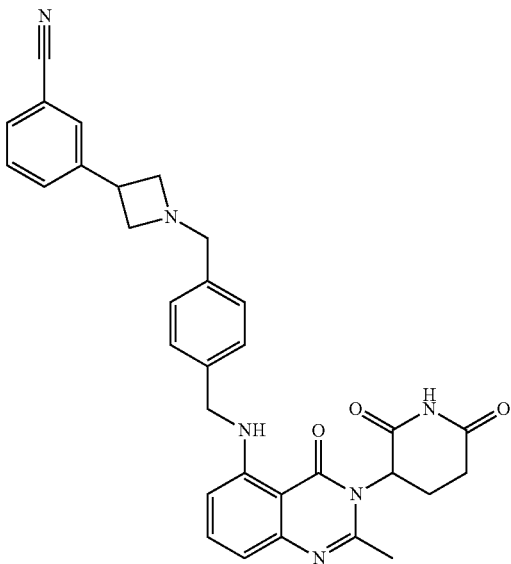 [SMILES: Cc1nc2cccc(NCc3ccc(CN4CC(c5cccc(C#N)c5)C4)cc3)c2c(=O)n1C1CCC(=O)NC1=O] | 3-(1-(4-(((3-(2,6-dioxopiperidin-3-yl)-2-methyl-4-oxo-3,4-dihydroquinazolin-5-yl)amino)methyl)benzyl)azetidin-3-yl)benzonitrile |
| --- | --- | --- |
| 107 | 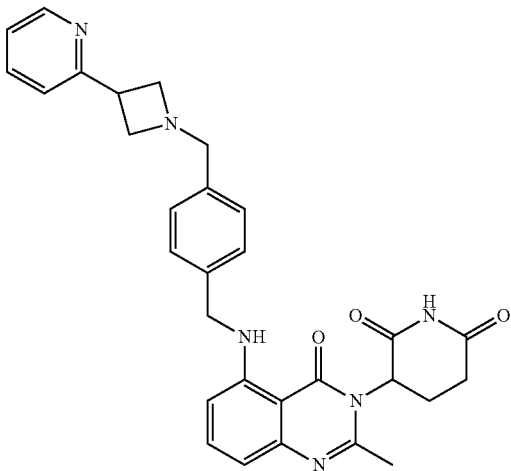 [SMILES: Cc1nc2cccc(NCc3ccc(CN4CC(c5ccccn5)C4)cc3)c2c(=O)n1C1CCC(=O)NC1=O] | 3-(2-methyl-4-oxo-5-((4-((3-(pyridin-2-yl)azetidin-1-yl)methyl)benzyl)amino)quinazolin-3(4H)-yl)piperidine-2,6-dione |
| 108 | 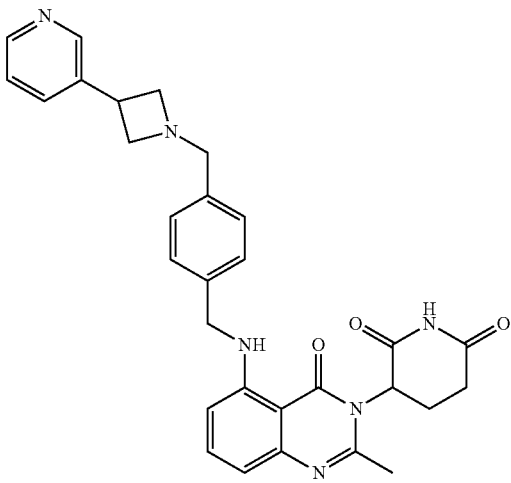 [SMILES: Cc1nc2cccc(NCc3ccc(CN4CC(c5cccnc5)C4)cc3)c2c(=O)n1C1CCC(=O)NC1=O] | 3-(2-methyl-4-oxo-5-((4-((3-(pyridin-3-yl)azetidin-1-yl)methyl)benzyl)amino)quinazolin-3(4H)-yl)piperidine-2,6-dione |

TABLE 3-continued
| 109 | 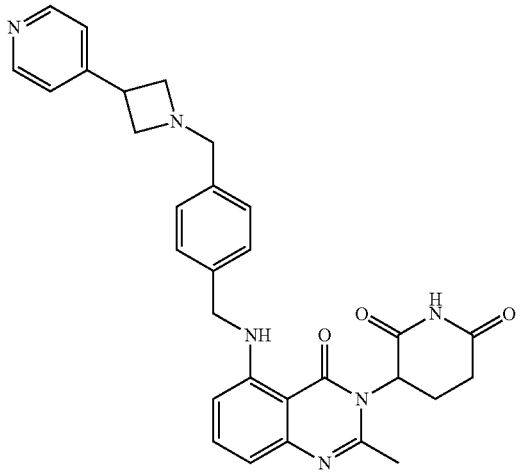 | 3-(2-methyl-4-oxo-5-((4-((3-(pyridin-4-yl)azetidin-1-yl)methyl)benzyl)amino)quinazolin-3(4H)-yl)piperidine-2,6-dione |
| 110 | 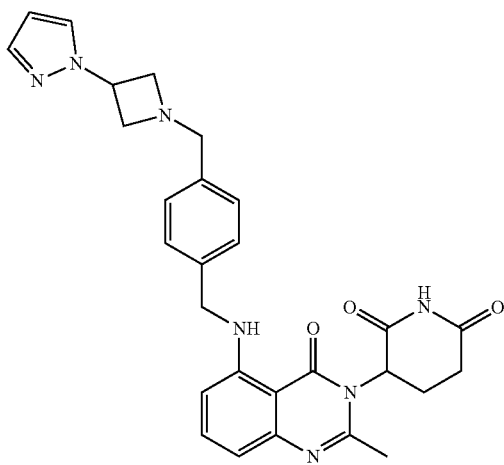 [SMILES: Cc1nc2cccc(NCc3ccc(CN4CC(n5cccn5)C4)cc3)c2c(=O)n1C1CCC(=O)NC1=O] | 3-(5-((4-((3-(1H-pyrazol-1-yl)azetidin-1-yl)methyl)benzyl)amino)-2-methyl-4-oxoquinazolin-3(4H)-yl)piperidine-2,6-dione |
| 111 | 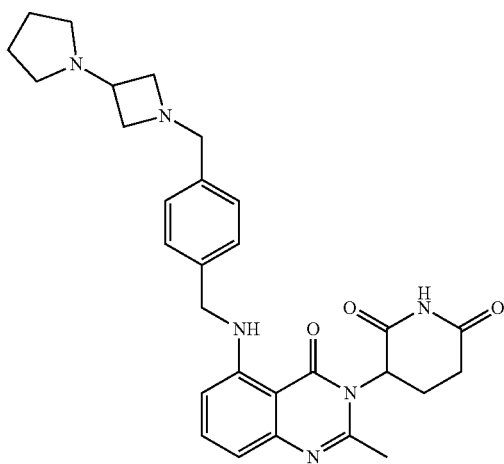 [SMILES: Cc1nc2cccc(NCc3ccc(CN4CC(N5CCCC5)C4)cc3)c2c(=O)n1C1CCC(=O)NC1=O] | 3-(2-methyl-4-oxo-5-((4-((3-(pyrrolidin-1-yl)azetidin-1-yl)methyl)benzyl)amino)quinazolin-3(4H)-yl)piperidine-2,6-dione |

TABLE 3-continued
| | | |
|---|---|---|
| 112 | 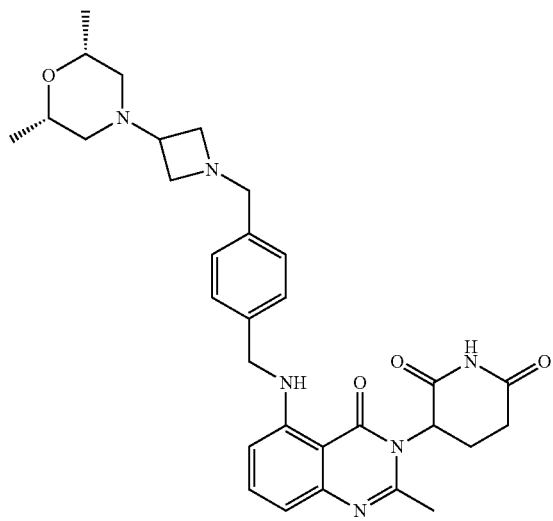 [SMILES: Cc1nc2cccc(NCc3ccc(CN4CC(N5C[C@@H](C)O[C@@H](C)C5)C4)cc3)c2c(=O)n1C1CCC(=O)NC1=O] | 3-(5-((4-((3-((2R,6S)-2,6-dimethylmorpholino)azetidin-1-yl)methyl)benzyl)amino)-2-methyl-4-oxoquinazolin-3(4H)-yl)piperidine-2,6-dione |
| 113 | 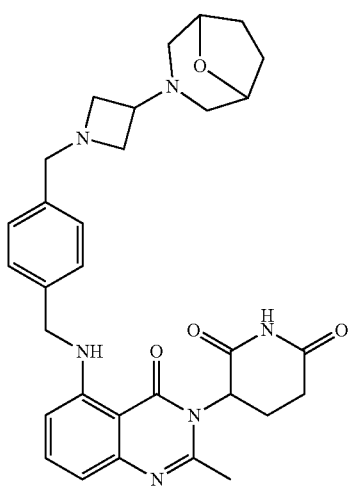 [SMILES: Cc1nc2cccc(NCc3ccc(CN4CC(N5CC6CCC(C5)O6)C4)cc3)c2c(=O)n1C1CCC(=O)NC1=O] | 3-(5-((4-((3-(8-oxa-3-azabicyclo[3.2.1]octan-3-yl)azetidin-1-yl)methyl)benzyl)amino)-2-methyl-4-oxoquinazolin-3(4H)-yl)piperidine-2,6-dione |
| 114 | 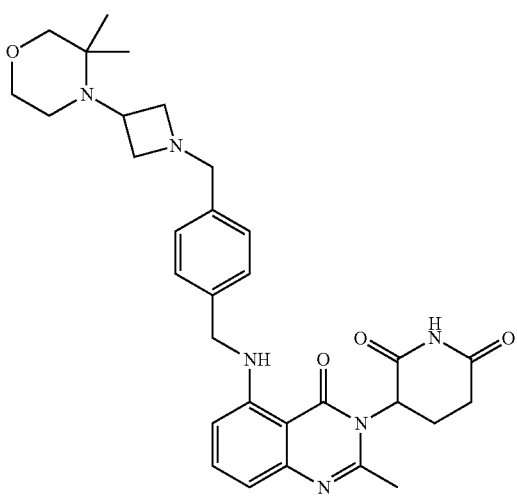 [SMILES: Cc1nc2cccc(NCc3ccc(CN4CC(N5CCOCC5(C)C)C4)cc3)c2c(=O)n1C1CCC(=O)NC1=O] | 3-(5-((4-((3-(3,3-dimethylmorpholino)azetidin-1-yl)methyl)benzyl)amino)-2-methyl-4-oxoquinazolin-3(4H)-yl)piperidine-2,6-dione |

TABLE 3-continued
| 115 | 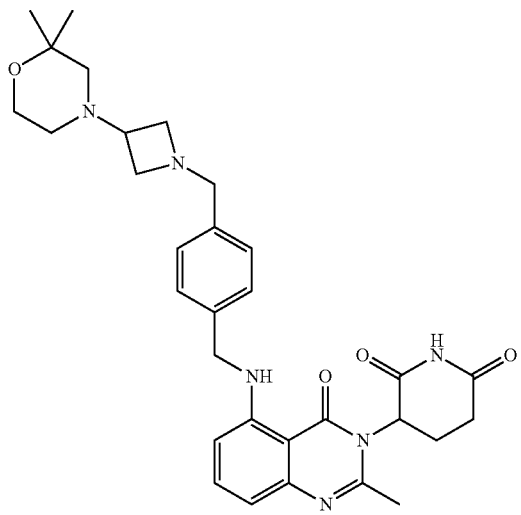 [SMILES: Cc1nc2cccc(NCc3ccc(CN4CC(N5CCOC(C)(C)C5)C4)cc3)c2c(=O)n1C1CCC(=O)NC1=O] | 3-(5-((4-((3-(2,2-dimethylmorpholino)azetidin-1-yl)methyl)benzyl)amino)-2-methyl-4-oxoquinazolin-3(4H)-yl)piperidine-2,6-dione |
| --- | --- | --- |
| 116 | 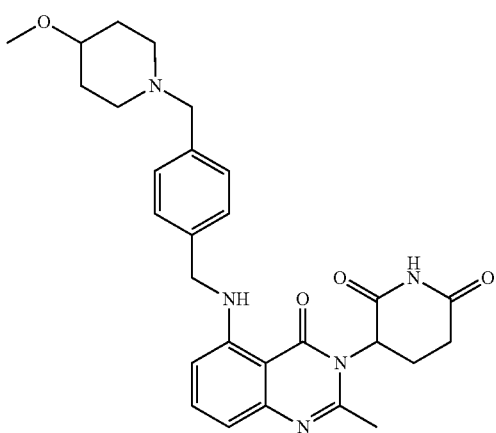 [SMILES: COC1CCN(Cc2ccc(CNc3cccc4nc(C)n(C5CCC(=O)NC5=O)c(=O)c34)cc2)CC1] | 3-(5-((4-((4-methoxypiperidin-1-yl)methyl)benzyl)amino)-2-methyl-4-oxoquinazolin-3(4H)-yl)piperidine-2,6-dione |
| 117 | 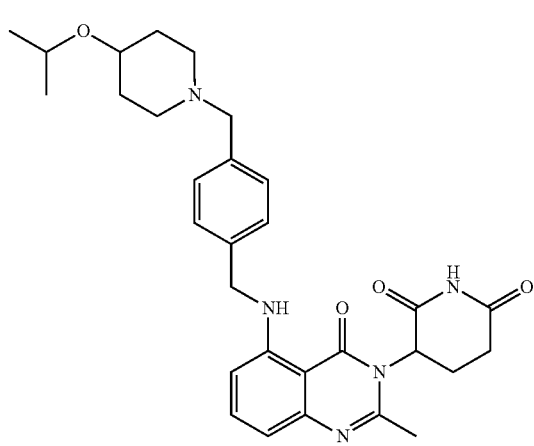 [SMILES: Cc1nc2cccc(NCc3ccc(CN4CCC(OC(C)C)CC4)cc3)c2c(=O)n1C1CCC(=O)NC1=O] | 3-(5-((4-((4-isopropoxypiperidin-1-yl)methyl)benzyl)amino)-2-methyl-4-oxoquinazolin-3(4H)-yl)piperidine-2,6-dione |

TABLE 3-continued
| | | |
|---|---|---|
| 118 | 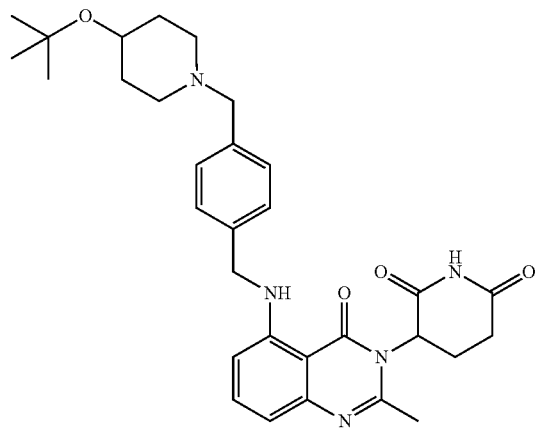 [SMILES: Cc1nc2cccc(NCc3ccc(CN4CCC(OC(C)(C)C)CC4)cc3)c2c(=O)n1C1CCC(=O)NC1=O] | 3-(5-((4-((4-(tert-butoxy)piperidin-1-yl)methyl)benzyl)amino)-2-methyl-4-oxoquinazolin-3(4H)-yl)piperidine-2,6-dione |
| 119 | 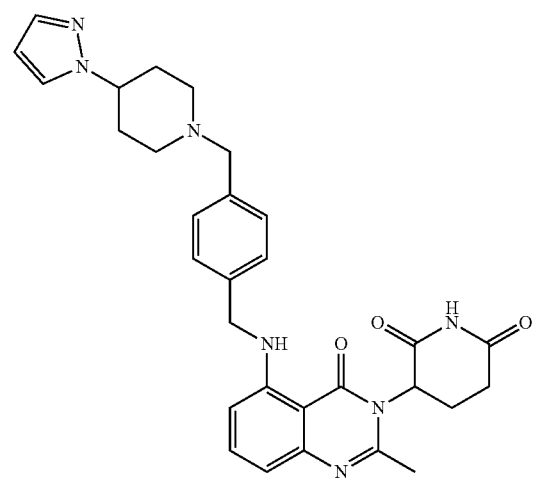 [SMILES: Cc1nc2cccc(NCc3ccc(CN4CCC(n5cccn5)CC4)cc3)c2c(=O)n1C1CCC(=O)NC1=O] | 3-(5-((4-((4-(1H-pyrazol-1-yl)piperidin-1-yl)methyl)benzyl)amino)-2-methyl-4-oxoquinazolin-3(4H)-yl)piperidine-2,6-dione |
| 120 | 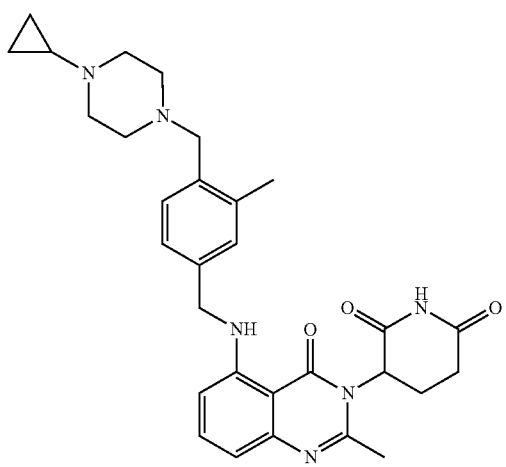 [SMILES: Cc1cc(CNc2cccc3nc(C)n(C4CCC(=O)NC4=O)c(=O)c23)ccc1CN1CCN(C2CC2)CC1] | 3-(5-((4-((4-cyclopropylpiperazin-1-yl)methyl)-3-methylbenzyl)amino)-2-methyl-4-oxoquinazolin-3(4H)-yl)piperidine-2,6-dione |

TABLE 3-continued
| 121 | 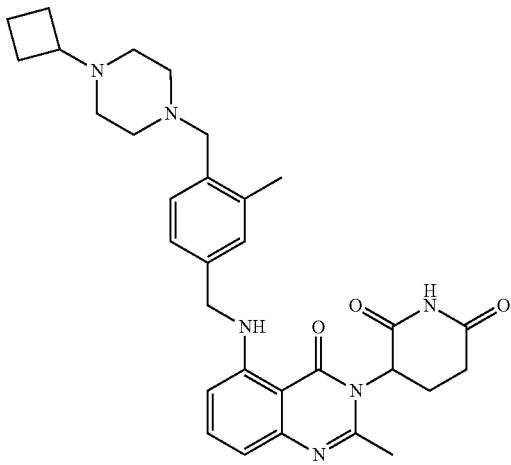 [SMILES: Cc1cc(CNc2cccc3nc(C)n(C4CCC(=O)NC4=O)c(=O)c23)ccc1CN1CCN(C2CCC2)CC1] | 3-(5-(((4-((4-cyclobutylpiperazin-1-yl)methyl)-3-methylbenzyl)amino)-2-methyl-4-oxoquinazolin-3(4H)-yl)piperidine-2,6-dione |
| 122 | 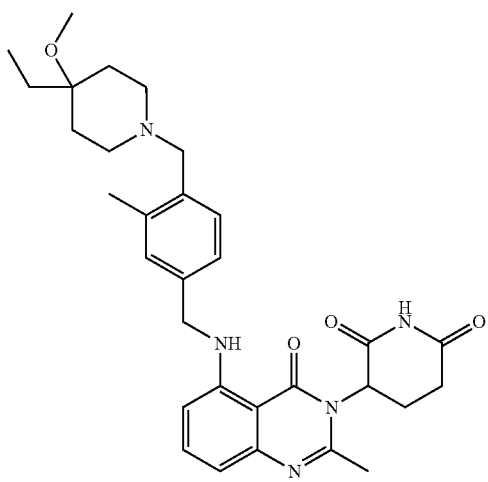 [SMILES: CCC1(OC)CCN(Cc2ccc(CNc3cccc4nc(C)n(C5CCC(=O)NC5=O)c(=O)c34)cc2C)CC1] | 3-(5-(((4-((4-ethyl-4-methoxypiperidin-1-yl)methyl)-3-methylbenzyl)amino)-2-methyl-4-oxoquinazolin-3(4H)-yl)piperidine-2,6-dione |
| 123 | 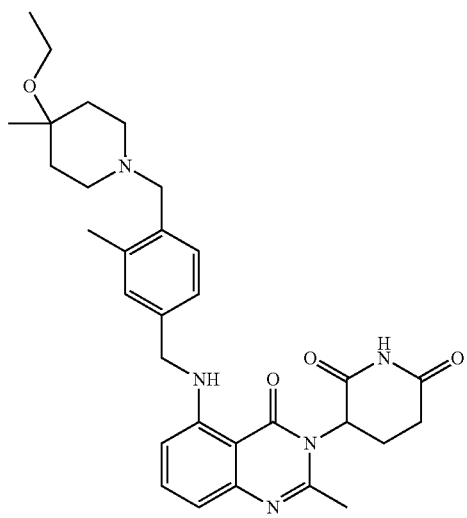 [SMILES: CCOC1(C)CCN(Cc2ccc(CNc3cccc4nc(C)n(C5CCC(=O)NC5=O)c(=O)c34)cc2C)CC1] | 3-(5-(((4-((4-ethoxy-4-methylpiperidin-1-yl)methyl)-3-methylbenzyl)amino)-2-methyl-4-oxoquinazolin-3(4H)-yl)piperidine-2,6-dione |

TABLE 3-continued
| 124 | 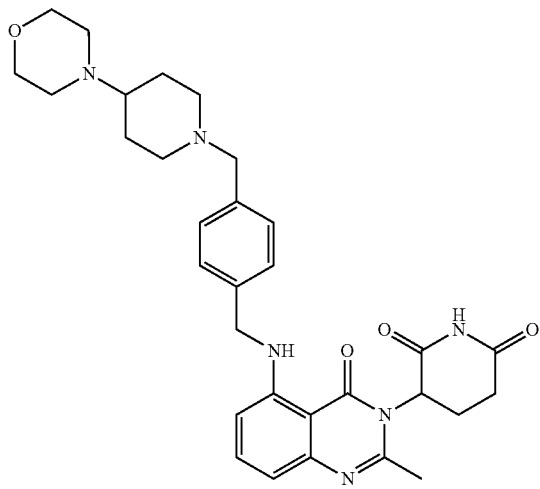 | 3-(2-methyl-5-((4-((4-morpholinopiperidin-1-yl)methyl)benzyl)amino)-4-oxoquinazolin-3(4H)-yl)piperidine-2,6-dione |
| 125 | 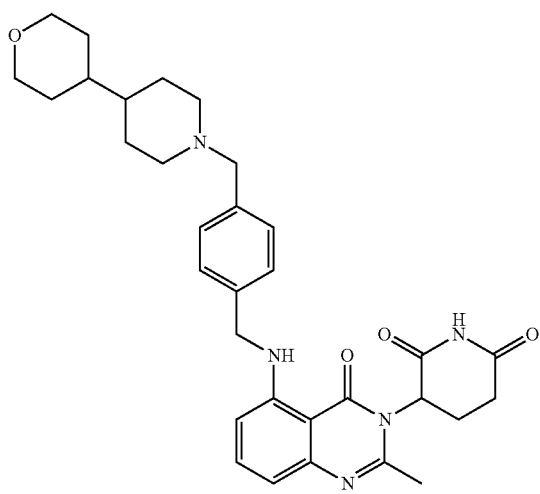 | 3-(2-methyl-4-oxo-5-((4-((4-(tetrahydro-2H-pyran-4-yl)piperidin-1-yl)methyl)benzyl)amino)quinazolin-3(4H)-yl)piperidine-2,6-dione |
| 126 | 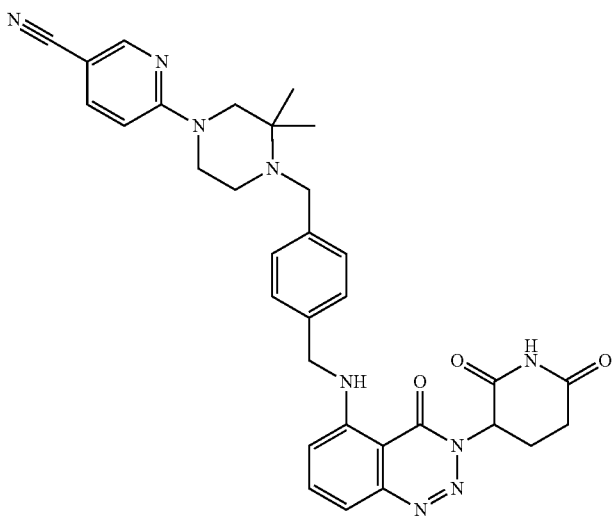 [SMILES: CC1(C)CN(c2ccc(C#N)cn2)CCN1Cc1ccc(CNc2cccc3nnn(C4CCC(=O)NC4=O)c(=O)c23)cc1] | 6-(4-(4-(((3-(2,6-dioxopiperidin-3-yl)-4-oxo-3,4-dihydrobenzo[d][1,2,3]triazin-5-yl)amino)methyl)benzyl)-3,3-dimethylpiperazin-1-yl)nicotinonitrile |

In a manner set forth above, each of the compounds of Table 1 supra already not exemplified herein could be prepared. It being understood that that list of compounds is exemplary in nature and non-limiting.

Example 127 NanoBRET CRBN Cellular Target Engagement Assay

The following example measures the extent to which a test compound of this invention binds to cereblon. In this example, a commercially available cereblon binding test kit (Promega Corporation, Madison, Wis., USA) was used but adapted to a 384 well format.

The kit comprises a tracer that binds to cereblon to form a tracer-cereblon complex. This complex is reversible. Upon addition of the test compound, competition between the tracer and the test compound for the binding site(s) on cereblon occurs. The extent of tracer release from cereblon correlates to the affinity of test compound to bind to cereblon. The higher the affinity, the more tracer is released from cereblon. Hence, test compounds binding with higher affinity to cereblon correlate to lower percent tracer bound to cereblon at the end of the assay.

The assay is a homogenous cell-based assay that used bioluminescence resonance energy transfer (BRET) to measure cereblon target compound binding which causes loss of BRET. Lower BRET values correlate to higher loss of tracer bound to cereblon and, accordingly, higher the levels of target compound binding to cereblon.

The specifics of the assay include HEK293T cells were transfected with a NanoLuc-CRBN expression plasmid using Fugene as described. Approximately 24 hr later, transfected cells were washed with 1× Phosphate Buffered Saline (PBS) and harvested using trypsin. Cells were resuspended in Opti-MEM (available from Thermo Fisher Scientific) at a concentration of 2×10$^5$ cells/mL. A ratio of 1 part 100× Tracer to 4 parts NanoBRET Tracer Dilution Buffer was used to make a 20× Tracer stock. Next, 40 µl cells per well containing 1× tracer was dispensed into 384 well white tissue culture treated plates. Compounds were then dispensed using a D330e Digital Dispenser (Tecan Trading AG) and plates were allowed to incubate for 2 hr at 37° C., 5% CO$_2$. Immediately prior to BRET measurements, a 3× Complete NanoBret Nano-Glo Substrate stock in Opti-MEM was prepared and 20 µl per well of substrate was subsequently added to the assay plates. Following a 2-3 minute incubation at room temperature, donor (450 nm) and acceptor (610 nm) emission values were read on a CLARIOStar multimode plate reader (BMG) in luminescence mode. Data were converted to milliBRET units by dividing acceptor emission values by donor emission and multiplying by 1000. Data are presented as % tracer bound and is reported in Table 4 below (where appropriate, the best fit available was used):

TABLE 4

| Test Compound tested at 10 µM | % tracer bound At the end of assay | % tracer removed From CBLN |
| --- | --- | --- |
| Example 1 | 47.3 | 52.7 |
| Example 2 | 47.4 | 52.6 |
| Example 3 | 27.3 | 72.7 |
| Example 4 | 40.9 | 59.1 |
| Example 5 | 23.8 | 76.2 |
| Example 6 | 26.6 | 73.4 |
| Example 7 | 22.9 | 77.1 |
| Example 8 | 47.7 | 52.3 |
| Example 9 | 30.2 | 69.8 |

TABLE 4-continued

| Test Compound tested at 10 µM | % tracer bound At the end of assay | % tracer removed From CBLN |
| --- | --- | --- |
| Example 10 | 20.2 | 79.8 |
| Example 11 | 30.2 | 69.8 |
| Example 12 | 0 | 100 |
| Example 13 | 16.0 | 84.0 |
| Example 14 | 11.5 | 88.5 |
| Example 15 | 23.9 | 76.1 |
| Example 16 | 20.9 | 79.1 |
| Example 17 | 34.8 | 65.2 |
| Example 18 | 21.3 | 78.7 |
| Example 19 | 29.7 | 71.3 |
| Example 20 | 12.1 | 87.9 |
| Example 21 | 9.9 | 90.1 |
| Example 34 | 27.4 | 72.6 |

The above data demonstrates that the compounds of this invention effectively bind cereblon.

Example 128 Stable Cell Line Fluorescent Reporter Degradation Assays

A. Generation of Stable Cell Lines

Polycistronic plasmids were constructed for the mammalian expression of fluorescent reporter fusions of human transcription factors IKZF1 (Ikaros) and IKZF3 (Aiolos). The respective protein sequences had their C-terminal end joined to a GGGGS linker repeated three times followed by mNeonGreen, P2A sequence, and mScarlet. IKZF1 expression was driven by a CMV promoter while IKZF3 was EF1α promoter driven. The plasmids contained the HygR resistance gene for positive selection of cells with genomic integration of the reporter constructs. The plasmids were transfected using cationic lipid reagents into adherent HEK 293T cells and stable integrants were selected by treatment with 200 ug/mL hygromycin B. Clonal populations were obtained from the population of stable integrants either by limiting dilution or fluorescence activated cell sorting. The clonal stable cell lines were maintained under constant 200 ug/mL hygromycin B selection while being passaged for use in the degradation assays. The fluorescence intensity of the IKZF1/2/3-mNeonGreen (FITC channel) and mScarlet (PE channel) reporters were routinely analyzed by flow cytometry to confirm consistent expression levels between experiments.

B. IKZF1 and IKZF3 Reporter Degradation Assay

Representative compounds were evaluated for their ability to degrade IKZF1 and IKZF3 in the following assay.

The IKZF1/IKZF3 degradation assays were carried out by harvesting the HEK 293T reporter cell lines and resuspending the cells in media formulated for reduced background fluorescence. The respective cell lines were seeded at a density of 4,000 cells/well into black-walled 384-well optical grade assay plates pre-coated by the manufacturer with PDL. The cells were incubated overnight to allow for attachment to the assay plate (37° C. with humidified air and 5% CO$_2$ for all incubations). Dilutions of the compounds were prepared in dimethyl sulfoxide (DMSO) from 10 mM compound stock solutions in DMSO. The assay plates were treated with appropriate concentrations of the compounds by dispensing the DMSO dilutions in quadruplicate wells with an upper limit of 0.5% final DMSO.

After a 24 hour incubation with the compounds, the assay plates were imaged on an ImageXpress Pico microscopy system (cells maintained at 37° C. during imaging) to obtain the fluorescent readouts. The assay plates were imaged in the FITC and TRITC channels to obtain the mNeonGreen fluorescence intensity (reporter degradation data) and mScarlet fluorescence intensity (for cell segmentation), respectively. 293T-IKZF1 and 293T-IKZF3 reporter cell lines were imaged with exposures of 500 milliseconds (ms) for both FITC and TRITC channels. The resulting data was analyzed with Cell Reporter Xpress software using the 2-channel cell scoring analysis with a "percent positive" readout. The TRITC channel was selected for the "nuclei" segmentation with a threshold of 20 while the FITC channel was selected for the "Marker 1" segmentation and a threshold of 100 for the IKZF1 and IKZF3 reporter lines. The minimum segmentation width was set to 6 micrometers and the maximum segmentation width was set to 15 micrometers for all cell lines.

The percent degradation amounts were calculated visually from the curves generated at a concentration of 10 micromolar. The results are as provided in Table 5 below:

TABLE 5

The percent degradation amounts were calculated visually from the curves generated at a concentration of 10 micromolar. The results are as provided in Table 5 below:

| Example No. | % Degradation IKZF1 @ 10 micromolar | % Degradation IKZF3 @ 10 micromolar |
| --- | --- | --- |
| 1 | 89.1 | 91.1 |
| 4 | 92.4 | 95.8 |
| 5 | 89.7 | 93.6 |
| 7 | 76.8 | 94.3 |
| 32 | 93.8 | 91.9 |
| 33 | 95.5 | 87.4 |
| 34 | 93.1 | 93.2 |
| 36 | 88.2 | 87.4 |
| 91 | 97.1 | 96.3 |
| 96 | 92.6 | 92.6 |
| 101 | 78.4 | 92.4 |

The data in Examples 127 and 128 show that the compounds described herein bind CBLN and also degrade IKZF1 and/or IKZF3.

The invention claimed is:
1. A compound of formula I-A:

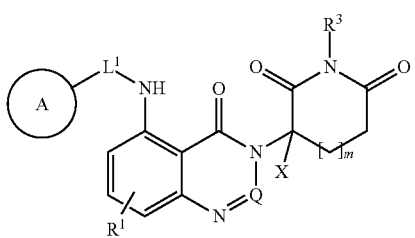

I-A or a pharmaceutical acceptable salt, solvate, stereoisomer, and/or tautomer thereof wherein:
m is zero, one or two;
$R^1$ is hydrogen, halo, or $C_1$-$C_4$ alkyl;
$R^2$ is hydrogen, $C_1$-$C_4$ alkyl, or cyclopropyl;
$R^3$ is hydrogen or —$CH_2$—$OR^5$ where $R^5$ is —C(O)—$R^6$ or —P(O)(OR$^7$)$_2$, where $R^6$ is $C_1$-$C_4$ alkyl or $C_1$-$C_4$ alkoxy, and each $R^7$ is independently hydrogen or $C_1$-$C_4$ alkyl;
X is hydrogen or deuterium;
$L^1$ is a $C_1$-$C_4$ alkylene or $C_1$-$C_4$ alkylene substituted with 1 to 2 substituents selected from halo, cyano, and $C_1$-$C_4$ alkoxy;

Q is N or $CR_2$;
ring A is a substituted aryl group of from 6 to 14 carbon atoms having from 1 to 3 substituents wherein each substituent is independently selected from:
amino,
$C_1$-$C_4$ alkylamino,
di-($C_1$-$C_4$ alkyl)-amino,
$C_1$-$C_4$ alkyl,
$C_1$-$C_4$ alkyl substituted with 1 to 3 substituents independently selected from amino, hydroxyl, or halo,
$C_1$-$C_4$ alkoxy,
$C_1$-$C_4$ alkoxy substituted with 1 to 3 substituents selected from amino, hydroxyl, or halo,
cyano,
halo,
hydroxyl, or
nitro;
wherein when ring A is 4-methoxyphenyl, Q is not N.

2. The compound of claim 1, wherein $L^1$ is a straight chain $C_1$-$C_4$ alkylene group.
3. The compound of claim 2, wherein $L^1$ is methylene or ethylene.
4. The compound of claim 1, wherein Q is C—$R^2$.
5. The compound of claim 1, wherein Q is N.
6. The compound of claim 1, wherein the aryl is a phenyl group having from 1 to 3 substituents each of which are independently selected from $C_1$-$C_4$ alkyl, hydroxy-$C_1$-$C_4$ alkyl, $C_1$-$C_4$ alkoxy, amino, $C_1$-$C_4$ alkylamino, di-($C_1$-$C_4$ alkyl)amino, halo, cyano, and nitro.
7. The compound of claim 1, wherein ring A is selected from: 2-methylphenyl, 3-methylphenyl, 4-methylphenyl, 2,4-dimethylphenyl, 2,6-dimethylphenyl, 3,5-dimethylphenyl, 2,4,6-trimethylphenyl, 2-methoxyphenyl, 3-methoxyphenyl, 4-methoxyphenyl, 2,4-dimethoxyphenyl, 2,6-dimethoxyphenyl, 2,5-dimethoxyphenyl, 3,4-dimethoxyphenyl, 3,5-dimethoxyphenyl, 2,4,6-trimethoxyphenyl, 2-fluorophenyl, 3-fluorophenyl, 4-fluorophenyl, 2,6-difluorophenyl, 3,5-difluorophenyl, 2,4-difluorophenyl, 2,5-difluorophenyl, 2,4,6-trifluorophenyl, 2-chlorophenyl, 3-chlorophenyl, 4-chlorophenyl, 2,6-dichlorophenyl, 3,5-dichlorophenyl, 2,4-dichlorophenyl, 2,5-dichlorophenyl, 2,4,6-trichlorophenyl, 2-hydroxymethylphenyl, 3-hydroxymethylphenyl, 4-hydroxymethylphenyl, trifluoromethylphenyl, 2,6-di-(trifluoromethyl)phenyl, 3,5-di-(trifluoromethyl)phenyl, 2-cyanophenyl, 3-cyanophenyl, 4-cyanophenyl, 2,4-dicyanophenyl, 2,6-dicyanophenyl, 2-methoxy-4-fluorophenyl, 2-ethyl-4-chlorophenyl, and 3-ethyl-5,8-dichloronaphth-2-yl.
8. A compound of formula I-B:

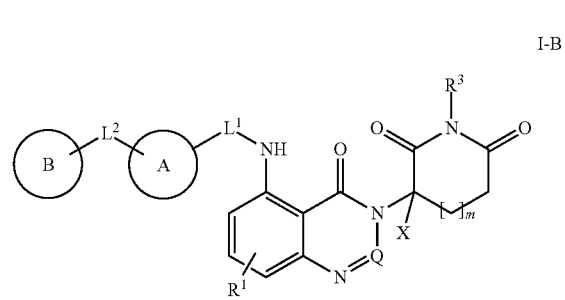

I-B or a pharmaceutical acceptable salt, solvate, stereoisomer, and/or tautomer thereof,
wherein:
m is zero, one or two;
X is hydrogen or deuterium;

L¹ is a C₁-C₄ alkylene or C₁-C₄ alkylene substituted with 1 to 2 substituents selected from hydroxy, halo, cyano, and C₁-C₄ alkoxy;

L² is a bond, C₁-C₄ alkylene, —O—C₁-C₄ alkylene or C₁-C₄ alkylene-O—;

Q is N or CR₂;

R¹ is hydrogen, halo, or C₁-C₄ alkyl;

R² is hydrogen, C₁-C₄ alkyl, or cyclopropyl;

R³ is hydrogen or —CH₂—OR⁵ where R⁵ is —C(O)—R⁶ or —P(O)(OR⁷)₂, where R⁶ is C₁-C₄ alkyl or C₁-C₄ alkoxy, and each R⁷ is independently hydrogen or C₁-C₄ alkyl;

Ring A is aryl or aryl having from 1 to 2 substituents wherein each substituent is independently selected from amino,
C₁-C₄ alkylamino,
di-(C₁-C₄ alkyl)-amino,
C₁-C₄ alkyl,
C₁-C₄ alkyl substituted with 1 to 3 substituents independently selected from amino, hydroxyl, or halo,
C₁-C₄ alkoxy,
C₁-C₄ alkoxy substituted with 1 to 3 substituents selected from amino, hydroxyl, or halo,
halo,
hydroxy,
cyano, or
nitro; and Ring B is aryl, substituted aryl, cycloalkyl, substituted cycloalkyl, heteroaryl, substituted heteroaryl, heterocyclic or substituted heterocyclic wherein each substituted aryl, substituted cycloalkyl, substituted heteroaryl and substituted heterocyclic have from 1 to 3 substituents selected from fluoro,
C₁-C₄ alkyl,
C₁-C₄ alkyl substituted with 1 to 3 substituents independently selected from amino, hydroxyl, or halo,
C₁-C₄ alkoxy, or
C₁-C₄ alkoxy substituted with 1 to 3 substituents selected from amino, hydroxyl, or halo.

9. The compound of claim 8, wherein L¹ is a straight chain C₁-C₄ alkylene group.

10. The compound of claim 9, wherein L¹ is methylene or ethylene.

11. The compound of claim 8, wherein L² is a bond or methylene.

12. The compound of claim 8, wherein Q is C—R².

13. The compound of claim 8, wherein Q is N.

14. The compound of claim 8, wherein the -Ring B-L²-Ring A group is selected from 4-(morpholin-N-yl-CH₂)-phenyl, 2-fluoro-4-(morpholin-N-yl-CH₂)-phenyl, 3-fluoro-4-(morpholin-N-yl-CH₂)-phenyl, 2,6-difluoro-4-(morpholin-N-yl-CH₂)-phenyl, 3,5-difluoro-4-(morpholin-N-yl-CH₂)-phenyl, 2,3-difluoro-4-(morpholin-N-yl-CH₂)-phenyl, 3-(morpholin-N-yl-CH₂)-phenyl, 2-fluoro-3-(morpholin-N-yl-CH₂)-phenyl, 4-fluoro-3-(morpholin-N-yl-CH₂)-phenyl, 2,6-difluoro-3-(morpholin-N-yl-CH₂)-phenyl, 2,5-difluoro-3-(morpholin-N-yl-CH₂)-phenyl, 2,4-difluoro-3-(morpholin-N-yl-CH₂)-phenyl, 2-(morpholin-N-yl-CH₂)-phenyl, 3-fluoro-2-(morpholin-N-yl-CH₂)-phenyl, 4-fluoro-2-(morpholin-N-yl-CH₂)-phenyl, 5-fluoro-2-(morpholin-N-yl-CH₂)-phenyl, 6-fluoro-2-(morpholin-N-yl-CH₂)-phenyl, 3,6-difluoro-2-(morpholin-N-yl-CH₂)-phenyl, 3,5-difluoro-2-(morpholin-N-yl-CH₂)-phenyl, 4,6-difluoro-2-(morpholin-N-yl-CH₂)-phenyl, 2-chloro-4-(morpholin-N-yl-CH₂)-phenyl, 3-chloro-4-(morpholin-N-yl-CH₂)-phenyl, 2,6-dichloro-4-(morpholin-N-yl-CH₂)-phenyl, 3,5-dichloro-4-(morpholin-N-yl-CH₂)-phenyl, 2,3-dichloro-4-(morpholin-N-yl-CH₂)-phenyl, 3-(morpholin-N-yl-CH₂)-phenyl, 2-chloro-3-(morpholin-N-yl-CH₂)-phenyl, 4-chloro-3-(morpholin-N-yl-CH₂)-phenyl, 2,6-dichloro-3-(morpholin-N-yl-CH₂)-phenyl, 2,5-dichloro-3-(morpholin-N-yl-CH₂)-phenyl, 2,4-dichloro-3-(morpholin-N-yl-CH₂)-phenyl, 2-(morpholin-N-yl-CH₂)-phenyl, 3-chloro-2-(morpholin-N-yl-CH₂)-phenyl, 4-chloro-2-(morpholin-N-yl-CH₂)-phenyl, 5-chloro-2-(morpholin-N-yl-CH₂)-phenyl, 6-chloro-2-(morpholin-N-yl-CH₂)-phenyl, 3,6-dichloro-2-(morpholin-N-yl-CH₂)-phenyl, 3,5-dichloro-2-(morpholin-N-yl-CH₂)-phenyl, 4,6-dichloro-2-(morpholin-N-yl-CH₂)-phenyl, 2-cyano-4-(morpholin-N-yl-CH₂)-phenyl, 2-cyano-6-fluoro-4-(morpholin-N-yl-CH₂)-phenyl, 4-benzyloxyphenyl, 4-(pyrid-2-yl-CH₂)-phenyl, 2-(pyrrolidin-N-yl-CH₂)-phenyl, 2-(piperidin-N-yl-CH₂)-phenyl, 4-(morpholin-N-yl-CH₂)-phenyl; 4-(piperazin-N-yl-CH₂)-phenyl, 2-fluoro-4-(piperazin-N-yl-CH₂)-phenyl, 2,6-difluoro-4-(piperazin-N-yl-CH₂)-phenyl, 3-fluoro-4-(piperazin-N-yl-CH₂)-phenyl, 3,5-difluoro-4-(piperazin-N-yl-CH₂)-phenyl, 2,3-difluoro-4-(piperazin-N-yl-CH₂)-phenyl; 2-chloro-4-(piperazin-N-yl-CH₂)-phenyl, 2,6-dichloro-4-(piperazin-N-yl-CH₂)-phenyl, 3-chloro-4-(piperazin-N-yl-CH₂)-phenyl, 3,5-dichloro-4-(piperazin-N-yl-CH₂)-phenyl, 2,3-dichloro-4-(piperazin-N-yl-CH₂)-phenyl, 2-cyclohexylphenyl, 2-cyclopentylphenyl, 4-(4,4-dimethylpiperidin-yl-CH₂)-phenyl, difluoropiperidin-yl-CH₂)-phenyl, 4-(4-trifluoromethylpiperidin-yl-CH₂)-phenyl, 4-(4-isopropylpiperidin-yl-CH₂)-phenyl, 4-(N'-isopropylpiperazin-N-yl-CH₂)-phenyl, 4-[(4-methoxypiperidin-N-yl)-CH₂—]phen-1-yl, 4-[(4-isopropoxypiperidin-N-yl)-CH₂-]phen-1-yl; 4-[(4-t-butoxypiperidin-N-yl)-CH₂—]phen-1-yl; 4-[(4-methoxy-4-ethylpiperidin-N-yl)-CH₂—]phen-1-yl; 3-methyl-4-[(4-methoxy-4-ethylpiperidin-N-yl)-CH₂—]phen-1-yl; 3-methyl-4-[(4-methoxy-4-methylpiperidin-N-yl)-CH₂—]phen-1-yl and 2-methyl-4-[(4-methoxy-4-ethylpiperidin-N-yl)-CH₂-]phen-1-yl.

15. A compound of formula I-C:

I-C or a pharmaceutical acceptable salt, solvate, stereoisomer, and/or tautomer thereof wherein:

m is zero, one or two;

L¹ is a C₁-C₄ alkylene or C₁-C₄ alkylene substituted with 1 to 2 substituents selected from hydroxy, halo, cyano, and C₁-C₄ alkoxy;

L² is a bond, C₁-C₄ alkylene, —O—C₁-C₄ alkylene or C₁-C₄ alkylene-O—;

T is a covalent bond or C₁-C₄ alkylene;

R¹ is hydrogen, halo, or C₁-C₄ alkyl;

R² is hydrogen, C₁-C₄ alkyl, or cyclopropyl;

R³ is hydrogen or —CH₂—OR⁵ where R⁵ is —C(O)—R⁶ or —P(O)(OR⁷)₂, where R⁶ is C₁-C₄ alkyl or C₁-C₄ alkoxy, and each R⁷ is independently hydrogen or C₁-C₄ alkyl;

Ring A is aryl or substituted aryl having from 1 to 3 substituents wherein each substituent is independently selected from:
amino,
C₁-C₄ alkylamino,
di-(C₁-C₄ alkyl)-amino
cyano,
halo,
nitro,
C₁-C₄ alkyl,
C₁-C₄ alkyl substituted with 1 to 3 substituents independently selected from amino, hydroxyl, or halo,
C₁-C₄ alkoxy, and
C₁-C₄ alkoxy substituted with 1 to 3 substituents selected from amino, hydroxyl, or halo;

Ring B is aryl, substituted aryl, heteroaryl, substituted heteroaryl, heterocyclic or substituted heterocyclic having 1 to 3 substituents selected from
amino,
C₁-C₄ alkylamino,
di-(C₁-C₄ alkyl)-amino
cyano,
halo,
nitro,
C₁-C₄ alkyl,
C₁-C₄ alkyl substituted with 1 to 3 substituents independently selected from amino, hydroxyl, or halo,
C₁-C₄ alkoxy, and
C₁-C₄ alkoxy substituted with 1 to 3 substituents selected from amino, hydroxyl, or halo; and Ring C is aryl, substituted aryl, cycloalkyl, substituted cycloalkyl, heteroaryl, substituted heteroaryl, heterocyclic or substituted heterocyclic wherein each substituted aryl, substituted cycloalkyl, substituted heteroaryl and substituted heterocyclic having from 1 to 3 substituents selected from
amino,
C₁-C₄ alkylamino,
di-(C₁-C₄ alkyl)-amino
cyano,
halo,
nitro,
C₁-C₄ alkyl,
C₁-C₄ alkyl substituted with 1 to 3 substituents independently selected from amino, hydroxyl, or halo,
C₁-C₄ alkoxy, and
C₁-C₄ alkoxy substituted with 1 to 3 substituents selected from amino, hydroxyl, or halo.

16. The compound of claim 15, wherein L¹ is a straight chain C₁-C₄ alkylene group.

17. The compound of claim 16, wherein L¹ is methylene or ethylene.

18. The compound of claim 17, wherein L² is a bond or methylene.

19. The compound of claim 15, wherein T is a bond.

20. The compound of claim 15, wherein the ring C-T-ring B-L²-ring A group is selected from:
3-[(2-fluoro-4-cyanophenyl)-N'-piperazinyl-N—CH₂—]phen-1-yl;
4-[(2-fluoro-4-cyanophenyl)-N'-piperazinyl-N—CH₂—]phen-1-yl;
4-[(2-fluoro-4-cyanophenyl)-N'-octahydropyrrolo-[3,4-c]-pyrrol-N-yl-CH₂]-phen-1-yl;
4-[(2-chloro-4-cyanophenyl)-N'-piperazin-N-yl-CH₂—]phen-1-yl;
4-[(4-fluorophenyl)-N'-piperazin-N-yl-CH₂—]phen-1-yl;
4-[(2,4-difluorophenyl)-N'-piperazin-N-yl-CH₂—]phen-1-yl;
4-[(3,5-difluorophenyl)-N'-piperazin-N-yl-CH₂—]phen-1-yl;
4-[(5-fluoropyrid-2-yl)-N'-piperazin-N-yl-CH₂-]phen-1-yl;
4-[(pyrid-2-yl)-N'-piperazin-N-yl-CH₂—]phen-1-yl;
4-[(pyrid-3-yl)-N'-piperazin-N-yl-CH₂—]phen-1-yl;
4-[(pyrid-4-yl)-N'-piperazin-N-yl-CH₂—]phen-1-yl;
4-[(2,3-dichlorophenyl)-N'-piperazin-N-yl-CH₂—]phen-1-yl;
4-[(4-cyanophenyl)-N'-piperazin-N-yl-CH₂—]phen-1-yl;
4-[1 (5-cyanopyrid-2-yl)-N'-2-methylpiperazin-N-yl-CH₂-]phen-1-yl;
4-[(3-trifluoromethylphenyl)-N'-piperazin-N-yl-CH₂—]phen-1-yl;
4-[(2-methoxyphenyl)-N'-piperazin-N-yl-CH₂—]phen-1-yl;
4-(3-(N-morpholino)-azetidin-N-yl-CH₂-phen-1-yl;
2-fluoro-4-[3-(N-morpholino)-azetidin-N-yl-CH₂—]pheny-1-yl;
2-methyl-4-[3-(N-morpholino)-azetidin-N-yl-CH₂—]pheny-1-yl;
3-methyl-4-[3-(N-morpholino)-azetidin-N-yl-CH₂—]pheny-1-yl;
3-fluoro-4-[(3-(N-morpholino)-azetidin-N-yl-CH₂—]pheny-1-yl;
2,6-difluoro-4-(3-(N-morpholino)-azetidin-N-yl-CH₂-pheny-1-yl;
3,5-difluoro-4-(3-(N-morpholino)-azetidin-N-yl-CH₂-pheny-1-yl;
3,6-difluoro-4-(3-(N-morpholino)-azetidin-N-yl-CH₂-pheny-1-yl;
2-fluoro-4-(3-(N-piperidinyl)-azetidin-N-yl-CH₂-pheny-1-yl;
3-fluoro-4-(3-(N-piperidinyl)-azetidin-N-yl-CH₂-pheny-1-yl;
2,6-difluoro-4-(3-(N-piperidinyl)-azetidin-N-yl-CH₂-pheny-1-yl;
3,5-difluoro-4-(3-(N-piperidinyl)-azetidin-N-yl-CH₂-pheny-1-yl;
3,6-difluoro-4-(3-(N-piperidinyl)-azetidin-N-yl-CH₂-pheny-1-yl;
2-fluoro-4-(3-(N-piperazinyl)-azetidin-N-yl-CH₂-pheny-1-yl;
3-fluoro-4-(3-(N-piperazinyl)-azetidin-N-yl-CH₂-pheny-1-yl;
2,6-difluoro-4-(3-(N-piperazinyl)-azetidin-N-yl-CH₂-pheny-1-yl;
3,5-difluoro-4-(3-(N-piperazinyl)-azetidin-N-yl-CH₂-pheny-1-yl,
4-cyano-(3-(N-piperidinyl)-azetidin-N-yl-CH₂-pheny-1-yl;
3-cyano-(3-(N-piperidinyl)-azetidin-N-yl-CH₂-pheny-1-yl;
4-[(pyrid-2-yl)-azetidin-N-yl-CH₂—]phen-1-yl;
4-[(pyrid-3-yl)-azetidin-N-yl-CH₂-]phen-1-yl;
4-[(pyrid-4-yl)-azetidin-N-yl-CH₂—]phen-1-yl;
4-[(pyrazol-N-yl)-azetidin-N-yl-CH₂—]phen-1-yl;
4-[(pyrrolidin-N-yl)-azetidin-N-yl-CH₂—]phen-1-yl;
4-[3-(2,6-dimethyl-N-morpholino)-azetidin-N-yl-CH₂—]pheny-1-yl;
4-[3-(3,3-dimethyl-N-morpholino)-azetidin-N-yl-CH₂-]pheny-1-yl;

4-[3-(2,2-dimethyl-N-morpholino)-azetidin-N-yl-CH₂—]pheny-1-yl;
4-[3-(8-oxa-3-aza-bicyclo[3.2.1]-octan-N-yl)-azetidin-N-yl-CH₂—]pheny-1-yl;
4-[(4-pyrrol-N-yl-piperidin-N-yl)-CH₂—]phen-1-yl;
3-methyl-4-[(N'-cyclopropylpiperazin-N-yl-CH₂—]phen-1-yl;
3-methyl-4-[(N'-cyclobutylpiperazin-N-yl-CH₂—]phen-1-yl; and
4-[4-(morpholin-N-yl)-piperidin-N-yl-CH₂—]phen-1-yl.

21. A compound or a pharmaceutical acceptable salt, solvate, stereoisomer, and/or tautomer thereof wherein said compound is selected from:

3-(5-((4-methoxybenzyl)-amino)-2-methyl-4-oxoquinazolin-3(4H)-yl)piperidine-2,6-dione;
3-(5-((2-methoxybenzyl)-amino)-2-methyl-4-oxoquinazolin-3(4H)-yl)piperidine-2,6-dione;
3-(5-((3-methoxybenzyl)-amino)-2-methyl-4-oxoquinazolin-3(4H)-yl)piperidine-2,6-dione;
3-(5-((4-fluorobenzyl)-amino)-2-methyl-4-oxoquinazolin-3 (4H)-yl)piperidine-2,6-dione;
3-(5-((3-fluorobenzyl)-amino)-2-methyl-4-oxoquinazolin-3 (4H)-yl)piperidine-2,6-dione;
3-(5-((2-fluorobenzyl)-amino)-2-methyl-4-oxoquinazolin-3 (4H)-yl)piperidine-2,6-dione;
3-(5-((3-methylbenzyl)-amino)-2-methyl-4-oxoquinazolin-3 (4H)-yl)piperidine-2,6-dione;
3-(5-((4-methylbenzyl)-amino)-2-methyl-4-oxoquinazolin-3 (4H)-yl)piperidine-2,6-dione;
3-(5-((2-chlorobenzyl)-amino)-2-methyl-4-oxoquinazolin-3 (4H)-yl)piperidine-2,6-dione;
3-(5-((3-chlorobenzyl)-amino)-2-methyl-4-oxoquinazolin-3 (4H)-yl)piperidine-2,6-dione;
3-(5-((2-methylbenzyl)-amino)-2-methyl-4-oxoquinazolin-3 (4H)-yl)piperidine-2,6-dione;
3-(5-(3,4-dimethoxybenzyl)-amino)-2-methyl-4-oxoquinazolin-3 (4H)-yl)piperidine-2,6-dione;
3-(5-((2-cyanobenzyl)-amino)-2-methyl-4-oxoquinazolin-3 (4H)-yl)piperidine-2,6-dione;
3-(5-((4-cyanobenzyl)-amino)-2-methyl-4-oxoquinazolin-3 (4H)-yl)piperidine-2,6-dione;
3-(5-((4-trifluoromethylbenzyl)-amino)-2-methyl-4-oxoquinazolin-3 (4H)-yl)piperidine-2,6-dione;
3-(5-((3,5-dimethoxybenzyl)-amino)-2-methyl-4-oxoquinazolin-3(4H)-yl)piperidine-2,6-dione;
3-(5-((2,4-dimethoxybenzyl)-amino)-2-methyl-4-oxoquinazolin-3(4H)-yl)piperidine-2,6-dione;
3-(5-((2,6-dichlorobenzyl)-amino)-2-methyl-4-oxoquinazolin-3 (4H)-yl)piperidine-2,6-dione;
3-(5-((2,5-dimethoxybenzyl)amino)-4-oxobenzo[d][1,2,3]triazin-3(4H)-yl)piperidine-2,6-dione;
3-(5-((2,5-dichlorobenzyl)amino)-2-methyl-4-oxoquinazolin-3(4H)-yl)piperidine-2,6-dione;
3-(5-((4-(hydroxymethyl)benzyl)amino)-2-methyl-4-oxoquinazolin-3(4H)-yl)piperidine-2,6-dione;
3-(5-((2,4-dimethoxybenzyl)amino)-4-oxobenzo[d][1,2,3]triazin-3(4H)-yl)piperidine-2,6-dione;
3-(2-cyclopropyl-5-((4-methoxybenzyl)amino)-4-oxoquinazolin-3(4H)-yl)piperidine-2,6-dione;
3-(2-methyl-5-((4-morpholinobenzyl)amino)-4-oxoquinazolin-3(4H)-yl)piperidine-2,6-dione;
3-(5-((2-fluoro-4-morpholinobenzyl)amino)-2-methyl-4-oxoquinazolin-3(4H)-yl)piperidine-2,6-dione;
3-(5-((4-methoxybenzyl)amino)-2,7-dimethyl-4-oxoquinazolin-3(4H)-yl)piperidine-2,6-dione;
3-(5-((2-cyclohexylbenzyl)amino)-2-methyl-4-oxoquinazolin-3(4H)-yl)piperidine-2,6-dione;
3-(5-((2-cyclopentylbenzyl)amino)-2-methyl-4-oxoquinazolin-3(4H)-yl)piperidine-2,6-dione;
3-(5-((4-(benzyloxy)benzyl)amino)-2-methyl-4-oxoquinazolin-3(4H)-yl)piperidine-2,6-dione;
3-(5-((4-methoxybenzyl)amino)-4-oxoquinazolin-3(4H)-yl)piperidine-2,6-dione;
3-(2-methyl-5-((4-(morpholinomethyl)benzyl)amino)-4-oxoquinazolin-3(4H)-yl)piperidine-2,6-dione;
4-(4-(3-(((3-(2,6-dioxopiperidin-3-yl)-2-methyl-4-oxo-3,4-dihydroquinazolin-5-yl)amino)methyl)benzyl)piperazin-1-yl)-3-fluorobenzonitrile;
4-(4-(4-(((3-(2,6-dioxopiperidin-3-yl)-2-methyl-4-oxo-3,4-dihydroquinazolin-5-yl)amino)methyl)benzyl)piperazin-1-yl)-3-fluorobenzonitrile;
3-(5-((2-fluoro-4-(morpholinomethyl)benzyl)amino)-2-methyl-4-oxoquinazolin-3(4H)-yl)piperidine-2,6-dione;
3-(5-((4-(morpholinomethyl)benzyl)amino)-4-oxobenzo[d][1,2,3]triazin-3(4H)-yl)piperidine-2,6-dione;
3-(5-((2-fluoro-4-(morpholinomethyl)benzyl)amino)-4-oxobenzo[d][1,2,3]triazin-3(4H)-yl)piperidine-2,6-dione;
3-(5-((4-(morpholinomethyl)benzyl)amino)-4-oxoquinazolin-3(4H)-yl)piperidine-2,6-dione;
3-(5-((2-fluoro-4-(morpholinomethyl)benzyl)amino)-4-oxoquinazolin-3(4H)-yl)piperidine-2,6-dione;
3-(5-((4-((4,4-dimethylpiperidin-1-yl)methyl)benzyl)amino)-2-methyl-4-oxoquinazolin-3(4H)-yl)piperidine-2,6-dione;
3-(5-((4-((4,4-dimethylpiperidin-1-yl)methyl)benzyl)amino)-2-methyl-4-oxoquinazolin-3(4H)-yl)piperidine-2,6-dione;
3-(5-((4-((4,4-dimethylpiperidin-1-yl)methyl)benzyl)amino)-4-oxobenzo[d][1,2,3]triazin-3(4H)-yl)piperidine-2,6-dione;
3-(5-((4-((4,4-dimethylpiperidin-1-yl)methyl)benzyl)amino)-4-oxoquinazolin-3(4H)-yl)piperidine-2,6-dione;
3-(5-((4-((4,4-difluoropiperidin-1-yl)methyl)benzyl)amino)-2-methyl-4-oxoquinazolin-3(4H)-yl)piperidine-2,6-dione;
3-(5-((4-((4,4-difluoropiperidin-1-yl)methyl)benzyl)amino)-4-oxobenzo[d][1,2,3]triazin-3(4H)-yl)piperidine-2,6-dione;
3-(5-((4-((4,4-difluoropiperidin-1-yl)methyl)benzyl)amino)-4-oxoquinazolin-3(4H)-yl)piperidine-2,6-dione;
3-(2-methyl-4-oxo-5-((4-((4-(trifluoromethyl)piperidin-1-yl)methyl)benzyl)amino)quinazolin-3(4H)-yl)piperidine-2,6-dione;
3-(4-oxo-5-((4-((4-(trifluoromethyl)piperidin-1-yl)methyl)benzyl)amino)benzo[d][1,2,3]triazin-3(4H)-yl)piperidine-2,6-dione;
3-(4-oxo-5-((4-((4-(trifluoromethyl)piperidin-1-yl)methyl)benzyl)amino)quinazolin-3(4H)-yl)piperidine-2,6-dione;
3-(5-((4-((4-isopropylpiperidin-1-yl)methyl)benzyl)amino)-2-methyl-4-oxoquinazolin-3(4H)-yl)piperidine-2,6-dione;
3-(5-((4-((4-isopropylpiperidin-1-yl)methyl)benzyl)amino)-4-oxobenzo[d][1,2,3]triazin-3(4H)-yl)piperidine-2,6-dione;
3-(5-((4-((4-isopropylpiperidin-1-yl)methyl)benzyl)amino)-4-oxoquinazolin-3(4H)-yl)piperidine-2,6-dione;

3-(5-((4-((4-isopropylpiperazin-1-yl)methyl)benzyl)amino)-2-methyl-4-oxoquinazolin-3(4H)-yl)piperidine-2,6-dione;

3-(5-((4-((4-isopropylpiperazin-1-yl)methyl)benzyl)amino)-4-oxobenzo[d][1,2,3]triazin-3(4H)-yl)piperidine-2,6-dione;

3-(5-((4-((4-isopropylpiperazin-1-yl)methyl)benzyl)amino)-4-oxoquinazolin-3(4H)-yl)piperidine-2,6-dione;

3-chloro-4-(4-(4-(((3-(2,6-dioxopiperidin-3-yl)-2-methyl-4-oxo-3,4-dihydroquinazolin-5-yl)amino)methyl)benzyl)piperazin-1-yl)benzonitrile;

3-(5-((4-((4-(4-fluorophenyl)piperazin-1-yl)methyl)benzyl)amino)-2-methyl-4-oxoquinazolin-3(4H)-yl)piperidine-2,6-dione;

3-(5-((4-((4-(2,4-difluorophenyl)piperazin-1-yl)methyl)benzyl)amino)-2-methyl-4-oxoquinazolin-3(4H)-yl)piperidine-2,6-dione;

4-(4-(4-(((3-(2,6-dioxopiperidin-3-yl)-2-methyl-4-oxo-3,4-dihydroquinazolin-5-yl)amino)methyl)benzyl)piperazin-1-yl)benzonitrile;

3-(5-((4-((4-(5-fluoropyridin-2-yl)piperazin-1-yl)methyl)benzyl)amino)-2-methyl-4-oxoquinazolin-3(4H)-yl)piperidine-2,6-dione;

3-(5-((4-((4-(2,3-dichlorophenyl)piperazin-1-yl)methyl)benzyl)amino)-2-methyl-4-oxoquinazolin-3(4H)-yl)piperidine-2,6-dione;

3-(2-methyl-4-oxo-5-((4-((4-(3-(trifluoromethyl)phenyl)piperazin-1-yl)methyl)benzyl)amino)quinazolin-3(4H)-yl)piperidine-2,6-dione;

3-(5-((4-((4-(2-methoxyphenyl)piperazin-1-yl)methyl)benzyl)amino)-2-methyl-4-oxoquinazolin-3(4H)-yl)piperidine-2,6-dione;

4-(4-(4-(((3-(2,6-dioxopiperidin-3-yl)-4-oxo-3,4-dihydrobenzo[d][1,2,3]triazin-5-yl)amino)methyl)benzyl)piperazin-1-yl)-3-fluorobenzonitrile;

3-chloro-4-(4-(4-(((3-(2,6-dioxopiperidin-3-yl)-4-oxo-3,4-dihydrobenzo[d][1,2,3]triazin-5-yl)amino)methyl)benzyl)piperazin-1-yl)benzonitrile;

3-(5-((4-((4-(4-fluorophenyl)piperazin-1-yl)methyl)benzyl)amino)-4-oxobenzo[d][1,2,3]triazin-3(4H)-yl)piperidine-2,6-dione;

3-(5-((4-((4-(2,4-difluorophenyl)piperazin-1-yl)methyl)benzyl)amino)-4-oxobenzo[d][1,2,3]triazin-3(4H)-yl)piperidine-2,6-dione;

4-(4-(4-(((3-(2,6-dioxopiperidin-3-yl)-4-oxo-3,4-dihydrobenzo[d][1,2,3]triazin-5-yl)amino)methyl)benzyl)piperazin-1-yl)benzonitrile;

3-(5-((4-((4-(5-fluoropyridin-2-yl)piperazin-1-yl)methyl)benzyl)amino)-4-oxobenzo[d][1,2,3]triazin-3(4H)-yl)piperidine-2,6-dione;

3-(5-((4-((4-(2,3-dichlorophenyl)piperazin-1-yl)methyl)benzyl)amino)-4-oxobenzo[d][1,2,3]triazin-3(4H)-yl)piperidine-2,6-dione;

3-(4-oxo-5-((4-((4-(3-(trifluoromethyl)phenyl)piperazin-1-yl)methyl)benzyl)amino)benzo[d][1,2,3]triazin-3(4H)-yl)piperidine-2,6-dione;

3-(5-((4-((4-(2-methoxyphenyl)piperazin-1-yl)methyl)benzyl)amino)-4-oxobenzo[d][1,2,3]triazin-3(4H)-yl)piperidine-2,6-dione;

4-(4-(4-(((3-(2,6-dioxopiperidin-3-yl)-4-oxo-3,4-dihydroquinazolin-5-yl)amino)methyl)benzyl)piperazin-1-yl)-3-fluorobenzonitrile;

3-chloro-4-(4-(4-(((3-(2,6-dioxopiperidin-3-yl)-4-oxo-3,4-dihydroquinazolin-5-yl)amino)methyl)benzyl)piperazin-1-yl)benzonitrile;

3-(5-((4-((4-(4-fluorophenyl)piperazin-1-yl)methyl)benzyl)amino)-4-oxoquinazolin-3(4H)-yl)piperidine-2,6-dione;

3-(5-((4-((4-(2,4-difluorophenyl)piperazin-1-yl)methyl)benzyl)amino)-4-oxoquinazolin-3(4H)-yl)piperidine-2,6-dione;

4-(4-(4-(((3-(2,6-dioxopiperidin-3-yl)-4-oxo-3,4-dihydroquinazolin-5-yl)amino)methyl)benzyl)piperazin-1-yl)benzonitrile;

3-(5-((4-((4-(5-fluoropyridin-2-yl)piperazin-1-yl)methyl)benzyl)amino)-4-oxoquinazolin-3(4H)-yl)piperidine-2,6-dione;

3-(5-((4-((4-(2,3-dichlorophenyl)piperazin-1-yl)methyl)benzyl)amino)-4-oxoquinazolin-3(4H)-yl)piperidine-2,6-dione;

3-(4-oxo-5-((4-((4-(3-(trifluoromethyl)phenyl)piperazin-1-yl)methyl)benzyl)amino)quinazolin-3(4H)-yl)piperidine-2,6-dione;

3-(5-((4-((4-(2-methoxyphenyl)piperazin-1-yl)methyl)benzyl)amino)-4-oxoquinazolin-3(4H)-yl)piperidine-2,6-dione;

4-(4-(3-(((2-cyclopropyl-3-(2,6-dioxopiperidin-3-yl)-4-oxo-3,4-dihydroquinazolin-5-yl)amino)methyl)benzyl)piperazin-1-yl)-3-fluorobenzonitrile;

4-(4-(3-(((3-(2,6-dioxopiperidin-3-yl)-4-oxo-3,4-dihydrobenzo[d][1,2,3]triazin-5-yl)amino)methyl)benzyl)piperazin-1-yl)-3-fluorobenzonitrile;

4-(4-(3-(((3-(2,6-dioxopiperidin-3-yl)-4-oxo-3,4-dihydroquinazolin-5-yl)amino)methyl)benzyl)piperazin-1-yl)-3-fluorobenzonitrile;

4-(5-(4-(((3-(2,6-dioxopiperidin-3-yl)-2-methyl-4-oxo-3,4-dihydroquinazolin-5-yl)amino)methyl)benzyl)hexahydropyrrolo[3,4-c]pyrrol-2(1H)-yl)-3-fluorobenzonitrile;

6-((3R)-4-(4-(((3-(2,6-dioxopiperidin-3-yl)-2-methyl-4-oxo-3,4-dihydroquinazolin-5-yl)amino)methyl)benzyl)-3-methylpiperazin-1-yl)nicotinonitrile;

4-(5-(4-(((3-(2,6-dioxopiperidin-3-yl)-4-oxo-3,4-dihydrobenzo[d][1,2,3]triazin-5-yl)amino)methyl)benzyl)hexahydropyrrolo[3,4-c]pyrrol-2(1H)-yl)-3-fluorobenzonitrile;

6-((3R)-4-(4-(((3-(2,6-dioxopiperidin-3-yl)-4-oxo-3,4-dihydrobenzo[d][1,2,3]triazin-5-yl)amino)methyl)benzyl)-3-methylpiperazin-1-yl)nicotinonitrile;

4-(5-(4-(((3-(2,6-dioxopiperidin-3-yl)-4-oxo-3,4-dihydroquinazolin-5-yl)amino)methyl)benzyl)hexahydropyrrolo[3,4-c]pyrrol-2(1H)-yl)-3-fluorobenzonitrile;

6-((3R)-4-(4-(((3-(2,6-dioxopiperidin-3-yl)-4-oxo-3,4-dihydroquinazolin-5-yl)amino)methyl)benzyl)-3-methylpiperazin-1-yl)nicotinonitrile;

3-(2-methyl-5-((4-((3-morpholinoazetidin-1-yl)methyl)benzyl)amino)-4-oxoquinazolin-3(4H)-yl)piperidine-2,6-dione;

3-(5-((2-fluoro-4-((3-morpholinoazetidin-1-yl)methyl)benzyl)amino)-2-methyl-4-oxoquinazolin-3(4H)-yl)piperidine-2,6-dione;

3-(2-methyl-5-((2-methyl-4-((3-morpholinoazetidin-1-yl)methyl)benzyl)amino)-4-oxoquinazolin-3(4H)-yl)piperidine-2,6-dione;

3-(5-((3-fluoro-4-((3-morpholinoazetidin-1-yl)methyl)benzyl)amino)-2-methyl-4-oxoquinazolin-3(4H)-yl)piperidine-2,6-dione;

3-(2-methyl-5-((3-methyl-4-((3-morpholinoazetidin-1-yl)methyl)benzyl)amino)-4-oxoquinazolin-3(4H)-yl)piperidine-2,6-dione;

3-(5-((4-((3-morpholinoazetidin-1-yl)methyl)benzyl)
amino)-4-oxobenzo[d][1,2,3]triazin-3(4H)-yl)piperi-
dine-2,6-dione;
3-(5-((2-fluoro-4-((3-morpholinoazetidin-1-yl)methyl)
benzyl)amino)-4-oxobenzo[d][1,2,3]triazin-3(4H)-yl)
piperidine-2,6-dione;
3-(5-((2-methyl-4-((3-morpholinoazetidin-1-yl)methyl)
benzyl)amino)-4-oxobenzo[d][1,2,3]triazin-3(4H)-yl)
piperidine-2,6-dione;
3-(5-((3-fluoro-4-((3-morpholinoazetidin-1-yl)methyl)
benzyl)amino)-4-oxobenzo[d][1,2,3]triazin-3(4H)-yl)
piperidine-2,6-dione;
3-(5-((3-methyl-4-((3-morpholinoazetidin-1-yl)methyl)
benzyl)amino)-4-oxobenzo[d][1,2,3]triazin-3(4H)-yl)
piperidine-2,6-dione;
3-(5-((4-((3-morpholinoazetidin-1-yl)methyl)benzyl)
amino)-4-oxoquinazolin-3(4H)-yl)piperidine-2,6-di-
one;
3-(5-((2-fluoro-4-((3-morpholinoazetidin-1-yl)methyl)
benzyl)amino)-4-oxoquinazolin-3(4H)-yl)piperidine-
2,6-dione;
3-(5-((2-methyl-4-((3-morpholinoazetidin-1-yl)methyl)
benzyl)amino)-4-oxoquinazolin-3(4H)-yl)piperidine-
2,6-dione;
3-(5-((3-fluoro-4-((3-morpholinoazetidin-1-yl)methyl)
benzyl)amino)-4-oxoquinazolin-3(4H)-yl)piperidine-
2,6-dione;
3-(5-((3-methyl-4-((3-morpholinoazetidin-1-yl)methyl)
benzyl)amino)-4-oxoquinazolin-3(4H)-yl)piperidine-
2,6-dione;
4-(1-(4-(((3-(2,6-dioxopiperidin-3-yl)-2-methyl-4-oxo-3,
4-dihydroquinazolin-5-yl)amino)methyl)benzyl)azeti-
din-3-yl)benzonitrile;
3-(1-(4-(((3-(2,6-dioxopiperidin-3-yl)-2-methyl-4-oxo-3,
4-dihydroquinazolin-5-yl)amino)methyl)benzyl)azeti-
din-3-yl)benzonitrile;
3-(2-methyl-4-oxo-5-((4-((3-(pyridin-2-yl)azetidin-1-yl)
methyl)benzyl)amino)quinazolin-3(4H)-yl)piperidine-
2,6-dione;
3-(2-methyl-4-oxo-5-((4-((3-(pyridin-3-yl)azetidin-1-yl)
methyl)benzyl)amino)quinazolin-3(4H)-yl)piperidine-
2,6-dione;
3-(2-methyl-4-oxo-5-((4-((3-(pyridin-4-yl)azetidin-1-yl)
methyl)benzyl)amino)quinazolin-3(4H)-yl)piperidine-
2,6-dione;
3-(5-((4-((3-(1H-pyrazol-1-yl)azetidin-1-yl)methyl)ben-
zyl)amino)-2-methyl-4-oxoquinazolin-3(4H)-yl)pip-
eridine-2,6-dione;
3-(2-methyl-4-oxo-5-((4-((3-(pyrrolidin-1-yl)azetidin-1-
yl)methyl)benzyl)amino)quinazolin-3(4H)-yl)piperi-
dine-2,6-dione;
3-(5-((4-((3-((2R,6S)-2,6-dimethylmorpholino)azetidin-
1-yl)methyl)benzyl)amino)-2-methyl-4-oxoquinazo-
lin-3(4H)-yl)piperidine-2,6-dione;
3-(5-((4-((3-(8-oxa-3-azabicyclo[3.2.1]octan-3-yl)azeti-
din-1-yl)methyl)benzyl)amino)-2-methyl-4-oxoqui-
nazolin-3(4H)-yl)piperidine-2,6-dione;
3-(5-((4-((3-(3,3-dimethylmorpholino)azetidin-1-yl)
methyl)benzyl)amino)-2-methyl-4-oxoquinazolin-3
(4H)-yl)piperidine-2,6-dione;
3-(5-((4-((3-(2,2-dimethylmorpholino)azetidin-1-yl)
methyl)benzyl)amino)-2-methyl-4-oxoquinazolin-3
(4H)-yl)piperidine-2,6-dione;
3-(5-((4-((4-methoxypiperidin-1-yl)methyl)benzyl)
amino)-2-methyl-4-oxoquinazolin-3(4H)-yl)piperi-
dine-2,6-dione;
3-(5-((4-((4-isopropoxypiperidin-1-yl)methyl)benzyl)
amino)-2-methyl-4-oxoquinazolin-3(4H)-yl)piperi-
dine-2,6-dione;
3-(5-((4-((4-(tert-butoxy)piperidin-1-yl)methyl)benzyl)
amino)-2-methyl-4-oxoquinazolin-3(4H)-yl)piperi-
dine-2,6-dione;
3-(5-((4-((4-(1H-pyrazol-1-yl)piperidin-1-yl)methyl)ben-
zyl)amino)-2-methyl-4-oxoquinazolin-3(4H)-yl)pip-
eridine-2,6-dione;
3-(5-((4-((4-cyclopropylpiperazin-1-yl)methyl)-3-meth-
ylbenzyl)amino)-2-methyl-4-oxoquinazolin-3(4H)-yl)
piperidine-2,6-dione;
3-(5-((4-((4-cyclobutylpiperazin-1-yl)methyl)-3-methyl-
benzyl)amino)-2-methyl-4-oxoquinazolin-3 (4H)-yl)
piperidine-2,6-dione;
3-(5-((4-((4-ethyl-4-methoxypiperidin-1-yl)methyl)-3-
methylbenzyl)amino)-2-methyl-4-oxoquinazolin-3
(4H)-yl)piperidine-2,6-dione;
3-(5-((4-((4-ethoxy-4-methylpiperidin-1-yl)methyl)-3-
methylbenzyl)amino)-2-methyl-4-oxoquinazolin-3
(4H)-yl)piperidine-2,6-dione;
3-(2-methyl-5-((4-((4-morpholinopiperidin-1-yl)methyl)
benzyl)amino)-4-oxoquinazolin-3(4H)-yl)piperidine-
2,6-dione; and
3-(2-methyl-4-oxo-5-((4-((4-(tetrahydro-2H-pyran-4-yl)
piperidin-1-yl)methyl)benzyl)amino)quinazolin-3
(4H)-yl)piperidine-2,6-dione.

22. A pharmaceutical composition comprising a pharmaceutically acceptable excipient and an effective amount of a compound of claim 1.

23. A pharmaceutical composition comprising a pharmaceutically acceptable excipient and an effective amount of a compound of claim 8.

24. A pharmaceutical composition comprising a pharmaceutically acceptable excipient and an effective amount of a compound of claim 15.

* * * * *